(12) United States Patent
Kohn et al.

(10) Patent No.: US 8,829,033 B2
(45) Date of Patent: *Sep. 9, 2014

(54) N-BENZYLAMIDE SUBSTITUTED DERIVATIVES OF 2-(ACYLAMIDO)ACETIC ACID AND 2-(ACYLAMIDO)PROPIONIC ACIDS: POTENT NEUROLOGICAL AGENTS

(75) Inventors: Harold L. Kohn, Chapel Hill, NC (US); Christophe Salomé, Herrlisheim-prés-Colmar (FR); Elise Salomé-Grosjean, Herrlisheim-prés-Colmar (FR)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/395,588

(22) PCT Filed: Sep. 17, 2010

(86) PCT No.: PCT/US2010/049258
§ 371 (c)(1),
(2), (4) Date: May 4, 2012

(87) PCT Pub. No.: WO2011/037833
PCT Pub. Date: Mar. 31, 2011

(65) Prior Publication Data
US 2012/0232015 A1  Sep. 13, 2012

Related U.S. Application Data

(60) Provisional application No. 61/244,914, filed on Sep. 23, 2009.

(51) Int. Cl.
*C07D 213/56* (2006.01)
*C07D 277/30* (2006.01)
*C07C 235/08* (2006.01)
*C07C 233/18* (2006.01)
*C07D 307/68* (2006.01)
*C07D 213/40* (2006.01)
*C07D 229/00* (2006.01)

(52) U.S. Cl.
CPC ............ *C07D 213/40* (2013.01); *C07C 233/18* (2013.01); *C07D 277/30* (2013.01); *C07C 235/08* (2013.01); *C07D 213/56* (2013.01); *C07D 307/68* (2013.01); *C07D 229/00* (2013.01)
USPC ........... 514/357; 514/365; 514/655; 546/337; 548/204; 564/158

(58) Field of Classification Search
None
See application file for complete search history.

(56) References Cited

U.S. PATENT DOCUMENTS

| 4,696,946 A | 9/1987 | Green et al. |
| 5,378,729 A | 1/1995 | Kohn et al. |
| 5,654,301 A | 8/1997 | Kohn et al. |
| 5,773,475 A | 6/1998 | Kohn |
| 6,803,481 B2 | 10/2004 | Selve |
| 7,416,864 B2 | 8/2008 | Stoehr |
| 7,427,601 B2 | 9/2008 | Stoehr |
| 7,687,553 B2 | 3/2010 | Beyreuther et al. |
| 7,718,161 B2 | 5/2010 | Stoehr |
| 7,820,857 B2 | 10/2010 | Stoehr et al. |
| 7,875,652 B2 | 1/2011 | Selve |
| 7,897,636 B2 | 3/2011 | Breslav et al. |
| 8,008,351 B2 | 8/2011 | Scheller et al. |
| 8,053,476 B2 | 11/2011 | Selve |

(Continued)

FOREIGN PATENT DOCUMENTS

| EP | 0 169 033 A2 | 1/1986 |
| WO | WO 92/14706 A1 | 9/1992 |

(Continued)

OTHER PUBLICATIONS

Letiran A et al. Design and evaluation of affinity labels of functionalized amino acid anticonvulsants. Journal of Medicinal Chemistry. Sep. 6, 2002; 45(21): 4762-4773.

Béguin C et al. Functionalized amido ketones: new anticonvulsant agents. Bioorganic & Medicinal Chemistry. Sep. 15, 2003; 11: 4275-4285.

(Continued)

*Primary Examiner* — Alicia L Otton
(74) *Attorney, Agent, or Firm* — Myers Bigel Sibley & Sajovec, P.A.

(57) ABSTRACT

A first aspect of the invention is a compound (sometimes also referred to herein as an "active agent" or "active compound") of Formula Ia, or more particularly Formula Ib, or a pharmaceutically acceptable salt or prodrug thereof. Compositions thereof and methods of using the same (e.g. for the treatment of a neurological disease) are also described.

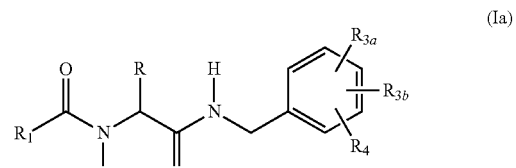

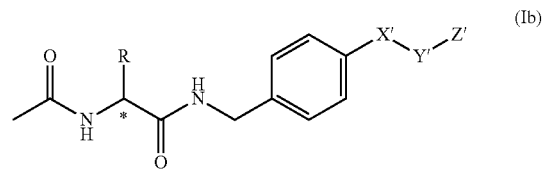

15 Claims, No Drawings

(56) References Cited

U.S. PATENT DOCUMENTS

| | | | |
|---|---|---|---|
| 2006/0100157 | A1 | 5/2006 | Rauschkolb-Loffler et al. |
| 2007/0042969 | A1 | 2/2007 | Rauschkolb-Loffler et al. |
| 2007/0048372 | A1 | 3/2007 | Beyreuther et al. |
| 2007/0197657 | A1 | 8/2007 | Beyreuther et al. |
| 2008/0280835 | A1 | 11/2008 | Beyreuther et al. |
| 2009/0018197 | A1 | 1/2009 | Rudd et al. |
| 2010/0240576 | A1 | 9/2010 | Stoehr |
| 2010/0256179 | A1 | 10/2010 | Stöhr et al. |
| 2010/0256241 | A1 | 10/2010 | Stoehr et al. |
| 2010/0260716 | A1 | 10/2010 | Stöhr et al. |
| 2010/0273714 | A1 | 10/2010 | Stoerhr |
| 2010/0324144 | A1 | 12/2010 | Heers et al. |
| 2011/0021482 | A1 | 1/2011 | Kohn et al. |

FOREIGN PATENT DOCUMENTS

| | | | | |
|---|---|---|---|---|
| WO | WO 2009/145816 | * | 12/2009 | ............ C07C 331/28 |
| WO | WO 2010/014236 | * | 2/2010 | ............ C07D 495/04 |
| WO | WO 2010/148300 | * | 12/2010 | ............ A01N 37/20 |

OTHER PUBLICATIONS

Shen M et al. Application of predictive QSAR models to database mining: identification and experimental validation of novel anticonvulsant compounds. Journal of Medicinal Chemistry. Mar. 20, 2004; 47(9): 2356-2364.

International Search Report and Written Opinion, PCT/US2010/049258, mailed May 19, 2011.

Supplementary European Search Report, EP 10819283, mailed Aug. 21, 2013.

Jones, J.B. et al., "Alkylations of the side-chain nucleophiles of cysteine, methionine, histidine, and lysine derivatives with allyl bromide, 1-bromo-2-butyne, and 2-bromoaceto-phenone", *Canadian Journal of Chemistry* (1971), 49(18), pp. 3012-3019, ISSN: 0008-4042.

European Search Report, EP 09 75 5179; Dated: Oct. 27, 2011; 7 pages.

Written Opinion of The International Searching Authority Corresponding to International Application No. PCT/US2009/001802; Date of Mailing: Dec. 17, 2009; 9 pages.

* cited by examiner

N-BENZYLAMIDE SUBSTITUTED DERIVATIVES OF 2-(ACYLAMIDO)ACETIC ACID AND 2-(ACYLAMIDO)PROPIONIC ACIDS: POTENT NEUROLOGICAL AGENTS

RELATED APPLICATIONS

This application is a 35 U.S.C. §371 national phase entry of PCT Application PCT/US2010/049258, filed Sep. 17, 2010, and published in English on Mar. 31, 2011, as International Publication No. WO 2011/037833, and which claims the benefit of under 35 U.S.C. §119(e) of U.S. Provisional Patent Application Ser. No. 61/244,914, filed Sep. 23, 2009, the disclosure of each of which is incorporated herein by reference in its entirety.

GOVERNMENT FUNDING

This invention was made with United States government support under grant number 5R01NS054112 from the National Institute of Neurological Disorders and grant number UL1 RR025747 from the National Center for Research Resources. The United States government has certain rights to this invention.

FIELD OF THE INVENTION

The present inventions concern compounds, pharmaceutical compositions, and methods of use thereof in treating neurological disorders such as epilepsy and neuropathic pain, and as neuroprotective agents.

BACKGROUND OF THE INVENTION

Epilepsy is a major neurological disorder that affects all populations (W. Hauser et al., The prevalence of epilepsy in Rochester, Minn., 1940-80. *Epilepsia* 1991 32, 429-445). Epilepsy describes the types of recurrent seizures produced by paroxysmal excessive neuronal discharges in the brain (Evans, J. H. Post-traumatic epilepsy. *Neurology* 1962, 12, 665-674; Lindsay, J. M. Genetics and epilepsy. *Epilepsia* 1971, 12, 47-54). In the United States alone, some 2 million people suffer from epilepsy and its sequelae; 340,000 are children. For many individuals afflicted with epilepsy the disabilities and associated neuropsychological and behavioral factors limit the quality of life. The restrictions on patients with epilepsy plus the expense for treatment and rehabilitation result in a large cost to society (See, e.g., Begley, C. E.; Lairson, D. R.; Reynolds, T. F.; Coan, S. Early treatment cost in epilepsy and how it varies with seizure type and frequency. *Epilepsia Res.* 2001, 47, 205-215).

The mainstay of treatment for epileptic disorders has been the long-term and consistent administration of anticonvulsant drugs (See, e.g., McNamara, J. O. In: *Goodman & Gilman's The Pharmacological Basis of Therapeutics*, 10th Ed.; Hardman, J. G.; Limbird, L. E., Ed.; McGraw-Hill: New York, 2001; Ch. 21, pp. 521-547; Aiken, S. P.; Brown, W. M. Treatment of epilepsy: Existing therapies and future developments. *Frontiers in Bioscience* 2000, 5, 124-15). Unfortunately, current medications are ineffective for approximately one-third of patients with epilepsy (See, e.g., Bauer, J.; Reuber, M. Medical treatment of epilepsy. *Expert Opinion on Emerging Drugs* 2003, 8, 457-467). Many continue to have seizures, while others experience disturbing side effects (e.g., drowsiness, dizziness, nausea, liver damage) (Pellock, J. M.; Willmore, L. J. A rational guide to monitoring in patients receiving anticonvulsants. *Neurology* 1991, 41, 961-964).

The shortcomings of current regimens highlight the need for new agents with novel mechanisms of action.

SUMMARY OF THE INVENTION

A first aspect of the invention is a compound (sometimes also referred to herein as an "active agent" or "active compound") of Formula Ia:

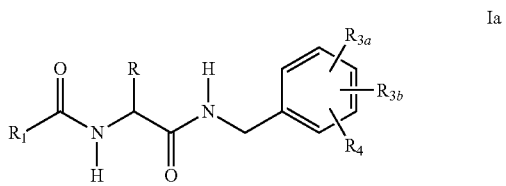

wherein:
R is $R_2$ or $CH_2X'R_5$, where X' is O, S, or N—$R_{6a}$ and $R_{6a}$ is hydrogen, alkyl, or cycloalkyl;

$R_1$ is alkyl or cycloalkyl, each of which can be unsubstituted or substituted with one or more (e.g., one, two, three, four) independently selected electron-donating or electron-withdrawing groups;

$R_2$ is alkyl, cycloalkyl, aryl, five- or six-membered cyclic heterocyclic or heteroaromatic groups, or —X—Y—Z, where X and Y=O, S, N—$R_6$, and Z=$R_6$, and where $R_6$ is hydrogen, alkyl, or cycloalkyl, each of which is unsubstituted or substituted with one or more (e.g., one, two, three, four) electron withdrawing or electron donating groups;

$R_5$ is alkyl, alkenyl (e.g., —$CH_2CH$=$CH_2$), alkynyl (e.g., —$CH_2C$≡$CH$, —$CH_2C$≡$CCH_3$), or arylalkyl, each of which is unsubstituted or substituted with one or more (e.g., one, two, three, four) electron donating or electron withdrawing groups;

$R_{3a}$ $R_{3b}$, and $R_4$ are each independently hydrogen, an electron donating or electron-withdrawing group, or alkyl, cycloalkyl, alkenyl, alkynyl, aryl, heterocyclo, heteroaryl, arylalkyl, heteroarylalkyl, heterocycloalkyl, arylalkyloxy, arylalkylamino, arylalkylthio, heteroarylalkyloxy, heteroarylalkylamino, heteroarylalkylthio, heterocycloalkyloxy, heterocycloalkylamino, heterocycloalkylthio, arylaminooxy, heteroarylaminooxy, heterocycloaminooxy, aryloxyamino, heteroaryloxyamino, heterocyclooxyamino, arylalkyl, heteroarylalkyl, heterocycloalkyl, arylalkenyl, heteroarylalkenyl, heterocycloalkenyl, arylalkynyl, heteroarylalkynyl, heterocycloalkynyl, arylhydrazino, heteroarylhydrazino, heterocyclohydrazino, arylazo, heteroarylazo, heterocycloazo, arylalkylaminoalkyl, heteroarylalkylaminoalkyl, heterocycloalkylaminoalkyl, arylalkyloxyalkyl, heteroarylalkyloxyalkyl, heterocycloalkyloxyalkyl, each of which can be unsubstituted or substituted with one or more (e.g., one, two, three, four) independently selected electron-donating or electron-withdrawing groups;

or a pharmaceutically acceptable salt or prodrug thereof.

A further aspect of the present invention is a pharmaceutical composition comprising, consisting of or consisting essentially of an active compound as described herein (e.g., compounds of Formula Ia) in a pharmaceutically acceptable carrier. The compositions may optionally further comprise or include at least one additional neurological or neuroprotective active agent.

A further aspect of the present invention is a method of treating a neurological disorder or imparting neuroprotection in a mammalian subject in need thereof, comprising administering (e.g., orally, intraveneously, or by inhalation) said subject an active compound as described herein in a treatment effective amount. The method may further comprise administering said subject at least one additional neurological or neuroprotective active agent in a treatment effective amount.

A further aspect of the invention is the use of an active agent as described herein for the preparation of a medicament for neuroprotection or treating a neurological disorder as described here.

A further aspect of the invention is an active agent as described herein for use in neuroprotection or treating a neurological disorder as described herein.

DETAILED DESCRIPTION OF EMBODIMENTS OF THE INVENTION

A. Definitions

"Neurological disorder" as used herein may be any central or peripheral nervous system disorder, including but not limited to acute and chronic pain (e.g., spontaneous chronic pain, mechanical allodynia, and thermal hyperalgesia, chronic muscle pain), migraine, neuropathic pain such as diabetic neruopathy, fibromyalgia, bipolar disorders, convulsions, mania, epilepsy, epileptogenesis, convulsions and other seizure disorders, dyskinesia, tremors, anxiety, depression, ischemia such as focal ischemia, etc.

"Neuroprotection" as used herein refers to any type of neuroprotection, such as against a neurotoxic agent, either prophylactically or after exposure to a neurotoxic agent.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. Such groups can be unsubstituted or substituted with one or more (e.g., one, two, three four, etc.) independently selected electron-donating or electron-withdrawing groups "Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise. Such groups can be unsubstituted or substituted with one or more (e.g., one, two, three four, etc.) independently selected electron-donating or electron-withdrawing groups.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. Such groups can be unsubstituted or substituted with one or more (e.g., one, two, three four, etc.) independently selected electron-donating or electron-withdrawing groups.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above. Such groups can be unsubstituted or substituted with one or more (e.g., one, two, three four, etc.) independently selected electron-donating or electron-withdrawing groups.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 3 to 8 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic and heterocyclic ring systems fused to an aryl group as defined herein, a cycloalkyl group as defined herein, or another monocyclic or heterocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. Such groups can be unsubstituted or substituted with one or more (e.g., one, two, three four, etc.) independently selected electron-donating or electron-withdrawing groups.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above. Such groups can be unsubstituted or substituted with one or more (e.g., one, two, three four, etc.) independently selected electron-donating or electron-withdrawing groups.

"Heteroaryl" as used herein is as described in connection with heterocyclo above. Such groups can be unsubstituted or substituted with one or more (e.g., one, two, three four, etc.) independently selected electron-donating or electron-withdrawing groups.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroarylalkyl" as used herein alone or as part of another group, refers to a heteroaryl group, as defined herein, appended to the parent molecular moiety through an alkyl group, as defined herein.

"Heterocycloalkyl" as used herein alone or as part of another group, refers to a heterocyclo group, as defined herein, appended to the parent molecular moiety through an alkyl group, as defined herein.

"Electron-withdrawing" and "electron donating" refer to the ability of a substituent to withdraw or donate electrons relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985), incorporated herein by reference. Examples of such electron withdrawing and electron donating groups or substituents include, but are not limited to halo, nitro, cyano, carboxy, alkylcarboxy, loweralkenyl, loweralkynyl, loweralkanoyl (e.g., formyl), carboxyamido, aryl, quaternary ammonium, aryl (loweralkanoyl), carbalkoxy and the like; acyl, carboxy, alkanoyloxy, aryloxy, alkoxysulfonyl, aryloxysulfonyl, and the like; hydroxy, alkoxy or loweralkoxy (including methoxy, ethoxy and the like); loweralkyl; amino, alkylamino, lower alkylamino, di(loweralkyl)amino, aryloxy (such as phenoxy), mercapto, loweralkylthio, lower alkylmercapto, disulfide (loweralkyldithio) and the like; 1-piperidino, 1-piperazino, 1-pyrrolidino, acylamino, hydroxyl, thiolo, alkylthio, arylthio, aryloxy, alkyl, ester groups (e.g., alkylcarboxy, arylcarboxy, heterocyclocarboxy), azido, isothiocyanato, isocyanato, thiocyanato, cyanato, and the like. One skilled in the art will appreciate that the aforesaid substituents may have electron donating or electron withdrawing properties under different chemical conditions. Moreover, the present invention contemplates any combination of substituents selected from the above-identified groups. See U.S. Pat. Nos. 6,133,261 and 5,654,301; see also U.S. Pat. No. 4,711,532.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkanoyl" refers to the group —C(O)R', wherein R' is lower alkyl. Hence "alkanoyl" groups are particular examples of "acyl" groups, as described above.

"Halo" or "halogen," as used herein refers to —Cl, —Br, —I or —F.

"Oxy" as used herein refers to an —O— group.

"Sulfonyl," as used herein, refers to an —SO$_2$— group.

"Thio" as used herein refers to an —S— group.

"Peptide coupling reagent" as used herein may be any suitable peptide coupling reagent, including but not limited to: N,N'-dicyclohexylcarbodiimide, dicyclohexylcarbodiimide plus hydroxysuccinimide, N,N'-dicyclohexylcarbodimide plus 1-hydroxy-benzotriazole, 1-benzotriazolyl diethyl phosphate, 1-chloro-N,N,2-trimethyl-1-propen-1-amine, diphenyl phosphoryl azide, diethylphosphorochloridate, di-loweralkyl (C1-C8) phosphorochloridates, diphenyl phosphorochloridate, phenyl phosphorodichloridate benzotriazol-1-yloxytris(dimethylamino)-phosphonium hexafluorophosphate, N,N'-bis[2-oxo-3-oxazolidinyl]-phosphorodiamidic chloride, diphenylphosphinyl chloride, diethoxyphosphoryl cyanide, bis(pentafluorophenyl)sulfite, N,N'-carbonyldiimidazole, or isobutyl chloroformate plus N-methylmorpholine, 2-chloro-1-methylpyridinium iodide, N,N'-disuccinimidyl carbonate, 1-bromo-N,N,2-trimethyl-1-propen-1-amine, 1-benzotriazolyl diethyl phosphate (see U.S. Pat. No. 5,189,023); dicyclohexylcarbodiimide (DCC), diisopropylcarbodiimide (DIPC), 1-ethyl-3-(3-dimethylaminopropyl)carbodiimide (EDC), benzotriazole-1-yloxy-tris (dimethylamino)phosphonium hexafluorophosphate (BOP) and diphenylphosphorylazide (DPPA) (see U.S. Pat. No. 6,172,067); DIC, TBTU, WSCDI, EEDQ, HBTU, TNTU, TSTU, HATU, BOP, BOP-Cl, PyBOP, PyBroP, IPCF, IBCF and propane phosphonic acid anhydride (see U.S. Pat. No. 5,977,302), and 4-(4,6-dimethoxy-1,3,5-triazin-2-yl)-4-methylmorpholinium chloride) (DMTMM), tetramethylfluoroformamidiniun hexafluorophosphate, etc.

"Subjects" as used herein are typically human subjects, but may also be other mammalian subjects such as dogs, cats, horses, etc. treated for veterinary purposes. Subjects may be male or female and may be neonate, infant, juvenile, adolescent, adult or geriatric subjects.

"Treat" as used herein refers to any type of treatment that imparts a benefit to a subject, including delaying the onset or progression of one or more symptom, reducing the severity of one or more symptom, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" as used herein means sufficiently close in time to produce a combined effect (that is, concurrently may be simultaneously, or it may be two or more events occurring within a short time period before or after each other).

B. Active Compounds

As noted above, the present invention provides compounds of Formula Ia:

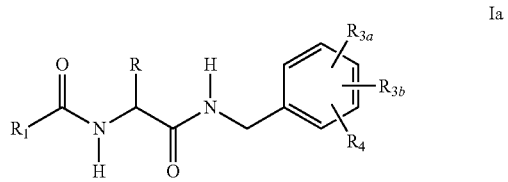

wherein:

R is $R_2$ or $CH_2X'R_5$, where X' is O, S, or N—$R_{6a}$ and $R_{6a}$ is hydrogen, alkyl, or cycloalkyl;

$R_1$ is alkyl or cycloalkyl, each of which can be unsubstituted or substituted with one or more (e.g., one, two, three, four) independently selected electron-donating or electron-withdrawing groups;

$R_2$ is alkyl, cycloalkyl, aryl, five- or six-membered cyclic heterocyclic or heteroaromatic groups, or —X—Y—Z, where X and Y=O, S, N—$R_6$, and Z=$R_6$, and where $R_6$ is hydrogen, alkyl, or cycloalkyl, each of which is unsubstituted or substituted with one or more (e.g., one, two, three, four) electron withdrawing or electron donating groups;

R$_5$ is alkyl, alkenyl, alkynyl, or arylalkyl, each of which is unsubstituted or substituted with one or more (e.g., one, two, three, four) electron donating or electron withdrawing groups;

R$_{3a}$ R$_{3b}$, and R$_4$ are each independently hydrogen, an electron donating or electron-withdrawing group, or alkyl, cycloalkyl, alkenyl, alkynyl, aryl, heterocyclo, heteroaryl, arylalkyl, heteroarylalkyl, heterocycloalkyl, arylalkyloxy, arylalkylamino, arylalkylthio, heteroarylalkyloxy, heteroarylalkylamino, heteroarylalkylthio, heterocycloalkyloxy, heterocycloalkylamino, heterocycloalkylthio, arylaminooxy, heteroarylaminooxy, heterocycloaminooxy, aryloxyamino, heteroaryloxyamino, heterocyclooxyamino, arylalkyl, heteroarylalkyl, heterocycloalkyl, arylalkenyl, heteroarylalkenyl, heterocycloalkenyl, arylalkynyl, heteroarylalkynyl, heterocycloalkynyl, arylhydrazino, heteroarylhydrazino, heterocyclohydrazino, arylazo, heteroarylazo, heterocycloazo, arylalkylaminoalkyl, heteroarylalkylaminoalkyl, heterocycloalkylaminoalkyl, arylalkyloxyalkyl, heteroarylalkyloxyalkyl, heterocycloalkyloxyalkyl, each of which can be unsubstituted or substituted with one or more (e.g., one, two, three, four) independently selected electron-donating or electron-withdrawing groups;

optionally but preferably wherein at least one of R$_{3a}$ and R$_4$ is not H;

and optionally but preferably wherein at least one, or both, of R$_{3a}$ and R$_4$ is a primary substituent selected from the group consisting of electron donating groups, electron-withdrawing groups, alkyl, cycloalkyl, alkenyl, alkynyl, aryl, heterocyclo, heteroaryl, arylalkyl, heteroarylalkyl, heterocycloalkyl, arylalkyloxy, arylalkylamino, arylalkylthio, heteroarylalkyloxy, heteroarylalkylamino, heterocycloalkyloxy, and heterocycloalkylamino, heterocycloalkylthio, heteroarylalkylthio, arylaminooxy, heteroarylaminooxy, heterocycloaminooxy, aryloxyamino, heteroaryloxyamino, heterocyclooxyamino, arylalkyl, heteroarylalkyl, heterocycloalkyl, arylalkenyl, heteroarylalkenyl, heterocycloalkenyl, arylalkynyl, heteroarylalkynyl, heterocycloalkynyl, arylhydrazino, heteroarylhydrazino, heterocyclohydrazino, arylazo, heteroarylazo, heterocycloazo, arylalkylaminoalkyl, heteroarylalkylaminoalkyl, heterocycloalkylaminoalkyl, arylalkyloxyalkyl, heteroarylalkyloxyalkyl, heterocycloalkyloxyalkyl;

and which primary substituent is in turn optionally but preferably substituted with one or more (e.g., one, two, three, four) secondary substituents independently selected from the group consisting of electron-donating groups, and electron-withdrawing groups (e.g., aryl such as phenyl); which secondary substituent can in turn be unsubstituted or substituted with one or more (e.g., one, two, three, four) additional independently selected electron-donating or electron-withdrawing groups (e.g., halo such as fluoro), etc.

or a pharmaceutically acceptable salt or prodrug thereof.

In some embodiments of the foregoing, R is R$_2$. In other embodiments of the foregoing, R is CH$_2$X'R$_5$.

In some embodiments of the foregoing, R$_{3b}$ is H.

In some embodiments of the foregoing, R$_1$ is CH$_3$.

In some embodiments of the foregoing, R$_2$ is 2-furan, 2-thiazole, 2-oxazole, 2-pyridine, 2-pyrimidine, 2-pyridazine, N(H)OCH$_3$, and N(CH$_3$)OCH$_3$, or N(H)N(H)CO$_2$CH$_3$.

In some embodiments of the foregoing, wherein X is O, and R$_5$ is CH$_3$, CH$_2$CH$_3$, CH(CH$_3$)$_2$, CH$_2$CH$_2$CHCH$_2$, CH$_2$CCH, CH$_2$CCR$_6$.

In some embodiments of the foregoing, either or both of R$_{3a}$ and R$_4$ are OCH$_2$C$_6$H$_4$(m-F), C$_6$H$_4$(m-F), OCF$_3$, N$_3$, CCCH$_2$OCH$_3$, CH$_2$OCH$_3$, (CH$_2$)$_3$OCH$_3$, C(N2)CF$_3$, C(O)C$_6$H$_5$ or CF$_3$.

Additional representative examples of R$_{3a}$ R$_{3b}$ and/or R$_4$ include OC(H)$_m$(W)$_n$ where W is a typical electron withdrawing or electron donating group and m can vary from 0-2 and n can vary from 1-3, CC—(CH$_2$)$_o$OR$_6$ and o can vary from 1-6, (CH$_2$)$_o$OR$_6$, 1-trifluorodiazinryl, azide, XCH$_2$C$_6$H$_5$, and where each of these atypical groups can be unsubstituted or substituted with one or more typical electron withdrawing and/or electron donating groups, or C(H)$_m$(W)$_n$ where W is a typical electron withdrawing or electron donating group and m can vary from 0-2 and n can vary from 1-3.

In some embodiments, compounds of the invention are compounds of Formula Ib:

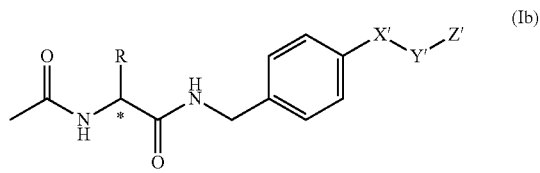

(Ib)

wherein:

R is:

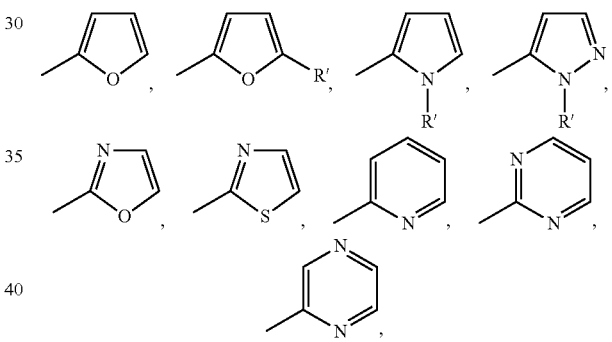

N(R')OR', CH$_2$OCH$_3$, CH$_2$OCH$_2$CH$_3$, CH$_2$OCH(CH$_3$)$_2$, CH$_2$OCD$_3$, CH$_2$OCD$_2$CD$_3$, CH$_2$OCD$_2$CH$_3$, CH$_2$OCD(CH$_3$)$_2$, CH$_2$OCD(CD$_3$)$_2$, CH$_2$OCF$_2$H, CH$_3$, CD$_3$, CF$_3$, CH$_2$F, CH$_2$CH$_3$, (CH$_2$)$_2$CH$_3$, CH(CH$_3$)$_2$, (CH$_2$)$_3$CH$_3$, C(CH$_3$)$_3$;

each R' is independently selected H or lower alkyl, unsubstituted or substituted with 1-3 electron-withdrawing or electron-donating groups;

X' is absent (that is, a direct covalent bond) or a linker that consists of one atom or two or three covalently connected atoms (e.g., atoms independently selected from C, O, N, and S) and which atoms may or may not be substituted, e.g., a saturated or unsaturated chain optionally containing zero, one, two or three heteroatoms independently selected from N, O, and S, and containing zero, one, two or three carbon atoms, which chain may be substituted or unsubstituted with one or more electron-withdrawing or electron-donating groups; e.g., Y' is an aromatic or heteroaromatic moiety (e.g., phenyl, pyridyl, pyrrolyl; furanyl, thiophenyl, pyrazolyl, oxazolyl, indolinyl, benzofuranyl, benzothiophenyl, etc.), unsubstituted or substituted with 1-3 electron-withdrawing or electron-donating groups; and Z' is H, F, Cl, Br, I, CF$_3$, CN, OCF$_3$, or N$_3$, or a pharmaceutically acceptable salt or prodrug thereof.

More particular examples of compounds of Formula Ib are compounds having the structures given below:
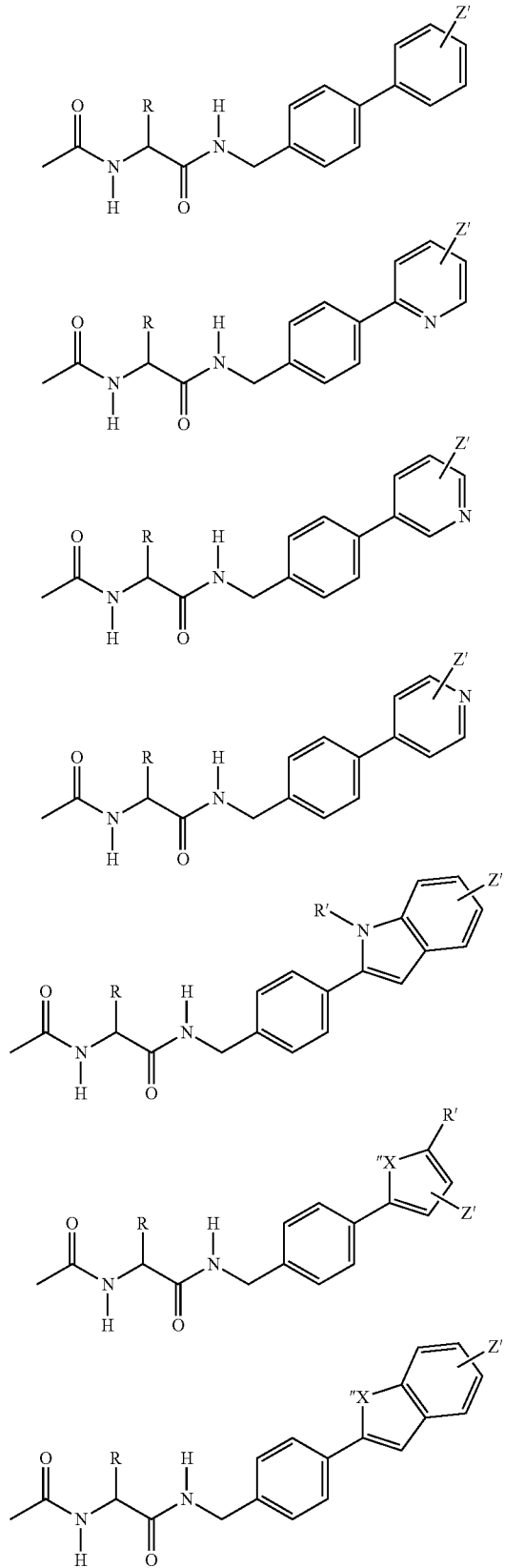
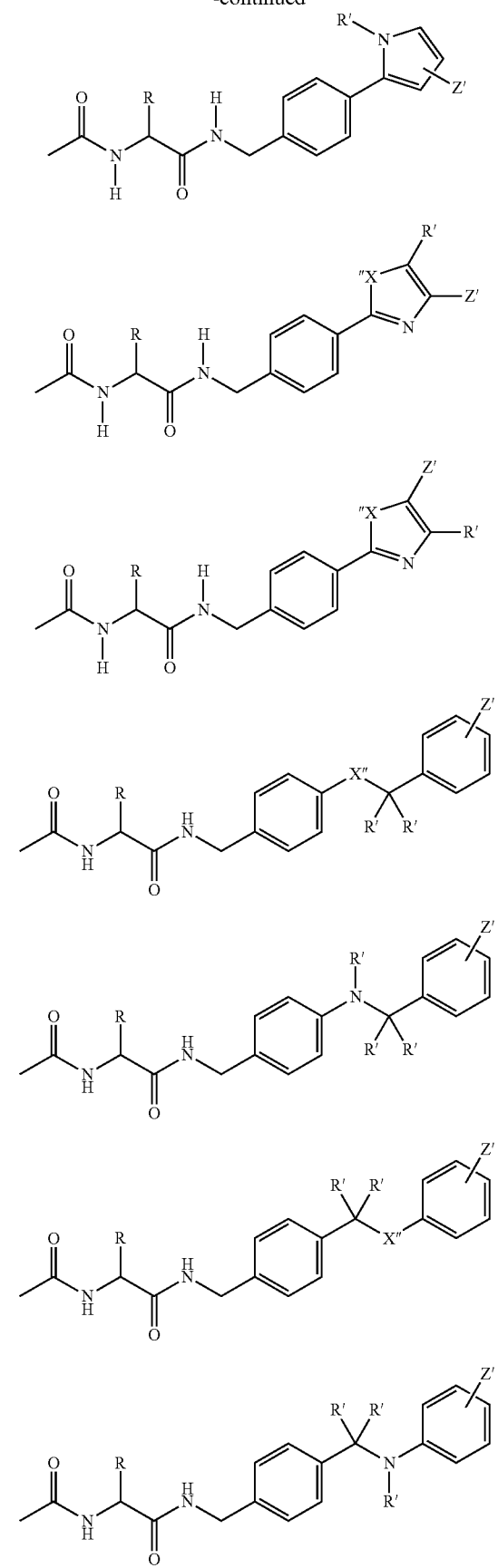

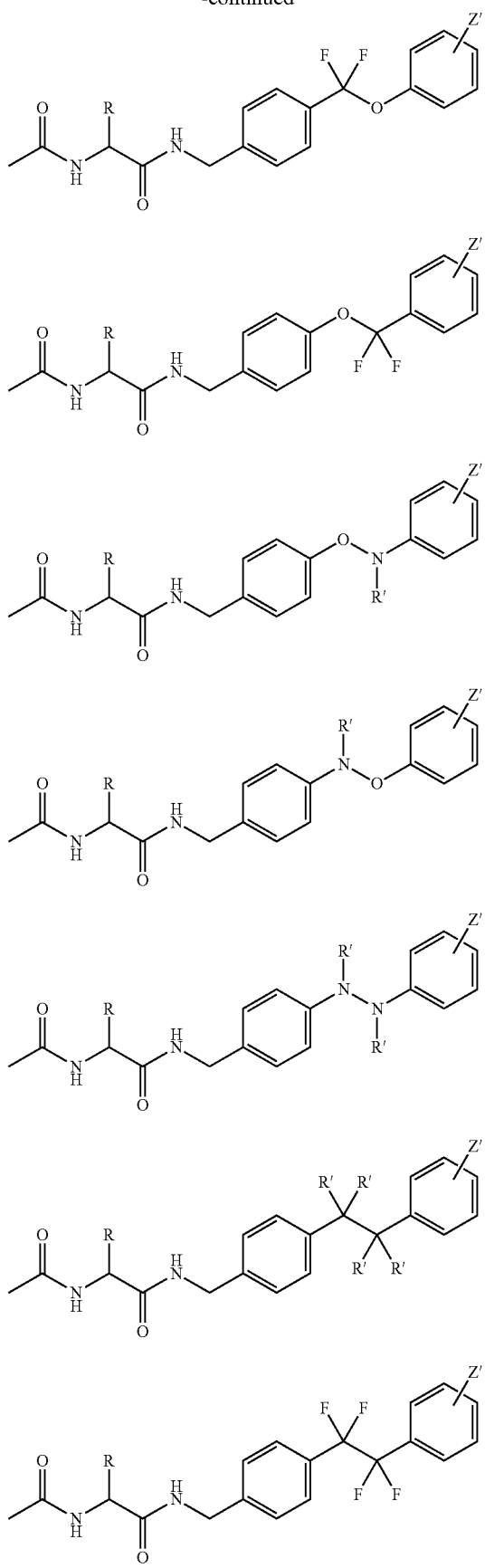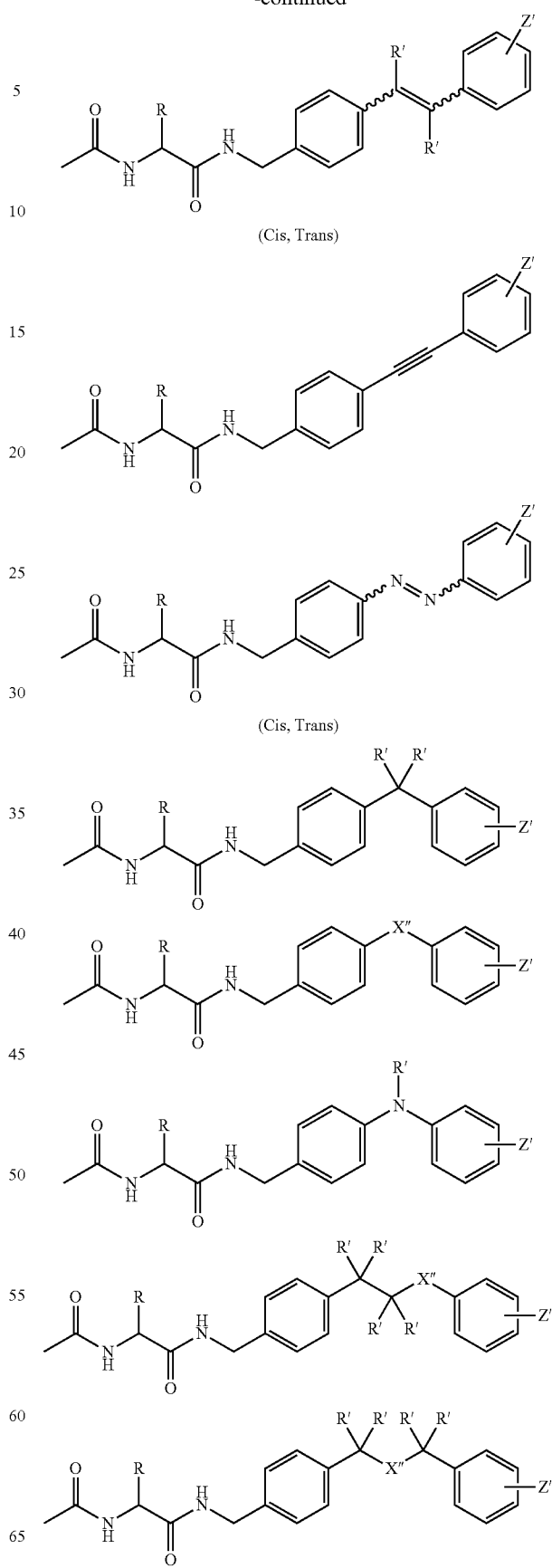

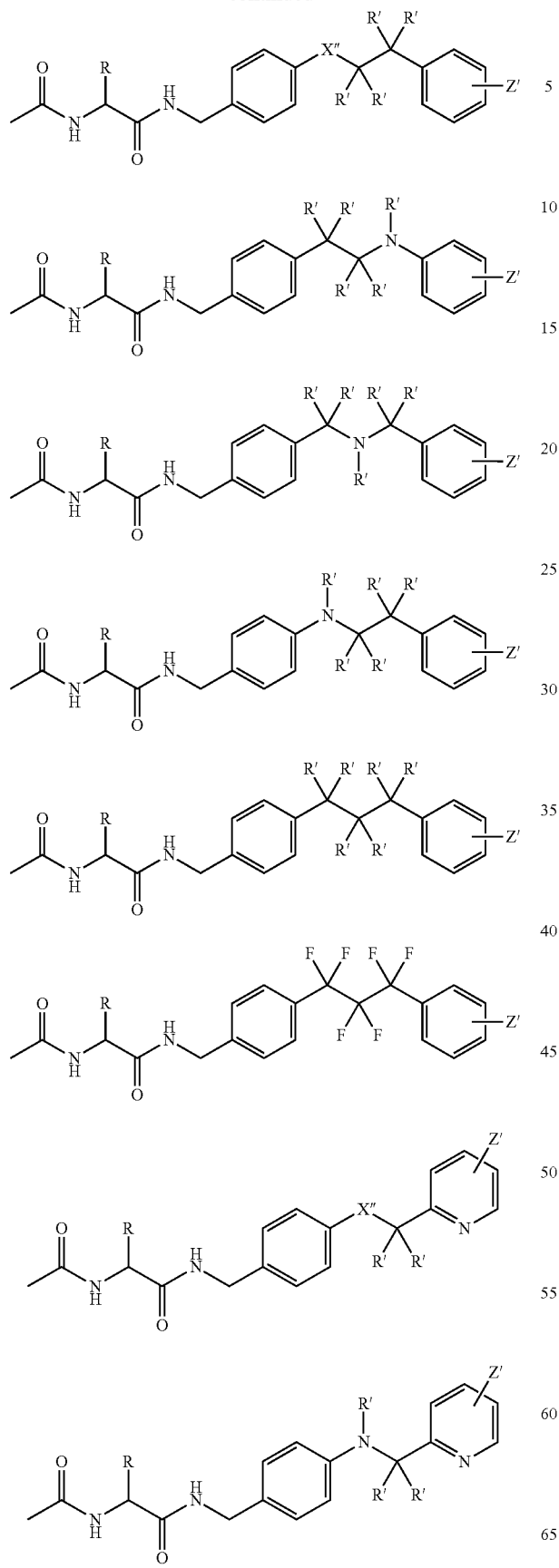
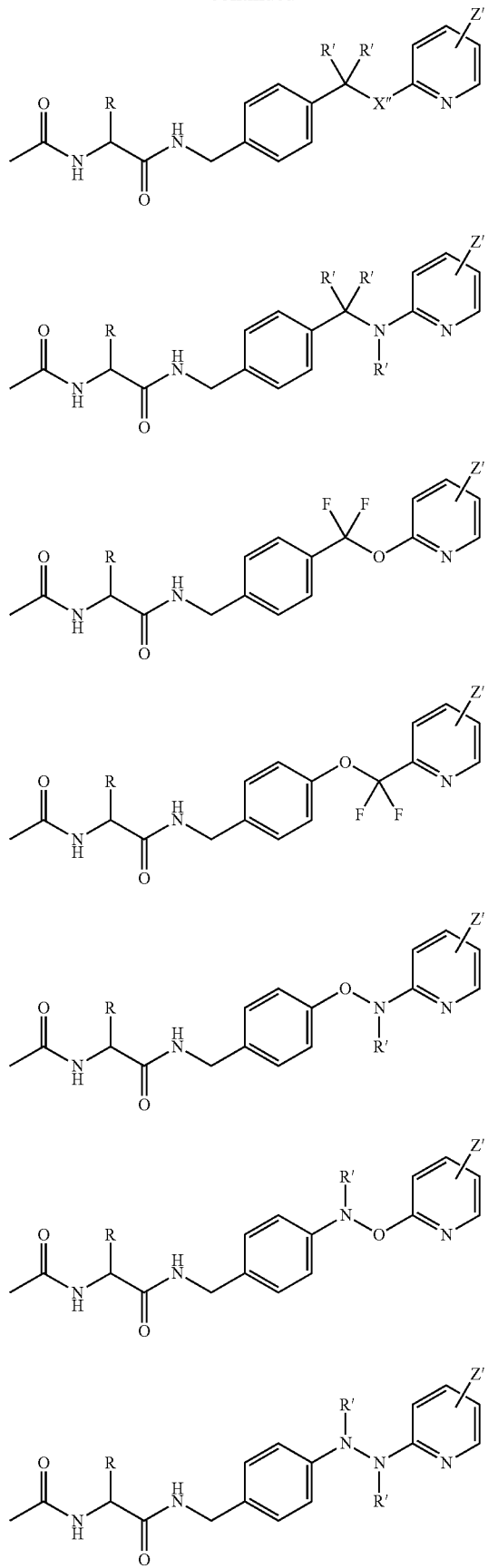

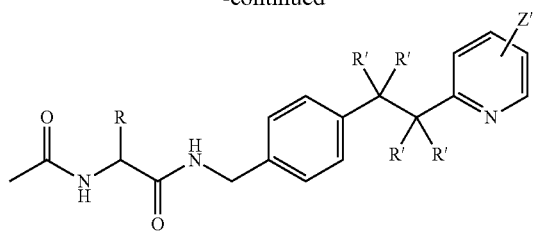
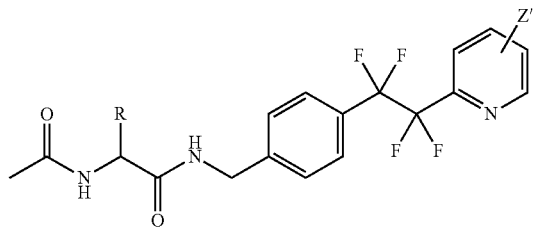
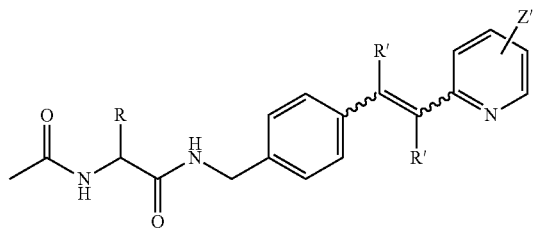
(Cis, Trans)
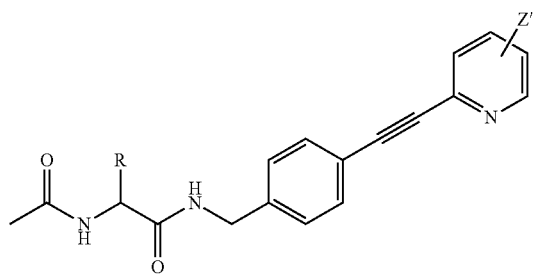
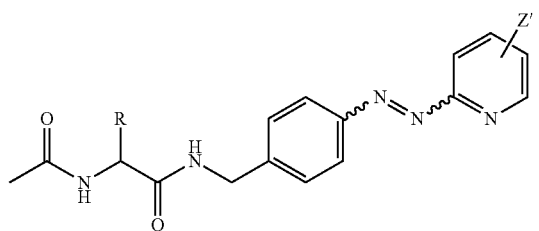
(Cis, Trans)
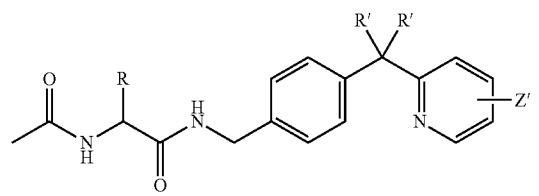
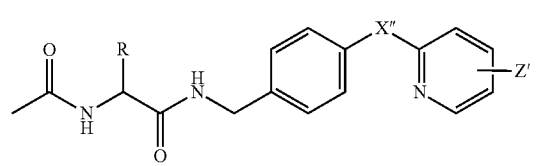
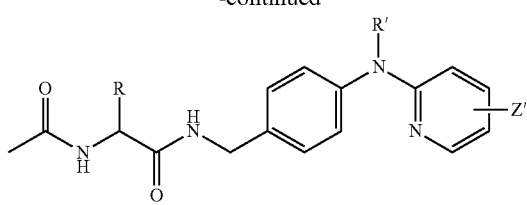
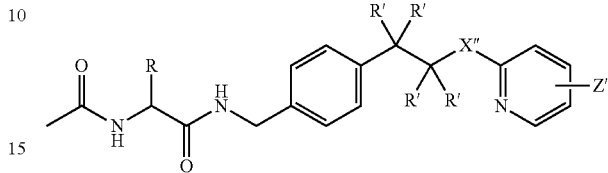
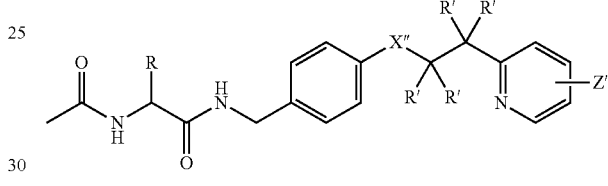
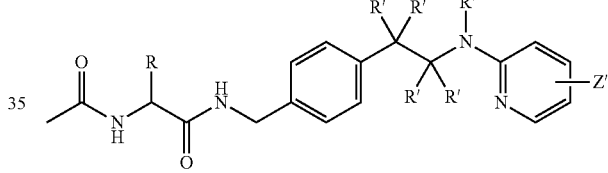
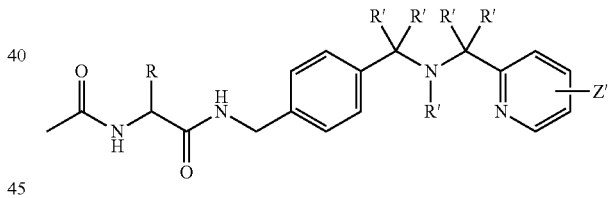
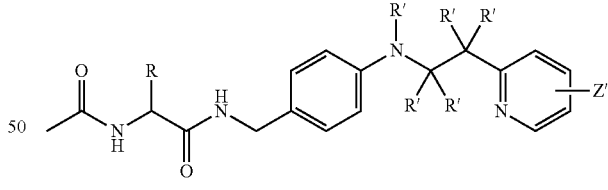
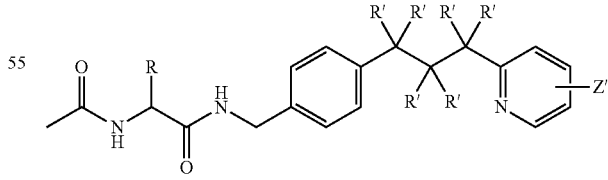
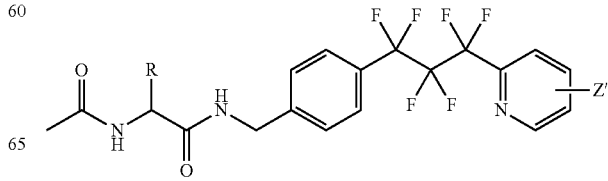

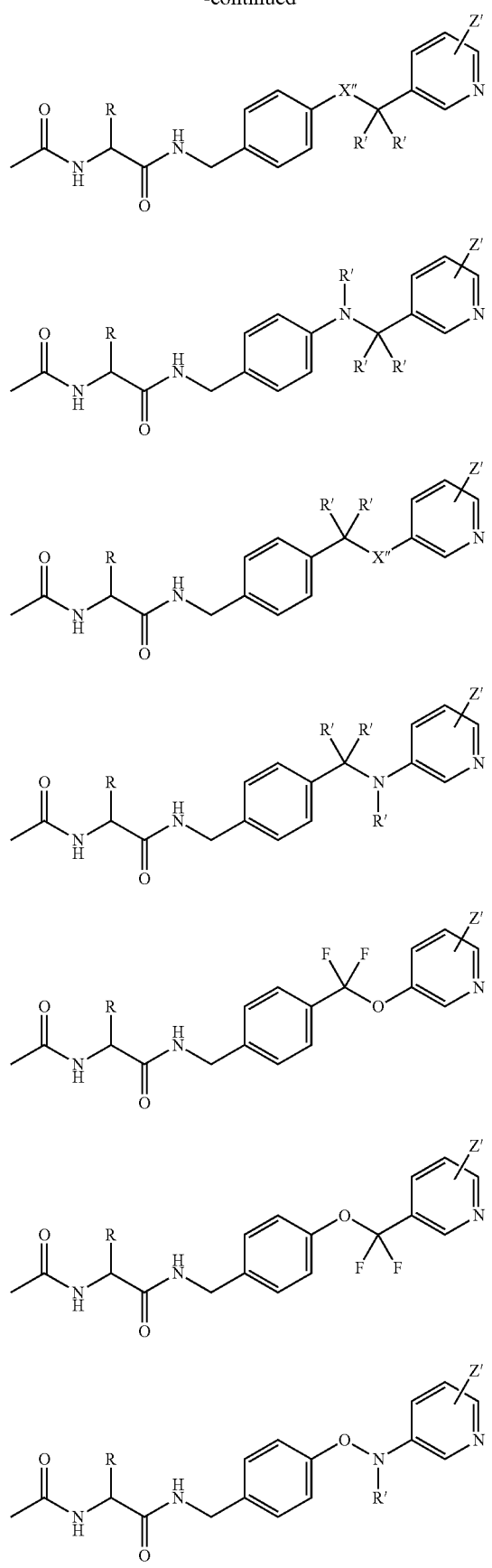
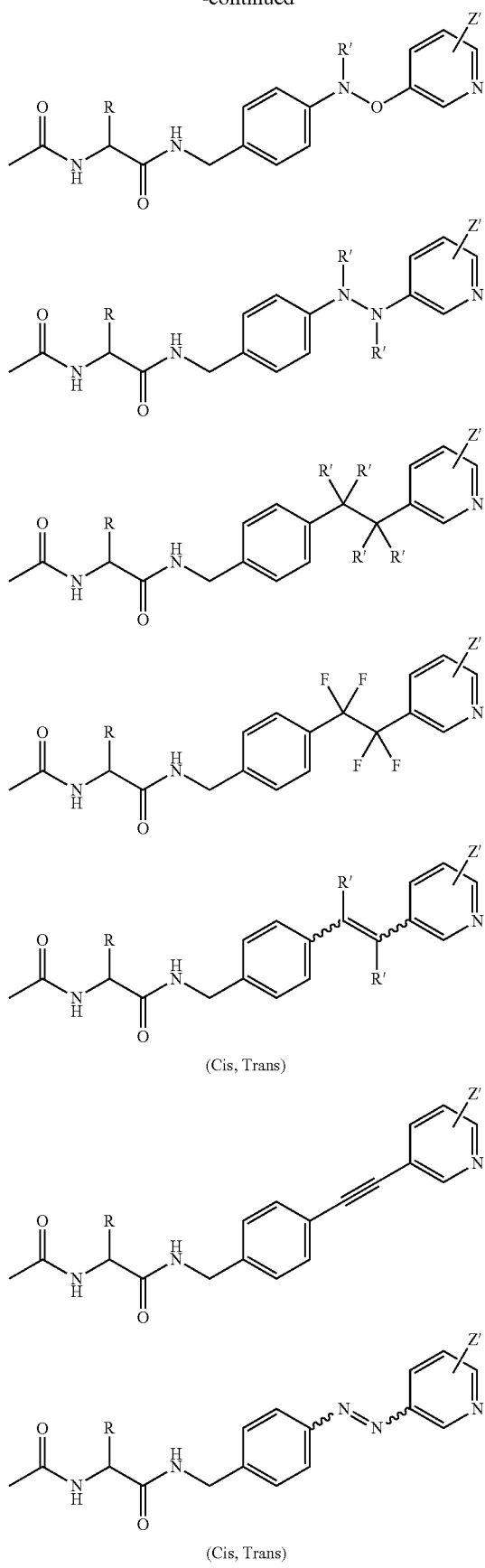

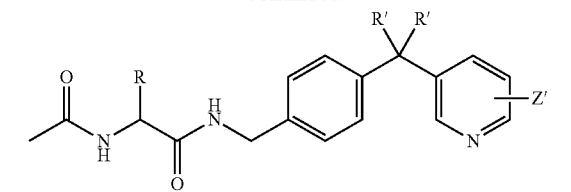
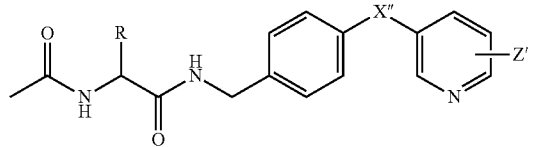
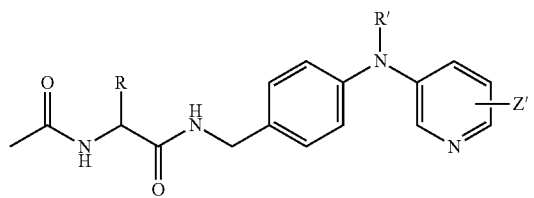
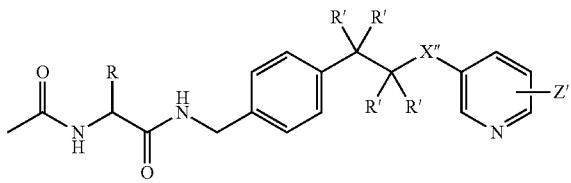
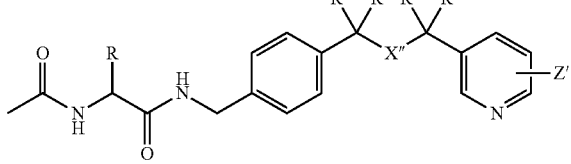
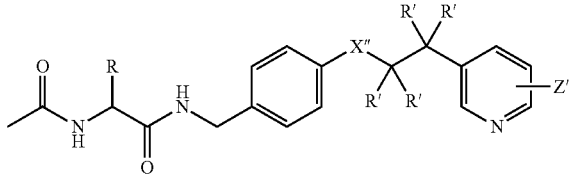
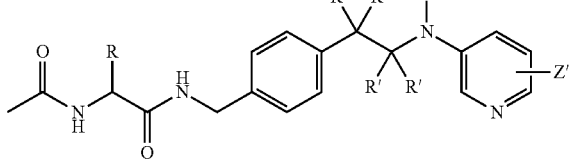
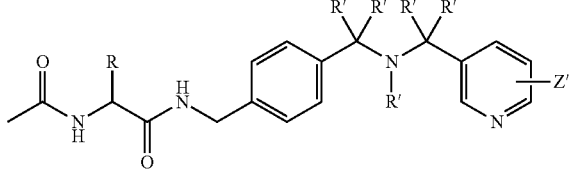
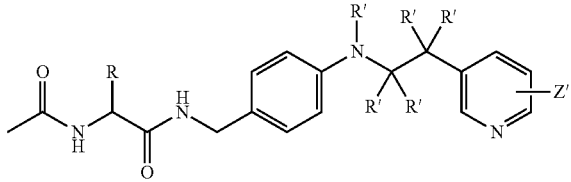
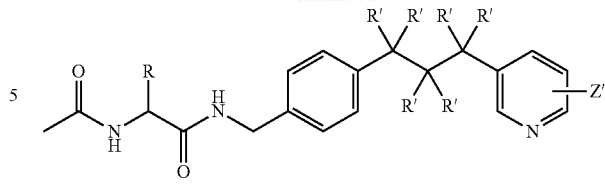
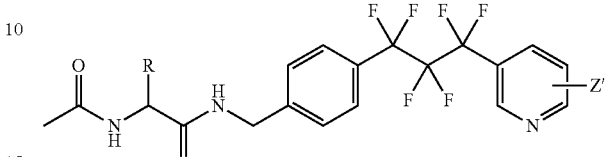
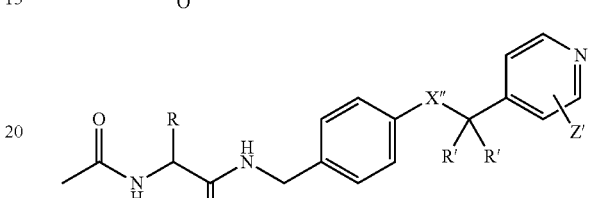
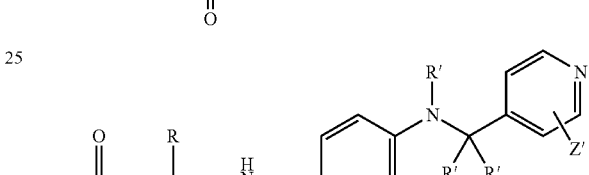
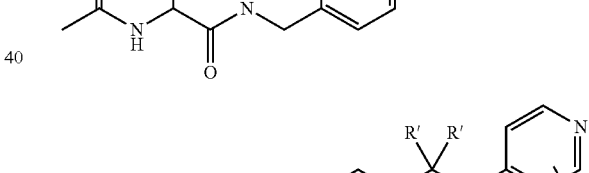
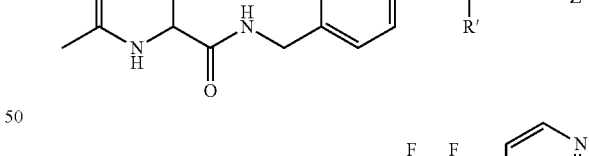
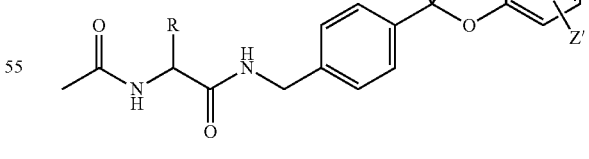
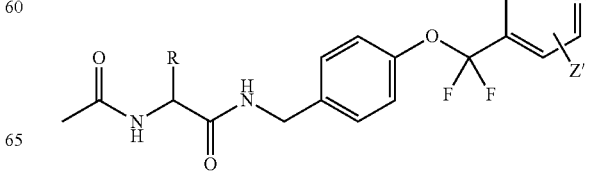

-continued
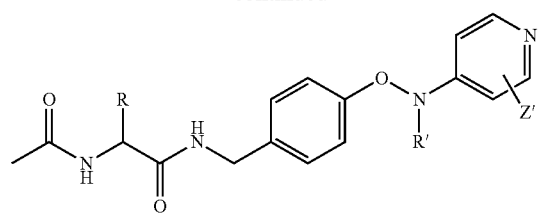
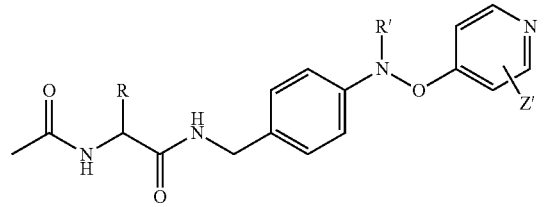
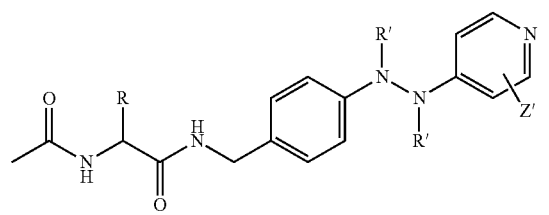
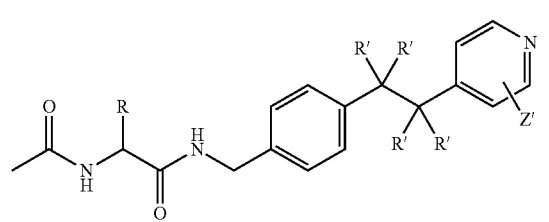
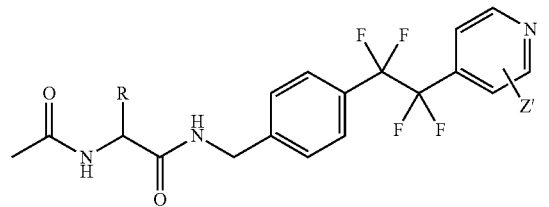
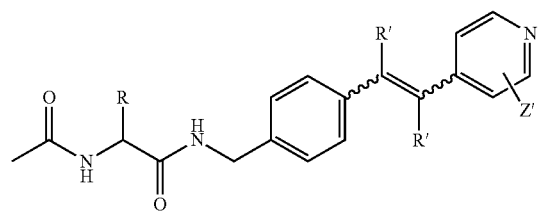
(Cis, Trans)
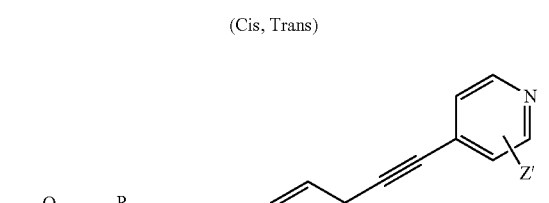
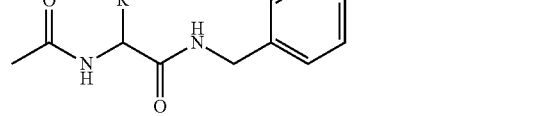
-continued
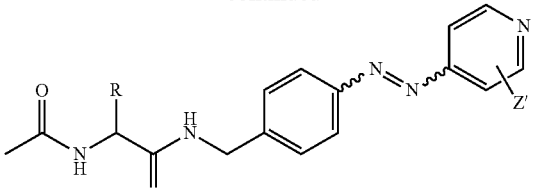
(Cis, Trans)
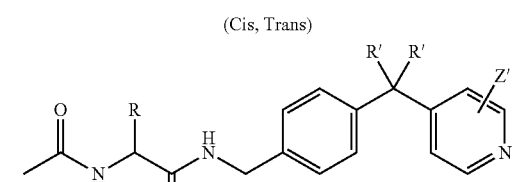
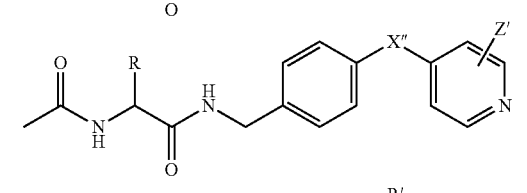
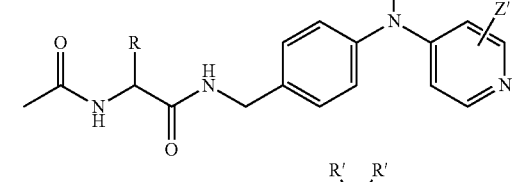
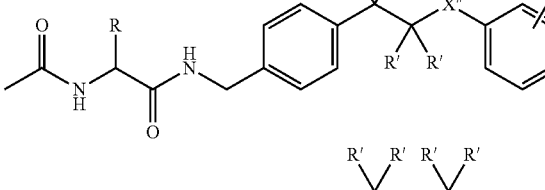
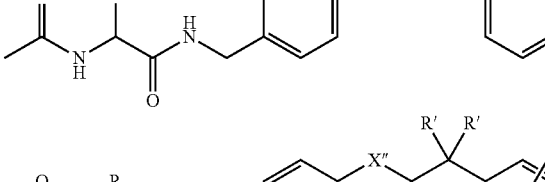
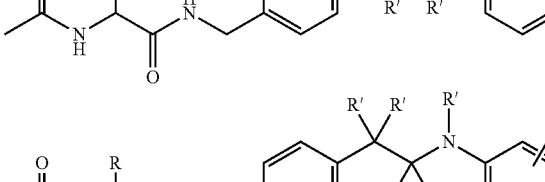
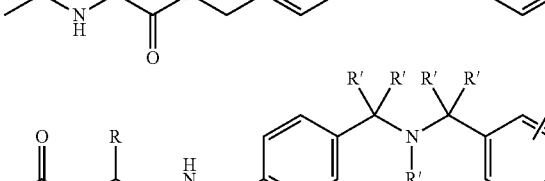

-continued
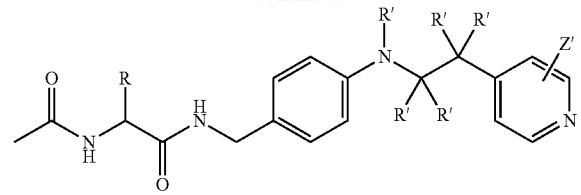
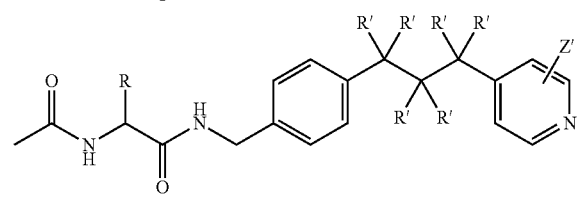
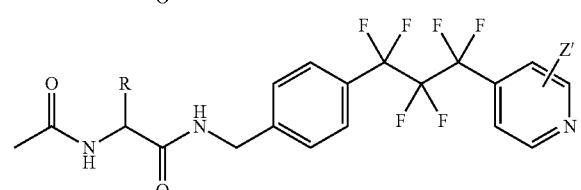
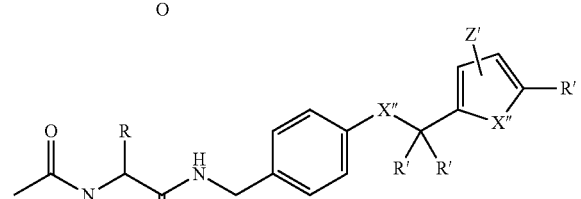
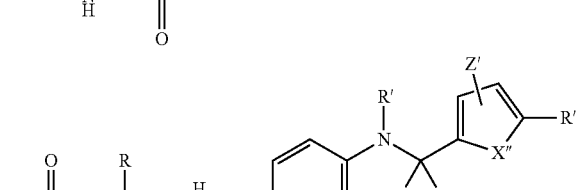
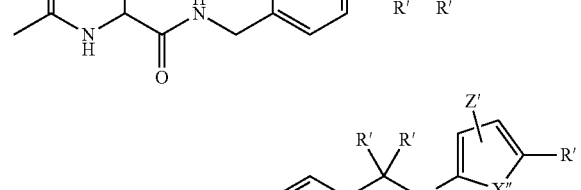
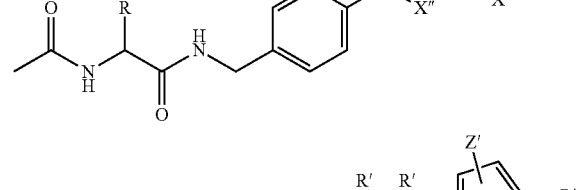
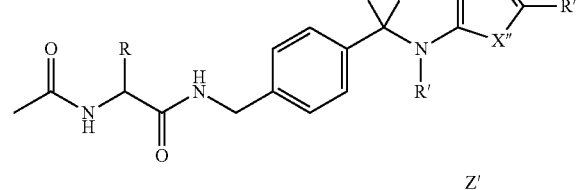
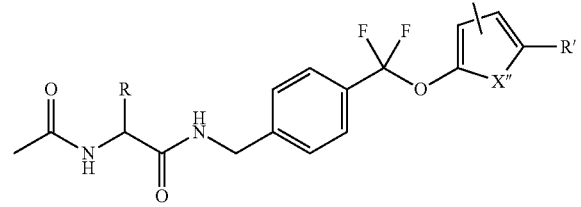
-continued
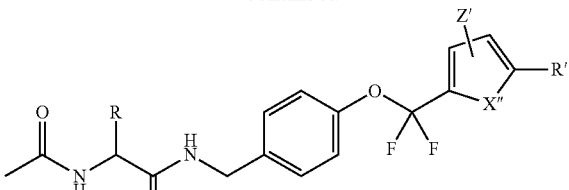
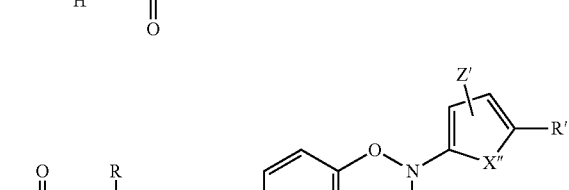
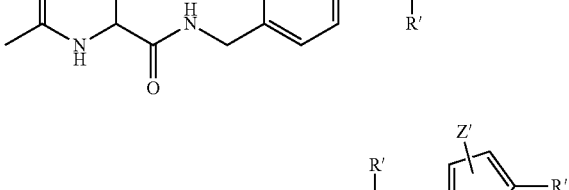
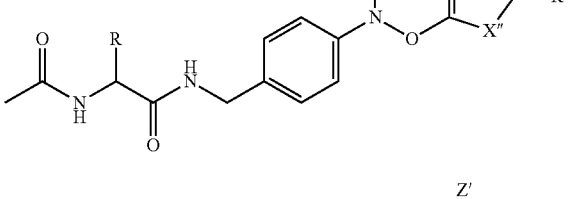
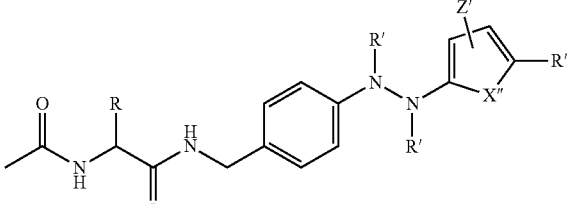
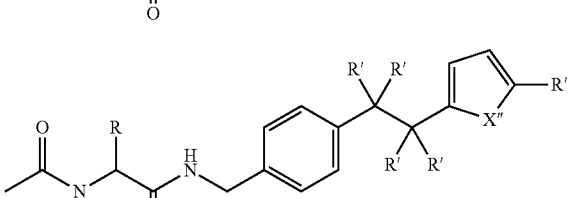
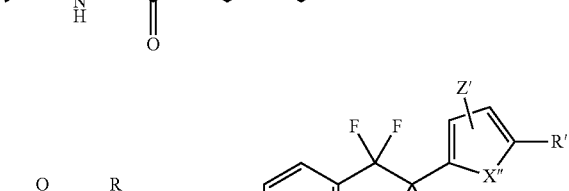
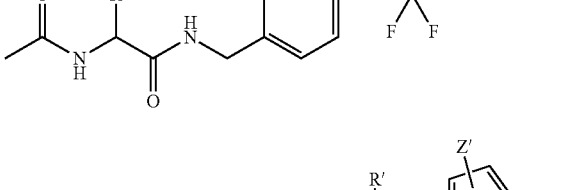
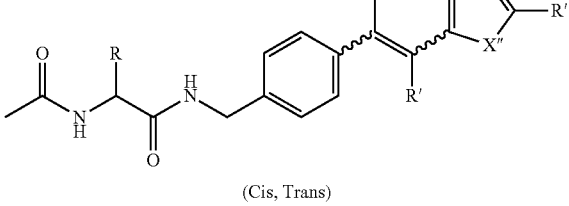
(Cis, Trans)

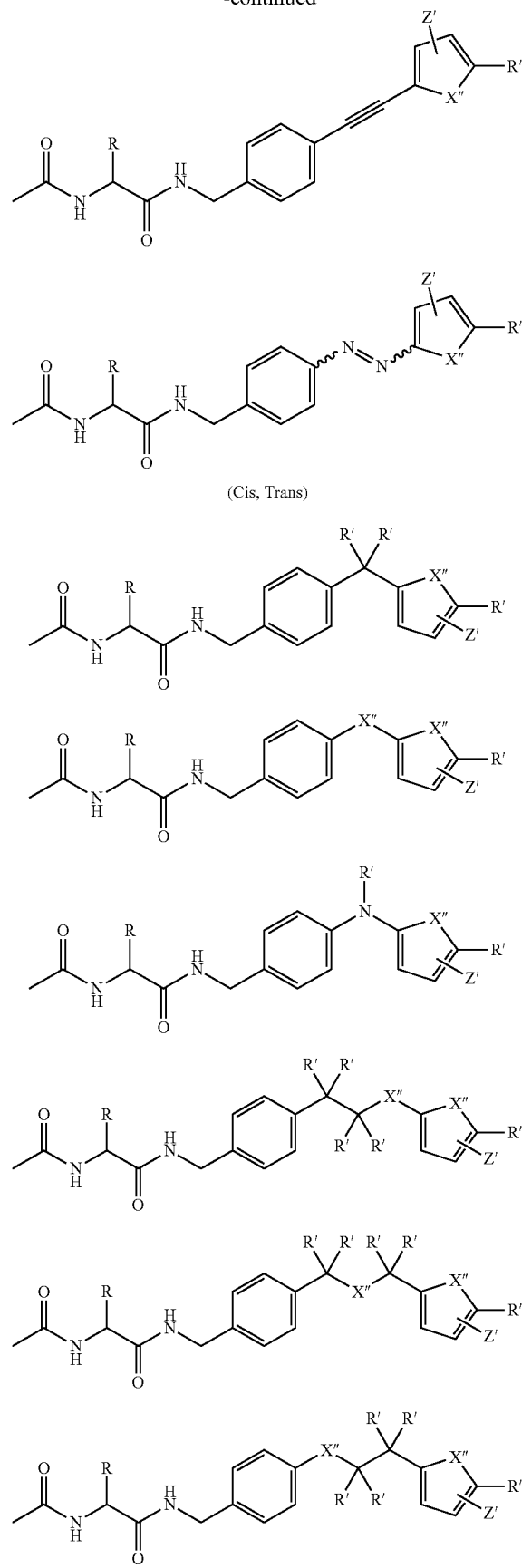
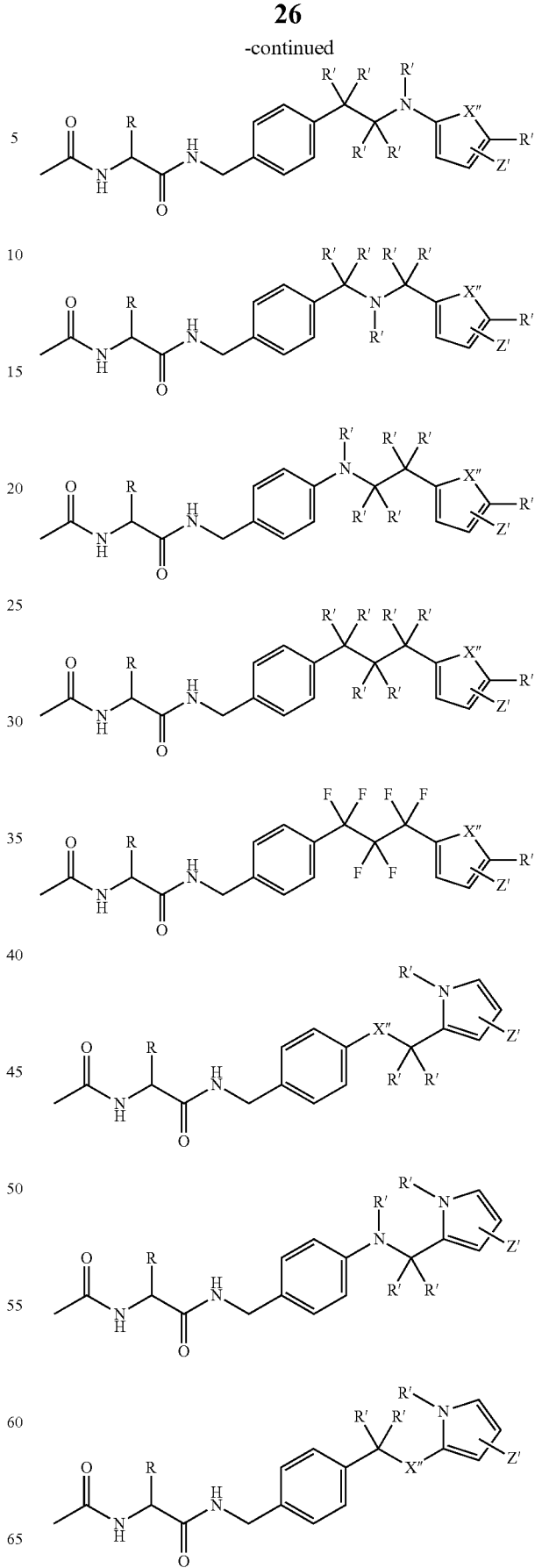

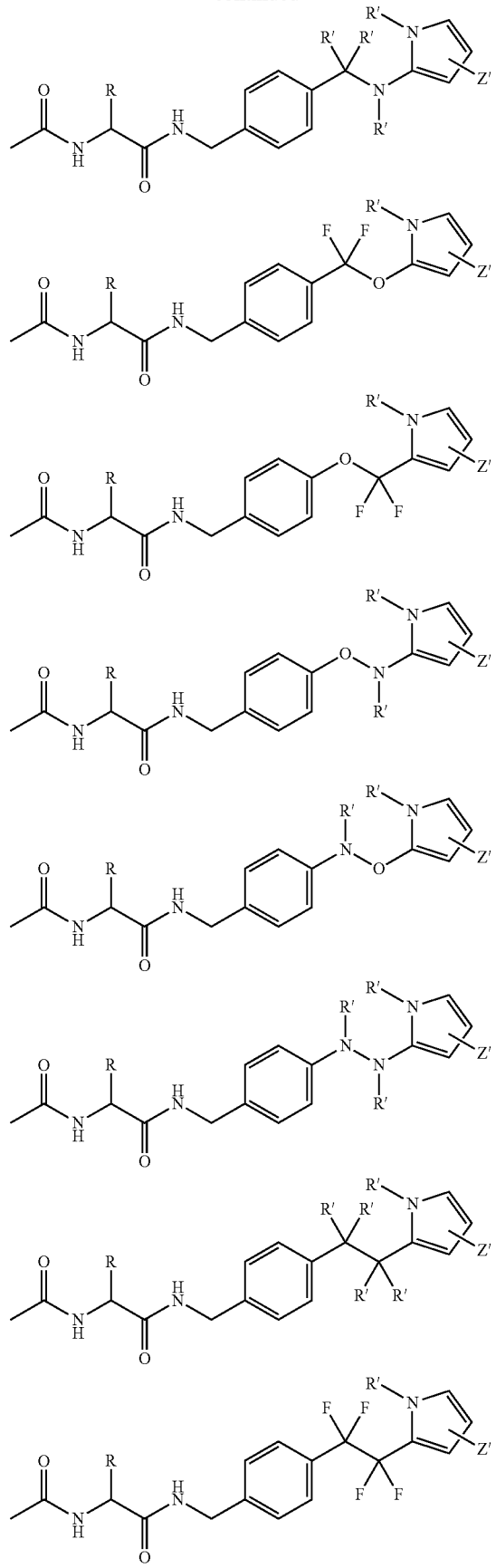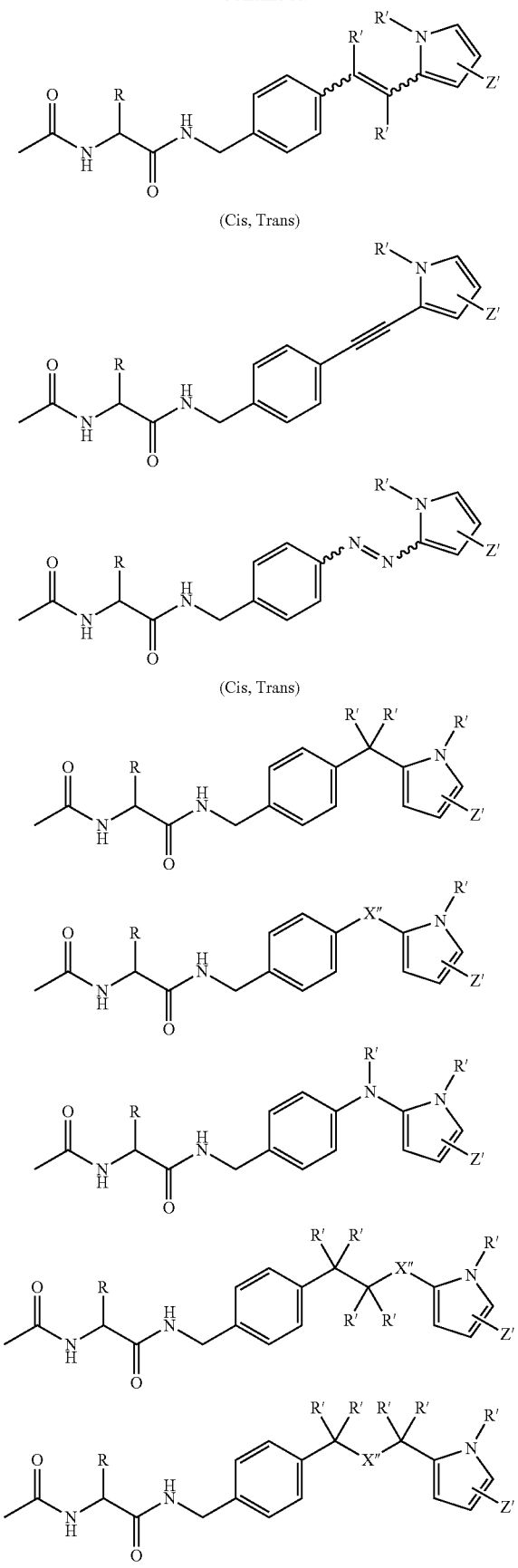
(Cis, Trans)
(Cis, Trans)

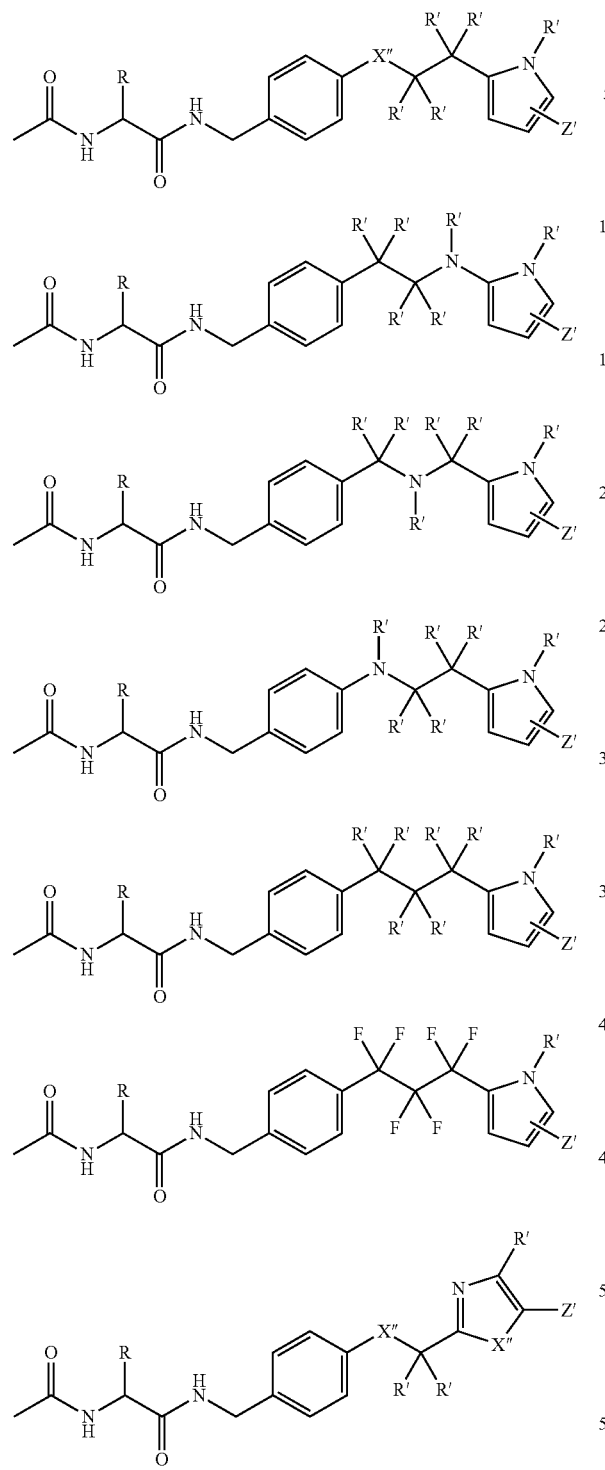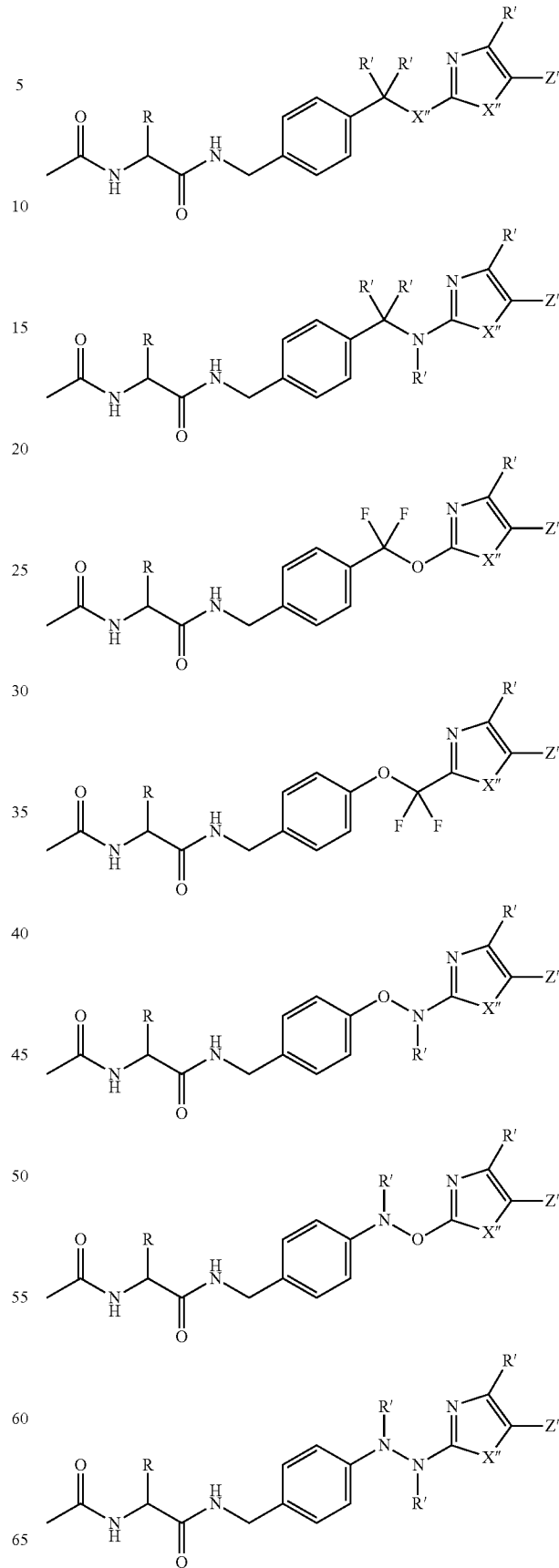

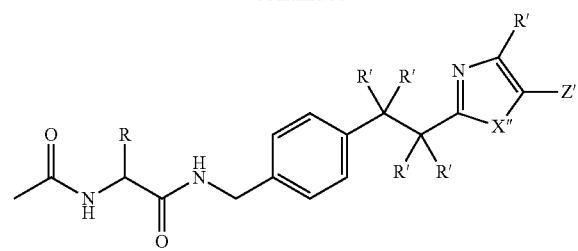
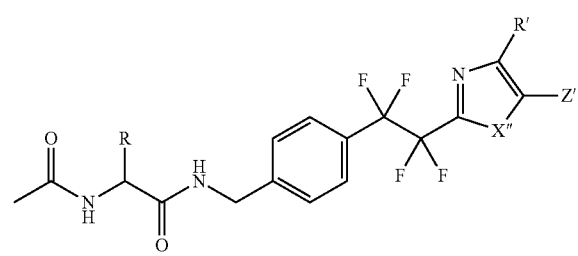
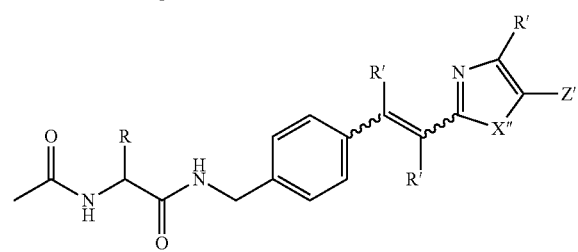
(Cis, Trans)
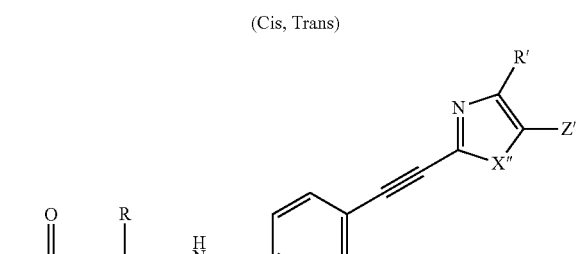
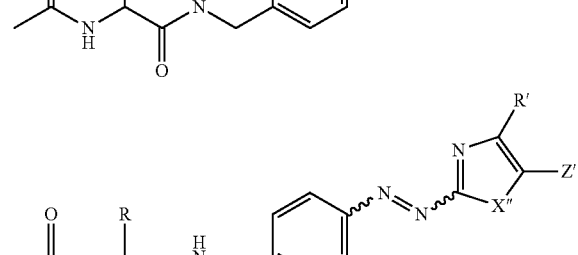
(Cis, Trans)
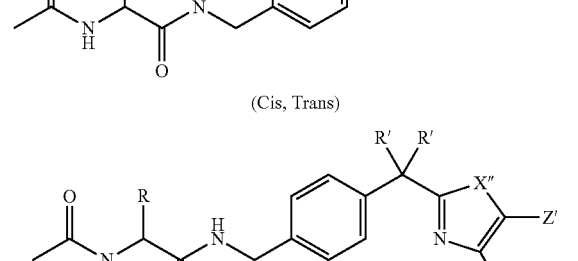
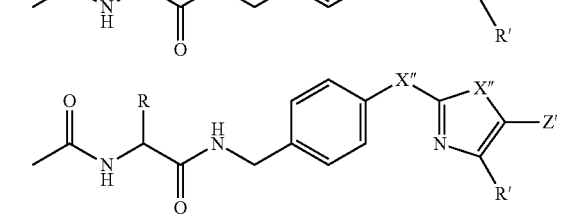
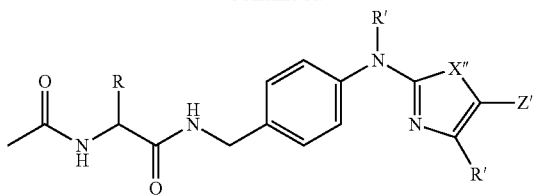
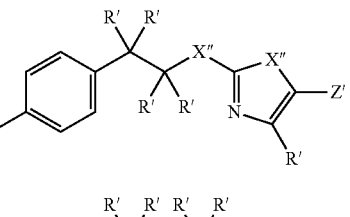
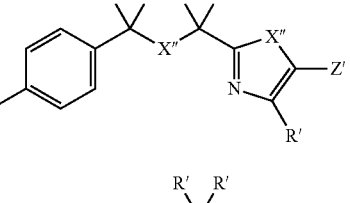
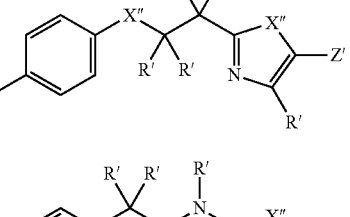
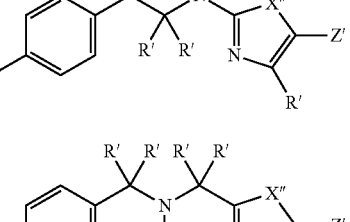
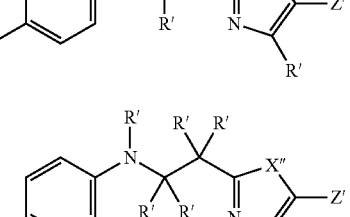
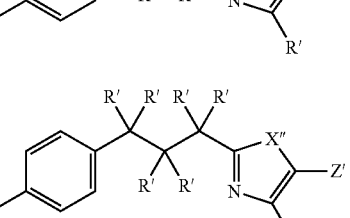
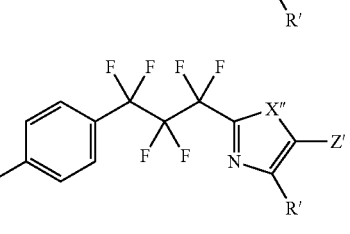

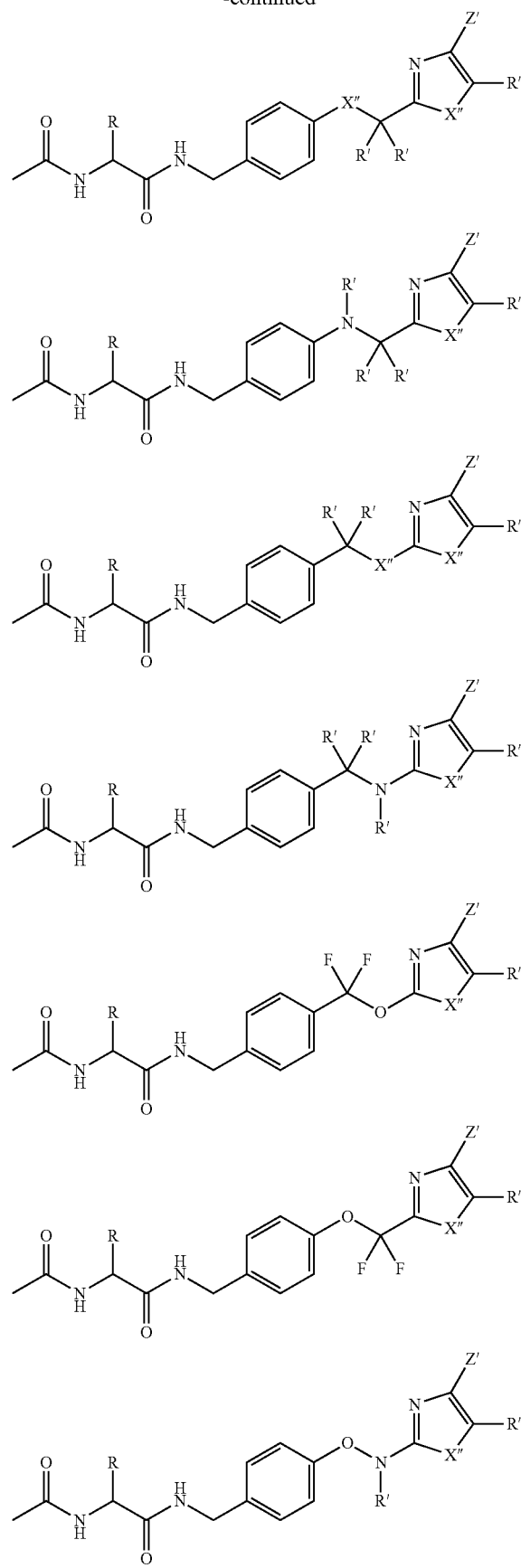
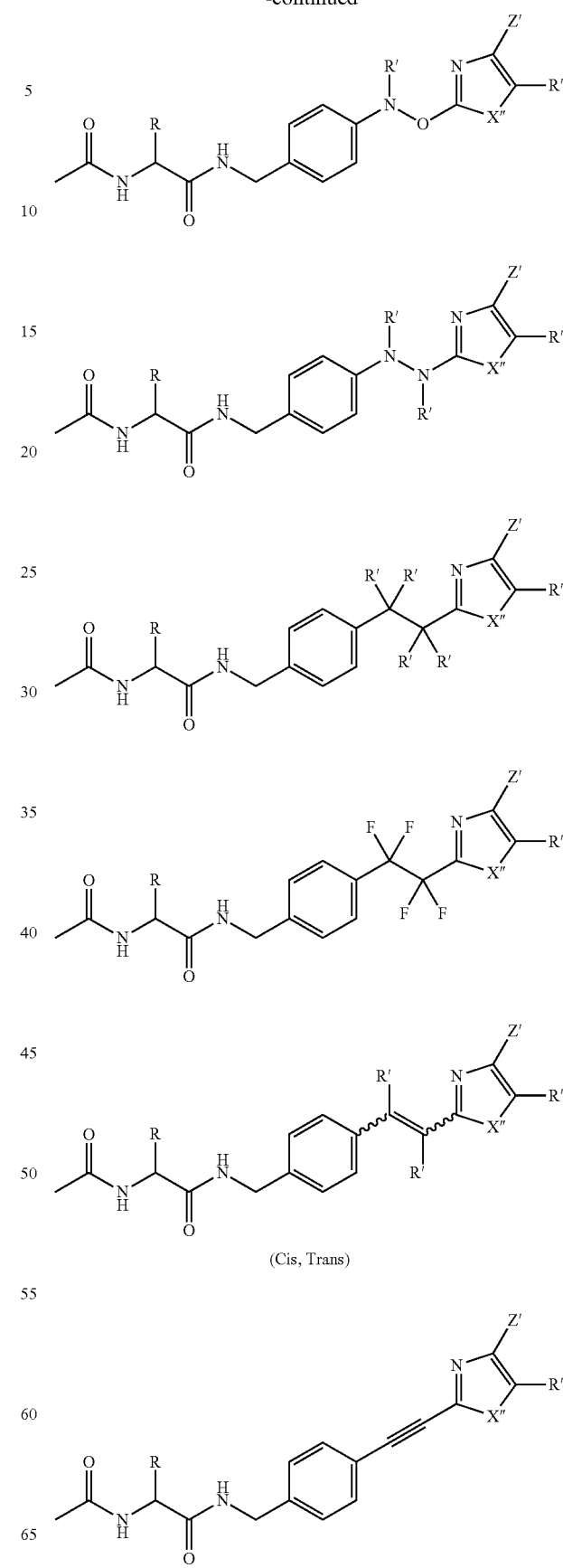
(Cis, Trans)

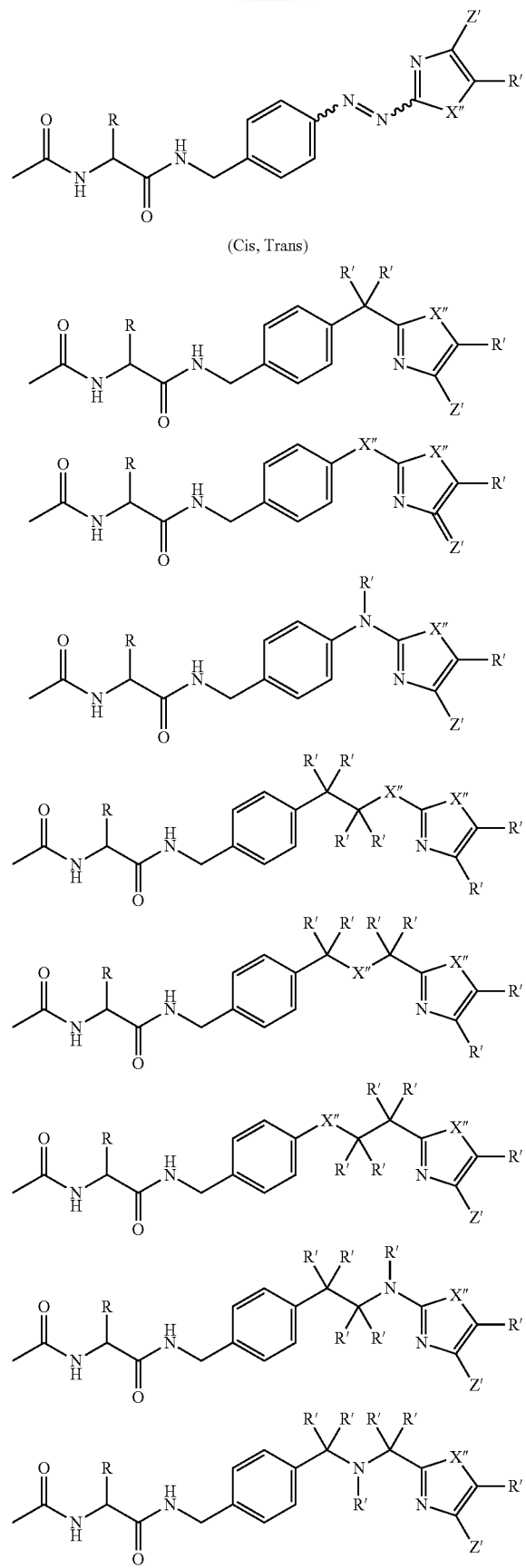
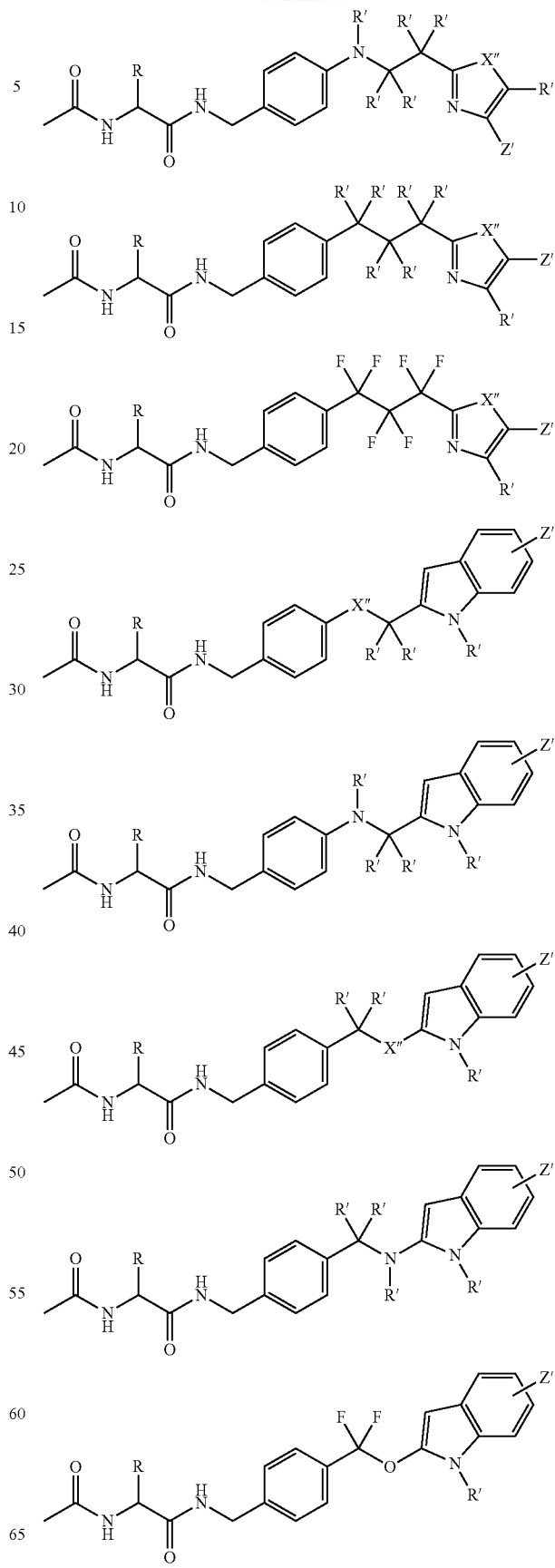

37
-continued
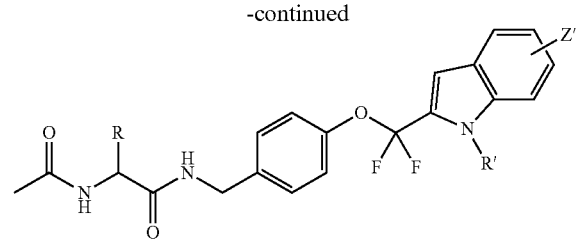
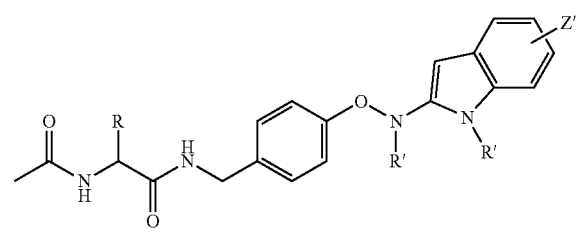
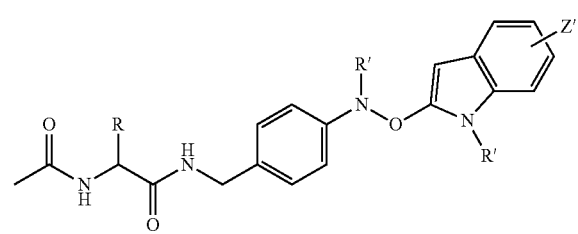
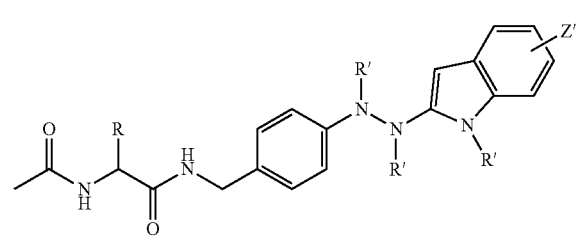
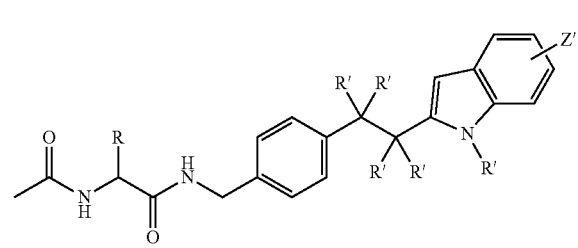
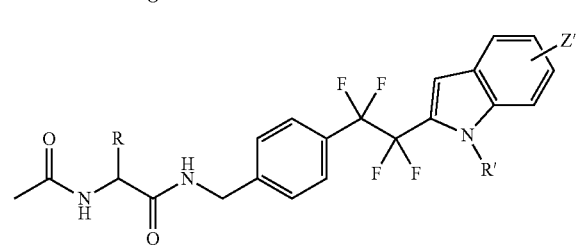
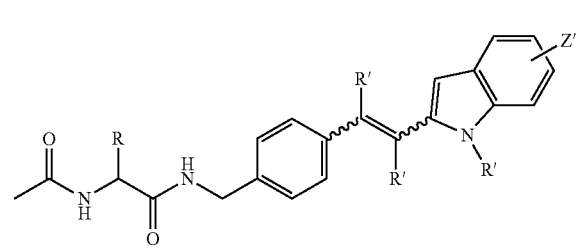
(Cis, Trans)
38
-continued
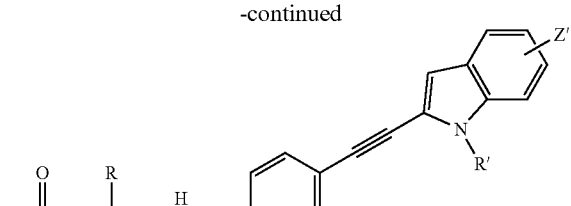
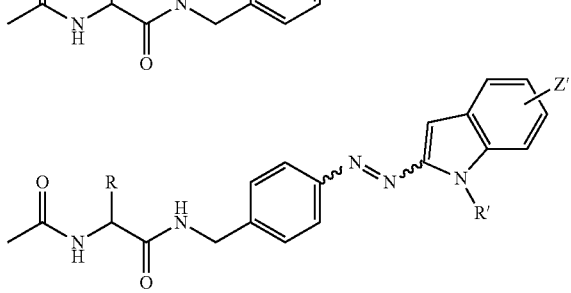
(Cis, Trans)
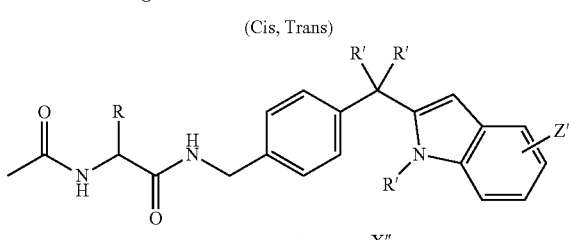
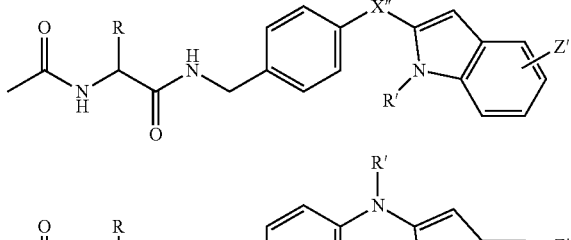
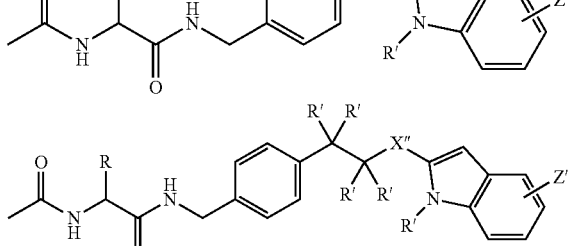
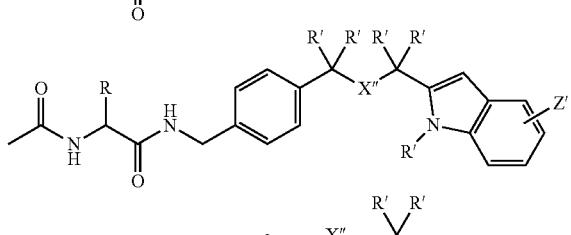
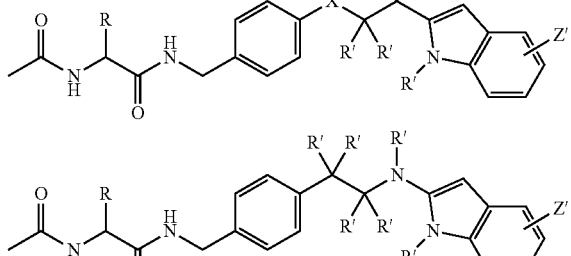

39
-continued
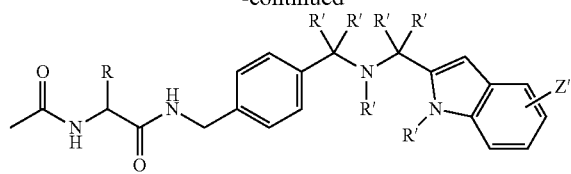
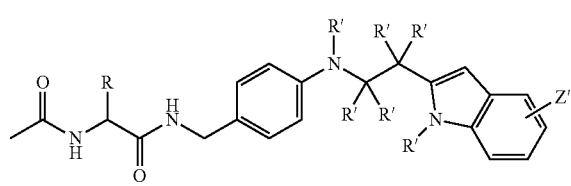
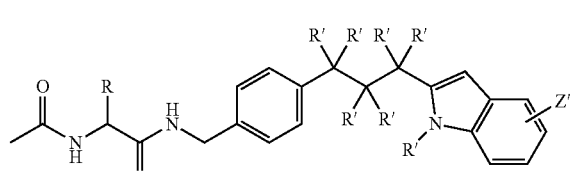
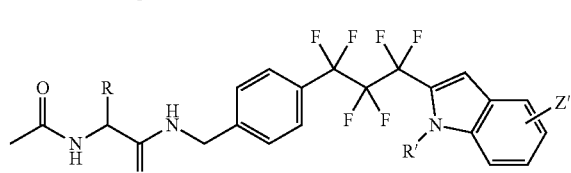
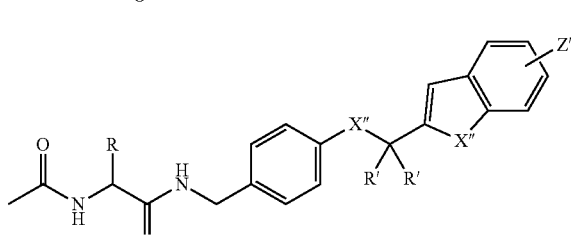
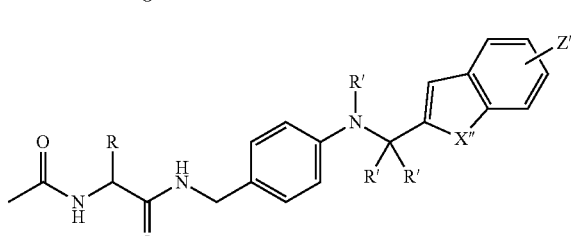
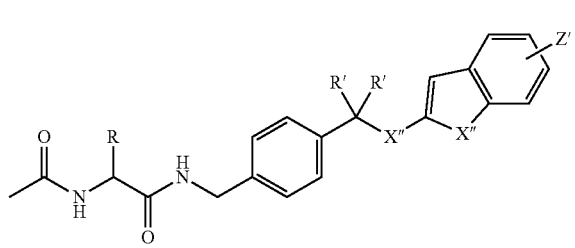
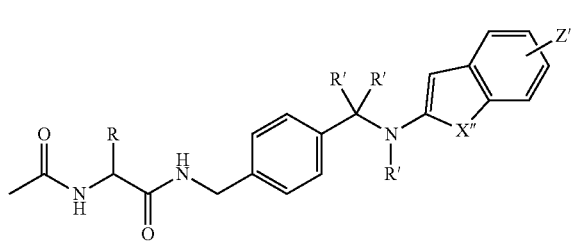
40
-continued
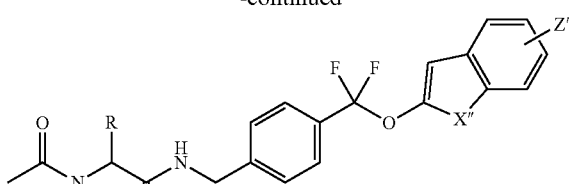
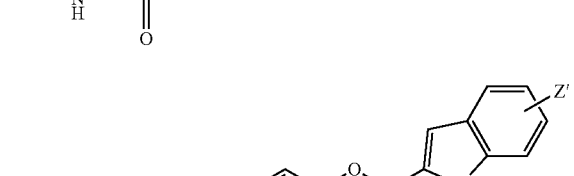
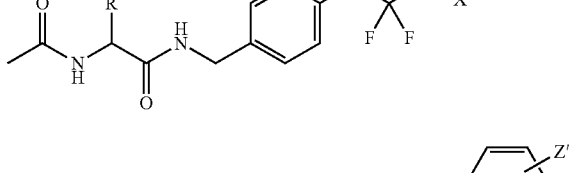
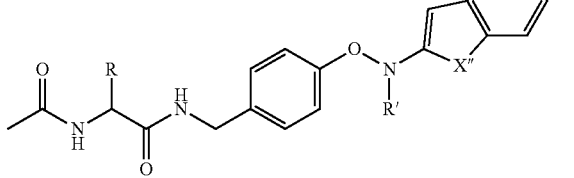
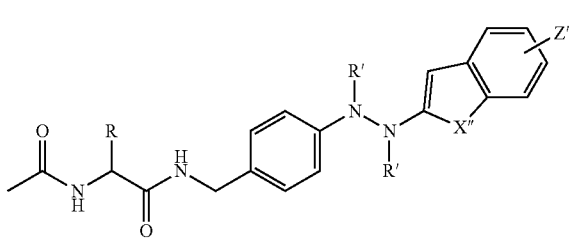
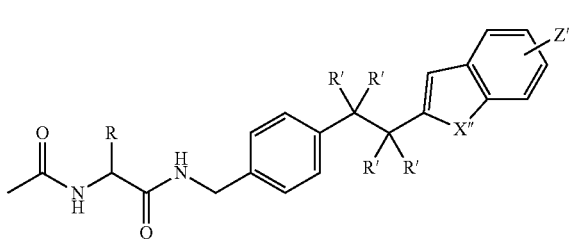
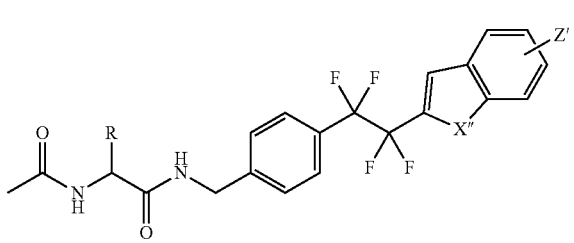

41
-continued

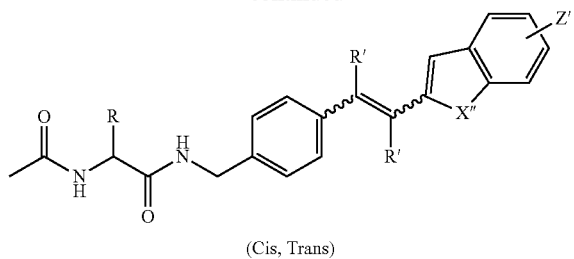
(Cis, Trans)

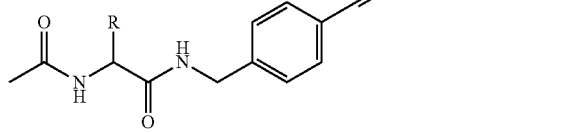
(Cis, Trans)

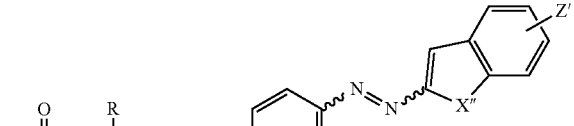

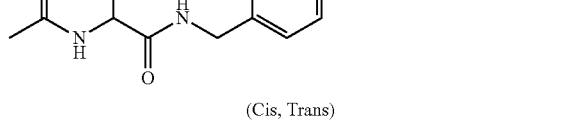

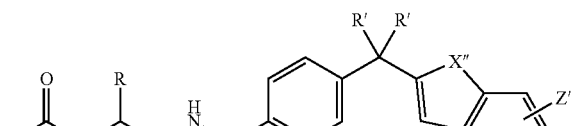

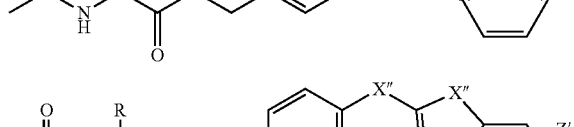

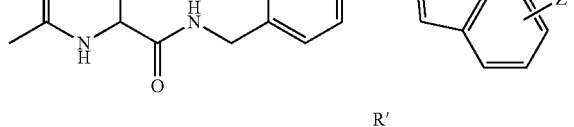

42
-continued

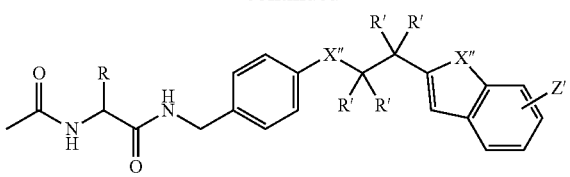

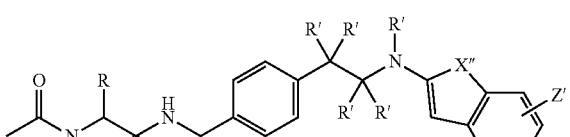

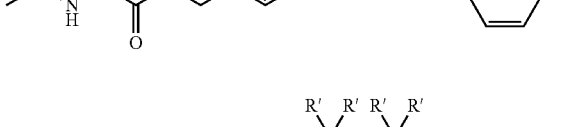

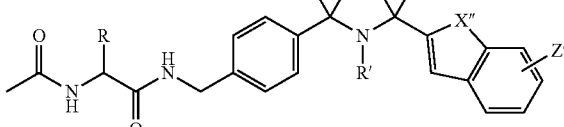

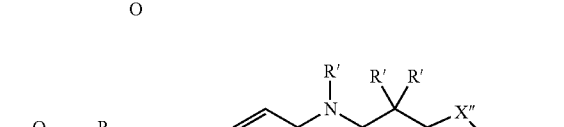

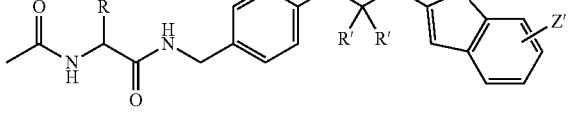 and

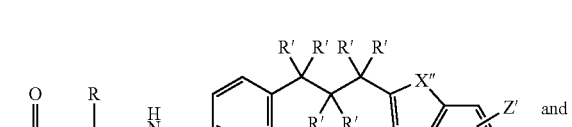

or a pharmaceutically acceptable salt or prodrug thereof, wherein each R and Z' is as given in connection with Formula Ib above, each R' is independently selected H or lower alkyl, unsubstituted or substituted with 1-3 electron-withdrawing or electron-donating groups, and where the different R' units within a given molecule may be the same or they may be different; and each X" is independently selected O or S.

In some embodiments of the foregoing, the active compounds are provided in the (R)-configuration.

In some embodiments of the foregoing, the active compounds are provided in isolated and/or purified form, or substantially pure form.

Compounds of the present invention can be prepared in accordance with known techniques or variations thereof that will be apparent to those skilled in the art based on the present disclosure, including but not limited to the methods shown in the Schemes below:

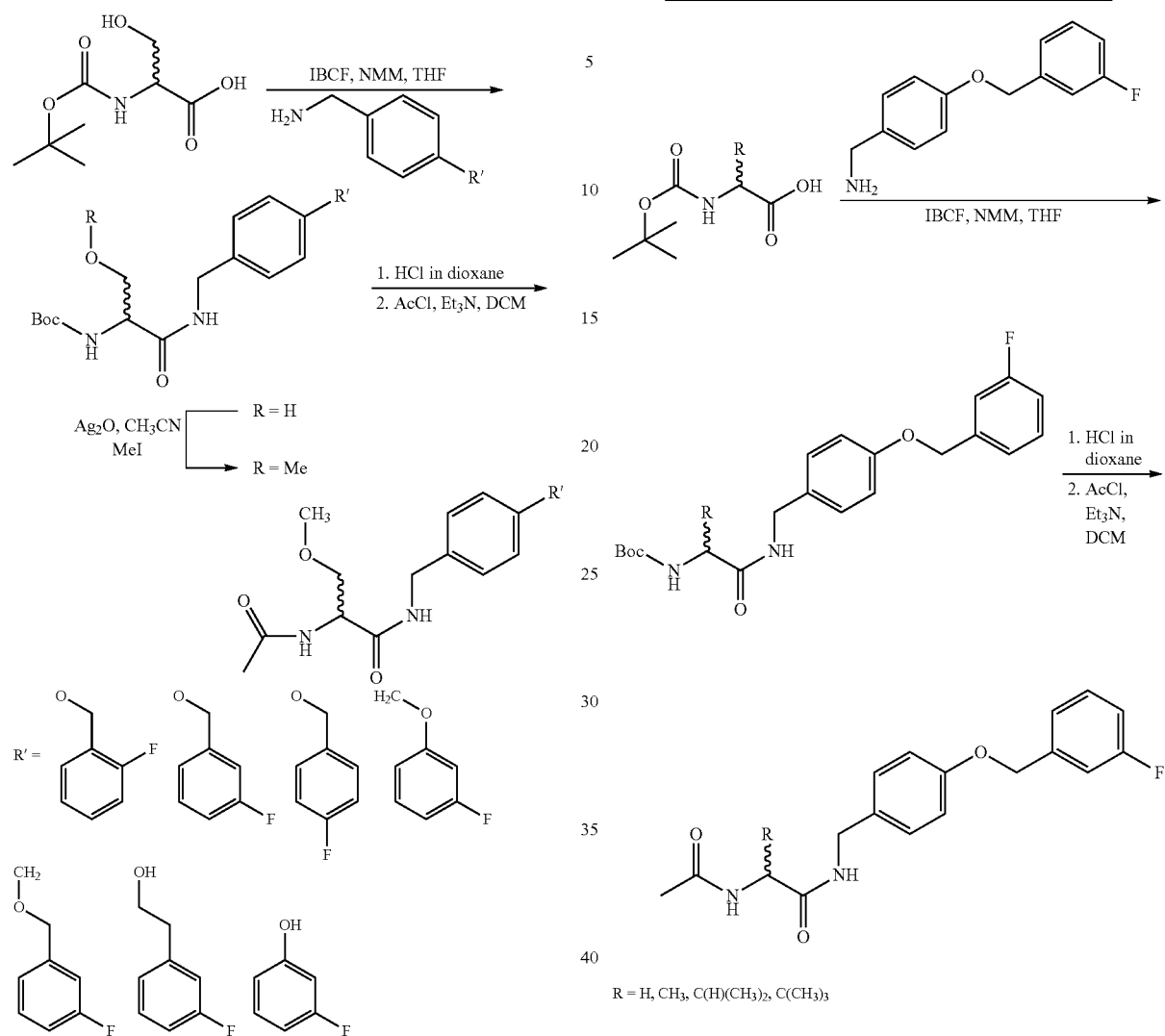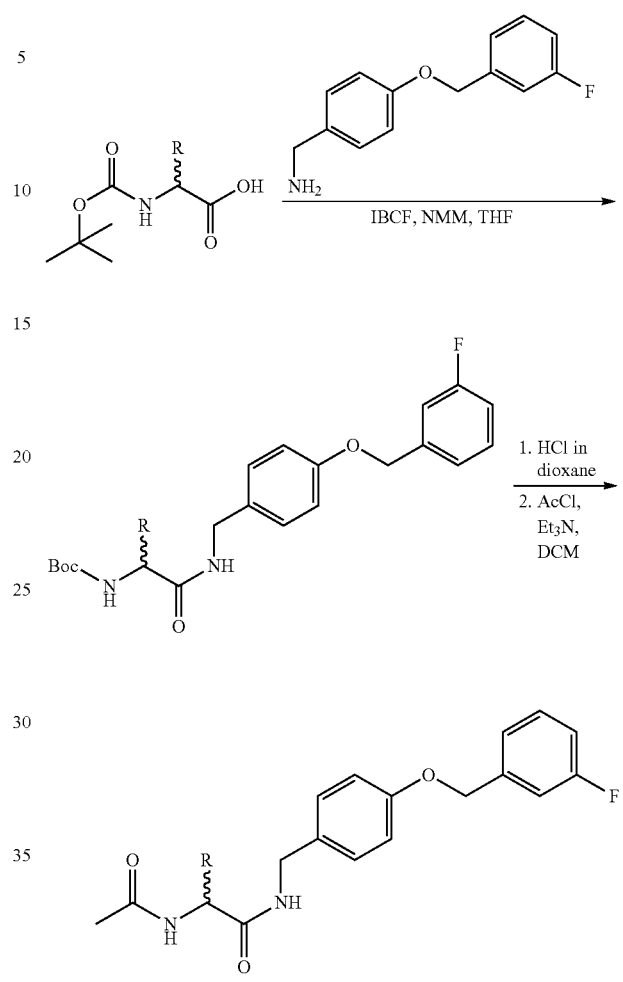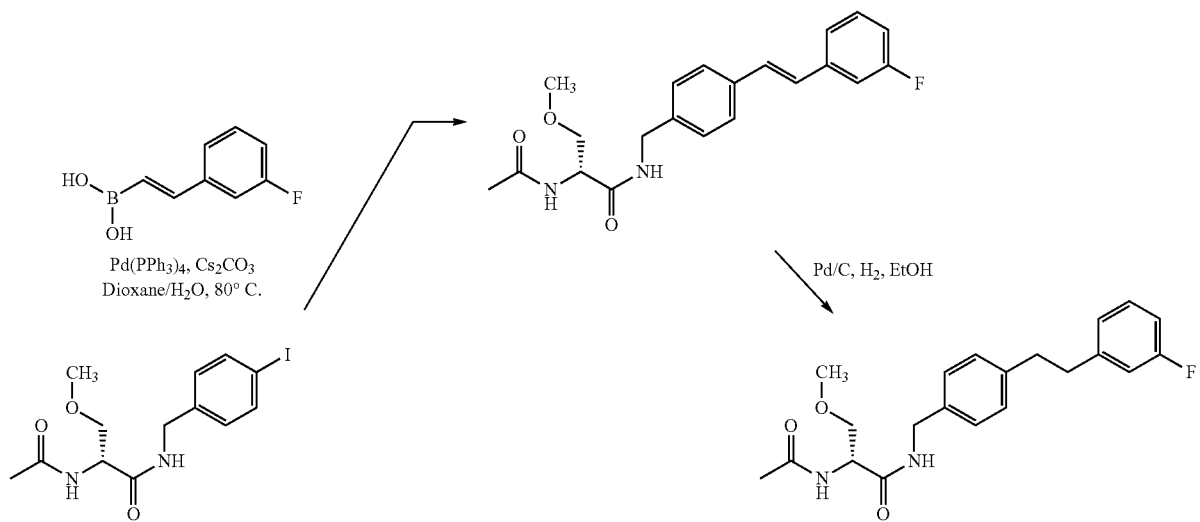

-continued
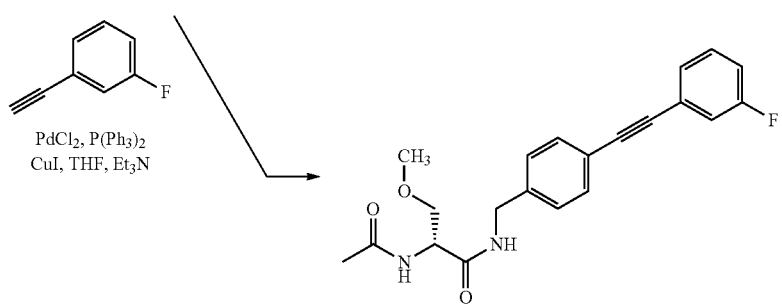
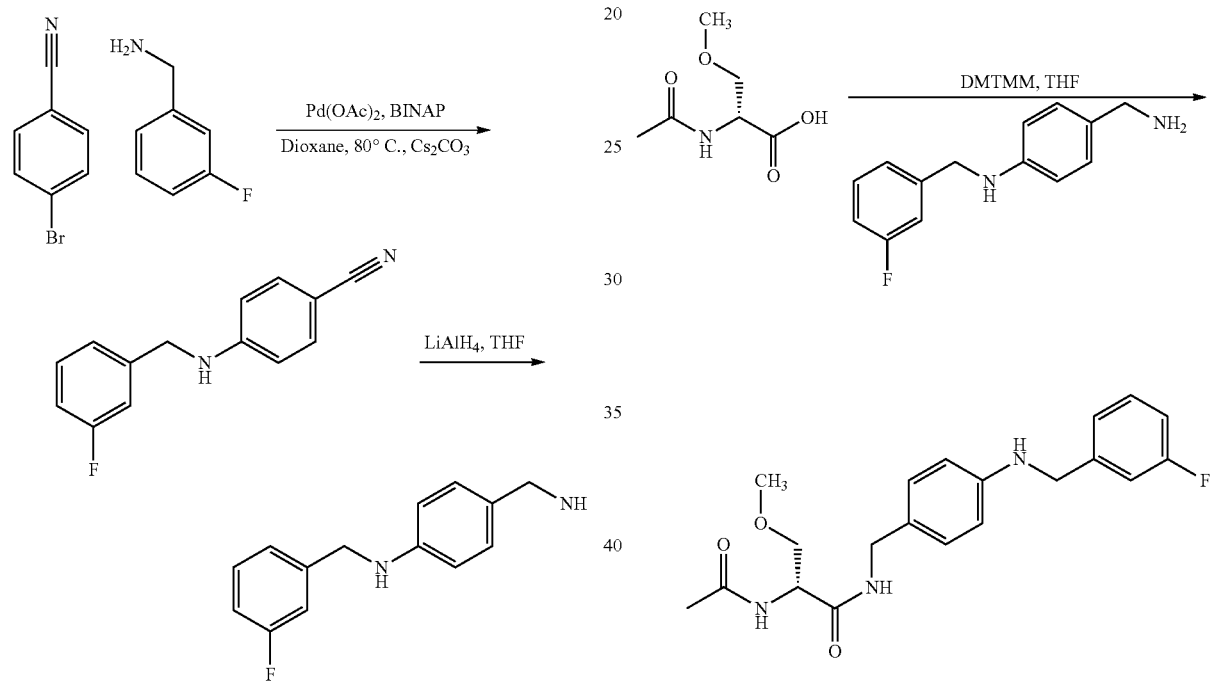
Scheme 4. Method "D" to Prepare Novel Neurological Agent
-continued
Scheme 5. Preparation of New Neurological Agent: 2-Acetamido-N-(4-(3-fluorobenzyloxy)benzyl)-2-(pyridin-2-yl)acetamide (Method "E")
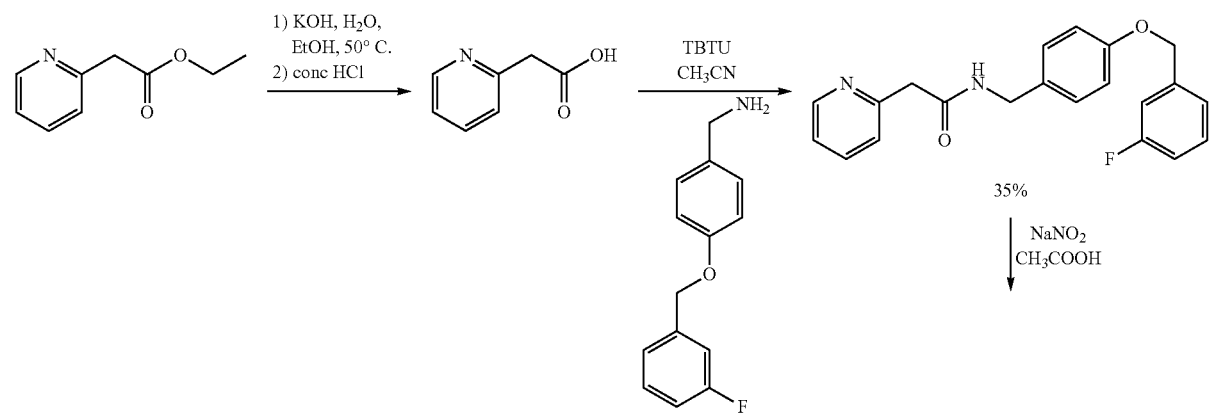

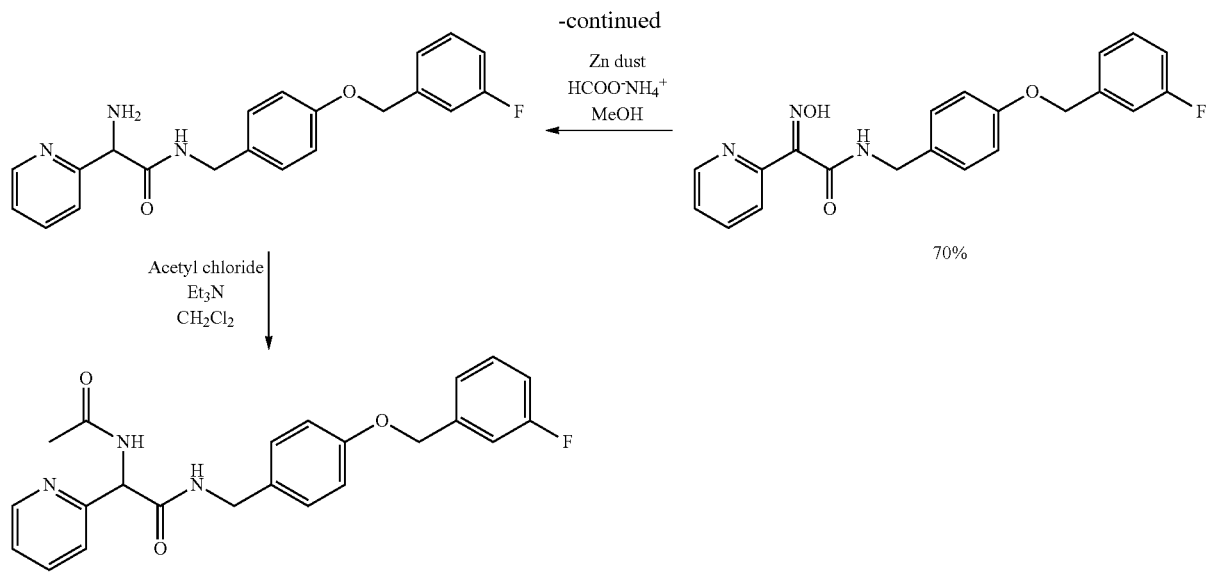
Scheme 6. Preparation of New Neurological Agent: 2-Acetamido-N-(4-(3-fluorobenzyloxy)benzyl)-2-(thiazol-2-yl)acetamide (Method "F")
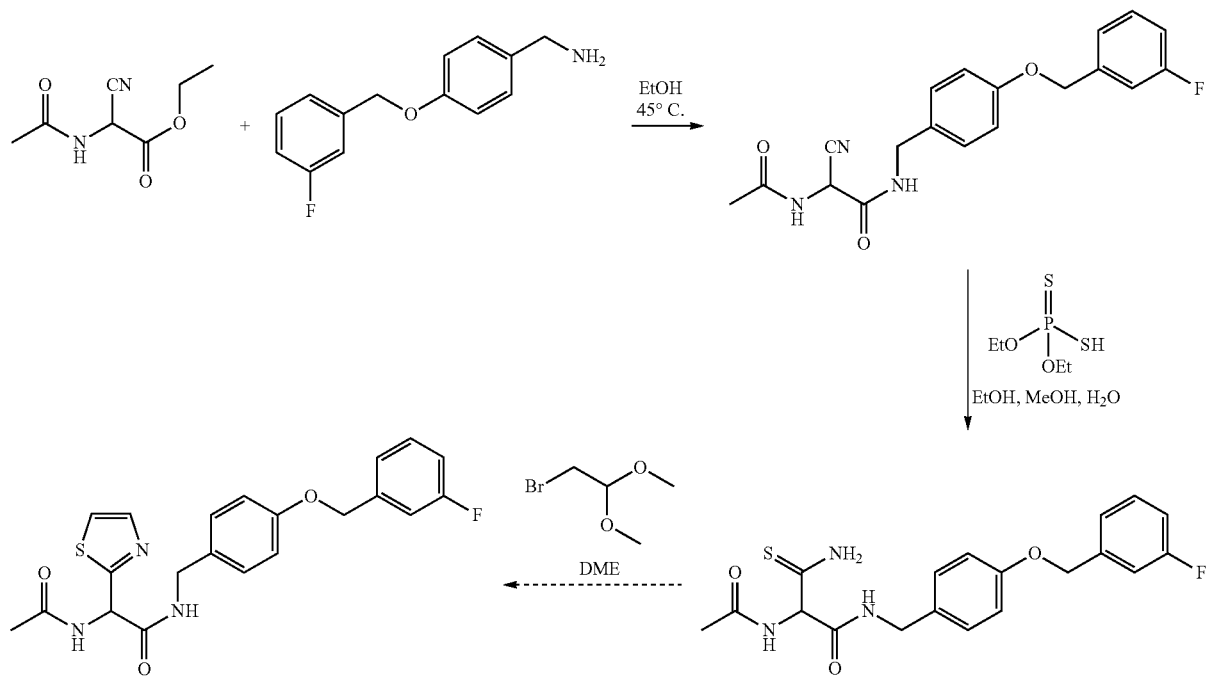
Specific examples of the active compounds of the invention include, but are not limited to:
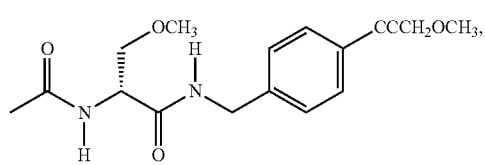
-continued
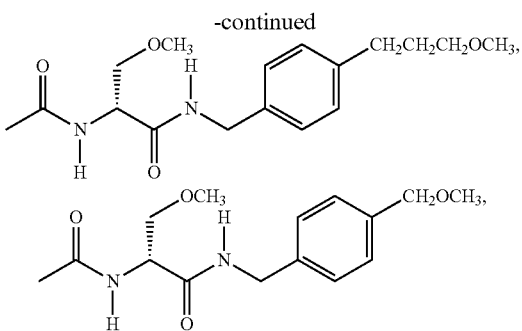

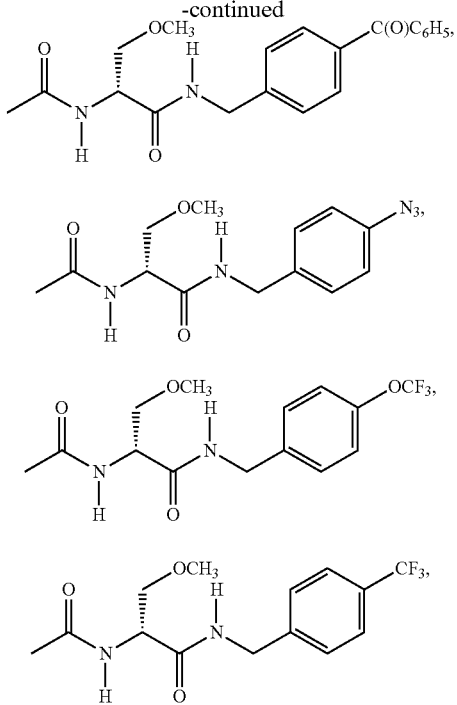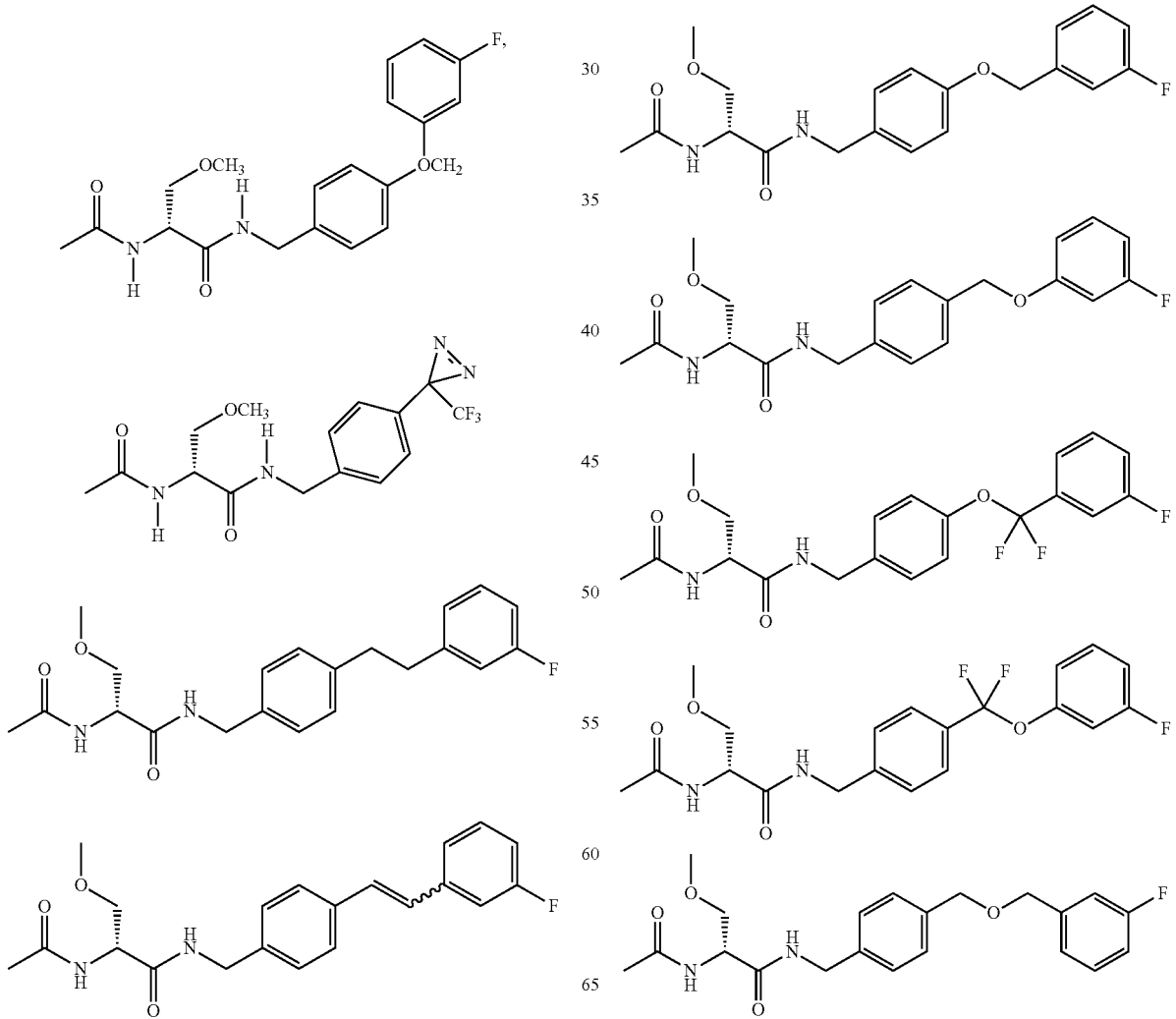

51
-continued
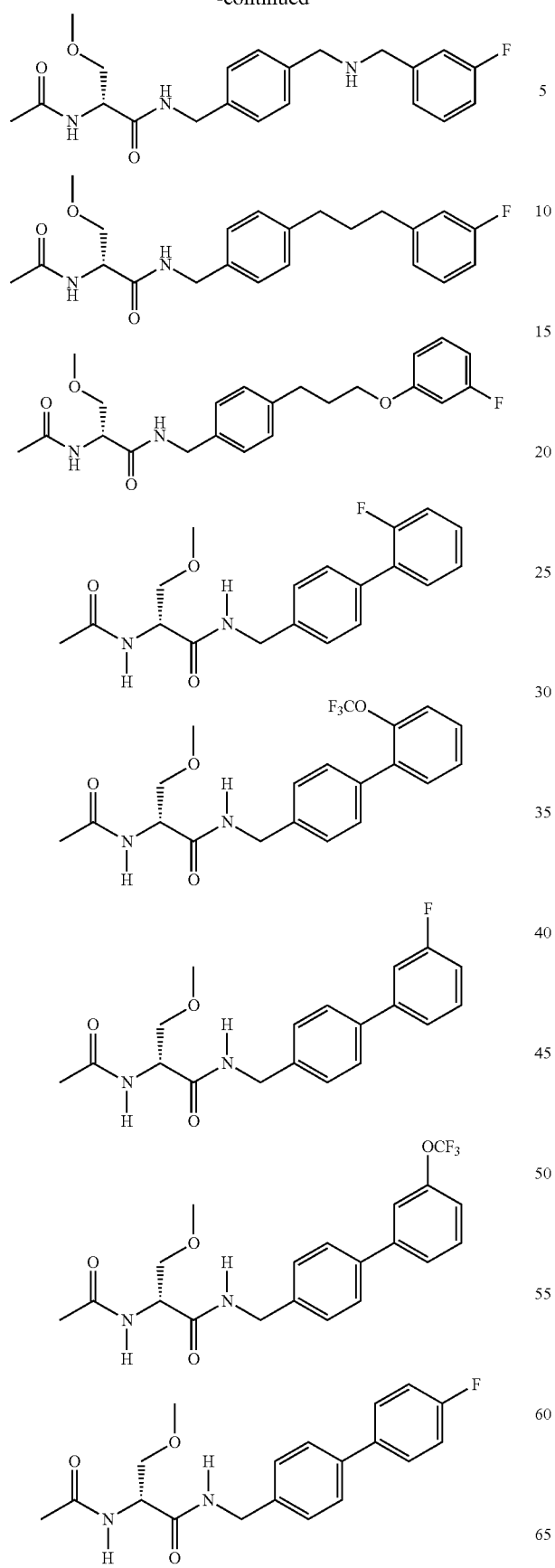
52
-continued
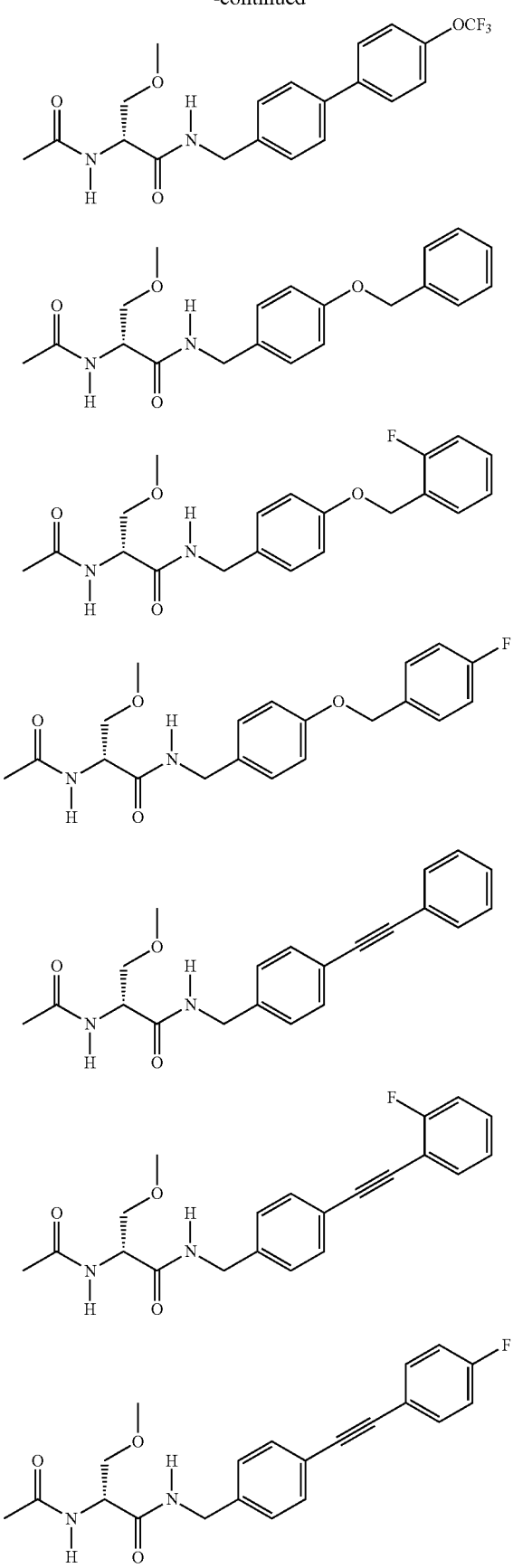

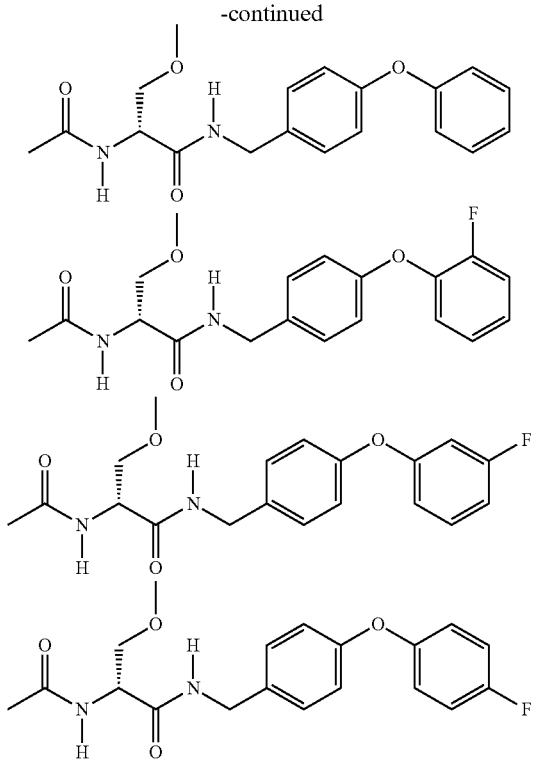

and pharmaceutically acceptable salts and prodrugs thereof.

In some embodiments of the foregoing, the active compounds are provided in the D-amino acid configuration.

In some embodiments of the foregoing, the active compounds are provided in isolated and/or purified form, or substantially pure form. In other embodiments, the compounds may exist as a racemic mixture or an unequal mixture of the D- and L-amino acid configurations at the chiral amino acid carbon.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

As also noted above, the compounds of the invention can be prepared as pharmaceutically acceptable prodrugs. Pharmaceutically acceptable prodrugs are those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A. C. S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

C. Pharmaceutical Formulations

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces such as by nasal administration or inhalation administration to nasal passages and/or to the lungs) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof. Formulations for inhalation administration may be administered as aqueous or dry powder particles by any suitable means, such as by a nebulizer or dry powder inhaler).

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

The formulations may be prepared as "timed release" formulations, e.g., by combining or mixing the active compound with a biodegradable or bioerodable polymer, by encapsulating the active compounds in a biodegradable capsule or with an enteric coating, or any other suitable technique In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

D. Dosage and Routes of Administration

As noted above, the present invention provides pharmaceutical formulations comprising the active compounds (including the pharmaceutically acceptable salts thereof), in pharmaceutically acceptable carriers for oral, inhalation, rectal, topical, buccal, parenteral, intramuscular, intradermal, intravenous, and transdermal administration.

The therapeutically effective dosage of any specific compound, the use of which is in the scope of present invention, will vary somewhat from compound to compound, and patient to patient, and will depend upon the condition of the patient and the route of delivery. In some embodiments, a dosage from about 0.1 or 1 up to about 1 or 2 g/patient will have therapeutic efficacy, with all weights being calculated based upon the weight of the active compound, including the cases where a salt is employed. Toxicity concerns at the higher level may restrict intravenous dosages to a lower level such as up to about 1 or 2 g/patient, with all weights being calculated based upon the weight of the active base, including the cases where a salt is employed.

For an oral administration form, the dosage may be from 50, 100 or 200 mg per subject up to 1 or 2 grams per subject, once or twice a day.

E. Combination Compositions and Treatment

The compounds above can be administered alone or in combination (concurrently) with the administration of other neurological active agents. The other neurological active agent can be administered separately, or included in the compositions described above that also contain the active agents described above.

Examples of other neurological active agents for the treatment of epilepsy, seizure disorders and the like, and which can be used to carry out the present invention, include but are not limited to: felbamate, gabapentin, lamotrigine, topiramate, tiagabine, levetiracetam, zonisamide, fosphenyloin, carbamazepine, oxcarbazepine, valproate sodium, diazepam, midazolam, propofol, ethosuximide, phensuximide, methsuximide, clonazepam, clorazepate dipotassium, phenyloin, mephenyloin, ethotoin, phenobarbital, mephobarbital, pyrimidone, pregabilin, etc. Such compounds may be administered to the subjects, or included in the compositions described above, in amounts known in the art.

Examples of other neurological active agents for the treatment of pain such as neuropathic pain, and which can be used to carry out the present invention, include but are not limited to: tricyclic antidepressants, serotonin reuptake inhibitors, anticonvulsants, nonopioid analgesics, etc. Particular examples include but are not limited to amitriptyline, desipramine, nortriptyline, fluoxetine, citalopram, venlafaxine, carbamazepine, phenyloin, gabapentin, lamotrigine, pregabilin, etc. Such compounds may be administered to the subjects, or included in the compositions described above, in amounts known in the art.

The present invention is explained in greater detail in the following non-limiting Examples.

Examples of Active Compounds of Formula Ia

Our laboratory has reported on the synthesis, characterization, and pharmacological activity of a class of compounds termed "functionalized amino acids" (FAAs, A). The protypical FAA is lacosamide (Vimpat®) (B), a compound that has recently been approved by the EMEA and FDA in Europe and the US, respectively, for the treatment of partial-onset seizures in adults with epilepsy. Lacosamide has also shown efficacy in phase III human trials for diabetic neuropathy and is under investigation for the treatment of migraines and fibromyalgia.

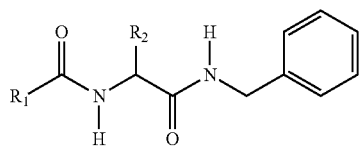

A

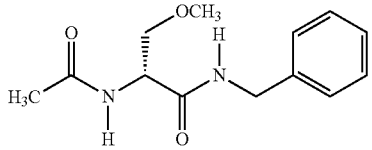

B

Recently, we have explored the structure-activity relationship (SAR) surrounding B and have discovered that select substituted N-benzylamide analogs exhibited unexpected and potent neurological activities in animal models for seizures and neuropathic pain. The potent activities of these N-benzyl substituted derivatives in animal models for seizures was surprising since similar studies with other FAAs showed that aryl substitution can lead to diminished activity. For example, we observed a sharp loss in seizure protection in mice (ip) in going from C (MES $ED_{50}$=32 mg/kg) to D (MES $ED_{50}$ ~300 mg/kg), where MES is the maximal electroshock seizure assay. A similar decrease in activity was observed upon N-benzylamide substitution of E (MES $ED_{50}$=4.5 mg/kg) to give F (MES $ED_{50}$>100, <300 mg/kg).

Our recently discovered compounds contain atypical substituents in the N-benzylamide unit. In general, an atypical substituent is a substituent that contains multiple groups or a substituent that is not easily characterized by its ability to either donate to or to withdraw electrons from the adjacent group (e.g., alkyl or aryl group). Correspondingly, typical substituents such as "electron withdrawing" and "electron donating" groups are well understood by one skilled in the art and are discussed in *Advanced Organic Chemistry* by J. March, John Wiley and Sons, New York, N.Y., pp 16-18 (1985) and the discussion therein is incorporated herein by reference. Typical electron withdrawing groups usually include halo, including bromo, fluoro, chloro, iodo and the like; nitro, carboxy, lower alkenyl, lower alkynyl, formyl, carboxyamido, aryl, quaternary ammonium, aryl lower alkanoyl, carbalkoxy and the like. Typical electron donating groups usually include such groups as hydroxyl, lower alkoxy, including methoxy, ethoxy and the like; lower alkyl, such as methyl, ethyl, and the like; amino, lower alkylamino, di(loweralkyl)amino, aryloxy such as phenoxy, mercapto, lower alkylthio, lower alkylmercapto, disulfide (lower alkyldithio) and the like.

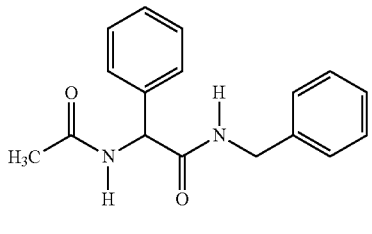

C (R,S) MES $ED_{50}$ 32 mg/kg

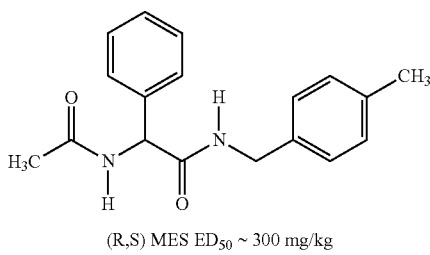

D (R,S) MES $ED_{50}$ ~ 300 mg/kg

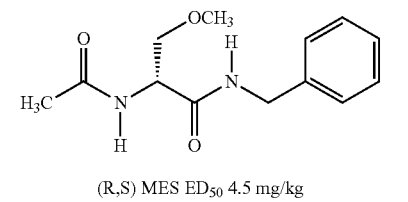

(R,S) MES ED$_{50}$ 4.5 mg/kg

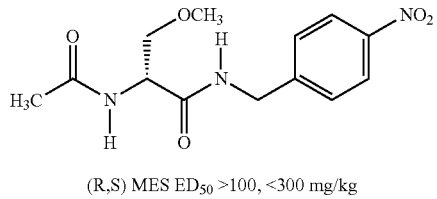

(R,S) MES ED$_{50}$ >100, <300 mg/kg

In this disclosure, we report the synthesis and characterization of compounds with atypical substituents attached to the N-benzylamido moiety of 2-(acylamido)acetic acid derivatives (1) and 2-(acylamido)propionic acid derivatives (2), and further disclose that the attachment of these moieties to the N-benzylamido substituent of 2-(acylamido)acetic acid derivatives (1) and the N-benzylamido substituent of 2-(acylamido)propionic acid derivatives (2) provides compounds with potent and efficacious activities against neurological disorders in mammals.

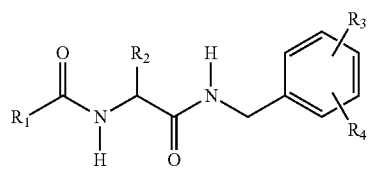

1

E

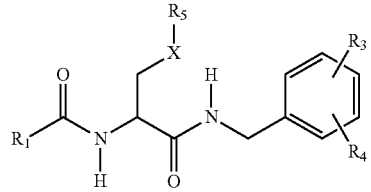

F

2

Results

We have prepared compounds 3-10 and evaluated their activities at the National Institutes of Health (NIH) NINDS Anticonvulsant Screening Program (ASP). All compounds were prepared as the (R)-stereoisomer, while for 3 and 5 the corresponding (S)-stereoisomer was also prepared. Previous studies have shown that maximal anticonvulsant activity resided in the D-amino acid configuration, which for these compounds corresponds to the (R)-configuration. The compounds were prepared by general synthetic methods similar to those outlined in Schemes 1-6 and those schemes given in the Experimental Section, and all compounds were fully characterized by established methods. The optical purity of each compound was assessed by a $^1$H NMR method and the optical activity recorded.

The pharmacological activities for 3-10 are summarized in Table 2. Unlike the dramatic reduction of anticonvulsant activity observed for D upon incorporation of a p-methyl unit in the N-benzylamide group of C or the attachment of a p-nitro group in E to give F, we found that N-benzylamide substitution led to compounds with excellent seizure protection in either mice (ip) and/or rats (po) (MES ED$_{50}$), and that these compounds exhibited minimal neurological toxicity (TD$_{50}$) in animal behavioral tests (e.g., the rotorod test in mice). The high TD$_{50}$ values compared with the low MES ED$_{50}$ value provided high Protective Index (PI) values (PI=TD$_{50}$/ED$_{50}$) that were comparable with proven antiepileptic agents (i.e., phenyloin, phenobarbital, valproic acid). Similar to previous findings for FAAs (A), we observed maximal activity for the (R)-stereoisomer.

TABLE 2

The Effect of N-Benzylamide Substitution.

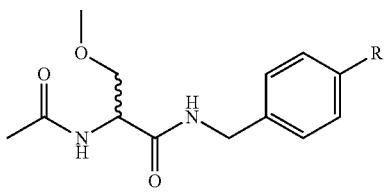

|  |  | Mice (ip)[a] | | | | Rat (po)[b] | | |
|---|---|---|---|---|---|---|---|---|
|  | R | MES, [d]ED$_{50}$ | 6 Hz, ED$_{50}$ | Tox, [e]TD$_{50}$ | PI[f] | MES, [d]ED$_{50}$ | Tox, [e]TD$_{50}$ | PI[f] |
| (R)-B | (R)-H | 4.5 [0.5] 3.7-5.5 |  | 27 [0.25] (26-28) | 5.2 | 3.9 [0.5] (2.6-6.2) | >500 | >130 |
| (S)-B | (S)-H | >100, >300 [0.5] |  | >300 [0.5] | >1.5 |  |  |  |
| (R)-3 | (R)-OCH$_2$H$_6$H$_4$(3'-F) | 13 [0.25] (11-16) | ~10 | 26 [0.5] (21-34) | ~2 | 14 [0.5] (6.1-27) [0.5] <30 [0.25 to 4.0] | >500 [0.5] >30 [0.25 to 4.0] | >36 |
| (S)-3 | (S)-OCH$_2$C$_6$H$_4$(3'-F) | >300 [0.5] |  | >300 [0.5] |  |  |  |  |

TABLE 2-continued
The Effect of N-Benzylamide Substitution.
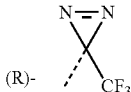
| | | Mice (ip)[a] | | | | Rat (po)[b] | | |
|---|---|---|---|---|---|---|---|---|
| | R | MES, [d]ED$_{50}$ | 6 Hz, ED$_{50}$ | Tox, [e]TD$_{50}$ | PI[f] | MES, [d]ED$_{50}$ | Tox, [e]TD$_{50}$ | PI[f] |
| (R)-4 | (R)-OCF$_3$ | [3; 10] [0.5] | | [10; 30] [0.5] | ~9.3 | >30 [0.25 to 4.0] | >30 [0.25 to 4.0] | |
| (R)-5 | (R)-N$_3$ | 8.4 [0.25] (5.7-12.2) | | 46.2 | 5.5 | 3.9 [0.5] (2.5-6.2) | >250 | >64 |
| (S)-5 | (S)-N$_3$ | >100, >300 | Around 100 | >300 | | >30 | >30 | |
| (R)-6 | (R)-C≡CCH$_2$OMe | 10 [0.25] (7.7-12) | | 15 [0.25] (13-17) | ~1.5 | 18 [1] (8.6-33) | 100 [0.5] (86-120) | 5.5 |
| (R)-7 | (R)-(CH$_2$)$_3$OMe | 20 [0.25] (18-23) | | 62 [0.25] (57-74) | ~3.1 | 16 [0.5] (8.8-25) [>2 h] | >500 [0.5 to 24] | >31.6 |
| (R)-8 | (R)-CH$_2$OMe | 73 [0.25] (62-88) | | 180 [0.25] (160-210) | ~2.3 | 45 [0.5] (29-76) | >500 [0.25 to 24]] | >11 |
| (R)-9 | (R)- N=N / CF$_3$ | 15.05 [0.25] (13.93-16.39) | | 68 [0.25] (58.78) | 4.4 | >30 [0.25 to 4.0] | >30 [0.25 to 4.0] | |
| (R)-10 | (R)-CF$_3$ | [3.10] [0.5] | | [100; 300] | ~3.1 | 4.9 [1] (2.7-7.6) | >280 | >57 |
| (R)-11 | (R)-CH$_2$OC$_6$H$_4$ [3'-F] | 5.9 [0.25] (4.3-7.3) | | 10 [0.25] (9.2-13) | ~1.8 | 19 [2] (13-25) | >400 [0.5] | >21 |
| | phenytoin[h] | 9.5 [2] (8.1-10) | | 66 [2] (53-72) | 6.9 | 30 [4] (22-39) | i | >100 |
| | Phenobarbital[h] | 22 [1] (15-23) | | 69 [0.5] (63-73) | 3.2 | 9.1 [5] (7.6-12) | 61 [0.5] (44-96) | 6.7 |
| | valproate[h] | 270 [0.25] (250-340) | | 430 [0.25] (370-450) | 1.6 | 490 [0.5] (350-730) | 280 [0.5] (190-350) | 0.6 |
EXPERIMENTAL SECTION
Scheme 1. Preparation pf (R)-3 and (S)-3.
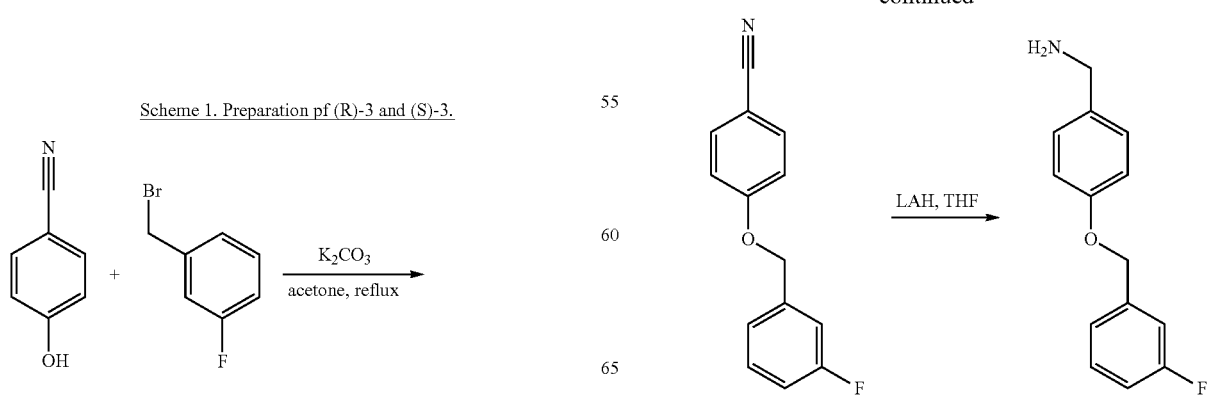

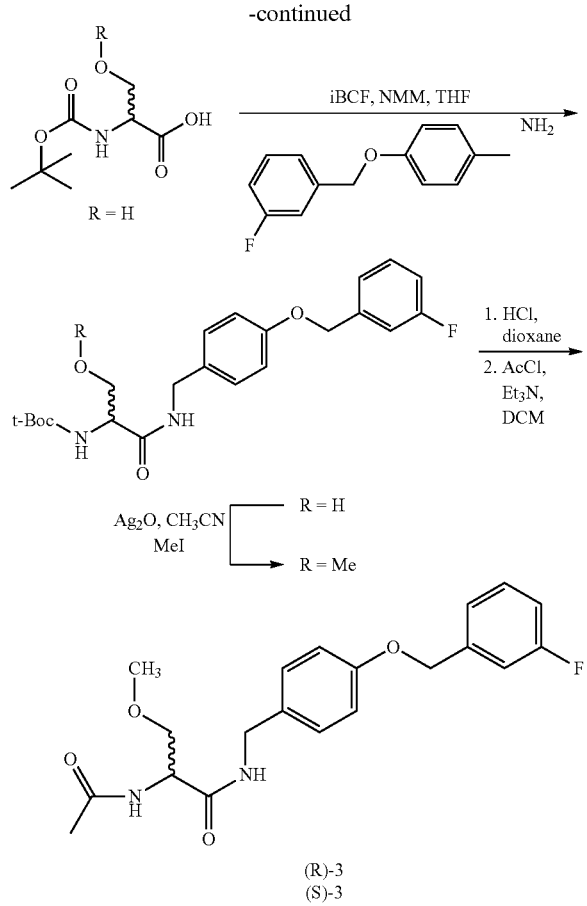

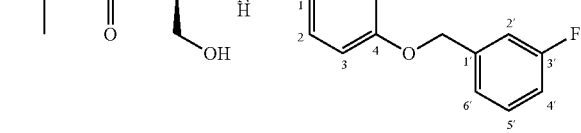

Preparation of 4-(3-Fluorobenzyloxy)benzonitrile (Nakamoto, Kazutaka; Tsukada, Itaru; Tanaka, Keigo; Matsukura, Masayuki; Haneda, Toru; Inoue, Satoshi; Ueda, Norihiro; Abe, Shinya; Hata, Katsura; Watanabe, Naoaki, WO 2005033079 (2005)). A mixture of 4-cyanophenol (11.91 g, 100.0 mmol), $K_2CO_3$ (55.20 g, 400.0 mmol), and 3-fluorobenzylbromide (22.68 g, 120.0 mmol) were heated in acetone (400 mL) at reflux (5 h). The volatiles were evaporated and the residue was diluted in $CH_2Cl_2$ (300 mL), and then washed with $H_2O$ (500 mL), dried ($MgSO_4$), and concentrated in vacuo to give white needles (19.81 g, 87%): $R_f$=0.45 (hexanes/EtOAc 9/1); mp 104-105° C.; $^1$H NMR (CDCl$_3$) δ 5.11 (s, CH$_2$O), 6.98-7.20 (m, 5 ArH), 7.33-7.41 (m, 1 ArH), 7.59 (d, J=8.7 Hz, 2 ArH); HRMS (M+Na$^+$) (ESI$^+$) 250.0641 [M+Na$^+$] (calcd for $C_{14}H_{10}NONa^+$ 250.0641).

Preparation of 4-(3-Fluorobenzyloxy)benzylamine (Aldrich data.) To a LiAlH$_4$ (5.02 g, 132.0 mmol) suspension in THF (400 mL) was added dropwise a THF (30 mL) solution of 4-(3-fluorobenzyloxy)benzonitrile (10.00 g, 44.0 mmol) at 0° C. The mixture was stirred at room temperature (16 h) and $H_2O$ (4 mL) was added dropwise at 0° C. followed by an aqueous NaOH solution (2 mL, 15% w/w), and then $H_2O$ (4 mL). The mixture was stirred at room temperature (2 h), and the precipitate filtered through a Celite® pad and the pad washed with $CH_2Cl_2$. The filtrate was concentrated in vacuo to obtain a white solid (8.82 g, 86%): $R_f$=0.00 (hexanes/EtOAc 9/1); $^1$H NMR (CDCl$_3$) δ 1.61 (br s, NH$_2$), 3.79 (s, CH$_2$NH$_2$), 5.04 (s, CH$_2$O), 6.90-7.04 (m, 3 ArH) 7.13-7.37 (m, 5 ArH); HRMS (M-NH$_2^+$) (ESI$^+$) 215.088 [M-NH$_2^+$] (calcd for $C_{14}H_{12}O^+$ 215.087).

Preparation of (R)-2-N-(tert.-Butoxy carbonyl) amino-3-hydroxy-N-(4-(3-fluorobenzyloxy)benzyl)-propanamide A THF solution (75 mL) of (R)-t-Boc-serine (4.00 g, 19.5 mmol) was stirred and cooled at −78° C. under Ar and then 4-methylmorpholine (NMM) (2.6 mL, 23.4 mmol) was added dropwise. After 2 min of stirring at this temperature, the isobutylchloroformate (IBCF) (3.0 mL, 23.4 mmol) was added dropwise leading to the precipitation of a white solid, and the reaction was allowed to proceed for additional 2 min. 4-(3-Fluorobenzyloxy)benzylamine (5.40 g, 23.4 mmol), was added portionwise at −78° C. The mixture was allowed to stir at room temperature (2 h), and then the white solid filtered and the organic layer concentrated in vacuo. The residue was purified by flash column chromatography on silica gel with EtOAc/hexanes (50/50 to 80/20) as the eluant to obtain (R)-2-N-(tert.-butoxycarbonyl)amino-3-hydroxy-N-(4-(3-fluorobenzyloxy)benzyl)-propanamide as a white solid (5.40 g, 66%): $R_f$ 0.33 (hexanes/EtOAc 5/5); mp 88-89° C.; $[α]^{25.8}_D$ +25.8° (c 1, CHCl$_3$); IR (nujol) 3319, 2966, 1659, 1527, 1456 1376, 1304, 1242, 1166, 1007, 864, 775, 673 cm$^{-1}$; $^1$H NMR (CDCl$_3$) δ1.41 (s, (CH$_3$)$_3$), 3.21-3.33 (br m, CHH), 3.59-3.72 (br m, CHH'), 4.04-4.20 (br m, CH, OH), 4.24-4.48 (br m, CH$_2$N), 5.03 (s, CH$_2$O), 5.56-5.66 (br d, NH), 6.86-6.92 (m, 2 ArH), 6.94-6.99 (m, 1 ArH, NH), 7.10-7.21 (m, 4 ArH), 7.30-7.38 (m, 1 ArH); $^{13}$C NMR (CDCl$_3$) 28.2 ((CH$_3$)$_3$), 42.8 (NCH$_2$), 55.2 (OCH$_2$CH), 62.8 (OCH$_2$CH), 69.1 (CH$_2$O), 80.5 (C(CH$_3$)$_3$), 114.1 (d, J=22.0 Hz, C$_{4'}$ or C$_{2'}$), 114.6 (d, J=21.0 Hz, C$_{2'}$ or C$_{4'}$), 114.9 (C$_1$), 122.6 (d, J=2.9 Hz, C$_{6'}$), 128.8 (ArC), 130.1 (d, J=8.2 Hz, C$_{5'}$), 130.3 (ArC), 139.5 (d, J=7.2 Hz, C$_{1'}$), 156.1 (NC(O)O), 157.8 (C$_4$), 162.9 (d, J=244.7 Hz, C$_{3'}$), 171.1 (C(O)); HRMS (M+H$^+$)(ESI$^+$) 419.1983 [M+H$^+$] (calcd for $C_{22}H_{27}FN_2O_6H^+$ 419.1982); Anal. Calcd. for $C_{22}H_{27}FN_2O_5$: C, 63.14; H, 6.50; N, 6.69; F, 4.54. Found: C, 63.12; H, 6.55; N, 6.65; F, 4.38.

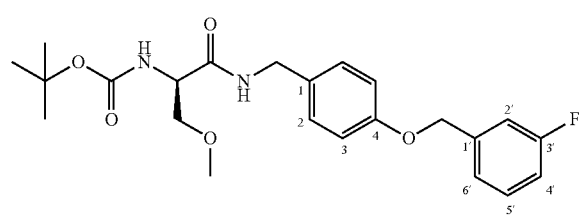 [SMILES: COC[C@@H](NC(=O)OC(C)(C)C)C(=O)NCc1ccc(OCc2cccc(F)c2)cc1]

Preparation of (R)-2-N-(tert.-Butoxycarbonyl)amino-3-methoxy-N-(4-(3-fluorobenzyloxy)benzyl)-propanamide Ag$_2$O (13.90 g, 60.0 mmol) was added to a CH$_3$CN solution (300 mL) of (R)-2-N-(tert.-butoxycarbonyl)amino-3-hydroxy-N-(4-(3-fluorobenzyloxy)benzyl)-propanamide (5.00 g, 12.0 mmol) and CH$_3$I (7.45 mL, 119.6 mmol) at room temperature under Ar. The reaction mixture was stirred at room temperature (3 d), filtered, and the filtrate concentrated in vacuo to obtain a white solid (5.10 g, 98%): R$_f$=0.29 (1/1 EtOAc/hexanes); mp 68-70° C.; [α]$^{24.3}_D$ −16.6° (c 1, CHCl$_3$); IR (nujol) 3308, 2951, 2857, 1648, 1523, 1457, 1376, 1317, 1168, 1088, 1046, 916, 862, 778, 677 cm$^{-1}$; $^1$H NMR (CDCl$_3$) δ 1.42 (s, (CH$_3$)$_3$), 3.36 (s, OCH$_3$), 3.49 (dd, J=6.3, 9.3 Hz, CHH'), 3.83 (dd, J=3.9, 9.3 Hz, CHH'), 4.18-4.31 (br m, CHCH$_2$), 4.36-4.44 (br m, CH$_2$N), 5.05 (s, OCH$_2$), 5.36-5.48 (br m, OC(O)NH), 6.64-6.72 (br t, CH$_2$NH), 6.91 (d, J=8.1 Hz, 2 ArH), 6.97-7.04 (m, 1 ArH), 7.11-7.24 (m, 4 ArH), 7.30-7.38 (m, 1 ArH); $^{13}$C NMR (CDCl$_3$) δ 28.2 ((CH$_3$)$_3$), 42.8 (NCH$_2$), 53.6 (OCH$_2$CH), 59.0 (OCH$_3$), 69.1 (CH$_2$O), 72.0 (OCH$_2$CH), 80.2 (C(CH$_3$)$_3$), 114.1 (d, J=22.0 Hz, C$_4'$ or C$_2'$), 114.6 (d, J=21.0 Hz, C$_2'$ or C$_4'$), 114.9 (C$_1$), 122.6 (d, J=2.9 Hz, C$_6'$), 128.8 (ArC), 130.0 (d, J=8.2 Hz, C$_5'$), 130.7 (ArC), 139.5 (d, J=7.3 Hz, C$_1'$), 155.0 (NC(O)O), 157.8 (C$_4$), 162.9 (d, J=244.8 Hz, C$_3'$), 170.1 (C(O)); HRMS (M+H$^+$) (ESI$^+$) 433.2139 [M+H$^+$] (calcd for C$_{23}$H$_{29}$FN$_2$O$_5$H$^+$ 433.2139); Anal. Calcd. for C$_{23}$H$_{29}$FN$_2$O$_5$: C, 63.87; H, 6.76; N, 6.48; F, 4.39. Found: C, 63.57; H, 6.75; N, 6.39; F, 4.13.

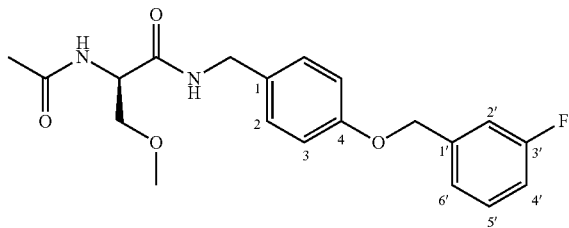 [SMILES: COC[C@@H](NC(C)=O)C(=O)NCc1ccc(OCc2cccc(F)c2)cc1]

Preparation of (R)-2-Acetamido-N-(4-(3-fluorobenzyloxy)benzyl)-3-methoxypropanamide ((R)-3)

A saturated HCl solution in dioxane (1 mmol/2 mL, 21.75 mL) was added to (R)-2-N-(tert.-butoxycarbonyl)amino-3-methoxy-N-(4-(3-fluorobenzyloxy)benzyl)-propanamide (4.70 g, 10.9 mmol) at 0° C. and the solution was stirred at room temperature (4 h). The reaction solution was concentrated in vacuo and dried (30 min): $^1$H NMR (CDCl$_3$) δ 3.23 (s, OCH$_3$), 3.80-4.00 (br m, CH$_2$), 4.14 (d, J=11.0 Hz, CHH'), 4.40 (d, J=11.0 Hz, CHH'), 4.58-4.35 (m, NC(H)CO), 4.87 (s, OCH$_2$), 6.79 (d, J=8.1 Hz, 2 ArH), 6.95 (t, J=8.4 Hz, 1 ArH), 7.01-7.20 (m, 4 ArH), 7.22-7.30 (m, 1 ArH), 8.11-8.28 (br s, NH$_3$), 8.55-8.61 (br s, NHC(O)); HRMS (M+H$^+$) (ESI$^+$) 333.1615 [M+H$^+$] (calcd for C$_{18}$H$_{21}$FN$_2$O$_3$H$^+$ 333.1614).

The residue was dissolved in CH$_2$Cl$_2$ (40 mL) and Et$_3$N (4.47 mL, 32.6 mmol) and AcCl (1.16 mL, 16.30 mmol) were successively added at 0° C. The mixture was stirred at room temperature (2 h), aqueous 10% citric acid (60 mL) was added and then the organic layer was separated. The aqueous layer was extracted with CH$_2$Cl$_2$ (2×30 mL). All of the organic layers were combined, washed with aqueous saturated NaHCO$_3$ (30 mL) and H$_2$O (30 mL), dried (MgSO$_4$), and concentrated in vacuo. The solid was recrystallized with EtOAc to obtain (R)-3 (2.60 g, 65%) as a white solid: R$_f$=0.29 (7/3 hexanes/EtOAc); mp 152° C.; [α]$^{24.5}_D$ −18.9° (c 1, CHCl$_3$); IR (nujol) 3284, 1633, 1552, 1457, 1376, 1305, 1247, 1137, 1050, 978, 722 cm$^{-1}$; $^1$H NMR (CDCl$_3$) δ 2.03 (s, CH$_3$CO), 3.37 (s, OCH$_3$), 3.43 (dd, J=7.2, 9.0 Hz, CHH'), 3.79 (dd, J=3.9, 9.0 Hz, CHH'), 4.40 (d, J=5.7 Hz, CH$_2$N), 4.49-4.55 (m, NC(H)CO), 5.05 (s, CH$_2$O), 6.43 (br d, J=7.2 Hz, NHC(O)CH$_3$), 6.64-6.83 (br m, CH$_2$NH), 6.89-7.05 (m, 3 ArH), 7.10-7.22 (m, 4 ArH), 7.31-7.38 (m, 1 ArH); addition of excess (R)-(−)-mandelic acid to a CDCl$_3$ solution of (R)-3 gave only one signal for the acetyl methyl and one signal for the ether methyl protons; $^{13}$C NMR (CDCl$_3$) δ 23.1 (CH$_3$C(O)), 43.0 (NCH$_2$), 52.4 (OCH$_2$CH), 59.0 (OCH$_3$), 69.1 (CH$_2$O), 71.7 (OCH$_2$CH), 114.1 (d, J=21.9 Hz, C$_4'$ or C$_2'$), 114.8 (d, J=21.1 Hz, C$_{2\alpha}$ or C$_4'$), 115.0 (C$_1$), 122.6 (d, J=2.9 Hz, C$_6'$), 128.8 (ArC), 130.1 (d, J=8.2 Hz, C$_5'$), 130.5 (ArC), 139.5 (d, J=7.3 Hz, C$_1'$), 157.8 (C$_4$), 162.9 (d, J=244.8 Hz, C$_3'$), 169.8, 170.3 (2C(O)); HRMS (M+H$^+$) (ESI$^+$) 375.1720 [M+H$^+$] (calcd for C$_{20}$H$_{23}$FN$_2$O$_4$H$^+$ 375.1720); Anal. Calcd. for C$_{20}$H$_{23}$FN$_2$O$_4$: C, 64.16; H, 6.19; N, 7.48, F, 5.07. Found: C, 64.14; H, 6.15; N, 7.37; F, 5.05.

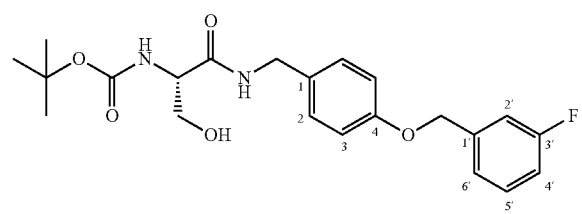 [SMILES: CC(C)(C)OC(=O)N[C@@H](CO)C(=O)NCc1ccc(OCc2cccc(F)c2)cc1]

Preparation of (S)-2-N-(tert.-Butoxycarbonyl)amino-3-hydroxy-N-(4-(3-fluorobenzyloxy)benzyl)-propanamide A THF solution (75 mL) of (S)-t-Boc-serine (4.00 g, 19.5 mmol) was stirred and cooled at −78° C. under Ar and then 4-methylmorpholine (NMM) (2.6 mL, 23.4 mmol) was added dropwise. After 2 min of stirring at this temperature, isobutylchloroformate (IBCF) (3.0 mL, 23.4 mmol) was added dropwise leading to the precipitation of a white solid. The reaction was allowed to proceed for additional 2 min and 4-(3-fluorobenzyloxy)benzylamine (5.40 g, 23.4 mmol) was added portionwise at −78° C. The mixture was allowed to stir at room temperature (2 h), and then the white solid filtered and the organic layer concentrated in vacuo. The residue was purified by flash column chromatography on silica gel with EtOAc/hexanes (50/50 to 80/20) as the eluant to obtain (S)-2-N-(tert.-butoxycarbonyl)amino-3-hydroxy-N-(4-(3-fluorobenzyloxy)benzyl)-propanamide as a white solid (5.10 g, 60%): R$_f$=0.33 (hexanes/EtOAc 5/5); mp 88-89° C.; [α]$^{25.8}_D$ −24.0° (c 1, CHCl$_3$); IR (nujol) 3322, 2944, 2858, 1659, 1525, 1457 1375, 1304, 1243, 1166, 1008, 868, 775, 725 cm$^{-1}$; $^1$H NMR (CDCl$_3$) δ 1.41 (s, (CH$_3$)$_3$), 3.21-3.39 (br m, CHH'), 3.59-3.74 (br m, CHH'), 4.04-4.20 (br m, CH, OH), 4.24-4.47 (br m, CH$_2$N), 5.03 (s, CH$_2$O), 5.63 (d, J=6.6 Hz, NH), 6.87-6.93 (d, J=9.0 Hz, 2 ArH), 6.94-7.09 (m, 1 ArH, NH), 7.10-7.21 (m, 4 ArH), 7.30-7.38 (m, 1 ArH); $^{13}$C NMR (CDCl$_3$) δ 28.2 ((CH$_3$)$_3$), 42.8 (NCH$_2$), 54.9 (OCH$_2$CH), 62.8 (OCH$_2$H), 69.1 (d, J=1.6 Hz, PhCH$_2$O), 80.6 (C(CH$_3$)$_3$), 114.1 (d, J=22.2 Hz, C$_4'$ or C$_2'$), 114.8 (d, J=21.0 Hz, C$_2'$ or C$_4'$), 115.0 (C$_1$), 122.6 (d, J=2.9 Hz, C$_6'$), 128.9 (ArC), 130.1 (d, J=8.0 Hz, C$_5'$), 130.3 (ArC), 139.5 (d, J=7.4 Hz, C$_1'$), 156.2 (NC(O)O), 157.9 (C$_4$), 162.9 (d, J=244.7 Hz, C$_{3'}$), 171.2 (C(O)); HRMS (M+H$^+$) (ESI$^+$) 419.1983 [M+H$^+$] (calcd for C$_{22}$H$_{27}$FN$_2$O$_5$H$^+$ 419.1982); Anal. Calcd. for C$_{22}$H$_{27}$FN$_2$O$_5$: C, 63.14; H, 6.50; N, 6.69; F, 4.54. Found: C, 63.31; H, 6.53; N, 6.77: F, 4.45.

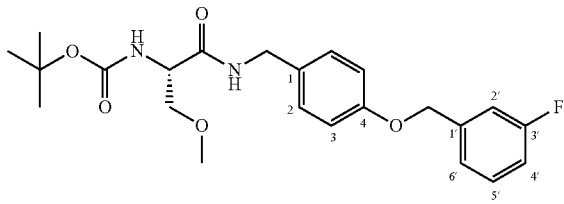 [SMILES: COC[C@H](NC(=O)OC(C)(C)C)C(=O)NCc1ccc(OCc2cccc(F)c2)cc1]

Preparation of (S)-2-N-(tert.-Butoxycarbonyl)amino-3-methoxy-N-(4-(3-fluorobenzyloxy)benzyl)-propanamide Ag$_2$O (13.65 g, 58.6 mmol) was added to a CH$_3$CN solution (300 mL) of (S)-2-N-(tert.-butoxycarbonyl)amino-3-hydroxy-N-(4-(3-fluorobenzyloxy)benzyl)-propanamide (4.90 g, 11.7 mmol) and CH$_3$I (7.3 mL, 117.0 mmol) at room temperature under Ar. The reaction mixture was stirred at room temperature in the dark (3 d), filtered, and the filtrate concentrated in vacuo to obtain a white solid (4.90 g, 98%): R$_f$=0.29 (1/1 EtOAc/hexanes); mp 70-71° C.; [α]$^{24.3}_D$ +16.8° (c 1, CHCl$_3$); IR (nujol) 3412, 3170, 3120, 1648, 1522, 1457, 1375, 1246, 1167, 1088, 1048, 918, 861, 778, 677 cm$^{-1}$; $^1$H NMR (CDCl$_3$) δ 1.42 (s, (CH$_3$)$_3$), 3.35 (s, OCH$_3$), 3.49 (dd, J=6.3, 9.3 Hz, CHH'), 3.83 (dd, J=3.9, 9.3 Hz, CHH'), 4.18-4.31 (br m, CHCH$_2$), 4.36-4.44 (br m, CH$_2$N), 5.05 (s, OCH$_2$), 5.36-5.48 (br m, OC(O)NH), 6.63-6.74 (br t, CH$_2$NH), 6.91 (d, J=8.7 Hz, 2 ArH), 6.97-7.04 (m, 1 ArH), 7.11-7.23 (m, 4 ArH), 7.30-7.38 (m, 1 ArH); $^{13}$C NMR (CDCl$_3$) δ 28.2 ((CH$_3$)$_3$), 42.8 (NCH$_2$), 54.0 (OCH$_2$CH), 59.0 (OCH$_3$), 69.1 (d, J=1.7 Hz, PhCH$_2$O), 72.0 (OCH$_2$CH), 80.2 (C(CH$_3$)$_3$), 114.1 (d, J=21.7 Hz, C$_{4'}$ or C$_{2'}$), 114.7 (d, J=21.1 Hz, C$_{2'}$ or C$_{4'}$), 114.9 (C$_1$), 122.6 (d, J=2.9 Hz, C$_{6'}$), 128.8 (ArC), 130.1 (d, J=8.5 Hz, C$_{5'}$), 130.6 (ArC), 139.5 (d, J=6.8 Hz, C$_{1'}$), 155.5 (NC(O)O), 157.8 (C$_4$), 162.9 (d, J=244.7 Hz, C$_{3'}$), 170.1 (C(O)); HRMS (M+H$^+$) (ESI$^+$) 433.2139 [M+H$^+$] (calcd for C$_{23}$H$_{29}$FN$_2$O$_6$H$^+$ 433.2139); Anal. Calcd. for C$_{23}$H$_{29}$FN$_2$O$_5$: C, 63.87; H, 6.76; N, 6.48; F, 4.39. Found: C, 63.75; H, 6.82; N, 6.51; F, 4.22.

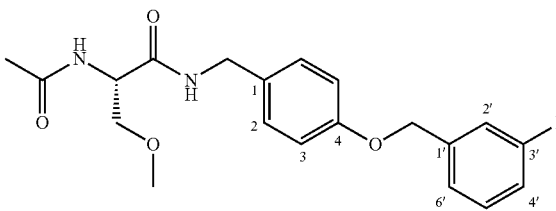

Preparation of (S)-2-Acetamido-N-(4-(3-fluorobenzyloxy)benzyl)-3-methoxypropanamide ((S)-3)

A saturated HCl solution in dioxane (1 mmol/2 mL, 20.8 mL) was added to (S)-2-N-(tert.-butoxycarbonyl)amino-3-methoxy-N-(4-(3-fluorobenzyloxy)benzyl)-propanamide (4.50 g, 10.4 mmol) at 0° C. and the solution was stirred at room temperature (4 h). The reaction solution was concentrated in vacuo and dried (30 min): $^1$H NMR (DMSO-d$_6$) δ 3.29 (s, OCH$_3$), 3.71 (d, J=4.8 Hz, CH$_2$), 3.94-4.06 (br m, CH), 4.27 (d, J=5.4 Hz, NCH$_2$), 5.13 (s, OCH$_2$), 6.97 (d, J=8.1 Hz, 2 ArH), 7.10-7.32 (m, 5 ArH), 7.40-7.47 (m, 1 ArH), 8.31-8.42 (br s, NH$_3$), 9.05-9.13 (br t, NHC(O)).

The residue was dissolved in CH$_2$Cl$_2$ (40 mL) and Et$_3$N (4.3 mL, 31.2 mmol) and AcCl (1.1 mL, 15.6 mmol) were successively added at 0° C. The mixture was stirred at room temperature (2 h), aqueous 10% citric acid (60 mL) was added and then the organic layer was separated. The aqueous layer was extracted with CH$_2$Cl$_2$ (2×30 mL). All of the organic layers were combined, washed with aqueous saturated NaHCO$_3$ (30 mL) and H$_2$O (30 mL), dried (MgSO$_4$), and concentrated in vacuo. The solid was recrystallized with EtOAc to obtain (S)-3 (3.10 g, 80%) as a white solid: R$_f$=0.29 (7/3 hexanes/EtOAc); mp 149-150° C.; [α]$^{24.5}_D$ +18.8° (c 1, CHCl$_3$); IR (nujol) 3281, 2946, 2890, 1634, 1553, 1457, 1376, 1304, 1246, 1135, 1050, 953, 720 cm$^{-1}$; $^1$H NMR (CDCl$_3$) δ 2.02 (s, CH$_3$CO), 3.36 (s, OCH$_3$), 3.43 (dd, J=7.5, 9.1 Hz, CHH'), 3.79 (dd, J=4.2, 9.1 Hz, CHH'), 4.40 (d, J=5.7 Hz, CH$_2$N), 4.50-4.55 (m, NC(H)CO), 5.05 (s, CH$_2$O), 6.47 (br d, J=6.0 Hz, NHC(O)CH$_3$), 6.70-6.79 (br m, CH$_2$NH), 6.90-7.05 (m, 3 ArH), 7.10-7.22 (m, 4 ArH), 7.31-7.38 (m, 1 ArH); addition of excess (R)-(−)-mandelic acid to a CDCl$_3$ solution of (S)-3 gave only one signal for the acetyl methyl and one signal for the ether methyl protons; $^{13}$C NMR (CDCl$_3$) δ 23.1 (CH$_3$C(O)), 42.9 (NCH$_2$), 52.4 (OCH$_2$CH), 59.0 (OCH$_3$), 69.1 (d, J=2.3 Hz, CH$_2$O), 71.8 (OCH$_2$CH), 114.1 (d, J=22.2 Hz, C$_{4'}$ or C$_{2'}$), 114.8 (d, J=21.1 Hz, C$_{2'}$ or C$_{4'}$), 114.9 (C$_1$), 122.6 (d, J=2.9 Hz, C$_{6'}$), 128.8 (ArC), 130.1 (d, J=8.0 Hz, C$_{5'}$), 130.5 (ArC), 139.5 (d, J=6.9 Hz, C$_{1'}$), 157.8 (C$_4$), 162.9 (d, J=244.7 Hz, C$_{3'}$), 169.8, 170.3 (2C(O)); HRMS (M+H$^+$) (ESI$^+$) 375.1720 [M+H$^+$] (calcd for C$_{20}$H$_{23}$FN$_2$O$_4$H$^+$ 375.1720); Anal. Calcd. for C$_{20}$H$_{23}$FN$_2$O$_4$: C, 64.16; H, 6.19; N, 7.48, F, 5.07. Found: C, 64.33; H, 6.23; N, 7.50; F, 5.01.

Scheme 2. Preparation of (R)-4.

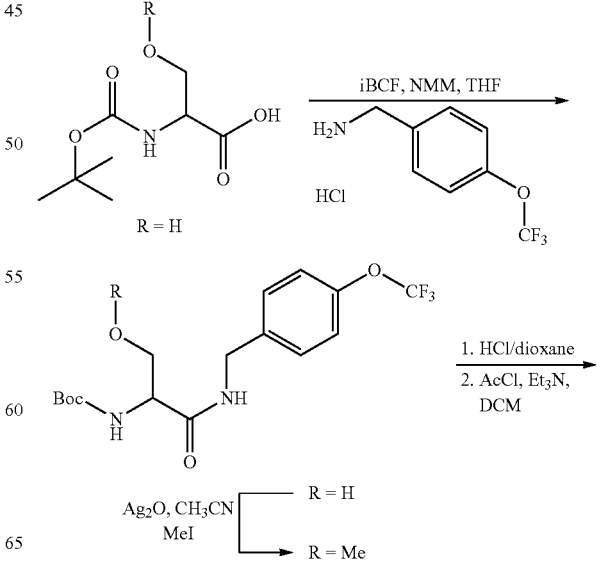

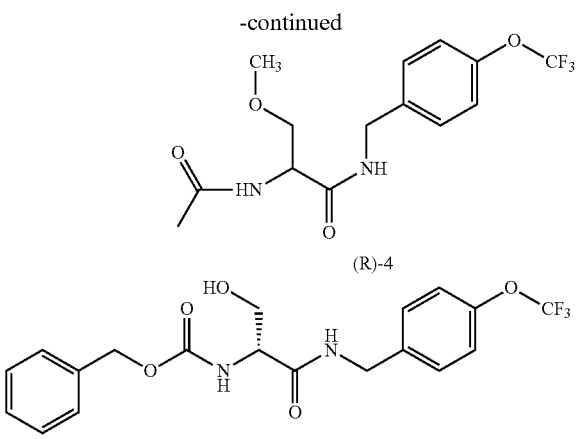

(R)-4

Preparation of (R)-2-N-(Benzyloxycarbonyl)amino-3-hydroxy-N-(4-trifluoromethoxybenzyl)-propanamide A THF solution (200 mL) of (R)-Cbz-serine (6.00 g, 25.1 mmol) was stirred and cooled at −78° C. under Ar and then 4-methylmorpholine (NMM) (3.3 mL, 30.1 mmol) was added dropwise. After 2 min of stirring at this temperature, isobutylchloroformate (IBCF) (3.9 mL, 30.1 mmol) was added dropwise leading to the precipitation of a white solid, and the reaction was allowed to proceed for additional 2 min and then 4-trifluoromethoxybenzylamine (4.6 mL, 30.1 mmol), was added portionwise at −78° C. The mixture was allowed to stir at room temperature (2 h), and then the white solid filtered and the organic layer concentrated in vacuo. The residue was recrystallized in EtOAc to obtain (R)-2-N-(benzyloxycarbonyl)amino-3-hydroxy-N-(4-trifluoromethoxybenzyl)-propanamide as a white solid (6.10 g, 59%): $R_f$=0.30 (hexanes/EtOAc 5/5); mp 189-190° C.; $[\alpha]^{27.4}_D$ −6.5° (c 1, DMSO); IR (nujol) 3278, 3143, 2926, 2866, 1691, 1645, 1539, 1457, 1374, 1278, 1224, 1157, 1025, 963 739, 690 cm$^{-1}$; $^1$H NMR (DMSO-d$_6$) δ 3.56 (m, CHH', CHH'), 4.05-4.12 (br dd, CH), 4.31 (d, J=5.7 Hz, CH$_2$N), 4.91 (t, J=5.5 Hz, OH), 5.04 (s, CH$_2$O), 7.25-7.38 (m, NH, 9 ArH), 8.50 (t, J=5.7 Hz, CH$_2$NH); $^{13}$C NMR (DMSO-d$_6$) δ 41.3 (NCH$_2$), 57.3 (OCH$_2$CH), 61.7 (OCH$_2$CH), 65.5 (PhCH$_2$O), 120.0 (q, J=254.4 Hz, OCF$_3$), 120.7, 127.6, 127.7, 128.2, 128.7, 136.9, 138.9, (7 ArC), 147.0 (q, J=1.7 Hz, COCF$_3$), 155.9 (NC(O)O), 170.3 (C(O)); HRMS (M+H$^+$) (ESI$^+$) 413.1325 [M+H$^+$] (calcd for C$_{19}$F$_{19}$F$_3$N$_2$O$_6$H$^+$ 413.1324); Anal. Calcd. for C$_{19}$H$_{19}$F$_3$N$_2$O$_6$: C, 55.34; H, 4.64; F, 13.82; N, 6.79. Found: C, 55.06; H, 4.61; F, 13.70; N, 6.74.

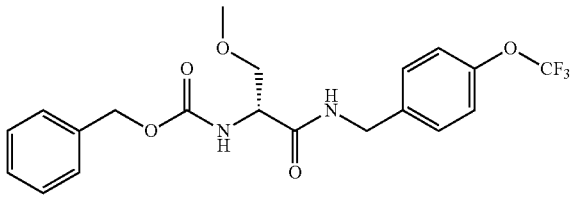 [SMILES: COC[C@@H](NC(=O)OCc1ccccc1)C(=O)NCc1ccc(OC(F)(F)F)cc1]

Preparation of (R)-2-N-(Benzyloxycarbonyl)amino-3-methoxy-N-(4-trifluoromethylbenzyl)-propanamide Ag$_2$O (15.56 g, 66.7 mmol) was added to a CH$_3$CN solution (250 mL) of (R)-2-N-(benzyloxycarbonyl)amino-3-hydroxy-N-(4-trifluoromethoxybenzyl)-propanamide (5.50 g, 13.4 mmol) and CH$_3$I (8.3 mL, 134.0 mmol) at room temperature under Ar. The reaction mixture was stirred at room temperature in the dark (3 d), filtered, and the filtrate concentrated in vacuo. The solid was purified by flash column chromatography on silica gel with EtOAc/hexanes (50/50) as the eluant to obtain (R)-2-N-(benzyloxycarbonyl)amino-3-methoxy-N-(4-trifluoromethylbenzyl)-propanamide as a white solid (4.40 g, 97%): $R_f$=0.77 (EtOAc/hexanes 5/5); mp 114-115° C.; $[0]^{24.5}_D$ −21.4° (c 1, CHCl$_3$); IR (nujol) 3279, 3089, 2958, 2858, 1638, 1553, 1456, 1377, 1285, 1221, 1148, 988, 918, 841, 725, 610 cm$^{-1}$; $^1$H NMR (CDCl$_3$) δ 3.36 (s, OCH$_3$), 3.49 (dd, J=6.3, 9.0 Hz, CHH'), 3.86 (dd, J=3.9, 9.0 Hz, CHH'), 4.29-4.40 (br m, CHCH$_2$), 4.46 (d, J=6.3 Hz, CH$_2$N), 5.12 (s, OCH$_2$), 5.53-5.64 (br s, NH), 6.74-6.84 (br m, NH), 7.15 (d, J=8.4 Hz, 2 ArH), 7.24-7.39 (m, 7 ArH); $^{13}$C NMR (CDCl$_3$) δ 42.7 (NCH$_2$), 54.4 (OCH$_2$CH), 59.1 (OCH$_3$), 67.3 (OCH$_2$), 71.9 (OCH$_2$CH), 120.4 (q, J=255.5 Hz, OCF$_3$), 121.2, 128.2, 128.3, 128.6, 128.7, 135.9, 136.7 (7 ArC), 148.5 (COCF$_3$), 156.1 (NC(O)O), 170.0 (C(O)); HRMS (M+H$^+$) (ESI$^+$) 427.1481 [M+H$^+$] (calcd for C$_{20}$H$_{21}$F$_3$N$_2$O$_6$H$^+$ 427.1481); Anal. Calcd. for C$_{20}$H$_{21}$F$_3$N$_2$O$_5$: C, 56.34; H, 4.96; F, 13.28; N, 6.57. Found: C, 56.34; H, 4.97; F, 13.28; N, 6.63.

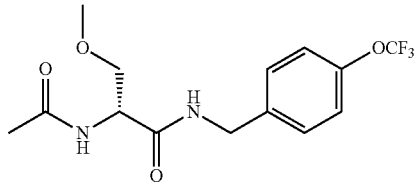 [SMILES: COC[C@@H](NC(C)=O)C(=O)NCc1ccc(OC(F)(F)F)cc1]

Preparation of (R)-2-Acetamido-3-methoxy-N-(4-trifluoromethylbenzyl)-propanamide ((R)-4)

An EtOH solution (400 mL) of (R)-2-N-(benzyloxycarbonyl)amino-3-methoxy-N-(4-trifluoromethylbenzyl)-propanamide ((R)-25) (3.90 g, 9.2 mmol) was treated with H$_2$ (1 atm) in presence of 10% Pd/C (390 mg) at room temperature (16 h). The mixture was carefully filtered through a bed of Celite® and the filtrate was evaporated in vacuo to obtain a brown oil: $^1$H NMR (CDCl$_3$) δ 1.44-1.95 (br s, NH$_2$), 3.38 (s, OCH$_3$), 3.50-3.67 (br m, CH$_2$, CH), 4.46 (d, J=5.7 Hz, NCH$_2$), 7.17 (d, J=8.0 Hz, 2 ArH), 7.31 (d, J=8.0 Hz, 2 ArH), 7.80-8.00 (br s, NHC(O)).

The oil was dissolved in CH$_2$Cl$_2$ (100 mL) and then triethylamine (1.5 mL, 11.0 mmol) and acetyl chloride (0.78 mL, 11.0 mmol) were carefully added at 0° C. and the resulting solution was stirred at room temperature (2 h). An aqueous 10% citric acid solution (100 mL) was added and the organic layer was extracted with CH$_2$Cl$_2$ (3×100 mL). The organic layers were combined, washed with a saturated NaHCO$_3$ solution (100 mL), dried (MgSO$_4$), and concentrated in vacuo. The residue was recrystallized in EtOAc to obtain (R)-4 as a white solid (2.50 g, 83%): $R_f$=0.49 (EtOAc); mp 134-135° C.; $[\alpha]^{24.9}_D$ −17.6° (c 0.5, CHCl$_3$); IR (nujol) 3279, 3088, 2958, 2858, 1638, 1553, 1456, 1377, 1285, 1221, 1148, 988, 918, 841, 725 cm$^{-1}$; $^1$H NMR (CDCl$_3$) δ 2.04 (s, CH$_3$CO), 3.39 (s, OCH$_3$), 3.44 (dd, J=7.5, 9.0 Hz, CHH'), 3.82 (dd, J=4.2, 9.0 Hz, CHH'), 4.44-4.52 (m, CH$_2$N), 4.52-4.59 (m, CH), 6.41 (br d, J=6.6 Hz, NHC(O)CH$_3$), 6.78-6.89 (br t, CH$_2$NH), 7.18 (d, J=8.1 Hz, 2 ArH), 7.29 (d, J=8.1 Hz, 2 ArH), addition of excess (R)-(−)-mandelic acid to a CDCl$_3$ solution of (R)-4 gave only one signal for the acetyl methyl and one signal for the ether methyl protons; $^{13}$C NMR (CDCl$_3$) 23.1 (CH$_3$CO), 42.7 (CH$_2$N), 52.5 (CHCH$_2$), 59.1 (OCH$_3$), 71.7 (CH$_2$OCH$_3$), 120.4 (q, J=255.5 Hz, CF$_3$), 121.2, 128.7, 136.7, (3 ArC), 148.4 (d, J=1.7 Hz, COCF$_3$), 170.1, 170.4 (2C(O)); HRMS (M+H$^+$) (ESI$^+$) 335.1219 [M+H$^+$] (calcd for C$_{14}$H$_{17}$F$_3$N$_2$O$_4$H$^+$ 335.1218); Anal. Calcd. for C$_{14}$H$_{17}$F$_3$N$_2$O$_4$: C, 50.30; H, 5.13; F, 17.05; N, 8.38. Found: C, 50.45; H, 5.13; F, 17.18; N, 8.39.

Scheme 3. Preparation of (R)-5 and (S)-5.

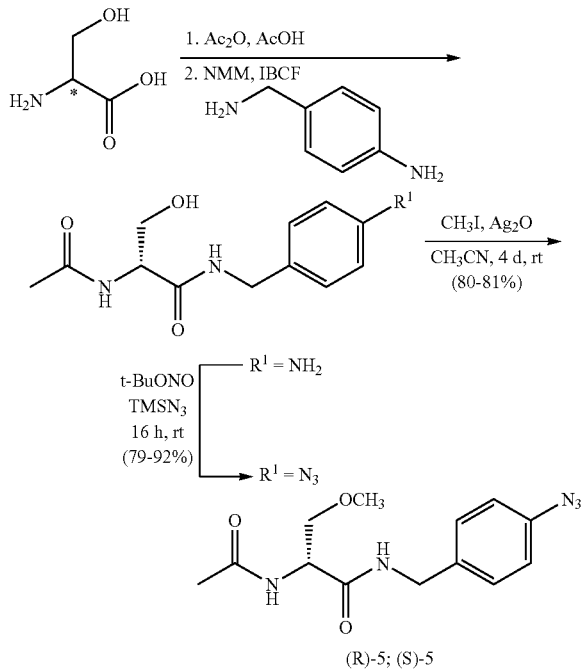

General Procedure for the Preparation N-Benzylamide Amino Acids Derivatives Using Mixed-Anhydride Coupling (MAC) (Method A).

A dry THF solution of the carboxylic acid (~0.2-1.0 M) was cooled to −78° C. under Ar, and 4-methylmorpholine (NMM) (1.3-1.5 equiv) was added. After stirring (2 min), isobutyl chloroformate (IBCF) (1.05-1.25 equiv) was added leading to the precipitation of a white solid. The reaction was allowed to proceed for an additional 5 min, and then benzylamine (1.05-1.2 equiv) was added at −78° C. The reaction mixture was allowed to stir at room temperature (1-2 h), and then the insoluble salts were filtered. The organic layer was concentrated in vacuo, and the product was purified by column chromatography on SiO$_2$ gel.

General Procedure for the Preparation 3-Methoxy-2-amidopropionamide Derivatives (Method B).

To a CH$_3$CN solution of the alcohol (0.05-0.1 M) was successively added Ag$_2$O (5 equiv) and MeI (10 equiv) at room temperature. The reaction mixture was maintained at room temperature (2-4 d), filtered, and the solvent was evaporated in vacuo. The residue was purified by column chromatography on SiO$_2$.

(R)—N-(4-Aminobenzyl)-2-acetamido-3-hydroxypropanamide

To a stirred AcOH (80 mL) suspension of D-serine (10.00 g, 95.24 mmol) was added Ac$_2$O (9.44 mL, 100.00 mmol), and then the reaction suspension was stirred at room temperature (24 h). The AcOH was removed in vacuo to give an oily residue, and then THF (600 mL) was added to the residue. Utilizing Method A, NMM (15.71 mL, 142.86 mmol), IBCF (15.71 mL, 120.09 mmol), and 4-aminobenzylamine (12.93 mL, 114.29 mmol) gave 3.35 g (14%) of (R)—N-(4-aminobenzyl)-2-acetamido-3-hydroxypropanamide after purification by column chromatography (SiO$_2$; 1/7 MeOH/CHCl$_3$) as a white solid: mp 158-160° C.; [α]$^{26}_D$ +18.3° (c 1.0, MeOH); R$_f$=0.30 (1/7 MeOH/CHCl$_3$); IR (nujol mull) 3302, 2924, 2359, 1630, 1551, 1458 cm$^{-1}$; $^1$H NMR (DMSO-d$_6$) δ 1.86 (s, CH$_3$C(O)), 3.55 (t, J=5.6 Hz, CH$_2$OH), 4.06 (½HH'$_q$, J=5.9, 14.7 Hz, CHH'Ar), 4.12 (½HH'$_q$, J=5.9, 14.7 Hz, CHH'Ar), 4.24-4.30 (m, CH), 4.85 (t, J=5.6 Hz, OH), 4.94 (s, NH$_2$), 6.46-6.50 (m, 2 ArH), 6.88-6.91 (m, 2 ArH), 7.88 (d, J=7.8 Hz, NHCH), 8.14 (1, J=5.9 Hz, NHCH$_2$); $^{13}$C NMR (DMSO-d$_6$) δ 22.7 (CH$_3$C(O)), 41.8 (CH$_2$Ph), 55.2 (CH), 61.8 (CH$_2$OH), 113.6, 126.1, 128.0, 147.4 (C$_6$H$_5$), 169.3, 169.8 (2C(O)); HRMS (ESI) 252.1344 [M+H$^+$] (calcd. for C$_{12}$H$_{18}$N$_3$O$_3$ 252.1348); Anal. (C$_{12}$H$_{17}$N$_3$O$_3$) Calcd.: C, 57.36%; H, 6.82%; N, 16.72%. Found: C, 57.13%; H, 6.87%; N, 16.55%.

(S)—N-(4-Aminobenzyl)-2-acetamido-3-hydroxypropanamide

Using L-serine (10.00 g, 95.24 mmol), Ac$_2$O (9.44 mL, 100.00 mmol), and the preceding procedure gave 3.30 g (14%) of (S)—N-(4-aminobenzyl)-2-acetamido-3-hydroxypropanamide as a white solid: mp 158.5-160° C.; [α]$^{26}_D$ −18.7° (c 1.0, MeOH); R$_f$=0.30 (1/7 MeOH/CHCl$_3$); IR (nujol mull) 3280, 2923, 1628, 1551, 1458 cm$^{-1}$; $^1$H NMR (DMSO-d$_6$) δ 1.86 (s, CH$_3$C(O)), 3.55 (t, J=5.6 Hz, CH$_2$OH), 4.06 (½HH'$_q$, J=5.9, 14.7 Hz, CHH'Ar), 4.12 (½HH'$_q$, J=5.9, 14.7 Hz, CHH'Ar), 4.24-4.30 (m, CH), 4.86 (t, J=5.6 Hz, OH), 4.94 (s, NH$_2$), 6.46-6.51 (m, 2 ArH), 6.88-6.91 (m, 2 ArH), 7.88 (d, J=7.8 Hz, NHCH), 8.14 (t, J=5.9 Hz, NHCH$_2$); $^{13}$C NMR (DMSO-d$_6$) δ 22.7 (CH$_3$C(O)), 41.8 (CH$_2$Ph), 55.2 (CH), 61.8 (CH$_2$OH), 113.7, 126.1, 128.1, 147.4 (C$_6$H$_5$), 169.3, 169.9 (2C(O)); HRMS (ESI) 252.1344 [M+H$^+$] (calcd. for C$_{12}$H$_{18}$H$_3$O$_3$ 252.1348); Anal. (C$_{12}$H$_{17}$N$_3$O$_3$) Calcd.: C, 57.36%; H, 6.82%; N, 16.72%. Found: C, 57.12%; H, 6.84%; N, 16.43%.

(R)—N-(4-Azidobenzyl)-2-acetamido-3-hydroxypropanamide

To a cooled (0° C.) CH$_3$CN solution (70 mL) of (R)—N-(4-aminobenzyl)-2-acetamido-3-hydroxypropanamide (2.40 g, 9.56 mmol) maintained under Ar, t-BuONO (3.41 mL, 28.68 mmol) followed by TMSN$_3$ (3.02 mL, 22.94 mmol) were slowly added. The resulting solution was allowed to stir at room temperature (16 h) under Ar. The solvent was removed in vacuo, and the product was purified by column chromatography (SiO$_2$; 1/9 MeOH/CHCl$_3$) to give 2.10 g (79%) of (R)—N-(4-azidobenzyl)-2-acetamido-3-hydroxypropanamide as a white solid: mp 161-163° C.; [α]$^{26}_D$ +13.2° (c 1.0, MeOH); R$_f$=0.35 (1/9 MeOH/CHCl$_3$); IR (nujol mull) 3268, 2924, 2128, 1649, 1553, 1459 cm$^{-1}$; $^1$H NMR (DMSO-d$_6$) δ 1.87 (s, CH$_3$C(O)), 3.58 (t, J=5.7 Hz, CH$_2$OH), 4.26-4.32 (m, CH$_2$Ar and CH), 4.91 (t, J=5.7 Hz, OH), 7.03-7.08 (m, 2 ArH), 7.28-7.31 (m, 2 ArH), 7.94 (d, J=8.1 Hz, NHCH), 8.40 (1, J=6.0 Hz, NHCH$_2$); $^{13}$C NMR (DMSO-d$_6$) δ 22.7 (CH$_3$C(O)), 41.5 (CH$_2$Ph), 55.3 (CH), 61.7 (CH$_2$OH), 118.9, 128.7, 136.5, 137.7 (C$_6$H$_5$), 169.4, 170.3 (2C(O)); HRMS (ESI) 278.1249 [M+H$^+$] (calcd. for C$_{12}$H$_{16}$N$_6$O$_3$ 278.1253); Anal. (C$_{12}$H$_{15}$N$_5$O$_3$) Calcd.: C, 51.98%; H, 5.45%; N, 25.26%. Found: C, 51.93%; H, 5.47%; N, 24.98%.

(S)—N-(4-Azidobenzyl)-2-acetamido-3-hydroxypropanamide

Using (S)—N-(4-aminobenzyl)-2-acetamido-3-hydroxypropanamide (2.80 g, 11.16 mmol), t-BuONO (3.98 mL, 33.48 mmol), TMSN$_3$ (3.52 mL, 26.78 mmol), and the preceding procedure gave 2.85 g (92%) of (S)—N-(4-azidobenzyl)-2-acetamido-3-hydroxypropanamide as a white solid: mp 161-162° C.; [α]$^{26}_D$ −13.6° (c 1.0, MeOH); R$_f$=0.35 (1/9 MeOH/CHCl$_3$); IR (nujol mull) 3267, 2924, 2129, 1648, 1552, 1459 cm$^{-1}$; $^1$H NMR (DMSO-d$_6$) δ 1.87 (s, CH$_3$C(O)), 3.58 (t, J=5.6 Hz, CH$_2$OH), 4.26-4.31 (m, CH$_2$Ar and CH), 4.91 (t, J=5.6 Hz, OH), 7.03-7.08 (m, 2 ArH), 7.27-7.32 (m, 2 ArH), 7.94 (d, J=7.8 Hz, NHCH), 8.40 (t, J=6.0 Hz, NHCH$_2$); $^{13}$C NMR (DMSO-d$_6$) δ 22.6 (CH$_3$C(O)), 41.5 (CH$_2$Ph), 55.3 (CH), 61.7 (CH$_2$OH), 118.9, 128.7, 136.5, 137.7 (C$_6$H$_5$), 169.4, 170.3 (2C(O)); HRMS (ESI) 278.1248 [M+H$^+$] (calcd. for C$_{12}$H$_{16}$N$_5$O$_3$ 278.1253); Anal. (C$_{12}$H$_{15}$N$_5$O$_3$) Calcd.: C, 51.98%; H, 5.45%; N, 25.26%. Found: C, 52.08%; H, 5.51%; N, 25.00%.

(R)—N-(4-Azidobenzyl)-2-acetamido-3-methoxypropanamide ((R)-5)

Utilizing Method B, (R)—N-(4-azidobenzyl)-2-acetamido-3-hydroxypropanamide (1.16 g, 4.19 mmol), Ag$_2$O (4.85 g, 20.94 mmol), and MeI (2.61 mL, 41.89 mmol) gave crude (R)-5 after 4 d. The product was purified by column chromatography (SiO$_2$; 1/9 MeOH/CHCl$_3$) to obtain 0.98 g (80%) of (R)-5 as a white solid: mp 149-150° C.; [α]$^{26}_D$ −15.2° (c 1.0, MeOH); R$_f$=0.5 (1/9 MeOH/CHCl$_3$); IR (nujol mull) 3285, 2931, 2113, 1635, 1560, 1456 cm$^{-1}$; $^1$H NMR (CDCl$_3$) δ 2.03 (s, CH$_3$C(O)), 3.38 (s, OCH$_3$), 3.44 (dd, J=7.5, 9.3 Hz, CHH'OCH$_3$), 3.80 (dd, J=4.2, 9.3 Hz, CHH'OCH$_3$), 4.40 (½HH'$_q$, J=6.2, 15.0 Hz, CHH'Ar), 4.46 (½HH'$_q$, J=6.2, 15.0 Hz, CHH'Ar), 4.52-4.58 (m, CH), 6.48 (br d, J=6.3 Hz, NHCH), 6.82-6.85 (br m, NHCH$_2$), 6.96-7.01 (m, 2 ArH), 7.23-7.28 (m, 2 ArH), addition of excess (R)-(−)-mandelic acid to a CDCl$_3$ solution of (R)-5 gave only a single signal for the acetyl methyl protons and the ether methyl protons, addition of excess (R)-(−)-mandelic acid to a CDCl$_3$ solution of (R)-5 and (S)-5 (1:2 ratio) gave two signals for the acetyl methyl protons (δ 1.995 (R) and 2.010 (S) (Δppm=0.015)), and two signals for the ether methyl protons (δ 3.302 (S) and 3.342 (R) (Δppm=0.040)); $^{13}$C NMR (CDCl$_3$) δ 23.4 (CH$_3$C(O)), 43.1 (CH$_2$Ph), 52.7 (CH), 59.3 (CH$_2$OCH$_3$), 71.8 (CH$_2$OCH$_3$), 119.5, 129.1, 134.9, 139.5 (C$_6$H$_5$), 170.2, 170.5 (2C(O)); HRMS (ESI) 292.1406 [M+H$^+$] (calcd. for C$_{13}$H$_{18}$N$_5$O$_3$ 292.1410); Anal. (C$_{13}$H$_{17}$N$_5$O$_3$) Calcd.: C, 53.60%; H, 5.88%; N, 24.04%. Found: C, 53.72%; H, 5.91%; N, 23.84%.

(S)—N-(4-Azidobenzyl)-2-acetamido-3-methoxypropanamide ((S)-5)

Utilizing Method B, (S)—N-(4-Azidobenzyl)-2-acetamido-3-hydroxypropanamide (2.40 g, 8.66 mmol), Ag$_2$O (10.04 g, 43.30 mmol), and MeI (5.40 mL, 86.60 mmol) gave crude (S)-5 after 4 d. The product was purified by column chromatography (SiO$_2$; 1/9 MeOH/CHCl$_3$) to obtain 2.05 g (81%) of (S)-5 as a white solid: mp 149-150° C.; [α]$^{26}_D$ +15.4° (c 1.0, MeOH); R$_f$=0.5 (1/9 MeOH/CHCl$_3$); IR (nujol mull) 3285, 2927, 2112, 1635, 1565, 1457 cm$^{-1}$; $^1$H NMR (CDCl$_3$) δ 2.03 (s, CH$_3$C(O)), 3.38 (s, OCH$_3$), 3.43 (dd, J=7.5, 9.0 Hz, CHH'OCH$_3$), 3.81 (dd, J=4.2, 9.0 Hz, CHH'OCH$_3$), 4.40 (½HH'$_q$, J=6.0, 15.0 Hz, CHH'Ar), 4.46 (½HH'$_q$, J=6.0, 15.0 Hz, CHH'Ar), 4.51-4.57 (m, CH), 6.43 (br d, J=6.3 Hz, NHCH), 6.78-6.83 (br m, NHCH$_2$), 6.96-7.01 (m, 2 ArH), 7.23-7.27 (m, 2 ArH), addition of excess (R)-(−)-mandelic acid to a CDCl$_3$ solution of (R)-5 gave only a single signal for the acetyl methyl protons and the ether methyl protons, addition of excess (R)-(−)-mandelic acid to a CDCl$_3$ solution of (R)-5 and (S)-5 (1:2 ratio) gave two signals for the acetyl methyl protons (δ 1.995 (R) and 2.010 (S) (Δppm=0.015)), and the ether methyl protons (δ 3.302 (S) and 3.342 (R) (Δppm=0.040)); $^{13}$C NMR (CDCl$_3$) δ 23.3 (CH$_3$C(O)), 43.1 (CH$_2$Ph), 52.7 (CH), 59.2 (CH$_2$OCH$_3$), 72.0 (CH$_2$OCH$_3$), 119.4, 129.1, 135.0, 139.4 (C$_6$H$_5$), 170.3, 170.6 (2C(O)); HRMS (ESI) 292.1405 [M+H$^+$] (calcd. for C$_{13}$H$_{18}$N$_5$O$_3$ 292.1410); Anal. (C$_{13}$H$_{17}$N$_5$O$_3$) Calcd.: C, 53.60%; H, 5.88%; N, 24.04%. Found: C, 53.76%; H, 5.97%; N, 24.22%.

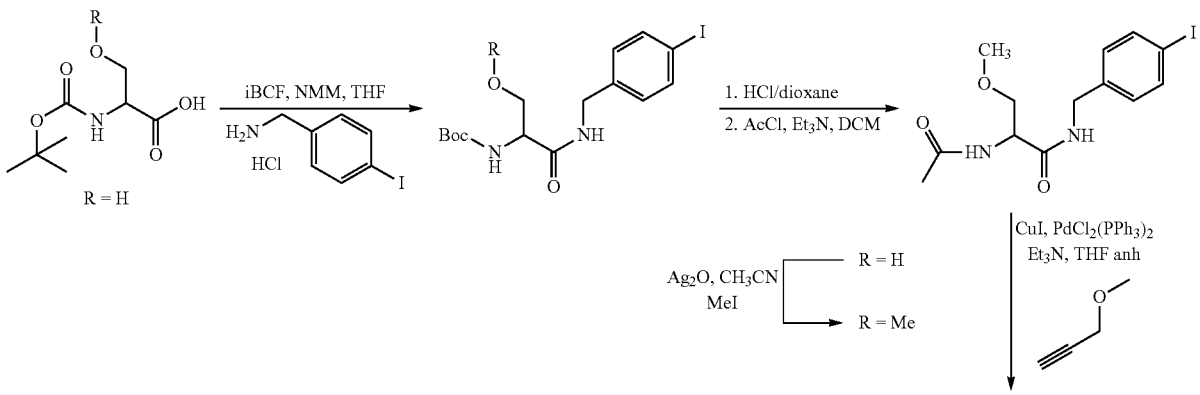

Scheme 4. Preparation of (R)-6 and (R)-7.

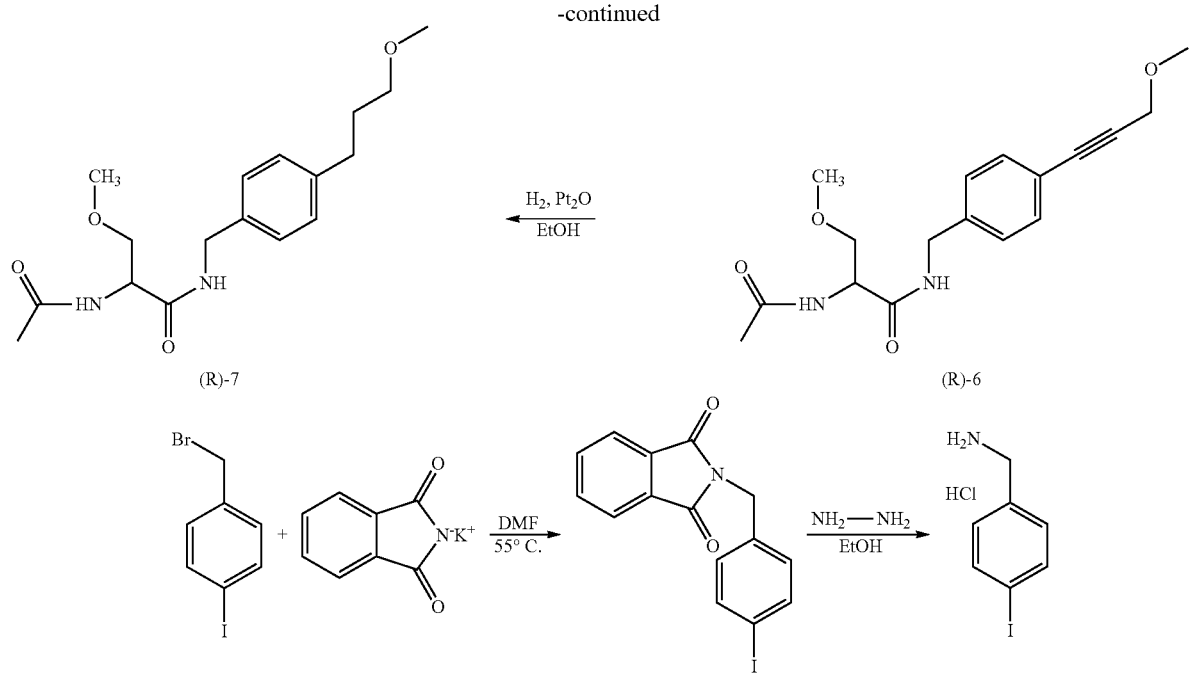

Preparation of N-(4-Iodobenzyl)phthalimide (Brown, Stephen; Grigg, Ronald; Hinsley, Joanne; Korn, Stewart; Sridharan, Visuvanathar; Uttley, Michael; Tetrahedron (2001), 57(52), 10347-10355.) A mixture of 4-iodobenzylchloride (40.0 g, 134.7 mmol), potassium phthalimide (26.20 g, 141.5 mmol) and dry DMF (150 mL) was heated overnight at 55° C. under Ar, and then the solvent was removed at reduced pressure. The solid residue was triturated with CHCl$_3$ (200 mL), filtered, and washed with CHCl$_3$ (3×200 mL). The combined organic extracts were successively washed with aqueous 0.2 M NaOH (200 mL) and H$_2$O (400 mL), and then dried (MgSO$_4$). The solvent was removed at reduced pressure to afford a crude solid, which was triturated with Et$_2$O to obtain a white solid (37.00 g, 75%): R$_f$=0.75 (1/1 EtOAc/hexanes); mp 138-139° C.; $^1$H NMR (CDCl$_3$) ☐ 4.77 (s, CH$_2$), 7.17 (d, J=8.6 Hz, 2 ArH), 7.63 (d, J=8.6 Hz, 2 ArH), 7.78 (dd, J=3.0, 5.7 Hz, 2 PhtH), 7.83 (dd, J=3.0, 5.7 Hz, 2 PhtH); $^{13}$C NMR (CDCl$_3$) δ 41.0 (CH$_2$), 93.5 (CI), 123.4, 130.6, 131.9, 134.1, 135.9, 137.7 (6 Ar), 167.2 (2C(O)); HRMS (ESI) 363.9831 [M+H$^+$] (calcd for C$_{17}$H$_{13}$NO$_2$H$^+$ 363.9835).

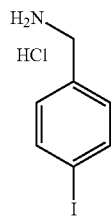

Preparation of 4-Iodobenzylamine Hydrochloride

An EtOH solution (50 mL) of hydrazine hydrate (7.28 mL, 152.9 mmol) was added to an EtOH solution (800 mL) of N-(4-iodobenzyl)phthalimide (37.00 g, 101.9 mmol) maintained at reflux under Ar. The solution was stirred at reflux (2.5 h), and then the solvent was removed at reduced pressure. The solid residue was dissolved in CHCl$_3$ (200 mL) and treated with aqueous 20% NaOH (200 mL). The aqueous phase was separated, extracted with CHCl$_3$ (3×300 mL), and the combined organic layers were dried (MgSO$_4$) and concentrated in vacuo to afford the free base as an oil.

The free base was converted to the corresponding hydrochloride salt by addition of a 4 M HCl solution in dioxane. The white precipitate was filtered and dried to obtain 25.00 g of 4-iodobenzylamine hydrochloride (91%): R$_f$=0.1 (EtOAc); mp >250° C. (lit. Aldrich data) mp 299-303° C.); $^1$H NMR (DMSO-d$_6$) δ 3.97 (d, J=5.4 Hz, CH$_2$), 7.34 (d, J=8.1 Hz, 2 ArH), 7.76 (d, J=8.1 Hz, 2 ArH), 8.50-8.85 (br s, NH$_3$); HRMS (ESI) 233.9780 (calcd for C$_{17}$H$_{13}$NO$_2$H$^+$ 233.9775).

Preparation of (R)-2-N-(tert.-Butoxycarbonyl)amino-3-hydroxy-N-(4-iodobenzyl)propanamide A THF solution (140 mL) of (R)-tert.-Boc-serine (1.72 g, 8.42 mmol) was stirred and cooled at −78° C. under Ar and then 4-methylmorpholine (NMM) (1.1 mL, 10.10 mmol) was added dropwise. The reaction was stirred at this temperature (2 min) and then isobutylchloroformate (IBCF) (1.3 mL, 10.10 mmol) was added dropwise leading to the precipitation of a white solid. The reaction was allowed to proceed for additional 2 min. A heterogeneous THF (10 mL) mixture of 4-iodobenzylamine hydrochloride (2.5 g, 9.26 mmol) and NMM (1.1 mL, 10.10 mmol) was added portionwise at −78° C. The mixture was allowed to stir at room temperature (2 h) and the white solid was filtered and the organic layer was concentrated in vacuum. The solid was recrystallized in EtOAc to obtain (R)-2-N-(tert.-butoxycarbonyl)amino-3-hydroxy-N-(4-iodobenzyl)propanamide (2.51 g, 71%) as a white solid: R$_f$=0.60 (EtOAc); mp 129-130° C.; [α]$^{24}_D$ +0.97° (c 2.8, DMSO); IR (nujol) 3327, 1656, 1521, 1458, 1375, 1302, 1244, 1164, 1009 cm$^{-1}$; $^1$H NMR (DMSO-d$_6$) δ 1.39 (s, (CH$_3$)$_3$C), 3.49-3.60 (br m, CHH'OH and CHH'OH), 3.95-4.01 (br m, CHCH$_2$), 4.18-4.31 (m, CH$_2$N), 4.86 (br s, OH), 6.68 (d, J=7.8 Hz, tert.-BocNH), 7.08 (d, J=8.1 Hz, 2 PhH), 7.64 (d, J=8.1 Hz, 2 PhH), 8.37 (br s, CH$_2$NH); $^{13}$C NMR (CDCl$_3$) δ 28.2 ((CH$_3$)$_3$C), 42.8 (NCH$_2$), 54.7 (OCH$_2$CH), 62.7 (OCH$_2$CH), 80.8 ((CH$_3$)$_3$C), 92.8 (CI), 129.3, 137.5, 137.7, (C$_6$H$_4$), 156.4 (C(O)), 171.5 (C(O)); HRMS (M+Na$^+$) (ESI$^+$) 443.0435 [M Na$^+$] (calcd for C$_{16}$H$_{21}$IN$_2$O$_4$Na$^+$ 443.0444); Anal. Calcd. for C$_{16}$H$_{21}$IN$_2$O$_4$: C, 42.87; H, 5.04; N, 6.67; I, 30.20. Found: C, 43.13; H, 5.14; N, 6.71; I, 29.96.

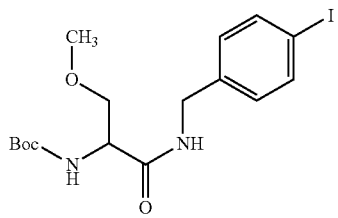 [SMILES: COCC(NC(=O)OC(C)(C)C)C(=O)NCc1ccc(I)cc1]

Preparation of (R)-2-N-(tert.-Butoxycarbonyl) amino-3-methoxy-N-(4-iodobenzyl)propanamide Ag$_2$O (23.40 g, 101.20 mmol) was added to a CH$_3$CN solution (300 mL) of (R)-2-N-(tert.-butoxycarbonyl)amino-3-hydroxy-N-(4-iodobenzyl)propanamide (8.50 g, 20.24 mmol) and then CH$_3$I (12.60 mL, 202.4 mmol) was added at room temperature under Ar. The reaction mixture was stirred at room temperature (3 d), filtered, and the filtrate concentrated in vacuo. The residue was purified by column chromatography (SiO$_2$; 2/3 EtOAc/hexanes) to obtain 7.56 g (85%) of a white solid: R$_f$=0.53 (111 EtOAc/hexanes); mp 86-87° C.; [α]$^{23}_D$ –3.4° (c 1, DMSO); IR (nujol) 3334, 1659, 1528, 1461, 1376, 1303, 1245, 1165, 1110, 1049, 954, 870, 788, 619 cm$^{-1}$; $^1$H NMR (CDCl$_3$) δ 1.43 (s, (CH$_3$)$_3$C), 3.37 (s, OCH$_3$) 3.48 (dd, J=6.3, 9.3 Hz, CHH'OH), 3.84 (dd, J=3.9, 9.3 Hz, CHH'OH), 4.20-4.28 (br m, CHCH$_2$), 4.41 (d, J=5.4 Hz, CH$_2$N), 5.39 (br s, tert.-BocNH), 6.75-6.80 (br t, CH$_2$NH), 7.01 (d, J=8.2 Hz, 2 PhH), 7.64 (d, J=8.2 Hz, 2 PhH); $^{13}$C NMR (CDCl$_3$) □ 28.2 ((CH$_3$)$_3$C), 42.8 (NCH$_2$), 54.0 (OCH$_2$CH), 59.1 (OCH$_3$), 71.9 (OCH$_2$CH), 80.5 ((CH$_3$)$_3$C), 92.7 (CI), 129.3, 137.7, 137.8, (C$_6$H$_4$), 155.5 (C(O)), 170.4 (C(O)); HRMS (M+H$^+$) (ESI$^+$) 435.0777 [M+H$^+$] (calcd for C$_{16}$H$_{23}$IN$_2$O$_4$H$^+$ 435.0781); Anal. Calcd. for C$_{16}$H$_{23}$IN$_2$O$_4$: C, 44.25; H, 5.34; N, 6.45; I, 29.22. Found: C, 44.51; H, 5.34; N, 6.41; I, 28.99.

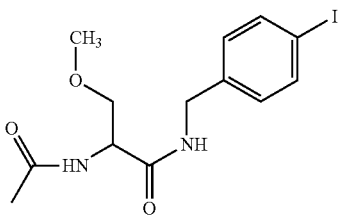 [SMILES: COCC(NC(C)=O)C(=O)NCc1ccc(I)cc1]

Preparation of (R)-2-Acetamido-3-methoxy-N-(4-iodobenzyl)propanamide

A saturated HCl solution in dioxane (1 mmol/2 mL, 17 mL) was added to (S)-2-N-(tert.-butoxycarbonyl)amino-3-methoxy-N-(4-iodobenzyl)propanamide ((S)-4) (3.70 g, 8.52 mmol) at 0° C. and the solution was stirred at room temperature (2 h). The reaction solution was concentrated in vacuo and dried (30 min). CH$_2$Cl$_2$ (30 mL) was added to the residue followed by the successive additions of Et$_3$N (3.6 mL, 25.60 mmol) and AcCl (906 μL, 12.30 mmol) at 0° C. The mixture was stirred at room temperature (2 h), aqueous 10% citric acid was added and then the organic layer was separated. The aqueous layer was extracted with CH$_2$Cl$_2$ (2×30 mL). The organic layers were combined, washed with aqueous saturated NaHCO$_3$ (30 ml) and H$_2$O (30 ml), dried (MgSO$_4$), and concentrated in vacuo. The solid was recrystallized with EtOAc to obtain (R)-2-acetamido-3-methoxy-N-(4-iodobenzyl)propanamide (2.43 g, 76%) as a white solid: R$_f$=0.76 (5/5 acetone/EtOAc); mp 159-160° C.; [α]$^{25}_D$=+3.3° (c 1, DMSO); IR (nujol) 3279, 1636, 1552, 1457, 1375, 1305, 1139, 725 cm$^{-1}$; $^1$H NMR (CDCl$_3$) δ 2.02 (s, CH$_3$CO), 3.38 (s, OCH$_3$), 3.44 (dd, J=7.2, 9.0 Hz, CHH'), 3.79 (dd, J=4.2, 9.0 Hz, CHH'), 4.38-4.41 (m, CH$_2$N), 4.52-4.59 (m, NC(H) CO), 6.46 (br d, J=6.6 Hz, NHC(O)CH$_3$), 6.85-6.93 (br t, CH$_2$NH), 7.00 (d, J=8.4 Hz, 2 PhH), 7.64 (d, J=8.4 Hz, 2 PhH); $^{13}$C NMR (CDCl$_3$) 23.1 (CH$_3$CO), 42.9 (CH$_2$N), 52.4 (CHCH$_2$), 59.1 (OCH$_3$), 71.6 (CH$_2$OCH$_3$), 92.7 (CI), 129.3, 137.7, 139.1 (C$_6$H$_4$), 170.1, 170.3 (2C(O)); HRMS (M+Na$^+$) (ESI$^+$) 399.0177 [M+Na$^+$] (calcd for C$_{13}$H$_{17}$IN$_2$O$_3$Na$^+$ 399.0182); Anal. Calcd. for C$_{13}$H$_{17}$IN$_2$O$_3$: C, 41.51; H, 4.55; N, 7.45; I, 33.73. Found: C, 41.70; H, 4.49; N, 7.39; I, 33.69.

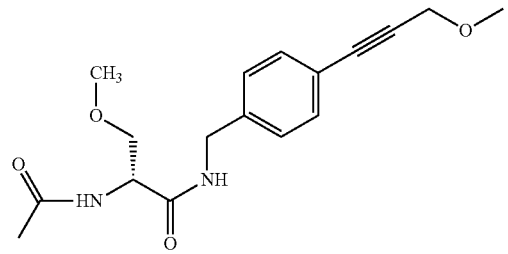 [SMILES: COCC#Cc1ccc(CNC(=O)[C@@H](COC)NC(C)=O)cc1]

Preparation of (R)-2-Acetamido-3-methoxy-N-(4-(3-methoxyprop-1-ynyl)benzyl)propanamide ((R)-6)

To an anhydrous THF (10 mL) solution of (R)-2-acetamido-3-methoxy-N-(4-iodobenzyl)propanamide (376 mg, 1.0 mmol), triethylamine (280 μL, 2.0 mmol), 3-methoxyprop-1-yne (125 μl, 1.5 mmol), dichlorobis(triphenylphosphine)-palladium (II) (70 mg, 0.1 mmol), and CuI (38 mg, 0.2 mmol) were sequentially added under Ar. The mixture was stirred at room temperature (4 h), and then Et$_2$O (10 mL) added and the precipitate filtered through a Celite pad. The filtrate was concentrated in vacuo and the residue was purified by flash chromatography on silica gel with EtOAc/MeOH (9/1) as the eluant to obtain (R)-6 (260 mg, 82%) as a beige solid: R$_f$=0.27 (EtOAc); mp 141-142° C.; [α]$^{27}_D$=+4.4° (c 1, DMSO); IR (nujol) 3278, 3096, 1640, 1554, 1458, 1370, 1304, 1257, 1192, 1099, 966, 903, 810, 732 cm$^{-1}$; $^1$H NMR (CDCl$_3$) δ 2.02 (s, CH$_3$CO), 3.37 (s, OCH$_3$), 3.45-3.47 (m, CHH' and OCH$_3$), 3.78 (dd, J=4.2, 9.0 Hz, CHH'), 4.32 (s, C≡CCH$_2$OCH$_3$) 4.38-4.52 (m, CH$_2$N), 4.54-4.61 (m, NC(H)CO), 6.52 (d, J=6.6 Hz, CHNH), 6.91-6.99 (br t, CH$_2$NH), 7.19 (d, J=7.9 Hz, 2 ArH), 7.41 (d, J=7.9 Hz, 2

ArH); $^{13}$C NMR (CDCl$_3$) δ 23.2 (CH$_3$CO), 43.2 (CH$_2$N), 52.5 (CHCH$_2$), 57.7 (C≡CCH$_2$OCH$_3$), 59.1 (OCH$_3$), 60.4 (C≡CCH$_2$OCH$_3$), 71.7 (CH$_2$OCH$_3$), 85.2 (C≡C), 86.0 (C≡C), 121.8, 127.3, 132.1, 138.4 (C$_6$H$_4$), 170.4 (2C(O)); HRMS (M+H$^+$) (ESI$^+$) 319.1652 [M+H$^+$] (calcd for C$_{17}$H$_{22}$N$_2$O$_4$H$^+$ 319.1658); Anal. Calcd. for C$_{17}$H$_{22}$N$_2$O$_4$·0.33H$_2$O: C, 62.95; H, 7.04; N, 8.64. Found: C, 62.98; H, 6.78; N, 8.47.

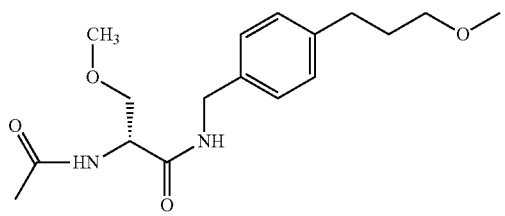 [SMILES: COCCCc1ccc(CNC(=O)[C@@H](COC)NC(C)=O)cc1]

Preparation of (R)-2-Acetamido-3-methoxy-N-(4-(3-methoxypropyl)benzyl)-propanamide ((R)-7)

An EtOH solution (30 mL) of (R)-2-acetamido-3-methoxy-N-(4-(3-methoxyprop-1-ynyl)benzyl)propanamide ((R)-6) (1.00 g, 3.1 mmol) was treated with H$_2$ (1 atm) in the presence of 10% PtO$_2$ (50 mg) at room temperature (16 h). The mixture was carefully filtered through a bed of Celite®. The filtrate was concentrated in vacuo and the residue was purified by flash chromatography on silica gel with EtOAc as the eluant to obtain (R)-7 (510 mg, 51%) as a white solid: R$_f$=0.27 (EtOAc); mp 105-107° C.; [α]$^{25}_D$ +3.0° (c 0.5, DMSO); IR (nujol) 3283, 3085, 1638, 1550, 1457, 1379, 1299, 1122, 979, 725, 605 cm$^{-1}$; $^1$H NMR (CDCl$_3$) δ 1.81-1.92 (m, CH$_2$), 2.03 (s, CH$_3$CO), 2.67 (t, J=7.8 Hz, CH$_2$Ph), 3.33-3.46 (m, CHH'O, CH$_2$O and 2 OCH$_3$), 3.80 (dd, J=4.0, 9.1 Hz, CHH'O), 4.44 (d, J=5.7 Hz, CH$_2$N), 4.50-4.57 (m, CH), 6.45 (br d, J=6.6 Hz, NHC(O)CH$_3$), 6.70-6.75 (br t, CH$_2$NH), 7.15-7.20 (m, 4 ArH); $^{13}$C NMR (CDCl$_3$) 23.2 (CH$_3$CO), 31.2, 31.9 (2 CH$_2$), 43.3 (CH$_2$N), 52.4 (CHCH$_2$), 58.6, 59.1 (2 OCH$_3$), 71.7, 71.9 (2 CH$_2$OMe), 127.5, 128.8, 135.3, 141.4 (C$_6$H$_4$), 169.9, 170.2 (2C(O)); HRMS (M+Na$^+$) (ESI$^+$) 317.1784 [M+Na$^+$] (calcd for C$_{17}$H$_{26}$N$_2$O$_4$Na$^+$ 345.1790); Anal. Calcd. for C$_{17}$H$_{26}$N$_2$O$_4$: C, 63.33; H, 8.13; N, 8.69. Found: C, 63.12; H, 8.13; N, 8.64.

Scheme 5. Preparation of (R)-8.

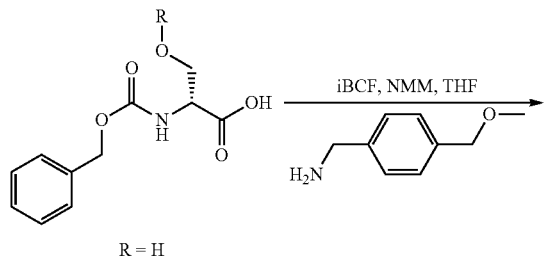

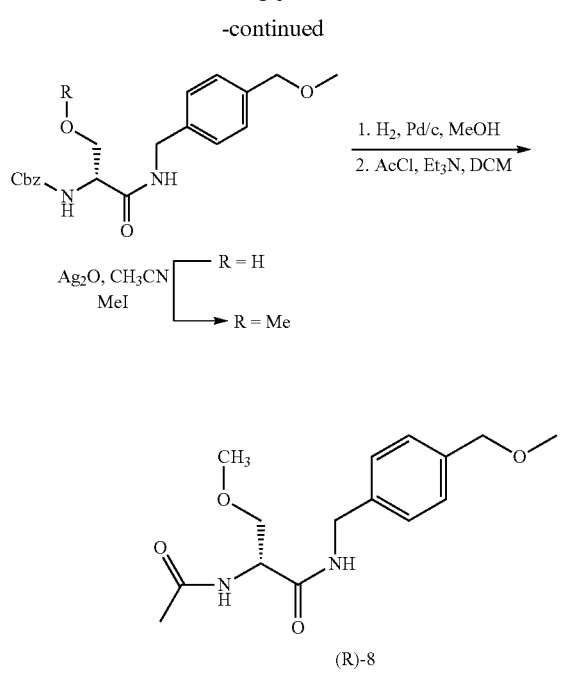

(R)-8

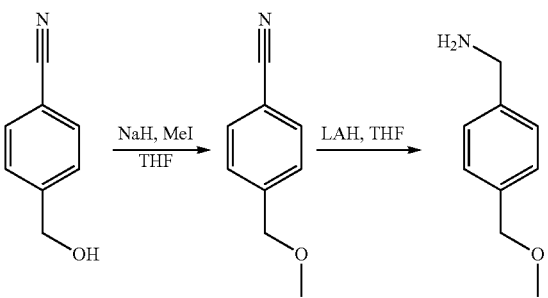

Preparation of 4-(Methoxymethyl)benzonitrile (Sebastien Fortin, Emmanuel Moreau, Alexandre Patenaude, Michel Desjardins, Jacques Lacroix, Jean L. C. Rousseau and René C-Gaudreault, Bioorganic & Medicinal Chemistry 15 (2007) 1430-1438.) A THF solution (250 mL) of 4-(hydroxymethyl)benzonitrile (10.00 g, 75.0 mmol) was added dropwise at 0° C. to a NaH (60% in mineral oil suspension, 11.50 g, 300.0 mmol) suspension in THF (600 mL). The mixture was stirred (10 min) and MeI (11.7 mL, 187.5 mmol) was added dropwise. The mixture was stirred at room temperature (3 h) and then a saturated aqueous NH$_4$Cl solution (100 mL) was added. The reaction mixture was extrated with CH$_2$Cl$_2$ (3×250 mL). The organic layers were combined, dried (Na$_2$SO$_4$), and concentrated in vacuo. The residue was distilled in vacuo (125° C., 5 torr) to obtain a colorless oil (10.50 g, 95%): R$_f$ 0.59 (hexanes/EtOAc 9/1); $^1$H NMR (CDCl$_3$) □ 3.43 (s, OCH$_3$), 4.51 (s, CH$_2$O), 7.44 (d, J=8.3 Hz, 2 ArH), 7.63 (d, J=8.3 Hz, 2 ArH); $^{13}$C NMR (CDCl$_3$) δ8.4 (CH$_3$O), 73.5 (CH$_2$OCH$_3$), 111.1 (CCN), 118.7 (CN), 127.6, 132.0, 143.8 (3 ArC); HRMS (M-CH$_3$$^+$) (ESI$^+$) 132.0443 [M-CH$_3$] (calcd for C$_8$H$_6$NO$^+$ 132.0443).

Preparation of 4-(Methoxymethyl)benzylamine (Braun, Julius; Zobel, Friedrich. Berichte der Deutschen Chemischen Gesellschaft (1923), 56B: 690-6.) To a LiAlH$_4$ (7.36 g, 193.7 mmol) suspension in THF (400 mL) was added dropwise a THF (30 mL) solution of 4-(methoxymethyl)benzonitrile (9.50 g, 64.6 mmol) at 0° C. The mixture was stirred at room temperature (16 h) and then H$_2$O (6 mL) was added dropwise at 0° C. followed by an aqueous NaOH solution (3 mL, 15% w/w) and then H$_2$O (6 mL). The mixture was stirred at room temperature (2 h) and the precipitate was filtered through Celite®, and the pad was washed with CH$_2$Cl$_2$. The filtrate was concentrated in vacuo to give 8.20 g of a colorless oil (84%): R$_f$=0.00 (hexanes/EtOAc 9/1); $^1$H NMR (CDCl$_3$) δ 1.41 (br s, NH$_2$), 3.88 (s, OCH$_3$), 3.86 (s, CH$_2$NH$_2$), 4.47 (s, CH$_2$O), 7.20-7.40 (br m, 4 ArH); $^{13}$C NMR (CDCl$_3$) δ6.2 (CH$_2$NH$_2$), 58.0 (CH$_3$O), 74.4 (CH$_2$OCH$_3$), 127.1, 128.0, 136.7, 142.8 (4 ArC); HRMS (M+H$^+$) (ESI$^+$) 152.1073 [M+H$^+$] (calcd for C$_9$H$_{13}$NO$^+$ 152.1075).

Preparation of (R)-2-N-(Benzyloxycarbonyl)amino-3-hydroxy-N-(4-methoxymethylbenzyl)propanamide A THF solution (75 mL) of (R)-Cbz-serine (5.30 g, 22.0 mmol) was stirred and cooled at −78° C. under Ar and then 4-methylmorpholine (NMM) (2.9 mL, 26.4 mmol) was added dropwise. After 2 min of stirring at this temperature, isobutylchloroformate (IBCF) (3.5 mL, 26.4 mmol) was added dropwise leading to the precipitation of a white solid, and the reaction was allowed to proceed for additional 2 min. 4-Methoxymethylbenzylamine (4.00 g, 26.4 mmol) was added portionwise at −78° C. and the mixture was stirred at room temperature (2 h). The white solid was filtered and the organic layer was concentrated in vacuo. The residue was triturated with EtOAc resulting in a solid that was filtered and recrystallized with EtOAc to give (R)-2-N-(benzyloxycarbonyl)amino-3-hydroxy-N-(4-methoxymethylbenzyl) propanamide as a white solid (7.20 g, 88%): R$_f$=0.63 (EtOAc); mp 138-140° C.; [α]$^{25.8}$$_D$ −34.0° (c 1, DMSO); IR (nujol) 3385, 3294, 3106, 2923, 2859, 1690, 1646, 1544, 1458, 1373, 1307, 1243, 1098, 1028, 919, 738, 694 cm$^{-1}$; $^1$H NMR (CDCl$_3$) δ 3.36 (s, OCH$_3$), 3.64 (dd, J=5.1, 10.8 Hz CHH'OH), 3.88-4.06 (br d, CHH'OH), 4.19-4.29 (m, CH), 4.34-4.45 (m, CH$_2$OCH$_3$, NCH$_2$), 5.06 (s, CH$_2$O), 6.96 (d, J=7.2 Hz, OC(O)NH), 7.02-7.14 (br s, NH), 7.19 (d, J=7.8 Hz, 2 ArH), 7.27 (d, J=7.8 Hz, 2 ArH), 7.30-7.38 (m, 5 ArH); $^{13}$C NMR (CDCl$_3$) δ 43.2 (NCH$_2$), 55.5 (OCH$_2$CH), 58.1 (CH$_3$O), 62.7 (OCH$_2$CH), 67.3 (CH$_2$O), 74.3 (CH$_2$OCH$_3$), 127.6, 128.0, 128.1, 128.3, 128.5, 135.9, 137.0, 137.5 (8 ArC), 156.7 (OC(O)N), 170.7 (C(O)); HRMS (M+H$^+$) (ESI$^+$) 373.1764 [M H$^+$] (calcd for C$_{20}$H$_{24}$N$_2$O$_5$H$^+$ 373.1763); Anal. Calcd. for C$_{20}$H$_{24}$N$_2$O$_5$.0.25H$_2$O: C, 63.73; H, 6.55; N, 7.43. Found: C, 63.35; H, 6.43; N, 7.29.

Preparation of (R)-2-N-(Benzyloxycarbonyl)amino-3-methoxy-N-(4-methoxymethylbenzyl)propanamide Ag$_2$O (12.40 g, 53.7 mmol) was added to a CH$_3$CN solution (100 mL) of (R)-2-N-(benzyloxycarbonyl)amino-3-hydroxy-N-(4-methoxymethylbenzyl)-propanamide (4.00 g, 10.7 mmol) and CH$_3$I (6.71 mL, 107.5 mmol) at room temperature under Ar. The reaction mixture was stirred at room temperature (2 d), filtered, and the filtrate concentrated in vacuo to obtain 3.90 g of the desired compound as a white solid (94%): R$_f$=0.79 (EtOAc); mp 107-108° C.; [α]$^{24.6}$$_D$ −22.1° (c 1, CHCl$_3$); IR (nujol) 3285, 2958, 2732, 2681, 1688, 1645, 1545, 1458, 1376, 1305, 1240, 1112, 1048, 966, 815, 729, 696 cm$^{-1}$; $^1$H NMR (CDCl$_3$) δ 3.36, 3.38 (2 s, 2 OCH$_3$), 3.49 (dd, J=6.6, 9.3 Hz, CHH'), 3.85 (dd, J=3.3, 9.3 Hz, CHH'), 4.28-4.38 (br m, CHCH$_2$), 4.43 (s, CH$_2$OCH$_3$), 4.46 (d, J=6.3 Hz, CH$_2$N), 5.11 (s, OCH$_2$), 5.64-5.72 (br m, OC(O)NH), 6.66-6.74 (br m, CH$_2$NH), 7.23 (d, J=8.4 Hz, 2 ArH), 7.29 (d, J=8.4 Hz, 2 ArH), 7.31-7.38 (m, 5 ArH); $^{13}$C NMR (CDCl$_3$) δ 43.2 (NCH$_2$), 54.3 (OCH$_2$CH), 58.0 (CH$_2$OCH$_3$) δ9.0 (OCH$_3$), 67.2 (PhCH$_2$O), 72.0 (OCH$_2$CH), 74.3 (CH$_2$OCH$_3$), 127.5, 128.0, 128.1, 128.2, 128.5, 136.0, 137.2, 137.6 (8 ArC), 156.1 (OC(O)), 169.8 (C(O)); HRMS (M+H$^+$) (ESI$^+$) 387.1920 [M+H$^+$] (calcd for C$_{21}$H$_{26}$N$_2$O$_5$H$^+$ 387.1920); Anal. Calcd. for C$_{21}$H$_{26}$N$_2$O$_5$: C, 65.27; H, 6.78; N, 7.25. Found: C, 65.27; H, 6.79; N, 7.38.

Preparation of (R)-2-Acetamido-3-methoxy-N-(4-methoxymethylbenzyl)propanamide ((R)-8)

A MeOH solution (400 mL) of (R)-2-N-(benzyloxycarbonyl)amino-3-methoxy-N-(4-methoxymethylbenzyl)propanamide (3.50 g, 9.1 mmol) was treated with H$_2$ (1 atm) in presence of 10% Pd/C (350 mg) at room temperature (16 h). The mixture was carefully filtered through a bed of Celite® and the filtrate was evaporated in vacuo to obtain a colorless oil. The oil was dissolved in CH$_2$Cl$_2$ (150 mL) and then triethylamine (1.52 mL, 10.9 mmol) and acetyl chloride (772 µL, 10.9 mmol) were carefully added at 0° C. and the resulting solution was stirred at room temperature (2 h). An aqueous 10% citric acid solution (150 mL) was added and the mixture was extracted with CH$_2$Cl$_2$ (3×100 mL). The organic layers were combined, washed with an aqueous saturated NaHCO$_3$ solution (100 mL), dried (MgSO$_4$), and concentrated in vacuo. The residue was triturated with EtOAc to give (R)-8 as a white solid (1.50 g, 56%): R$_f$=0.35 (EtOAc); mp 119-120° C.; [α]$^{25}$$_D$ −25.4° (c 0.5, CHCl$_3$); IR (nujol) 3266, 3069, 2935, 2863, 1635, 1550, 1458, 1457, 1382, 1282, 1226, 1194, 1125, 948, 836, 792, 726 cm$^{-1}$; $^1$H NMR (CDCl$_3$) δ 2.03 (s, CH$_3$CO), 3.37, 3.38 (2 s, 2 OCH$_3$), 3.43 (dd, J=7.5, 9.1, CHH'), 3.80 (dd, J=4.2, 9.1 Hz, CHH'), 4.41-4.49 (m, CH$_2$OCH$_3$, CH$_2$N), 4.51-4.58 (m, CH), 6.42-6.52 (br d, NHC(O)CH$_3$), 6.75-6.84 (br t, CH$_2$NH), 7.24 (d, J=7.9 Hz, 2 ArH), 7.30 (d, J=7.9 Hz, 2 ArH); addition of excess (R)-(−)-mandelic acid to a CDCl$_3$ solution of (R)-8 gave only one signal for the acetyl methyl and one signal for the ether methyl protons; $^{13}$C NMR (CDCl$_3$) 23.2 (CH$_3$CO), 43.3 (CH$_2$N), 52.5 (CHCH$_2$), 58.1 (OCH$_3$), 59.1 (OCH$_3$), 71.8 (CH$_2$OCH$_3$), 74.3 (CH$_2$OMe), 127.5, 128.1, 137.3, 137.5 (4 ArC), 170.0, 170.3 (2C(O)); HRMS (M+Na$^+$) (ESI$^+$) 295.1658 [M+Na$^+$] (calcd for C$_{15}$H$_{22}$N$_2$O$_4$H$^+$ 295.1658); Anal. Calcd. for C$_{15}$H$_{22}$N$_2$O$_4$: C, 61.21; H, 7.45; N, 9.52. Found: C, 60.88; H, 7.45; N, 9.35.

Scheme 6. Preparation of (R)-9.

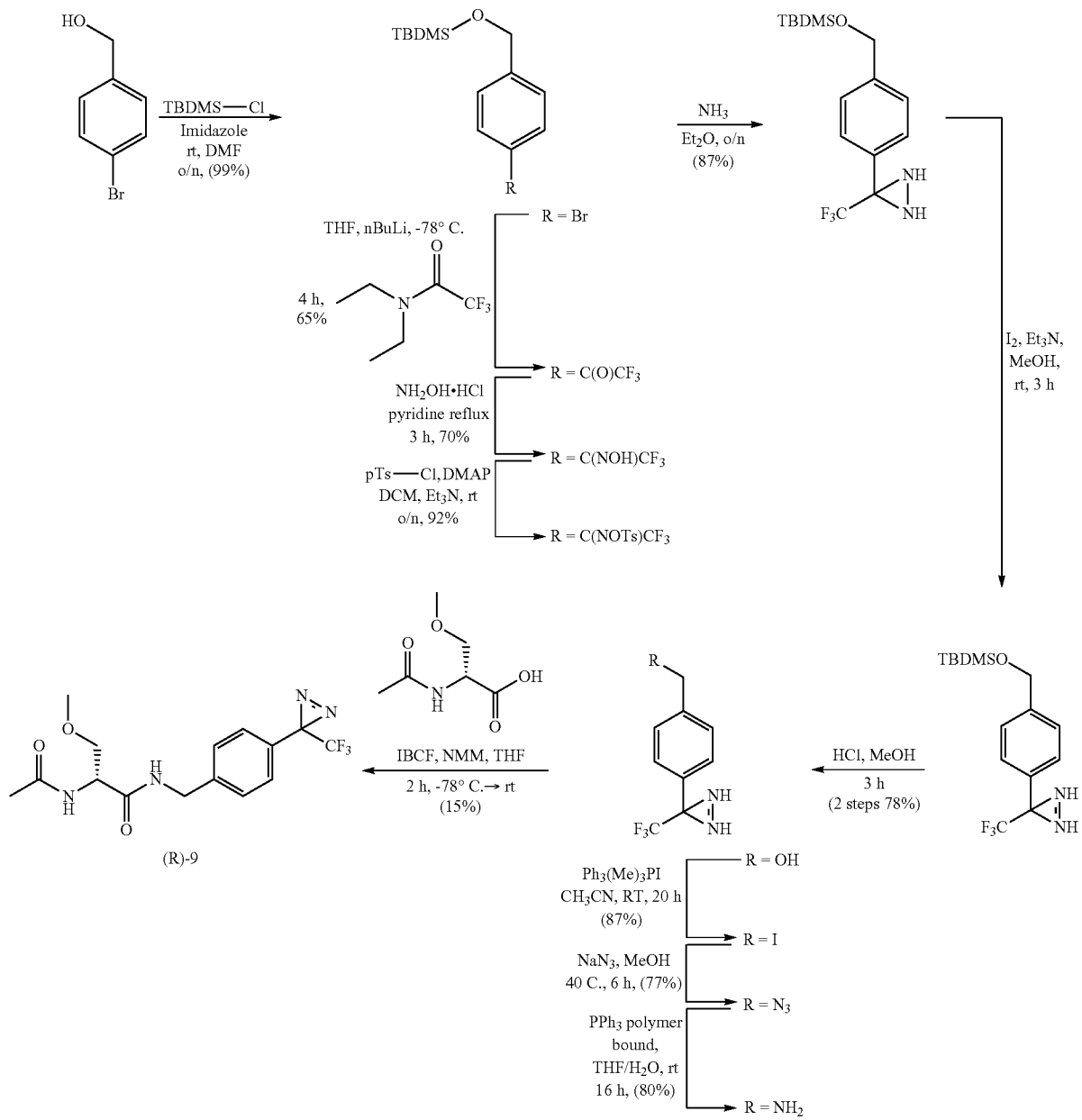

Preparation of (4-Bromobenzyloxy(tert.-butyl)-dimethylsilane

4-Bromobenzyl alcohol (50.00 g, 267.3 mmol), tert.-butyldimethylsilyl chloride (52.38 g, 347.5 mmol), and imidazole (23.66 g, 347.5 mmol) were dissolved in anhydrous DMF (300 mL). This solution was allowed to stir at room temperature overnight and then poured into ice-water (600 mL). The organic layer was separated off and washed with saturated aqueous sodium bicarbonate (2×200 mL) and water (2×200 mL). We obtained colorless oil (71.9 g, 88%): $^1$H NMR (CDCl$_3$): δ 0.10 (s, (CH$_3$)$_2$Si), 0.94 (s, (CH$_3$)$_3$C), 4.7 (s, CH$_2$O), 7.20 (d, J=7.8 Hz, C$_6$H$_4$), 7.45 (d, J=7.8 Hz, C$_6$H$_4$); $^{13}$C NMR (CDCl$_3$): δ.

Preparation of 1-(4-((tert.-Butyldimethylsilyloxy)methyl)phenyl)-2,2,2-Trifluoroethanone To a stirred solution of the (4-bromobenzyloxy)-(tert.-butyl)-dimethylsilane (24.94 g, 82.8 mmol) in THF (420 mL) at −78° C. was added dropwise a 1.6 M solution of nBuLi in hexane (62 mL, 99.2 mmol) over a 1 h period. After stirring the mixture at the same temperature for 75 min, a solution of N,N-diethyltrifluoroacetamide (19.19 g, 113 nmol) in THF (60 mL) was added dropwise over 1 h. Following the addition the mixture at −78° C. for a further 75 min before the reaction was quenched with an aqueous solution of NH$_4$Cl. Ether was added and the organic layer was extracted 3 times with ether (3×300 mL). The organic layers were combined, dried over Na$_2$SO$_4$ and concentrated in vacuum. The resulting pale yellow liquid was distillated in vacuo to give the 1-(4-((tert-butyldimethylsilyloxy)methyl)phenyl)-2,2,2-trifluoroethanone (65%) as a colorless liquid; b.p. 170-180° C. (10 torr), $^1$H NMR (CDCl$_3$): δ 0.12 (s, (CH$_3$)$_2$Si), 0.96 (s, CH$_3$)$_3$C), 4.83 (s, CH$_2$), 7.50 (d, J=8.2 Hz, C$_6$H$_4$), 8.05 (d, J=8.2 Hz, C$_6$H$_4$); $^{13}$C NMR (CDCl$_3$): δ −5.4 (CH$_3$Si), 18.3 (C(CH$_3$)$_3$), 25.8 (C(CH$_3$)$_3$), 64.2 (CH$_2$O), 116.7 (q, J=289.7 Hz, CF$_3$), 126.2 (C$_6$H$_2$), 128.6 (C$_6$H$_2$), 130.2 (C$_6$H$_2$), 150.1, (C$_6$H$_2$), 180.2 (q, J=34.5 Hz, CO).

Preparation of 1-(4-((tert.-Butyldimethylsilyloxy)methyl)phenyl)-2,2,2-Trifluoroethanone Oxime Hydroxylamine hydrochloride (6.55 g, 94.3 mmol) was added to a pyridine (30 mL) solution of 1-(4-((tert.-butyldimethylsilyloxy)methyl)phenyl)-2,2,2-trifluoroethanone (10 g, 31.4 mmol). The solution was stirred a reflux (4 h). The pyridine was evaporated and 150 mL of an aqueous solution of citric acid (10%) and CH$_2$Cl$_2$ (100 mL) were added to the residue and the organic layer was extracted. The aqueous layer was washed 2 times with CH$_2$Cl$_2$ (2×100 mL). Finally, the organic layers were combined and concentrated in vacuum. The residue was purified by silica gel flash chromatography (MPLC) to obtain 8.4 g of a white solid. R$_f$=0.31 (1/9 EtOAc/hexanes); mp 63-65° C.; $^1$H NMR (CDCl$_3$): δ 0.12 (s, (CH$_3$)$_2$Si), 0.96 (s, CH$_3$)$_3$C), 4.73 (s, CH$_2$), 7.44 (d, J=8.2 Hz, C$_6$H$_4$), 7.50 (d, J=8.2 Hz, C$_6$H$_4$), 8.61 (s, OH); $^{13}$C NMR (CDCl$_3$): δ −5.3 (CH$_3$Si), 18.4 (C(CH$_3$)$_3$), 25.9 (C(CH$_3$)$_3$), 64.4 (CH$_2$O), 120.6 (q, J=273.2 Hz, CF$_3$), 124.4 (C$_6$H$_2$), 125.9 (C$_6$H$_2$), 128.6 (C$_6$H$_2$), 144.2, (C$_6$H$_2$), 147.9 (q, J=32.1 Hz, CN).

Preparation of 1-(4-((tert.-Butyldimethylsilyloxy)methyl)phenyl)-2,2,2-trifluoroethanone O-Tosyl Oxime An anhydrous CH$_2$Cl$_2$ solution of pTs-Cl (10.10 g, 53.3 mmol) was added portionwise to an anhydrous CH$_2$Cl$_2$ solution of 1-(4-((tert.-butyldimethylsilyloxy)methyl)phenyl)-2,2,2-trifluoroethanone oxime, Et$_3$N and DMAP. The solution was stirred at it (overnight). 200 mL of an aqueous solution of citric acid (10%) was added to the reaction solution and the organic layer was extracted. The aqueous layer was washed 2 times with CH$_2$Cl$_2$ (2×200 mL). The organic layers were combined, dried (Na$_2$SO$_4$) and concentrated in vacuum. The residue was purified by silica gel flash chromatography to obtain 11.80 g of a colorless oil (92%). R$_f$=0.58 (1/9 EtOAc/hexanes); $^1$H NMR (CDCl$_3$): δ 0.12 (s, (CH$_3$)$_2$Si), 0.96 (s, CH$_3$)$_3$C), 2.48 (s, CH$_3$Ph), 4.78 (s, CH$_2$), 7.37-7.45 (m, 6 C$_6$H$_4$), 7.89 (d, J=8.4 Hz, 2 C$_6$H$_4$); $^{13}$C NMR (CDCl$_3$): δ −5.3 (CH$_3$Si), 18.4 (C(CH$_3$)$_3$), 21.7 (CH$_3$), 25.8 (C(CH$_3$)$_3$), 64.2 (CH$_2$O), 119.7 (q, J=275.5 Hz, CF$_3$), 122.9 (C$_6$H$_2$), 126.0 (C$_6$H$_2$), 128.4 (C$_6$H$_2$), 129.3 (C$_6$H$_2$), 129.8 (C$_6$H$_2$), 131.3 (C$_6$H$_2$), 145.6 (C$_6$H$_2$), 146.0 (C$_6$H$_2$), 154.0 (q, J=33.0 Hz, CN).

Preparation of 3-(4-((tert.-Butyldimethylsilyloxy)methyl)phenyl)-3-(trifluoromethyl)diaziridine Liquid ammonia (2 mL) was added a −78° C. to an ether (15 mL) solution of 1-(4-((tert.-butyldimethylsilyloxy)methyl)phenyl)-2,2,2-trifluoroethanone O-tosyl oxime (4.00 g, 8.2 mmol) in a sealed tube. The solution was stirred at rt (16 h). The mixture was carefully cooled at −78° C. and the sealed tube was opened. The ammonia was evaporated and the white precipitate was filtered and washed with ether. The filtrate was concentrated in vacuum to obtain 2.4 g of a colorless oil (87%); NMR (CDCl$_3$): δ 0.10 (s, (CH$_3$)$_2$Si), 0.95 (s, CH$_3$)$_3$C), 2.21 (d, J=8.1 Hz, NH), 2.77 (d, J=8.1 Hz, NH), 4.76 (s, CH$_2$), 7.38 (d, J=8.4 Hz, 2 C$_6$H$_4$), 7.58 (d, J=8.4 Hz, 2 C$_6$H$_4$); $^{13}$C NMR (CDCl$_3$): δ −5.3 (CH$_3$Si), 18.4 (C(CH$_3$)$_3$), 25.9 (C(CH$_3$)$_3$), 58.0 (q, J=35.8 Hz, C diaziridine), 64.4 (CH$_2$O), 123.6 (q, J=276.0 Hz, CF$_3$), 126.2 (C$_6$H$_2$), 128.0 (C$_6$H$_2$), 130.2 (C$_6$H$_2$), 143.8 (C$_6$H$_2$).

Preparation of 4-[3-(Trifluoromethyl)-3H-Diazirin-3-yl]-Benzenemethanol

I$_2$ (1.14 g, 4.5 mmol) was added to a MeOH (4 mL) solution of Et$_3$N (1.2 mL) and 3-(4-((tert.-butyldimethylsilyloxy)methyl)phenyl)-3-(trifluoromethyl)-diaziridine (1.65 g, 5.00 mmol). The solution was stirred at rt (3 h). Aqueous citric acid 10% (50 mL) and NaS$_2$O$_3$ were added. The organic layer was extracted 3 times with ether (3×30 mL). The organic layers were combined, dried and concentrated in vacuum to obtain a yellow oil; $^1$H NMR (CDCl$_3$): δ 0.09 (s, (CH$_3$)$_2$Si), 0.94 (s, CH$_3$)$_3$C), 4.74 (s, CH$_2$), 7.15 (d, J=8.0 Hz, 2 C$_6$H$_4$), 7.35 (d, J=8.0 Hz, 2 C$_6$H$_4$). HCl in dioxane (4 M, 5 mL, 20 mmol) was added to a MeOH (10 mL) solution of the yellow residue. The solution was stirred at rt (3 h) and the volatiles were evaporated. The residue was purified by silica gel flash chromatography to obtain 840 mg (78%) of a yellow liquid: R$_f$=0.19 (1/9 EtOAc/hexanes); $^1$H NMR (CDCl$_3$): δ 1.95-2.05 (br, OH), 4.70 (s, CH$_2$), 7.18 (d, J=8.4 Hz, 2 C$_6$H$_4$), 7.38 (d, J=8.4 Hz, 2C$_6$H$_4$); $^{13}$C NMR (CDCl$_3$): δ 28.3 (q, J=40.4 Hz, C diazirine), 64.4 (CH$_2$O), 122.1 (q, J=273.0 Hz, CF$_3$), 126.7 (C$_6$H$_2$), 127.1 (C$_6$H$_2$), 128.3 (C$_6$H$_2$), 142.5 (C$_6$H$_2$).

Preparation of 3-[4-(Iodomethyl)phenyl]-3-(Trifluoromethyl)-3H-Diazirine

PPh$_3$MeI (3.35 g, 7.4 mmol) was added to a 4-[3-(trifluoromethyl)-3H-diazirin-3-yl]-benzenemethanol (8) (0.80 g, 3.7 mmol) in anhydrous acetonitrile (6 mL). The solution was stirred at rt and in the dark (20 h). Ether (30 mL) and an aqueous NaOH 1 M (30 mL) were added successively. The organic layer was extracted and the aqueous one was washed with ether (2×30 mL). The organic layers were combined and concentrated in vacuum. Finally, the residue was purified by silica gel flash chromatography (0→20 EtOAc in hexanes) to obtain 1.06 g (87%) of a colorless liquid: R$_f$=0.95 (1/9 EtOAc/hexanes); $^1$H NMR (CDCl$_3$): δ 4.42 (s, CH$_2$), 7.11 (d, J=8.3 Hz, 2 C$_6$H$_4$), 7.39 (d, J=8.3 Hz, 2 C$_6$H$_4$); $^{13}$C NMR (CDCl$_3$): δ 28.3 (q, J=40.1 Hz, C diazirine), 33.8 (CH$_2$I), 122.0 (q, J=273.2 Hz, CF$_3$), 126.9 (C$_6$H$_2$), 128.7 (C$_6$H$_2$), 129.1 (C$_6$H$_2$), 141.1 (C$_6$H$_2$).

Preparation of 3-[4-(Azidomethyl)phenyl]-3-(Trifluoromethyl)-3H-Diazirine

NaN$_3$ (0.42 g, 6.2 mmol) was added to a MeOH (30 mL) solution of 3-[4-(iodomethyl)phenyl]-3-(trifluoromethyl)-3H-diazirine (1.01 g, 3.1 mmol). The solution was stirred at 45° C. (6 h). The methanol was evaporated and CH$_2$Cl$_2$ (30 mL) and water (30 mL) were added. The organic layer was extracted and the aqueous layer was washed with $CH_2Cl_2$ (1×30 mL). The organic layers were combined and concentrated in vacuum. Finally, the residue was purified by silica gel flash chromatography (0→30% EtOAc in hexanes) to obtain 570 mg (77%) of a pale yellow liquid: $R_f$=0.85 (1/9 EtOAc/hexanes); IR (nujol) 3298, 2927, 2859, 2100 ($N_3$), 1694, 1615, 1459, 1374, 1236, 1162, 1055, 939, 805, 728 $cm^{-1}$; $^1$H NMR ($CDCl_3$): δ 4.37 (s, $CH_2$), 7.21 (d, J=7.9 Hz, 2 $C_6H_4$), 7.35 (d, J=7.9 Hz, 2 $C_6H_4$); $^{13}$C NMR ($CDCl_3$): δ 28.3 (q, J=40.2 Hz, C diazirine), 54.1 ($CH_2N_3$), 122.1 (q, J=273.0 Hz, $CF_3$), 127.0 ($C_6H_2$), 128.5 ($C_6H_2$), 129.2 ($C_6H_2$), 137.2 ($C_6H_2$).

Preparation of 4-[3-(Trifluoromethyl)-3H-Diazirin-3-yl]-Benzenemethanamine

Triphenylphosphine polymer bound (Fluka, cat #93094) (1.6 g/mol, 6.3 mmol) was added to an aqueous (378 μL, 21.0 mmol)/THF (10 mL) solution of 3-[4-(azidomethyl)phenyl]-3-(trifluoromethyl)-3H-diazirine (506 mg, 2.1 mmol). The mixture was shaken until the starting material was no longer evident by TLC analysis (18 h). The triphenylphosphine-based support was filtered, washed with $CH_2Cl_2$, and the filtrate was concentrated in vacuum to obtain 350 mg (80%) of a yellow oil corresponding to the free amine: $^1$H NMR ($CDCl_3$) δ 1.35-1.50 (br s, $NH_2$), 3.89 (s, $CH_2$), 7.17 (d, J=8.2 Hz, 2 $C_6H_4$), 7.35 (d, J=8.2 Hz, 2 $C_6H_4$); $^{13}$C NMR ($CDCl_3$): δ 28.4 (q, J=39.9 Hz, C diazirine), 45.9 ($CH_2NH_2$), 122.2 (q, J=273.2 Hz, $CF_3$), 126.7 ($C_6H_2$), 127.5 ($C_6H_2$), 145.0 ($C_6H_2$) (one peak is overlapped with an other one).

Preparation of (R)-2-Acetamido-3-methoxy-N-(4-(3-(trifluoromethyl)-3H-diazirin-3-yl)benzyl)propanamide ((R)-9)

4-[3-(Trifluoromethyl)-3H-diazirin-3-yl]-benzenemethanamine hydrochloride (933 mg, 3.7 mmol) was added to a THF (31 mL) solution of the (R)-2-acetamido-3-methoxypropanoic acid (500 mg, 3.1 mmol), and the mixture was stirred at room temperature (5 min) and then NMM (0.41 mL, 3.7 mmol) was added. The mixture was stirred a room temperature (5 min) and DMTMM (1.03 g, 3.7 mmol) was added, and the mixture was stirred at room temperature (16 h). The white precipitate was filtered and the filtrate was concentrated in vacuo. The residue was purified by flash column chromatography on silica gel with EtOAc/acetone (10/0→6/4) as the eluant to obtain a white solid (810 mg, 73%): $R_f$=0.74 (EtOAc); mp 195° C. (decomp); $[α]^{25}_D$ −11.0° (c 0.5, $CHCl_3$); IR (nujol) 3278, 1635, 1554, 1458, 1375, 1236, 1186, 1148, 1054, 940, 805, 731 $cm^{-1}$; $^1$H NMR ($CDCl_3$) δ 2.02 (s, $CH_3C(O)$), 3.38 (s, $OCH_3$), 3.44 (dd, J=7.2, 9.0 Hz, CHH'), 3.80 (dd, J=4.2, 9.0 Hz, CHH'), 4.40-4.51 (m, $CH_2$), 4.52-4.59 (m, CH), 6.45 (d, J=6.0 Hz, $NHC(O)CH_3$), 6.89-6.98 (br t, $NHCH_2$), 7.15 (d, J=8.2 Hz, 2 ArH), 7.29 (d, J=8.2 Hz, 2 ArH); addition of excess (R)-(−)-mandelic acid to a $CDCl_3$ solution of (R)-18 gave only one signal for the acetyl methyl and one signal for the ether methyl protons; $^{13}$C NMR ($CDCl_3$): δ 23.2 ($CH_3O(O)$), 28.3 (q, J=40.1 Hz, C diazirine), 43.0 ($CH_2N$), 52.5 (CH), 59.1 ($OCH_3$), 71.5 ($CH_2OCH_3$), 122.1 (q, J=273.1 Hz, $CF_3$), 126.9, 127.8, 128.3, 139.9 (4 ArC), 170.2, 170.4 (2 CO); HRMS ($M+H^+$)($ESI^+$) 359.1334 $[M+Na^+]$ (calcd $C_{15}H_{17}F_3N_4O_3H^+$ 359.1331); Anal. Calcd. for $C_{15}H_{17}F_3N_4O_3 \cdot 0.05C_3H_6O$: C, 50.34; H, 4.81; N, 15.56; F, 15.83. Found: C, 50.59; H, 4.76; N, 15.24; F, 15.46.

Example 2

Formalin Test

Compounds of the present invention were active in treating pain in a formalin test carried out in accordance with standard techniques, as described in S. Hunskaar et al., *J. Neurosci. Methods* 14: 69-76 (1985). Briefly, 0.5% formalin is injected into the mouse hind paw to elicit a bi-phasic licking response, where the first acute phase is thought to correspond to the direct stimulation of peripheral fibers and the second (inflammatory) phase is caused by the release of inflammatory mediators. Results areas shown in Table 2 below.

TABLE 2

Formalin Test Results of Formula IA Compounds.

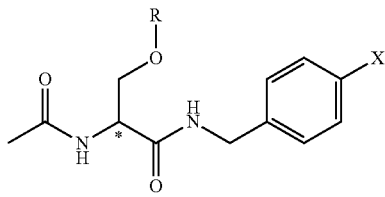

| | | | | | \multicolumn{4}{c|}{Area Under the Curve} | |
| R | X | Stereo | Dose (mg/kg) | Test | Control | Drug Tested | % of Control | S.E.M | P value |
| --- | --- | --- | --- | --- | --- | --- | --- | --- | --- |
| $CH_2C\equiv CH$ | H | (R) | 16.0 | Acute | 295.1 | 142.9 | 48.42 | 3.52 | <0.01 |
| | | | 16.0 | Inflammatory | 797.3 | 468.3 | 54.99 | 14.75 | <0.05 |
| $CH_3$ | $N_3$ | (R) | 8.0 | Acute | 224.0 | 131.4 | 58.67 | 12.49 | <0.05 |
| | | | 8.0 | Inflammatory | 653.8 | 694.5 | 106.22 | 9.5 | >0.05 |
| $CH_2C\equiv CH$ | $N_3$ | (R) | 20.0 | Acute | 205.8 | 119.9 | 58.28 | 9.68 | <0.05 |
| | | | 20.0 | Inflammatory | 530.0 | 414.3 | 78.17 | 14.84 | >0.05 |

Example 3

Additional Compounds

Reaction overview

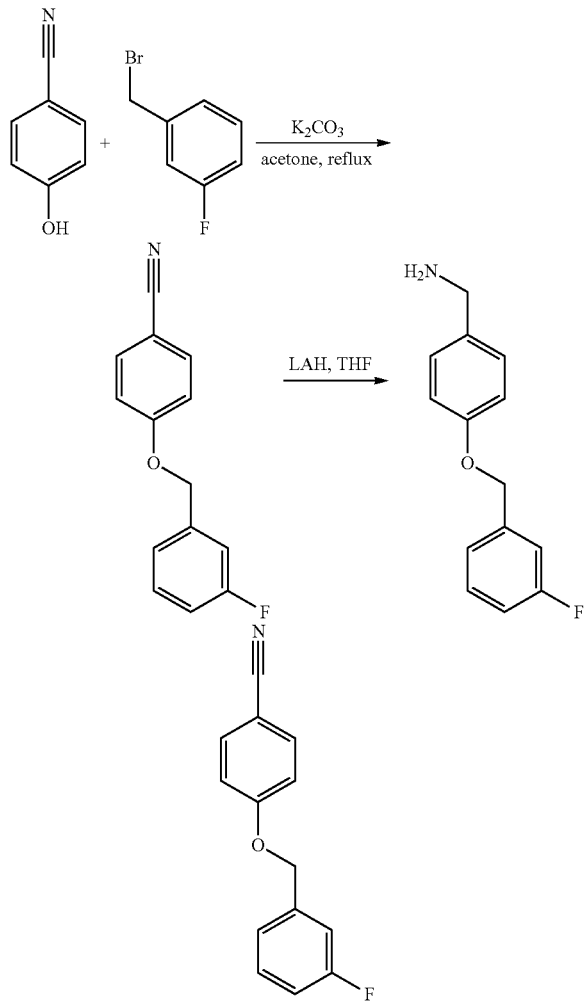

Preparation of 4-(3-Fluorobenzyloxy)benzonitrile (Nakamoto, Kazutaka; Tsukada, Itaru; Tanaka, Keigo; Matsukura, Masayuki; Haneda, Toru; Inoue, Satoshi; Ueda, Norihiro; Abe, Shinya; Hata, Katsura; Watanabe, Naoaki, WO 2005033079 (2005).)

A mixture of 4-cyanophenol (11.91 g, 100.0 mmol), $K_2CO_3$ (55.20 g, 400.0 mmol), and 3-fluorobenzylbromide (22.68 g, 120.0 mmol) were heated in acetone (400 mL) at reflux (5 h). The volatiles were evaporated and the residue was diluted in $CH_2Cl_2$ (300 mL), and then washed with $H_2O$ (500 mL), dried ($MgSO_4$), and concentrated in vacuo to give white needles (19.81 g, 87%): $R_f$=0.45 (hexanes/EtOAc 9/1); mp 104-105° C.; $^1$H NMR (CDCl$_3$) δ 5.11 (s, CH$_2$O), 6.98-7.20 (m, 5 ArH), 7.33-7.41 (m, 1 ArH), 7.59 (d, J=8.7 Hz, 2 ArH); HRMS (M+Na$^+$) (ESI$^+$) 250.0641 [M+Na$^+$] (calcd for $C_{14}H_{10}NONa^+$ 250.0641).

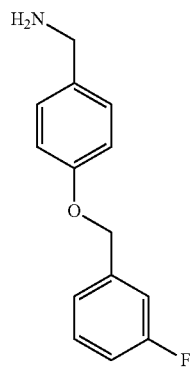

Preparation of 4-(3-Fluorobenzyloxy)benzylamine[1]

To a LiAlH$_4$ (5.02 g, 132.0 mmol) suspension in THF (400 mL) was added dropwise a THF (30 mL) solution of 4-(3-fluorobenzyloxy)benzonitrile (10.00 g, 44.0 mmol) at 0° C. The mixture was stirred at room temperature (16 h) and $H_2O$ (4 mL) was added dropwise at 0° C. followed by an aqueous NaOH solution (2 mL, 15% w/w), and then $H_2O$ (4 mL). The mixture was stirred at room temperature (2 h), and the precipitate filtered and washed with $CH_2Cl_2$. The filtrate was concentrated in vacuo to obtain a white solid (8.82 g, 86%): $R_f$=0.00 (hexanes/EtOAc 9/1); mp 44-45° C.; $^1$H NMR (CDCl$_3$) δ 1.61 (br s, NH$_2$), 3.79 (s, CH$_2$NH$_2$), 5.04 (s, CH$_2$O), 6.90-7.04 (m, 3 ArH) 7.13-7.37 (m, 5 ArH); HRMS (M-NH$_2^+$) (ESI$^+$) 215.088 [M-NH$_2^+$] (calcd for $C_{14}H_{12}O^+$ 215.087).

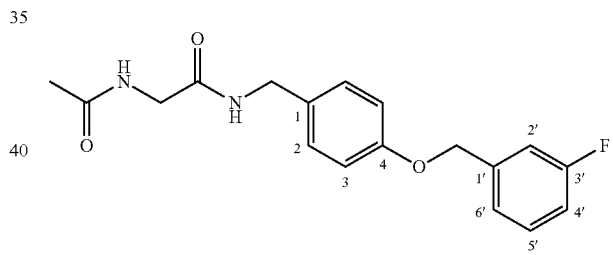

Preparation of N-4-(3-Fluorobenzyloxy)benzyl 2-Acetamidoacetamide

A THF solution (120 mL) of N-acetylglycine (1.50 g, 12.8 mmol) was stirred and cooled at −78° C. under Ar and then 4-methylmorpholine (NMM) (1.7 mL, 15.4 mmol) was added dropwise. After 2 min of stirring at this temperature, isobutylchloroformate (IBCF) (2.0 mL, 15.4 mmol) was added dropwise leading to the precipitation of a white solid. The reaction was allowed to proceed for additional 2 min and 4-(3-fluorobenzyloxy)benzylamine (3.26 g, 14.1 mmol) was added portionwise at −78° C. The mixture was allowed to stir at room temperature (2 h), and then the white solid filtered and the organic layer concentrated in vacuo. The solid was purified by flash column chromatography on silica gel with methanol/EtOAc (0/10→5/5) as the eluant to obtain N-4-(3-fluorobenzyloxy)benzyl 2-acetamidoacetamide as white solid (1.30 g, 31%): $R_f$=0.11 (EtOAc); mp 155-156° C.; IR (nujol) 3305, 3070, 2921, 2862, 1647, 1549, 1457, 1374, 1249, 1145, 1017, 933, 879, 825, 781, 724 cm$^{-1}$; $^1$H NMR (CDCl$_3$) δ 2.03 (s, C(O)CH$_3$), 3.92 (d, J=5.1 Hz, CH$_2$N), 4.38

(d, J=5.7 Hz, NCH$_2$Ar), 5.05 (s, CH$_2$O), 6.24-6.35 (br m, 2 NH), 6.92 (m, 2 ArH), 6.97-7.04 (m, 1 ArH), 7.11-7.21 (m, 4 ArH), 7.30-7.38 (m, 1 ArH); $^{13}$C NMR (CDCl$_3$) δ 22.9 (C(O)CH$_3$), 43.0, 43.4 (2 CH$_2$), 69.2 (d, J=1.7 Hz, PhCH$_2$O), 114.1 (d, J=22.1 Hz, C$_{4'}$ or C$_{2'}$), 114.8 (d, J=21.1 Hz, C$_{2'}$ or C$_{4'}$), 115.0 (CA 122.6 (d, J=2.9 Hz, C$_{6'}$), 129.1 (ArC), 130.1 (d, J=8.5 Hz, C$_{5'}$), 130.3 (ArC), 139.5 (d, J=7.4 Hz, C$_{1'}$), 157.9 (C$_4$), 163.0 (d, J=244.7 Hz, C$_{3'}$), 168.6, 170.7 (2C(O)); MS (M+H$^+$) (ESI$^+$) 331.1 [M+H$^+$] (calcd for C$_{18}$H$_{19}$FN$_2$O$_3$H$^+$ 331.1); Anal. Calcd. for C$_{18}$H$_{19}$FN$_2$O$_3$·0.35H$_2$O: C, 64.21; H, 5.90; F, 5.64; N, 8.32. Found: C, 63.83; H, 5.56; F, 5.49; N, 8.22.

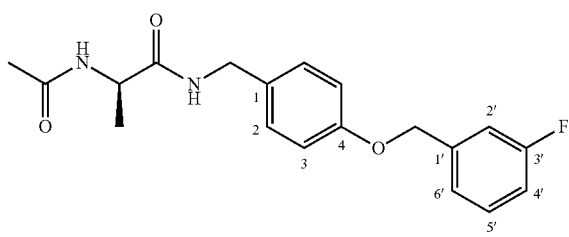 [SMILES: CC(=O)N[C@H](C)C(=O)NCc1ccc(OCc2cccc(F)c2)cc1]

Preparation of (R)—N-4-(3-Fluorobenzyloxy)benzyl 2-Acetamido-propionamide

A THF solution (100 mL) of (R)—N-acetylalanine (1.50 g, 11.4 mmol) was stirred and cooled at –78° C. under Ar and then 4-methylmorpholine (NMM) (1.5 mL, 13.7 mmol) was added dropwise. After 2 min of stirring at this temperature, isobutylchloroformate (IBCF) (1.8 mL, 13.7 mmol) was added dropwise leading to the precipitation of a white solid. The reaction was allowed to proceed for additional 2 min and 4-(3-fluorobenzyloxy)benzylamine (2.90 g, 12.6 mmol) was added portionwise at –78° C. The mixture was allowed to stir at room temperature (2 h), and then the white solid filtered and the organic layer concentrated in vacuo. The solid was recrystallized with EtOAc to obtain (R)—N-4-(3-fluorobenzyloxy)benzyl 2-acetamidopropionamide as a white solid (905 mg, 22%): R$_f$=0.16 (EtOAc); mp 158° C.; [α]$^{26.2}_D$ +27.3° (c 1, CHCl$_3$); IR (nujol) 3284, 2937, 2862, 1629, 1546, 1457, 1375, 1242, 1151, 1020, 778, 722 cm$^{-1}$; $^1$H NMR (CDCl$_3$) δ 1.37 (d, J=6.9 Hz, CH$_3$), 1.94 (s, C(O)CH$_3$), 4.32 (d, J=5.7 Hz, CH$_2$N), 4.46-4.56 (m, CH), 5.02 (s, CH$_2$O), 6.41 (d, J=7.5 Hz, NH), 6.79-6.85 (br m, NH), 6.87-6.92 (m, 2 ArH), 7.00 (td, J=2.4, 8.4 Hz, 1 ArH), 7.10-7.20 (m, 4 ArH), 7.30-7.37 (m, 1 ArH), addition of excess (R)-(–)-mandelic acid to a CDCl$_3$ solution of R)—N-4-(3-fluorobenzyloxy)benzyl 2-acetamidopropionamide gave only one signal for the acetyl methyl and one signal for the ether methyl protons; $^{13}$C NMR (CDCl$_3$) δ 18.5 (CH$_3$), 23.1 (C(O)CH$_3$), 43.0 (NCH$_2$), 48.8 (CH), 69.1 (d, J=1.6 Hz, PhCH$_2$O), 114.1 (d, J=21.6 Hz, C$_{4'}$ or C$_{2'}$), 114.8 (d, J=21.0 Hz, C$_{2'}$ or C$_{4'}$), 115.0 (C$_1$), 122.6 (d, J=2.9 Hz, C$_{6'}$), 129.0 (ArC), 130.1 (d, J=8.5 Hz, C$_{5'}$), 130.5 (ArC), 139.5 (d, J=7.4 Hz, C$_{1'}$), 157.9 (C$_4$), 163.0 (d, J=244.7 Hz, C$_{3'}$), 170.0, 172.2 (2C(O)); MS (M+H$^+$) (ESI$^+$) 345.2 [M+H$^+$] (calcd for C$_{19}$H$_{21}$FN$_2$O$_3$H$^+$ 344.2); Anal. Calcd. for C$_{19}$H$_{21}$FN$_2$O$_3$: C, 66.26; H, 6.15; F, 5.44; N, 8.13. Found: C, 65.98; H, 6.10; F, 5.41; N, 8.03.

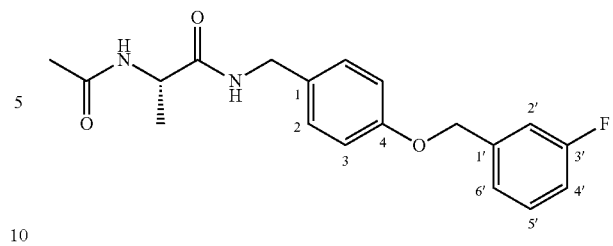

Preparation of (S)—N-4-(3-Fluorobenzyloxy)benzyl 2-Acetamidopropionamide

A THF solution (80 mL) of (S)—N-acetylalanine (1.50 g, 11.4 mmol) was stirred and cooled at –78° C. under Ar and then 4-methylmorpholine (NMM) (1.5 mL, 13.7 mmol) was added dropwise. After 2 min of stirring at this temperature, isobutylchloroformate (IBCF) (1.8 mL, 13.7 mmol) was added dropwise leading to the precipitation of a white solid. The reaction was allowed to proceed for additional 2 min and 4-(3-fluorobenzyloxy)benzylamine (2.90 g, 12.6 mmol) was added portionwise at –78° C. The mixture was allowed to stir at room temperature (2 h), and then the white solid filtered and the organic layer concentrated in vacuo. The solid was recrystallized with EtOAc to obtain (S)—N-4-(3-fluorobenzyloxy)benzyl 2-acetamidopropionamide as a white solid (1.50 g, 38%): R$_f$=0.16 (EtOAc); mp 153-154° C.; [α]$^{26.2}_D$ –28.1° (c 1, CHCl$_3$); IR (nujol) 3286, 2921, 2862, 1631, 1544, 1457, 1375, 1304, 1247, 1151, 1044, 778, 723 cm$^{-1}$; $^1$H NMR (CDCl$_3$) δ 1.38 (d, J=7.2 Hz, CH$_3$), 1.94 (s, C(O)CH$_3$), 4.32 (d, J=5.7 Hz, CH$_2$N), 4.46-4.57 (m, CH), 5.02 (s, CH$_2$O), 6.38-6.46 (br d, NH), 6.78-6.85 (br m, NH), 6.89 (d, J=8.4 Hz, 2 ArH), 6.98-7.04 (m, 1 ArH), 7.10-7.20 (m, 4 ArH), 7.30-7.37 (m, 1 ArH); $^{13}$C NMR (CDCl$_3$) δ 18.4 (CH$_3$), 23.1 (C(O)CH$_3$), 43.0 (NCH$_2$), 48.8 (CH), 69.2 (d, J=1.6 Hz, PhCH$_2$O), 114.1 (d, J=21.6 Hz, C$_{4'}$ or C$_{2'}$), 114.8 (d, J=21.0 Hz, C$_{2'}$ or C$_{4'}$), 115.0 (C$_1$), 122.6 (d, J=2.9 Hz, C$_{6'}$), 129.0 (ArC), 130.1 (d, J=8.0 Hz, C$_{5'}$), 130.5 (ArC), 139.5 (d, J=7.4 Hz, C$_{1'}$), 157.9 (C$_4$), 163.0 (d, J=244.7 Hz, C$_{3'}$), 170.1, 172.1 (2C(O)); MS (M+H$^+$) (ESI$^+$) 345.2 [M+H$^+$] (calcd for C$_{19}$H$_{21}$FN$_2$O$_3$H$^+$ 345.2); Anal. Calcd. for C$_{19}$H$_{21}$FN$_2$O$_3$: C, 66.26; H, 6.15; F, 5.44; N, 8.13. Found: C, 65.98; H, 6.11; F, 5.44; N, 8.05.

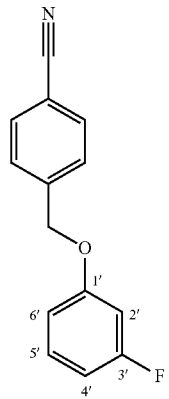 [SMILES: N#Cc1ccc(COc2cccc(F)c2)cc1]

Preparation of 4-((3-Fluorophenoxy)methyl)benzonitrile

A mixture of 4-(bromomethyl)benzonitrile (23.50 g, 120.0 mmol), K$_2$CO$_3$ (55.20 g, 400.0 mmol) and 3-fluorophenol (11.21 g, 100.0 mmol) were heated at reflux in acetone (400 mL) (16 h). The volatiles were evaporated and the residue was diluted with CH$_2$Cl$_2$ (300 mL). The organic layer was washed with H$_2$O (300 mL), dried (MgSO$_4$) and concentrated in vacuo to give white needles (19.81 g, 87%): R$_f$=0.40 (9/1 hexanes/ethyl acetate); mp 69-70° C.; $^1$H NMR (CDCl$_3$) δ 5.02 (s, CH$_2$O), 6.56-6.67 (m, 3 ArH), 7.16 (q, J=7.7 Hz, 1 ArH), 7.45 (d, J=7.1 Hz, 2 ArH), 7.59 (d, J=8.1 Hz, 2 ArH); $^{13}$C NMR (CDCl$_3$) δ 60.1 (CH$_2$O), 102.8 (d, J=24.4 Hz, C$_{2'}$ or C$_{4'}$), 108.3 (d, J=21.1 Hz, C$_{4'}$ or C$_{2'}$), 110.4 (d, J=2.8 Hz, C$_{6'}$), 111.9 (Are), 118.6 (CN), 127.5 (ArC), 130.4 (d, J=9.7 Hz, C$_{5'}$), 132.4, 141.9 (2 Are), 159.4 (d, J=10.8 Hz, C$_{1'}$), 163.6 (d, J=244.2 Hz, C$_{3'}$); LRMS (M+Na$^+$) (ESI$^+$) 250.0 [M+Na$^+$] (calcd for C$_{14}$H$_{10}$NONa$^+$ 250.0).

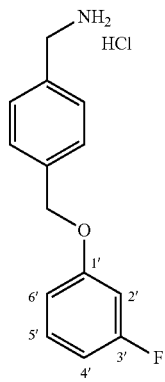 [SMILES: NCc1ccc(COc2cccc(F)c2)cc1 ; Cl]

Preparation of
4-((3-Fluorophenoxy)methyl)benzylamine
Hydrochloride

To a LiAlH$_4$ (5.02 g, 132.0 mmol) suspension in THF (400 mL) was added dropwise at 0° C., a THF (30 mL) solution of 4-((3-fluorophenoxy)methyl)benzonitrile (10.00 g, 44.0 mmol). The mixture was stirred at room temperature (16 h). Then, H$_2$O (4 mL) was added dropwise at 0° C. followed by an aqueous NaOH solution (2 mL, 15% w/w) and H$_2$O (4 mL). The mixture was stirred at room temperature (2 h), and the precipitate was filtered and the pad was washed with CH$_2$Cl$_2$. The filtrate was concentrated in vacuo. The residue was solubilized in Et$_2$O (50 mL) and then HCl in Et$_2$O (1 M) was added dropwise at 0° C. The white precipitate was filtered to obtain 9.16 g (78%) of 3 as a white solid: R$_f$=0.00 (hexanes/EtOAc 9/1); mp 240-245° C.; IR (nujol mull) 2896, 2726, 1595, 1458, 1376, 1275, 1135, 1029, 963, 828, 768 cm$^{-1}$; $^1$H NMR (DMSO-d$_6$) δ 4.01 (s, CH$_2$NH$_2$), 5.14 (s, CH$_2$O), 6.74-6.91 (m, 2 ArH), 7.20-7.39 (m, 2 ArH), 7.48 (d, J=7.9 Hz, 2 ArH), 7.53 (d, J=7.9 Hz, 2 ArH), 8.38-8.64 (br s, NH$_3$Cl); $^{13}$C NMR (CDCl$_3$) δ 41.7 (CH$_2$NH$_3$), 60.0 (CH$_2$O), 102.3 (d, J=24.4 Hz, C$_{2'}$ or C$_{4'}$), 107.3 (d, J=21.0 Hz, C$_{4'}$ or C$_{2'}$), 111.1 (d, J=2.8 Hz, C$_{6'}$), 127.8, 129.1 (2 ArC), 130.6 (d, J=10.2 Hz, C$_{5'}$), 133.7, 136.7 (2 ArC), 159.6 (d, J=11.3 Hz, C$_{1'}$), 162.9 (d, J=241.3 Hz, C$_{3'}$); HRMS (M+H$^+$) (ESI$^+$) 232.1138 [M+H$^+$] (calcd for C$_{14}$H$_{14}$FNOH$^+$ 232.1137).

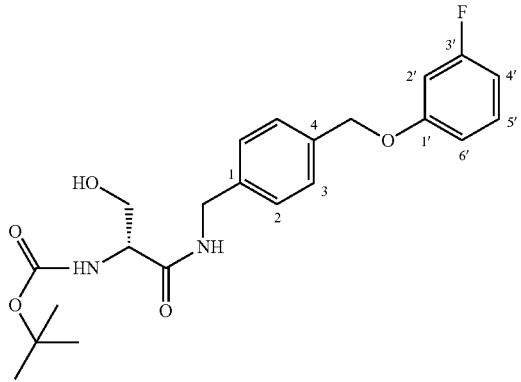 [SMILES: CC(C)(C)OC(=O)N[C@H](CO)C(=O)NCc1ccc(COc2cccc(F)c2)cc1]

Preparation of (R)—N-(4-(3-Fluorophenoxy)methyl)
benzyl 2-N-(tert-Butoxycarbonyl)amino-3-hydroxypropionamide Using Method C, (R)-t-Boc-serine (5.00 g, 24.4 mmol), 4-methylmorpholine (NMM) (3.2 mL, 29.3 mmol), isobutylchloroformate (IBCF) (3.8 mL, 29.3 mmol), THF (300 mL) and 4-((3-fluorophenoxy)methyl)benzylamine (6.20 g, 26.8 mmol) gave (R)—N-(4-(3-fluorophenoxy)methyl)benzyl 2-N-(tert-butoxycarbonyl)amino-3-hydroxypropionamide as a white solid (5.20 g, 51%): R$_f$=0.40 (EtOAc); mp 85-86° C.; [α]$^{23.4}_D$ +27.9° (c 1, CHCl$_3$); IR (nujol mull) 3324, 2927, 1652, 1524, 1457, 1378, 1306, 1275, 1242, 1166, 1011, 835, 766, 674, 572 cm$^{-1}$; $^1$H NMR (CDCl$_3$) δ 1.41 (s, (CH$_3$)$_3$C), 3.42-3.58 (br m, CHH'), 3.61-3.72 (br m, CHH'), 4.02-4.11 (m, CH), 4.13-4.22 (br m, OH), 4.33-4.42 (br m, CH$_2$N), 5.00 (s, OCH$_2$), 5.63-5.74 (br m, NH), 6.34-6.75 (m, 3 ArH), 7.09-7.26 (m, 4 ArH), 7.35 (d, J=7.5 Hz, ArH); $^{13}$C NMR (CDCl$_3$) δ 28.2 ((CH$_3$)$_3$C), 43.0 (NCH$_2$), 54.9 (OCH$_2$CH), 62.8 (OCH$_2$CH), 69.8 (OCH$_2$) 80.6 ((CH$_3$)$_3$C), 102.6 (d, J=24.5 Hz, C$_{4'}$ or C$_{2'}$), 107.8 (d, J=21.1 Hz, C$_{2'}$ or C$_{4'}$), 110.6 (d, J=2.9 Hz, C$_{6'}$), 127.7, 127.8 (2 ArC), 130.2 (d, J=9.7 Hz, C$_{5'}$), 135.7, 137.7 (2 ArC), 156.3 (OC(O)NH), 160.0 (d, J=10.8 Hz, C$_{1'}$), 163.6 (d, J=243.6 Hz, C$_{3'}$), 171.4 (C(O)); HRMS (M+H$^+$) (ESI$^+$) 419.1982 [M+H$^+$] (calcd for C$_{22}$H$_{27}$FN$_2$O$_5$H$^+$ 419.1982); Anal. Calcd. for C$_{22}$H$_{27}$FN$_2$O$_5$: C, 63.14; H, 6.50; F, 4.54; N, 6.69. Found: C, 62.90; H, 6.83; F, 4.18; N, 7.03.

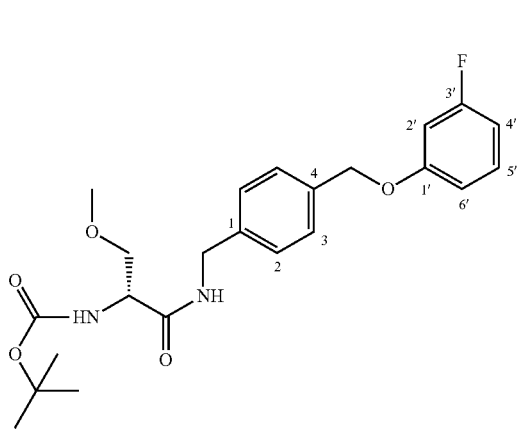 [SMILES: COC[C@@H](NC(=O)OC(C)(C)C)C(=O)NCc1ccc(COc2cccc(F)c2)cc1]

Preparation of (R)—N-(4-(3-Fluorophenoxy)methyl) benzyl 2-N-(tert-Butoxycarbonyl)amino-3-methoxypropionamide Ag$_2$O (12.80 g, 55.0 mmol) was added to a CH$_3$CN solution (200 mL) of (R)—N-(4-(3-fluorophenoxy)methyl)benzyl 2-N-(tert-butoxycarbonyl)amino-3-hydroxypropionamide (4.60 g, 11.0 mmol) and then CH$_3$I (6.85 mL, 110.0 mmol) was added at room temperature under Ar. The reaction mixture was stirred at room temperature (4 d), filtered, and the filtrate concentrated in vacuo. The residue was purified by column chromatography (SiO$_2$; 1/1 EtOAc/hexanes) to obtain 4.30 g (91%) of a white solid: R$_f$=0.55 (1/1 EtOAc/hexanes); mp 77-79° C.; [α]$^{26}_D$ −17.8° (c 1, CHCl$_3$); IR (nujol mull) 3101, 2927, 2860, 1689, 1648, 1529, 1458, 1375, 1323, 1266, 1165, 1087, 1048, 961, 825, 762, 674 cm$^{-1}$; $^1$H NMR (CDCl$_3$) δ 1.43 (s, (CH$_3$)$_3$C), 3.36 (s, OCH$_3$), 3.50 (dd, J=6.3, 9.3 Hz, CHH'OCH$_3$), 3.82-3.87 (m, CHH'OCH$_3$), 4.22-4.33 (br m, CHCHH'), 4.49 (d, J=5.1 Hz, CH$_2$N), 5.02 (s, CH$_2$O), 5.39-5.46 (br m, NH), 6.66-6.76 (m, 3 ArH, NH), 7.14-7.23 (m, 1 ArH), 7.28 (d, J=7.9 Hz, 2 ArH), 7.37 (d, J=7.9 Hz, 2 ArH); $^{13}$C NMR (CDCl$_3$) δ 28.2 ((CH$_3$)$_3$C), 43.1 (NCH$_2$), 54.1 (OCH$_2$CH), 59.1 (OCH$_3$), 69.9 (OCH$_2$), 72.0 (OCH$_2$CH), 80.6 ((CH$_3$)$_3$C), 102.6 (d, J=24.5 Hz, C$_4'$ or C$_2'$), 107.8 (d, J=21.0 Hz, C$_2'$ or C$_4'$), 110.6 (d, J=2.9 Hz, C$_6'$), 127.7, 127.8 (2 ArC), 130.2 (d, J=9.7 Hz, C$_5'$), 135.7, 138.0 (2 ArC), 155.5 (OC(O)NH), 160.0 (d, J=10.8 Hz, C$_1'$), 163.6 (d, J=243.6 Hz, C$_3'$), 170.3 (C(O)); Anal. Calcd. For C$_{23}$H$_{29}$FN$_2$O$_5$: C, 63.87; H, 6.76; F, 4.39; N, 6.48. Found: C, 63.43; H, 6.76; F, 4.25; N, 6.57.

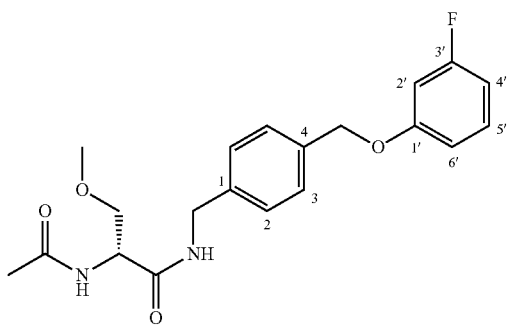 [SMILES: COC[C@@H](NC(C)=O)C(=O)NCc1ccc(COc2cccc(F)c2)cc1]

Preparation of (R)—N-4-((3-Fluorophenoxy)methyl) benzyl 2-Acetamido-3-methoxypropionamide A saturated HCl solution in dioxane (1 mmol/2 mL, 102 mL) was added to (R)—N-(4-(3-fluorophenoxy)methyl)benzyl2-N-(tert-butoxycarbonyl)amino-3-methoxypropionamide (2.20 g, 5.1 mmol) at 0° C. and the solution was stirred at room temperature (2 h). The reaction solution was concentrated in vacuo and dried (30 min) to provide (R)-2-amino-N-4-((3-fluorophenoxy)methyl)benzyl-3-methoxypropionamide hydrochloride as a white solid (1.80 g, quant.): mp 128-130° C.; [α]$^{23.8}_D$ +17.6° (c 0.5, H$_2$O); IR (nujol mull) 3145, 2915, 1660, 1569, 1459, 1376, 1274, 1138, 1017, 961, 832, 777, 724, 683 cm$^{-1}$; $^1$H NMR (DMSO-d$_6$) δ 3.30 (s, OCH$_3$), 3.72 (d, J=5.1 Hz, CH$_2$), 3.99-4.11 (br m, CH), 4.35 (d, J=3.6 Hz, NCH$_2$), 5.10 (s, OCH$_2$), 6.74-6.91 (m, 3 ArH), 7.26-7.35 (m, 3 ArH), 7.41 (d, J=7.8 Hz, 2 ArH), 8.28-8.41 (br s, NH$_3$), 9.11-9.19 (br t, NHC(O)); $^{13}$C NMR (DMSO-d$_6$) δ 42.0 (NCH$_2$), 52.1 (OCH$_2$CH), 58.4 (OCH$_3$), 69.2 (CH$_2$O), 70.3 (OCH$_2$CH), 102.2 (d, J=24.5 Hz, C$_4'$ or C$_2'$), 107.3 (d, J=21.1 Hz, C$_2'$ or C$_4'$), 111.0-111.2 (br d, C$_6'$), 127.3, 127.8 (2 ArC), 130.1 (d, J=9.7 Hz, C$_5'$), 135.2, 138.3 (2 ArC), 159.7 (d, J=10.9 Hz, C$_1'$), 162.9 (d, J=241.3 Hz, C$_3'$), 166.3 (C(O)); HRMS (M+H$^+$)(ESI) 333.1614 [M+H$^+$] (calcd for C$_{18}$H$_{21}$FN$_2$O$_3$H$^+$ 333.1614). Anal. Calcd. For C$_{18}$H$_{22}$ClFN$_2$O$_3$: C, 58.62; H, 6.01; Cl, 9.61; F, 5.15; N, 7.58. Found: C, 58.41; H, 6.19; Cl, 9.81; F, 4.93; N, 7.58.

Triethylamine (1.5 mL, 5.2 mmol) and acetyl chloride (380 μL, 10.7 mmol) were carefully added at 0° C. to a CH$_2$Cl$_2$ (20 mL) solution of (R)—N-4-((3-fluorophenoxy)methyl)benzyl 2-amino-3-methoxypropionamide hydrochloride (1.30 g, 3.5 mmol) and the resulting solution was stirred at room temperature (2 h). An aqueous 10% citric acid solution (30 mL) was added and the organic layer was extracted with CH$_2$Cl$_2$ (3×30 mL). The organic layers were combined, washed with a saturated aqueous NaHCO$_3$ solution (40 mL), dried (MgSO$_4$), and concentrated in vacuo. The solid was recrystallized (EtOAc) to obtain 900 mg (68%) of the desired product as a white solid: R$_f$=0.18 (EtOAc); mp 140-142° C.; [α]$^{26.9}_D$ −21.0° (c 1, CHCl$_3$); IR (nujol mull) 3279, 2947, 2858, 1739, 1629, 1552, 1457, 1374, 1273, 1203, 1133, 1103, 1044, 960, 914, 829, 768, 724 cm$^{-1}$; $^1$H NMR (CDCl$_3$) δ 2.04 (s, CH$_3$CO), 3.41 (s, OCH$_3$), 3.43 (dd, J=7.5, 9.2 Hz, CHH'), 3.82 (dd, J=3.9, 9.2 Hz, CHH'), 4.47-4.59 (m, CH$_2$N, CH), 5.03 (s, OCH$_2$), 6.38-6.43 (br d, NHC(O)CH$_3$), 6.64-6.78 (m, 3 ArH, CH$_2$NH), 7.14-7.30 (m, 3 ArH), 7.40 (d, J=8.4 Hz, 2 ArH), addition of excess (R)-(−)-mandelic acid to a CDCl$_3$ solution of (R)—N-4-((3-fluorophenoxy)methyl)benzyl 2-acetamido-3-methoxypropionamide gave only one signal for the acetyl methyl and one signal for the ether methyl protons; $^{13}$C NMR (CDCl$_3$) 23.2 (C(O)CH$_3$), 43.2 (NCH$_2$), 52.4 (CHCH$_2$), 59.1 (OCH$_3$), 69.9 (ArCH$_2$O), 71.7 (CH$_2$O), 102.6 (d, J=25.1 Hz, C$_4'$ or CA 107.8 (d, J=21.6 Hz, C$_2'$ or C$_4'$), 110.5 (d, J=2.9 Hz, C$_6'$), 127.7, 129.8 (2 ArC), 130.2 (d, J=9.7 Hz, C$_5'$), 135.7, 137.9 (2 ArC), 160.0 (d, J=10.8 Hz, C$_1'$), 163.6 (d, J=244.2 Hz, C$_3'$), 170.0, 170.3 (2C(O)); LRMS (M+Na$^+$) (ESI$^+$) 397.1 [M+Na$^+$] (calcd for C$_{20}$H$_{23}$FN$_2$O$_4$H$^+$ 397.1); Anal. Calcd. for C$_{20}$H$_{23}$FN$_2$O$_4$: C, 64.16; H, 6.19; F, 5.07; N, 7.48. Found: C, 63.86; H, 6.13; F, 4.88; N, 7.50.

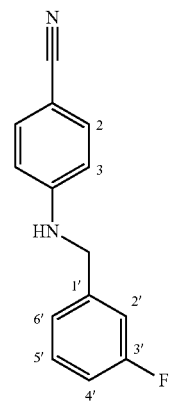 [SMILES: N#Cc1ccc(NCc2cccc(F)c2)cc1]

Preparation of 4-(3-Fluorobenzylamino)benzonitrile

In a flame-dried Schlenk tube, Pd(OAc)$_2$ (304 mg, 1.3 mmol), Binap (1.69 g, 2.7 mmol), and 4-bromobenzonitrile (5.00 g, 27.1 mmol) were added under Ar to a stirring solution of 3-fluorobenzylamine (3.80 g, 30.4 mmol) and Cs$_2$CO$_3$ (13.20 g, 40.6 mmol) in dioxane (55 mL). The mixture was stirred at 80° C. (16 h) and then the volatiles were evaporated. CH$_2$Cl$_2$ (100 mL) and H$_2$O (100 mL) were added and the layers separated. The aqueous layer was washed with CH$_2$Cl$_2$ (2×100 mL). The organic layers were combined, dried and concentrated under vacuum. The crude residue was purified by column chromatography (SiO$_2$; EtOAc/hexanes 0/10 to 3/7) to obtain 4.90 g (78%) of a yellow solid: $R_f$=0.36 (1/9 EtOAc/hexanes); mp 63-64° C.; IR (nujol mull) 2934, 2861, 2214, 1739, 1605, 1527, 1457, 1375, 1285, 1248, 1164, 915, 824, 784, 730 cm$^{-1}$; $^1$H NMR (CDCl$_3$) δ 4.39 (s, CH$_2$N), 4.59-4.74 (br m, NH), 6.57 (d, J=8.8 Hz, 2H$_3$), 6.94-7.05 (m, 2ArH), 7.11 (d, J=7.5 Hz, H$_{6'}$), 7.28-7.36 (m, 1 ArH), 7.42 (d, J=8.8 Hz, 2H$_2$); $^{13}$C NMR (CDCl$_3$) δ 46.8 (d, J=1.7 Hz, NCH$_2$), 99.9 (CN), 112.4 (ArC), 113.9 (d, J=22.2 Hz, C$_{4'}$ or C$_{2'}$), 114.4 (d, J=21.1 Hz, C$_{2'}$ or C$_{4'}$), 120.3 (ArC), 122.5 (d, J=2.9 Hz, C$_{6'}$), 130.3 (d, J=8.6 Hz, C$_{5'}$), 133.7 (ArC), 140.6 (d, J=6.8 Hz, C$_{1'}$), 150.9 (ArC), 163.1 (d, J=245.3 Hz, C$_{3'}$); HRMS (M+H$^+$) (ESI$^+$) 227.0985 [M+H$^+$] (calcd for C$_{14}$H$_{11}$FN$_2$H$^+$227.0984).

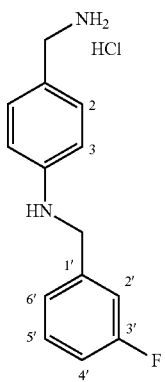 [SMILES: NCc1ccc(NCc2cccc(F)c2)cc1 ; Cl]

Preparation of 4-(3-Fluorobenzylamino)benzylamine Hydrochloride

To a LiAlH$_4$ (1.01 g, 26.5 mmol) suspension in THF (75 mL) was added dropwise a THF (15 mL) solution of 4-(3-fluorobenzylamino)benzonitrile (2.00 g, 8.8 mmol) at 0° C. The mixture was stirred at room temperature (16 h) and then H$_2$O (815 μL) was added dropwise at 0° C. followed by an aqueous NaOH solution (407 μL, 15% w/w) and then H$_2$O (815 μL). The mixture was stirred at room temperature (2 h) and the precipitate was filtered and was washed with CH$_2$Cl$_2$. The filtrate was concentrated in vacuo, and then Et$_2$O (10 mL) followed by HCl (1 M) in Et$_2$O (13.3 mL, 13.3 mmol) were added to give 1.80 g of a yellow solid (78%): $R_f$=0.00 (hexanes/EtOAc 9/1); mp 211° C. (decomp.) $^1$H NMR (DMSO-d$_6$) δ 2.51 (br t, J=1.8 Hz, NH), 3.79-3.90 (m, CH$_2$N), 4.39 (s, CH$_2$N), 6.87 (d, J=7.8 Hz, 2H$_3$), 7.03-7.12 (m, 1 ArH), 7.24-7.41 (m, 5 ArH), 8.21-8.32 (br s, NH$_3$); $^{13}$C NMR (DMSO-d$_6$) δ 47.4, 47.8 (2 CH$_2$N), 113.9 (d, J=20.5 Hz, C$_{4'}$ or C$_{2'}$), 114.6 (d, J=21.1 Hz, C$_{2'}$ or C$_{4'}$), 115.3, 124.0 (2 ArC), 124.4 (br m, Ca 130.0 (ArC), 130.2 (d, J=8.5 Hz, C$_{5'}$), 133.7 (ArC), 140.7-140.8 (br m, C$_{1'}$), 144.8 (ArC), 162.1 (d, J=241.9 Hz, C$_{3'}$); HRMS (M+H$^+$) (ESI$^+$) 231.1298 [M+H$^+$] (calcd for C$_{14}$H$_{16}$FN$_2$H$^+$231.1297).

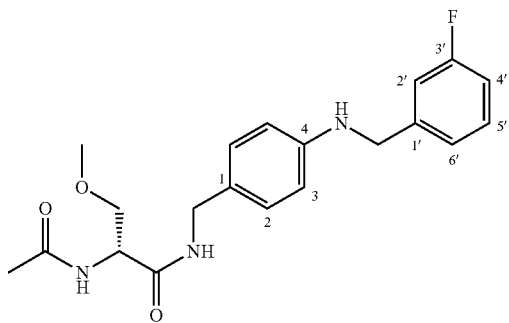 [SMILES: COC[C@@H](NC(C)=O)C(=O)NCc1ccc(NCc2cccc(F)c2)cc1]

Preparation of (R)—N-4-(3-Fluorobenzylamino)benzyl 2-Acetamido-3-methoxypropionamide 4-(3-Fluorobenzylamino)benzylamine hydrochloride (293 mg, 1.1 mmol) was added to a THF (10 mL) solution of the (R)-2-acetamido-3-methoxypropanoic acid (161 mg, 1.0 mmol) and the mixture was stirred at room temperature (5 min) and then NMM (121 μL, 1.1 mmol) was added. The mixture was stirred at room temperature (5 min) and DMTMM (332 mg, 1.2 mmol) was added, and the mixture was stirred at room temperature (16 h). The white precipitate was filtered and the filtrate was concentrated in vacuo. The residue was purified by flash column chromatography on silica gel with EtOAc/hexanes (5/5) to EtOAc/acetone (5/5) as the eluant to obtain (R)—N-4-(3-fluorobenzylamino)benzyl 2-acetamido-3-methoxypropionamide as a yellow solid (140 mg, 35%): $R_f$=0.37 (EtOAc); mp 78-81° C.; $[α]^{26.9}_D$ −15.0° (c 0.5, CHCl$_3$); IR (nujol mull) 3160, 2919, 2857, 1736, 1630, 1523, 1457, 1375, 1259, 1125, 784, 726 cm$^{-1}$; $^1$H NMR (CDCl$_3$): δ 2.03 (s, CH$_3$CO), 3.36 (s, OCH$_3$), 3.40 (dd, J=7.2, 9.0 Hz, CHH'), 3.82 (dd, J=4.2, 9.0 Hz, CHH'), 4.12-4.19 (br m, CH$_2$NH), 4.31-4.37 (m, 2 CH$_2$N), 4.46-4.52 (m, CH), 6.38-6.45 (br m, NHC(O)CH$_3$), 6.57 (d, J=9.0 Hz, 2 ArH, NH), 6.91-6.89 (m, 1 ArH), 7.05-7.15 (m, 4 ArH), 7.27-7.34 (m, 1 ArH), addition of excess (R)-(−)-mandelic acid to a CDCl$_3$ solution of (R)—N-4-(3-fluorobenzylamino) benzyl 2-acetamido-3-methoxypropionamide gave only one signal for the acetyl methyl and one signal for the ether methyl protons; $^{13}$C NMR (CDCl$_3$) 23.2 (C(O)CH$_3$), 43.3 (NCH$_2$), 47.7 (d, J=1.7 Hz, CH$_2$N(H)Ph), 52.4 (CHCH$_2$), 59.0 (OCH$_3$), 71.7 (CH$_2$O), 113.0 (C$_3$), 114.0 (d, J=20.5 Hz, C$_{2'}$ or C$_{4'}$), 114.1 (d, J=21.7 Hz, C$_{2'}$ or C$_{4'}$), 122.7 (d, J=2.3 Hz, C$_{6'}$), 126.8 (C$_1$), 128.9 (C$_2$), 130.1 (d, J=8.6 Hz, C$_{5'}$), 142.1 (d, J=6.8 Hz, C$_{1'}$), 147.2 (C$_4$), 163.1 (d, J=224.5 Hz, C$_{3'}$), 169.7, 170.2 (2C(O)); HRMS (M+H$^+$) (ESI$^+$) 374.1880 [M+H$^+$] (calcd for C$_{20}$H$_{24}$FN$_3$O$_3$H$^+$ 374.1879).

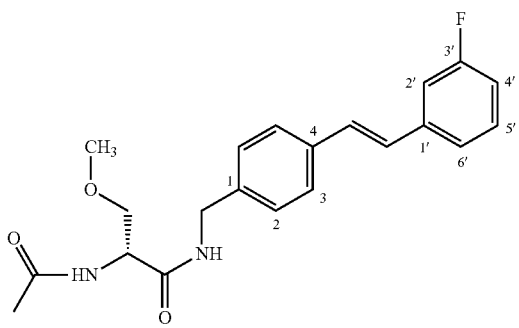 [SMILES: COC[C@@H](NC(C)=O)C(=O)NCc1ccc(/C=C/c2cccc(F)c2)cc1]

Preparation of (2-R,E)-N-4-(3-Fluorostyryl)benzyl 2-Acetamido-3-methoxypropionamide To a flame-dried Schlenck tube, under Ar, containing a dioxane (22.5 mL) solution of (R)—N-(4-iodo)benzyl 2-acetamido-3-methoxypropionamide (1.50 g, 4.0 mmol), palladiumtetrakis(triphenylphosphine) (464 mg, 0.402) and trans-2-(3-fluorophenyl)vinylboronic acid (800 mg, 4.82 mmol) was added an aqueous solution (9 mL) of $Cs_2CO_3$ (2.60 g, 8.0 mmol). The mixture was stirred at reflux (16 h). Then, MeOH and silica gel were added. The volatiles were concentrated in vacuo and the residue was purified by flash chromatography on silica gel with EtOAc/MeOH (10/0 to 9/1) as the eluant to obtain (2-R,E)-N-4-(3-fluorostyryl)benzyl 2-acetamido-3-methoxypropionamide (0.90 g, 60%) as a yellowish solid. To remove traces of palladium impurities, the solid was treated with 6.00 g of resin scavenger (SPM32, PhosPhonics) in $CH_2Cl_2$. The mixture was stirred at room temperature (2 h), and filtered, the filtrate evaporated under vacuum to obtain 560 mg (37%) of (R,E)-N-4-(3-fluorostyryl)benzyl 2-acetamido-3-methoxypropionamide as a white solid: $R_f$=0.53 (EtOAc); mp 206-208° C.; $[\alpha]^{27}_D$=−20.6° (c 0.5, $CHCl_3$); IR (nujol mull) 3280, 3098, 2918, 2859, 1640, 1556, 1456, 1375, 1304, 1264, 1138, 1045, 963, 856, 780, 736, 605 $cm^{-1}$; $^1H$ NMR ($CDCl_3$) δ 2.04 (s, $CH_3C(O)$), 3.40 (s, $OCH_3$), 3.40-3.48 (m, CHH'O), 3.83 (d, J=3.9, 8.7 Hz, CHH'O), 4.47-4.56 (m, $CH_2N$, NC(H)CO), 6.41-6.49 (br d, $NHC(O)CH_3$), 6.75-7.02 (br t, $CH_2NH$), 6.92-7.01 (m), 7.07 (d, J=2.7 Hz), 7.18-7.35 (m), 7.47 (d, J=8.4 Hz) (8 ArH, 2 vinyl H), addition of excess (R)-(−)-mandelic acid to a $CDCl_3$ solution of (R,E)-N-4-(3-fluorostyryl)benzyl 2-acetamido-3-methoxypropionamide gave only one signal for the acetyl methyl and one signal for the ether methyl protons; $^{13}C$ NMR (DMSO-$d_6$) δ 22.5 ($CH_3CO$), 41.7 ($CH_2N$), 52.6 ($CHCH_2$), 58.1 ($OCH_3$), 72.0 ($CH_2OCH_3$), 112.3 (d, J=22.2 Hz, $C_{2'}$ or $C_{4'}$), 114.1 (d, J=20.5 Hz, $C_{4'}$ or $C_{2'}$), 122.7-122.8 (br d, $C_{6'}$), 126.4 ($C_2$ or $C_3$), 126.7 (CH=CH), 127.3 ($C_3$ or $C_2$), 129.7 (CH=CH'), 130.5 (d, J=8.5 Hz, $C_{1'}$ or $C_{5'}$), 135.1, 139.1 ($C_1$, $C_4$), 139.7 (d, J=8.6 Hz, $C_{1'}$ or $C_{5'}$), 162.5 (d, J=241.3 Hz, $C_{3'}$), 169.3, 169.7 (2C(O)); LRMS (M+$Na^+$) ($ESI^+$) 393.1 [M+$Na^+$] (calcd for $C_{21}H_{23}FN_2O_3Na^+$ 393.1); Anal. Calcd. for $C_{21}H_{23}FN_2O_3$: C, 68.09; H, 6.26; F, 5.13; N, 7.56. Found: C, 67.81; H, 6.32; F, 4.88; N, 7.34.

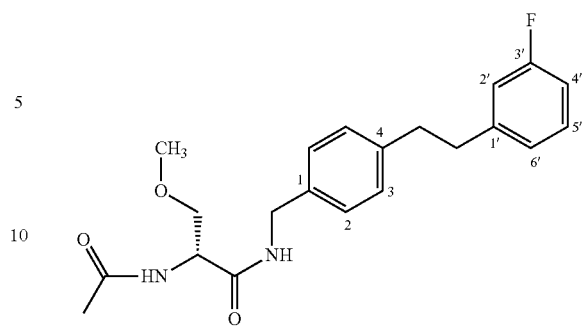

Preparation of (R)—N (4-(3-Fluorophenethyl)benzyl 2-Acetamido-3-methoxypropionamide Pd/C (18 mg) was added to an EtOH solution of (2-R,E)-N-4-(3-fluorostyryl)benzyl 2-acetamido-3-methoxypropionamide (180 mg, 0.49 mmol), and the mixture was stirred at room temperature under $H_2$ (1 atm) (36 h). The reaction mixture was filtered through a pad of Celite®, and the pad was washed successively with EtOH and $CH_2Cl_2$. The filtrate was concentrated under vacuum to obtain (R)—N-(4-(3-fluorophenethyl)benzyl 2-acetamido-3-methoxypropionamide (170 mg, 94%) as a white solid: $R_f$=0.29 (EtOAc); mp 134-136° C.; $[\alpha]^{24.4}_D$=−12.3° (c 0.48, $CHCl_3$); IR (nujol) 3140, 2943, 2870, 2729, 2670, 1631, 1542, 1457, 1374, 1305, 1136, 938, 842, 726 $cm^{-1}$; $^1H$ NMR (400 MHz, $CDCl_3$) δ 2.03 (s, $CH_3C(O)$), 2.90 (s, 2 $CH_2Ar$), 3.38 (s, $OCH_3$), 3.43 (dd, J=7.6, 9.2 Hz, CHH'), 3.81 (dd, J=4.0, 9.2 Hz, CHH'), 4.40-4.47 (m, $CH_2N$), 4.50-4.55 (m, NC(H)CO), 6.41-6.47 (br m, CHNH), 6.68-6.75 (br m, $CH_2NH$), 6.84-6.94 (m, 3 ArH), 7.11-7.25 (m, 5 ArH), addition of excess (R)-(−)-mandelic acid to a $CDCl_3$ solution of (R)—N-(4-(3-fluorophenethyl)benzyl 2-acetamido-3-methoxypropionamide gave only one signal for the acetyl methyl and one signal for the ether methyl protons; $^{13}C$ NMR (75 MHz, $CDCl_3$) δ 23.2 ($CH_3CO$), 37.1 ($CH_2Ph$), 37.4 (d, J=1.7 Hz, $CH_2Ph$), 43.3 ($CH_2N$), 52.4 ($CHCH_2$), 59.1 ($OCH_3$), 71.7 ($CH_2OCH_3$), 112.8 (d, J=21.1 Hz, $C_{2'}$ or $C_{4'}$), 115.2 (d, J=20.5 Hz, $C_{4'}$ or $C_{2'}$), 124.1 (d, J=2.8 Hz, $C_{6'}$), 127.5, 128.7 ($C_2$, $C_3$), 129.7 (d, J=8.0 Hz, $C_{1'}$), 135.6 ($C_1$), 140.5 ($C_4$), 144.1 (d, J=6.8 Hz, $C_{5'}$), 162.8 (d, J=243.6 Hz, $C_{3'}$), 169.9, 170.3 (2C(O)); HRMS (M+$H^+$) ($ESI^4$) 373.1927 [M $H^+$] (calcd for $C_{21}H_{25}FN_2O_3H^+$ 373.1927); Anal. Calcd. for $C_{21}H_{25}FN_2O_3 \cdot 0.32H_2O$: C, 66.70; H, 6.83; N, 7.41. Found: C, 66.35; H, 6.59; N, 7.28.

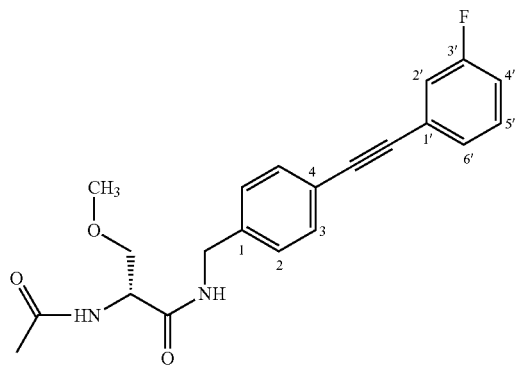 [SMILES: COC[C@@H](NC(C)=O)C(=O)NCc1ccc(C#Cc2cccc(F)c2)cc1]

Preparation of (R)—N-4-((3-Fluorophenyl)ethynyl)benzyl 2-Acetamido-3-methoxypropionamide To an anhydrous THF (70 mL) solution of (R)—N-(4-iodo) benzyl 2-acetamido-3-methoxypropionamide (2.60 g, 7.0 mmol) were sequentially added triethylamine (0.95 mL, 14.0 mmol), (3-fluoro)phenylacetylene (1.20 ml, 10.37 mmol), dichlorobis(triphenylphosphine)palladium (II) (491 mg, 0.70 mmol), and CuI (200 mg, 0.1.05 mmol) under Ar. The mixture was stirred at room temperature (16 h), and then MeOH and silica gel were added. The volatiles were concentrated in vacuo and the residue was purified by flash chromatography on silica gel with EtOAc/MeOH (9/1) as the eluant to obtain (R)—N-4-((3-fluorophenyl)ethynyl)benzyl 2-acetamido-3-methoxypropionamide (2.40 g, 93%) as a yellowish solid. To remove traces of palladium impurities, the solid was treated with 21.00 g of resin scavenger (SPM32, PhosPhonics) in CH$_2$Cl$_2$. The mixture was stirred at room temperature (2 h), and filtered, the filtrate evaporated under vacuum. The solid was recrystallized with EtOAc to obtain 1.20 g (46%) of (R)—N-4-((3-fluorophenyl)ethynyl)benzyl 2-acetamido-3-methoxypropionamide as a white solid: R$_f$=0.26 (EtOAc); mp 200-202° C.; [α]$^{24}_D$=−2.6° (c 0.5, CHCl$_3$); IR (nujol mull) 3285, 3097, 2934, 2862, 2356, 1638, 1566, 1457, 1375, 1307, 1264, 1203, 1135, 1104, 1045, 941, 863, 777, 737, 608, 524 cm$^{-1}$; $^1$H NMR (DMSO-d$_6$) δ 1.88 (s, CH$_3$C(O)), 3.27 (s, OCH$_3$), 3.48-3.57 (m, CH$_2$O), 4.33 (d, J=6.1 Hz, CH$_2$N), 4.45-4.53 (m, NC(H)CO), 7.25-7.32 (m, 3 ArH), 7.38-7.53 (m, 5 ArH), 8.13 (d, J=6.3 Hz, NHC(O)CH$_3$), 8.56 (br t, J=6.1 Hz, CH$_2$NH), addition of excess (R)-(−)-mandelic acid to a CDCl$_3$ solution of (R)—N-4-((3-fluorophenyl)ethynyl)benzyl 2-acetamido-3-methoxypropionamide gave only one signal for the acetyl methyl and one signal for the ether methyl protons; $^{13}$C NMR (DMSO-d$_6$) δ 22.5 (CH$_3$CO), 41.7 (CH$_2$N), 52.6 (CHCH$_2$), 58.1 (OCH$_3$), 72.0 (CH$_2$OCH$_3$), 87.6 (CC), 90.2 (CC), 115.9 (d, J=20.5 Hz, C$_{2'}$ or C$_{4'}$), 117.8 (d, J=22.7 Hz, C$_{4'}$ or C$_{2'}$), 119.9 (C$_4$), 124.2 (d, J=9.7 Hz, C$_{1'}$ or C$_{5'}$), 127.2 (C$_2$), 127.6 (d, J=2.2 Hz, C$_{6'}$), 130.8 (d, J=8.6 Hz, C$_1$ or C$_5$), 131.3 (C$_3$), 140.6 (C$_1$), 161.8 (d, J=243.1 Hz, C$_{3'}$), 169.4, 169.8 (2C(O)); HRMS (M+H$^+$) (ESI$^+$) 369.1614 [M+H$^+$] (calcd for C$_{21}$H$_{21}$FN$_2$O$_3$H$^+$ 369.1614); Anal. Calcd. for C$_{21}$H$_{21}$FN$_2$O$_3$: C, 68.46; H, 5.75; F, 5.16; N, 7.60. Found: C, 68.51; H, 5.92; F, 5.34; N, 7.56.

Reaction overview

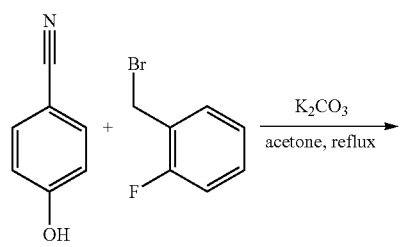

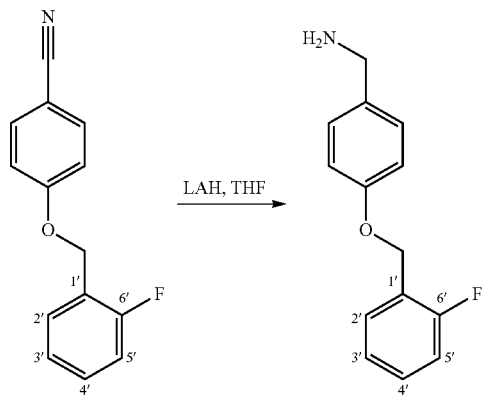

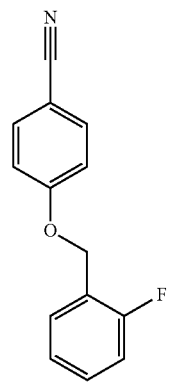

Preparation of 4-(2-Fluorobenzyloxy)benzonitrile

A mixture of 4-cyanophenol (11.91 g, 100.0 mmol), K$_2$CO$_3$ (55.20 g, 400.0 mmol), and 2-fluorobenzylbromide (22.68 g, 120.0 mmol) were heated in acetone (400 mL) at reflux (5 h). The volatiles were evaporated and the residue was diluted in CH$_2$Cl$_2$ (300 mL), and then washed with H$_2$O (500 mL), dried (MgSO$_4$), and concentrated in vacuo. The solid was recrystallized with MeOH to give white needles (14.10 g, 62%): R$_f$=0.90 (hexanes/EtOAc 9/1); mp 118-119° C.; IR (nujol) 3068, 2939, 2885, 2213, 1601, 1507, 1459, 1376, 1300, 1249, 1159, 994, 827, 720, 547, 509 cm$^{-1}$; $^1$H NMR (CDCl$_3$) δ 5.18 (s, CH$_2$O), 7.01-7.21 (m, 4 ArH), 7.32-7.39 (m, 1 ArH), 7.47 (td, J=1.5, 7.2 Hz, 1 ArH), 7.60 (d, J=9.0 Hz, 2 ArH); $^{13}$C NMR (CDCl$_3$) δ 63.9 (d, J=4.5 Hz, CH$_2$O), 104.5 (CCN), 115.4 (ArC), 115.5 (d, J=21.0 Hz, C$_{3'}$), 119.1 (CN), 122.9 (d, J=14.2 Hz, C$_{1'}$), 124.4 (d, J=3.7 Hz, C$_{5'}$), 129.7 (d, J=3.7 Hz, C$_{6'}$ or C$_{4'}$), 130.2 (d, J=8.2 Hz, C$_{4'}$ or C$_{6'}$), 134.0 (ArC), 160.5 (d, J=245.9 Hz, C$_{2'}$), 161.7 (ArC); Anal. Calcd. for C$_{14}$H$_{10}$FNO$_2$: C, 74.00; H, 4.44; F, 8.36; N, 6.16. Found: C, 74.06; H, 4.28; F, 8.26; N, 6.16.

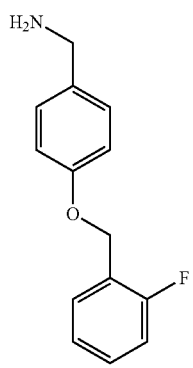 [SMILES: NCc1ccc(OCc2ccccc2F)cc1]

Preparation of 4-(2-Fluorobenzyloxy)benzylamine

To a LiAlH₄ (6.50 g, 171.9 mmol) suspension in THF (500 mL) was added dropwise a THF (40 mL) solution of 4-(2-fluorobenzyloxy)benzonitrile (13.00 g, 57.3 mmol) at 0° C. The mixture was stirred at room temperature (16 h) and H₂O (5.4 mL) was added dropwise at 0° C. followed by an aqueous NaOH solution (2.7 mL, 15% w/w), and then H₂O (5.4 mL). The mixture was stirred at room temperature (2 h), and the precipitate filtered and washed with CH₂Cl₂. The filtrate was concentrated in vacuo to obtain a colorless oil (8.00 g, 64%): $R_f$=0.00 (hexanes/EtOAc 911); IR (hydrochloride salt, nujol) 3081, 1608, 1519, 1457, 1380, 1300, 1240, 1181, 1051, 967, 836, 754, 558 cm⁻¹; ¹H NMR (CDCl₃) δ 1.63 (br 5, NH₂), 3.80 (s, CH₂NH₂), 5.12 (s, CH₂O), 6.96 (d, J=9.0 Hz, 2 ArH), 7.05-7.34 (m, 5 ArH), 7.50 (td, J=1.5, 7.5 Hz, 1 ArH).

Reaction Overview

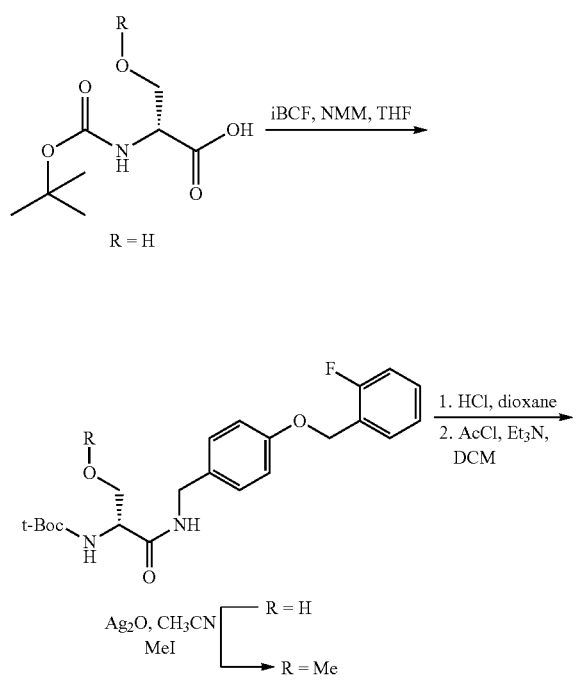

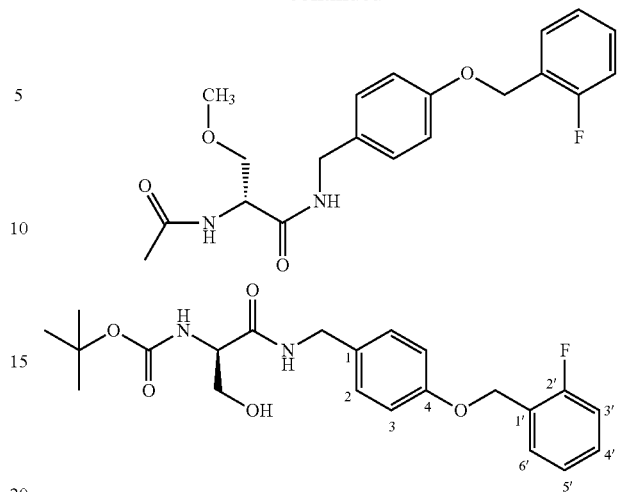

Preparation of (R)—N-4-(2-Fluorobenzyloxy)benzyl 2-N-(tert.-Butoxycarbonyl)amino-3-hydroxypropionamide A THF solution (100 mL) of (R)-t-Boc-serine (5.00 g, 24.4 mmol) was stirred and cooled at −78° C. under Ar and then 4-methylmorpholine (NMM) (3.2 mL, 29.3 mmol) was added dropwise. After 2 min of stirring at this temperature, isobutylchloroformate (IBCF) (3.8 mL, 29.3 mmol) was added dropwise leading to the precipitation of a white solid, and the reaction was allowed to proceed for additional 2 min, and then 4-(2-fluorobenzyloxy)benzylamine (6.70 g, 29.3 mmol) was added portionwise at −78° C. The mixture was allowed to stir at room temperature (2 h), and the white solid filtered and the organic layer concentrated in vacuo. The residue was purified by flash column chromatography on silica gel with EtOAc/hexanes (50/50 to 100/00) as the eluant to obtain (R)—N-4-(2-fluorobenzyloxy)benzyl 2-N-(tert.-butoxycarbonyl)amino-3-hydroxypropionamide as a white solid (6.90 g, 68%): $R_f$=0.51 (hexanes/EtOAc 4/6); mp 99-100° C.; $[\alpha]^{25.2}_D$ +14.2° (c 1, CHCl₃); IR (nujol) 3175, 2966, 1691, 1650, 1526, 1458, 1378, 1305, 1238, 1167, 1044, 1004, 828, 718, 664, 566 cm⁻¹; ¹H NMR (400 MHz, CDCl₃) δ 1.41 (s, (CH₃)₃), 3.21-3.33 (br m, CHH'), 3.64-3.70 (br m, CHH'), 4.09-4.16 (br m, CH, OH), 4.29-4.43 (br m, CH₂N), 5.01 (s, CH₂O), 5.56-5.66 (br d, NH), 6.92 (d, J=8.4 Hz, 2 ArH), 6.96-7.04 (br m, NH), 7.05-7.19 (m, 4 ArH), 7.28-7.34 (m, 1 ArH), 7.48 (td, J=1.2, 9.2 Hz, 1 ArH); ¹³C NMR (100 MHz, CDCl₃) δ 28.3 ((CH₃)₃), 42.9 (NCH₂), 54.9 (OCH₂CH), 62.8 (OCH₂CH), 63.7 (d, J=4.6 Hz, CH₂O), 80.6 (C(CH₃)₃), 115.0 (C₃), 115.4 (d, J=21.2 Hz, C₃'), 124.1 (d, J=14.2 Hz, C₁'), 124.3 (d, J=3.2 Hz, C₅'), 128.9 (ArC), 129.6 (d, J=7.7 Hz, C₄' or C₆'), 129.7 (d, J=11.5 Hz, C₆' or C₄'), 130.3 (ArC), 156.3 (NC(O)O), 158.0 (C₄), 160.4 (d, J=245.0 Hz, C₂'), 171.3 (C(O)); HRMS (M+H⁺) (ESI⁺) 419.1982 [M+H⁺] (calcd for C₂₂H₂₇FN₂O₆H⁺ 419.1982); Anal. Calcd. for C₂₂H₂₇FN₂O₅: C, 63.14; H, 6.50; F, 4.54; N, 6.69. Found: C, 63.09; H, 6.50; F, 4.36; N, 6.69.

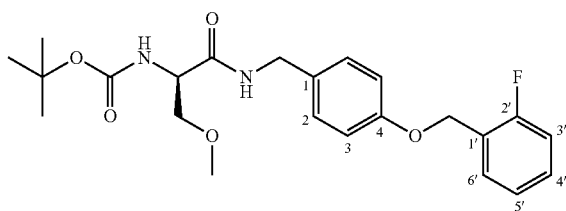 [SMILES: COC[C@@H](NC(=O)OC(C)(C)C)C(=O)NCc1ccc(OCc2ccccc2F)cc1]

Preparation of (R)—N-4-(2-Fluorobenzyloxy)benzyl 2-N-(tert.-Butoxycarbonyl)amino-3-methoxypropionamide Ag$_2$O (18.80 g, 81.2 mmol) was added to a CH$_3$CN solution (400 mL) of (R)—N-4-(2-fluorobenzyloxy)benzyl 2-N-(tert.-butoxycarbonyl)amino-3-hydroxypropionamide (6.80 g, 16.3 mmol) and CH$_3$I (10.12 mL, 162.5 mmol) at room temperature under Ar. The reaction mixture was stirred at room temperature (3 d), filtered, and the filtrate concentrated in vacuo. The residue was purified by flash column chromatography on silica gel with EtOAc/hexanes (3/7) as the eluant to obtain (R)—N-4-(2-fluorobenzyloxy)benzyl 2-N-(tert.-butoxycarbonyl)amino-3-methoxypropionamide as a white solid (6.10 g, 87%): R$_f$=0.56 (3/7 EtOAc/hexanes); mp 82-85° C.; [α]$^{24.6}_D$ −16.7° (c 1, CHCl$_3$); IR (nujol) 3305, 2855, 1689, 1648, 1524, 1457, 1378, 1313, 1241, 1171, 1092, 1048, 916, 834, 757, 680 cm$^{-1}$; $^1$H NMR (400 MHz, CDCl$_3$) δ 1.35 (s, (CH$_3$)$_3$), 3.28 (s, OCH$_3$), 3.41 (dd, J=6.4, 8.8 Hz, CHH'), 3.73-3.77 (m, CHH'), 4.16-4.20 (br m, CH), 4.30-4.36 (br m, CH$_2$N), 5.05 (s, OCH$_2$), 5.30-5.34 (br m, OC(O)NH), 6.58-6.62 (br m, CH$_2$NH), 6.86 (d, J=8.8 Hz, 2 ArH), 7.01 (t, J=8.8 Hz, 1 ArH), 7.06-7.14 (m, 3 ArH), 7.20-7.26 (m, 1 ArH), 7.42 (t, J=7.6 Hz, 1 ArH); $^{13}$C NMR (CDCl$_3$) δ 28.3 ((CH$_3$)$_3$), 42.8 (NCH$_2$), 54.0 (OCH$_2$CH), 59.0 (OCH$_3$), 63.6 (d, J=4.0 Hz, CH$_2$O), 72.0 (OCH$_2$CH), 80.2 (C(CH$_3$)$_3$), 114.9 (C$_3$), 115.2 (d, J=21.1 Hz, C$_{3'}$), 124.1 (d, J=14.1 Hz, C$_{1'}$), 124.2 (d, J=3.4 Hz, C$_{5'}$), 128.8 (ArC), 129.5-129.7 (br t, C$_{4'}$, C$_{6'}$), 130.6 (ArC), 155.4 (NC(O)O), 157.8 (C$_4$), 160.3 (d, J=245.9 Hz, C$_{2'}$), 170.1 (C(O)); HRMS (M+H$^+$) (ESI$^+$) 433.2139 [M+H$^+$] (calcd for C$_{23}$H$_{29}$FN$_2$O$_5$H$^+$ 433.2139); Anal. Calcd. for C$_{23}$H$_{29}$FN$_2$O$_5$: C, 63.87; H, 6.76; N, 6.48; F, 4.39. Found: C, 64.05; H, 6.76; N, 6.46; F, 4.21.

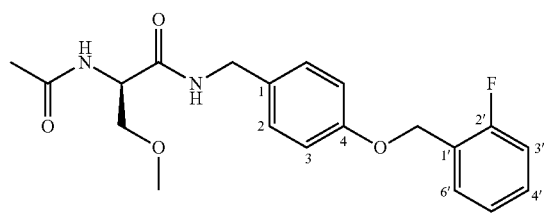

Preparation of (R)—N-4-(2-Fluorobenzyloxy)benzyl 2-Acetamido-3-methoxypropionamide A saturated HCl solution in dioxane (1 mmol/2 mL, 11.57 mL) was added to (R)—N-4-(2-fluorobenzyloxy)benzyl 2-N-(tert.-butoxycarbonyl)amino-3-methoxypropionamide (2.50 g, 5.8 mmol) at 0° C. and the solution was stirred at room temperature (16 h). The reaction solution was concentrated in vacuo and dried (30 min): $^1$H NMR (400 MHz, DMSO-d$_6$) δ 3.30 (s, OCH$_3$), 3.67 (d, J=5.2 Hz, CH$_2$), 3.98-4.02 (br app t, CH), 4.28 (d, J=5.6 Hz, CH$_2$N), 5.13 (s, OCH$_2$), 7.00 (d, J=8.8 Hz, 2 ArH), 7.19-7.27 (m, 4 ArH), 7.39-7.45 (m, 1 ArH), 7.54 (td, J=1.6, 7.6 Hz, 1 ArH), 8.18-8.24 (br s, NH$_2$), 8.56 (t J=5.8 Hz, NH); HRMS (M+H$^+$) (ESI$^+$) 333.1624 [M+H$^+$] (calcd for C$_{18}$H$_{21}$FN$_2$O$_3$H$^+$ 333.1614); Anal. Calcd. for C$_{18}$H$_{21}$ClFN$_2$O$_3$: C, 58.62; H, 6.01; Cl, 9.61; F, 5.15; N, 7.60. Found: C, 58.56; H, 5.98; Cl, 9.42; F, 5.06; N, 7.57.

The residue (1.70 g, 5.1 mmol) was dissolved in CH$_2$Cl$_2$ (20 mL) and Et$_3$N (2.10 mL, 15.3 mmol) and AcCl (550 µL, 7.6 mmol) were successively added at 0° C. The mixture was stirred at room temperature (2 h), aqueous 10% citric acid (60 mL) was added and then the organic layer was separated. The aqueous layer was extracted with CH$_2$Cl$_2$ (2×30 mL). All of the organic layers were combined, washed with aqueous saturated NaHCO$_3$ (30 mL) and H$_2$O (30 mL), dried (MgSO$_4$), and concentrated in vacuo. The solid was recrystallized with EtOAc to obtain (R)—N-4-(2-fluorobenzyloxy)benzyl 2-acetamido-3-methoxypropionamide (1.25 g, 65%) as a white solid: R$_f$=0.28 (EtOAc); mp 173-174° C.; [α]$^{24.6}_D$ −20.7° (c 1, CHCl$_3$); IR (nujol) 3276, 3230, 3167, 3094, 2750, 1635, 1550, 1457, 1375, 1298, 1236, 1147, 1236, 1147, 1113, 1011, 761, 724, 587 cm$^{-1}$; $^1$H NMR (400 MHz, CDCl$_3$) δ 2.03 (s, CH$_3$CO), 3.37 (s, OCH$_3$), 3.42 (dd, J=7.6, 9.0 Hz, CHH'), 3.79 (dd, J=4.0, 9.0 Hz, CHH'), 4.34-4.44 (m, CH$_2$N), 4.49-4.54 (m, NC(H)CO), 5.12 (s, CH$_2$O), 6.43 (br d, J=6.4 Hz, NHC(O)CH$_3$), 6.66-6.72 (br t, CH$_2$NH), 6.94 (d, J=8.0 Hz, 2 ArH), 7.06-7.21 (m, 4 ArH), 7.28-7.34 (m, 1 ArH), 7.49 (td, J=1.6, 7.6 Hz, 1 ArH), addition of excess (R)-(−)-mandelic acid to a CDCl$_3$ solution of (R)—N-4-(2-fluorobenzyloxy)benzyl 2-acetamido-3-methoxypropionamide gave only one signal for the acetyl methyl and one signal for the ether methyl protons; $^{13}$C NMR (CDCl$_3$) δ 23.2 (CH$_3$C(O)), 43.0 (NCH$_2$), 52.4 (OCH$_2$CH), 59.1 (OCH$_3$), 63.7 (d, J=4.5 Hz, CH$_2$O), 71.6 (OCH$_2$CH), 115.0 (C$_3$), 115.3 (d, J=21.2 Hz, C$_{3'}$), 114.8 (d, J=14.1 Hz, C$_{1'}$), 124.2 (d, J=3.3 Hz, C$_{5'}$), 128.8 (ArC), 129.6 (d, J=12.2 Hz, C$_{4'}$ or C$_{6'}$), 129.7 (d, J=8.4 Hz, C$_{6'}$ or C$_{4'}$), 130.4 (ArC), 158.0 (C$_4$), 160.4 (d, J=245.7 Hz, C$_{3'}$), 169.8, 170.2 (2C(O)); HRMS (M+H$^+$) (ESI$^+$) 375.1720 [M+H$^+$] (calcd for C$_{20}$H$_{23}$FN$_2$O$_4$H$^+$ 375.1720); Anal. Calcd. for C$_{20}$H$_{23}$FN$_2$O$_4$: C, 64.16; H, 6.19; F, 5.07; N, 7.48. Found: C, 63.95; H, 6.20; F, 5.14; N, 7.46.

Reaction Overview

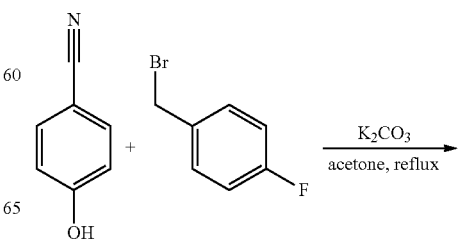

-continued

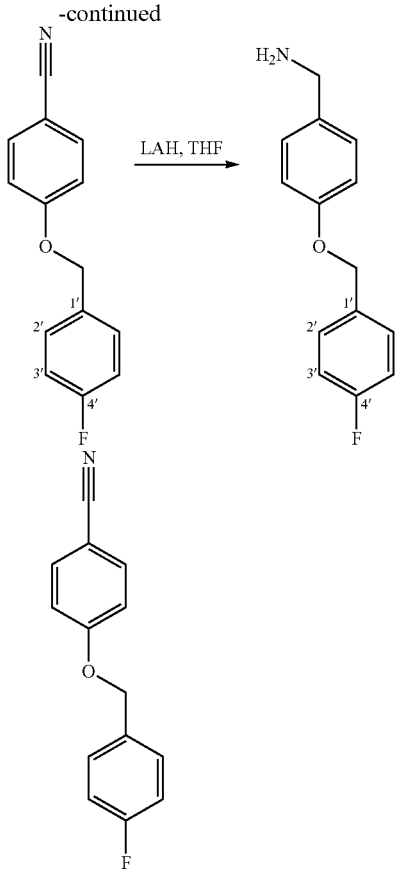

Preparation of 4-(4-Fluorobenzyloxy)benzonitrile

A mixture of 4-cyanophenol (11.91 g, 100.0 mmol), $K_2CO_3$ (55.20 g, 400.0 mmol), and 4-fluorobenzylbromide (22.68 g, 120.0 mmol) were heated in acetone (400 mL) at reflux (5 h). The volatiles were evaporated and the residue was diluted in $CH_2Cl_2$ (300 mL), and then washed with $H_2O$ (500 mL), dried ($MgSO_4$), and concentrated in vacuo. The solid was recrystallized with MeOH to give white needles (18.50 g, 81%): $R_f$=0.89 (hexanes/EtOAc 911); mp 82-83° C.; $^1$H NMR (CDCl$_3$) δ 5.07 (s, CH$_2$O), 7.01 (d, J=9.0 Hz, 2 ArH), 7.09 (t, J=8.7 Hz, 2 ArH), 7.37-7.42 (m, 2 ArH), 7.59 (d, J=9.0 Hz, 2 ArH); $^{13}$C NMR (CDCl$_3$) δ 69.5 (CH$_2$O), 104.2 (CCN), 115.5 (ArC), 115.6 (d, J=22.5 Hz, C$_{3'}$), 119.0 (CN), 129.4 (d, J=7.9 Hz, C$_{2'}$), 131.4 (C$_{1'}$), 133.9 (ArC), 161.7 (ArC), 162.6 (d, J=245.6 Hz, C$_{4'}$); Anal. Calcd. for C$_{14}$H$_{10}$FNO$_2$: C, 74.00; H, 4.44; F, 8.36; N, 6.16. Found: C, 74.06; H, 4.28; F, 8.26; N, 6.16.

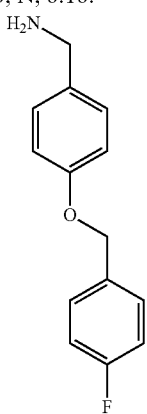

Preparation of 4-(4-Fluorobenzyloxy)benzylamine

To a LiAlH$_4$ (6.50 g, 171.9 mmol) suspension in THF (500 mL) was added dropwise a THF (40 mL) solution of 4-(4-fluorobenzyloxy)benzonitrile (13.00 g, 57.3 mmol) at 0° C. The mixture was stirred at room temperature (16 h) and H$_2$O (5.4 mL) was added dropwise at 0° C. followed by an aqueous NaOH solution (2.7 mL, 15% w/w), and then H$_2$O (5.4 mL). The mixture was stirred at room temperature (2 h), and the precipitate filtered and washed with CH$_2$Cl$_2$. The filtrate was concentrated in vacuo to obtain a white solid (12.00 g, 92%): $R_f$=0.00 (hexanes/EtOAc 9/1); $^1$H NMR (CDCl$_3$) δ 1.43-1.79 (br s, NH$_2$), 3.81 (s, CH$_2$NH$_2$), 5.02 (s, CH$_2$O), 6.93 (d, J=9.0 Hz, 2 ArH), 7.07 (1, J=8.2 Hz, 2 ArH), 7.23 (d, J=9.0 Hz, 2 ArH), 7.38-7.43 (m, 2 ArH); $^{13}$C NMR (CDCl$_3$) δ 45.7 (CH$_2$N), 69.2 (CH$_2$O), 114.7 (ArC), 115.3 (d, J=21.4 Hz, C$_{3'}$), 128.6 (ArC), 129.1 (d, J=8.2 Hz, C$_{4'}$), 132.6-132.7 (br d, C$_{1'}$), 135.8 (ArC), 157.3 (ArC), 162.3 (d, J=244.7 Hz, C$_{2'}$).

Reaction Overview

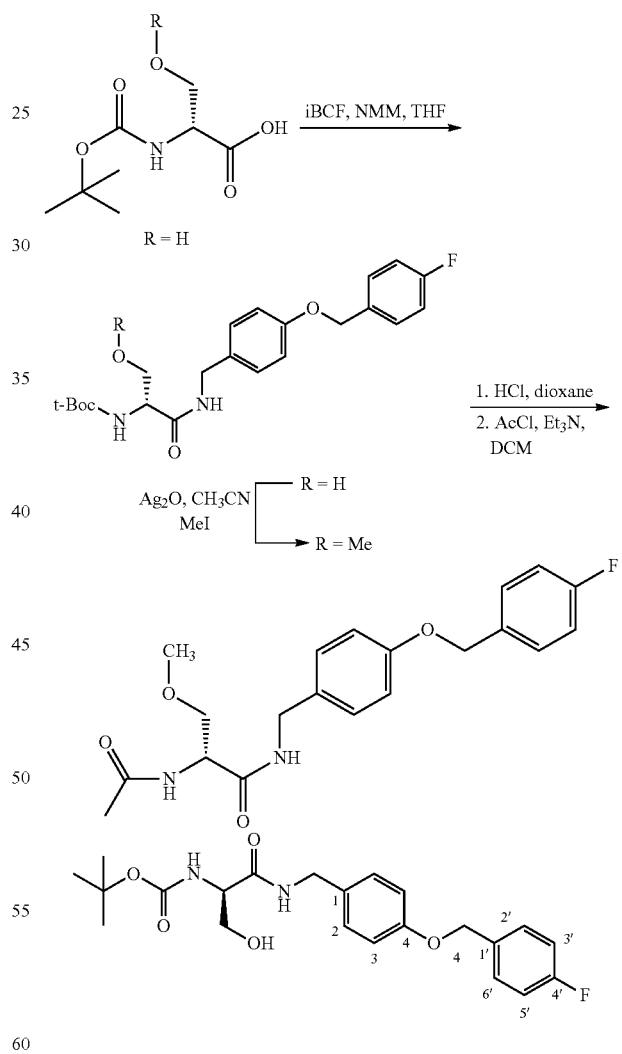

Preparation of (R)—N-4-(4-Fluorobenzyloxy)benzyl 2-N-(tert.-Butoxycarbonyl)amino-3-hydroxypropionamide A THF solution (100 mL) of (R)-t-Boc-serine (5.00 g, 24.4 mmol) was stirred and cooled at −78° C. under Ar and then 4-methylmorpholine (NMM) (3.2 mL, 29.3 mmol) was added dropwise. After 2 min of stirring at this temperature, isobutylchloroformate (IBCF) (3.8 mL, 29.3 mmol) was added dropwise leading to the precipitation of a white solid, and the reaction was allowed to proceed for additional 2 min, and then 4-(4-fluorobenzyloxy)benzylamine (6.70 g, 29.3 mmol) was added portionwise at −78° C. The mixture was allowed to stir at room temperature (2 h), and the white solid filtered, and the organic layer concentrated in vacuo. The residue was purified by flash column chromatography on silica gel with EtOAc/hexanes (50/50 to 70/30) as the eluant to obtain (R)—N-4-(4-fluorobenzyloxy)benzyl 2-N-(tert.-butoxycarbonyl)amino-3-hydroxypropionamide as a white solid (7.10 g, 69%): $R_f$=0.33 (hexanes/EtOAc 4/6); mp 93-95° C.; $[\alpha]^{25.6}_D$ +14.3° (c 1, $CHCl_3$); IR (nujol) 3160, 2942, 2838, 1685, 1637, 1513, 1454, 1373, 1304, 1237, 1164, 1012, 860, 818, 724, 600, 509 $cm^{-1}$; $^1H$ NMR (400 MHz, $CDCl_3$) δ 1.40 (s, $(CH_3)_3$), 3.30-3.69 (br m, CHH', OH), 4.06 (d, J=7.5 Hz, CHH'), 4.12-4.20 (br m, CH), 4.33-4.39 (br m, $CH_2N$), 4.98 (s, $CH_2O$), 5.61-5.69 (br t, NH), 6.88 (d, J=6.2 Hz, 2 ArH), 7.03-7.09 (br m, 2 ArH, NH), 7.16 (d, J=6.2 Hz, 2 ArH), 7.38 (t, J=5.1 Hz, 2 ArH); $^{13}C$ NMR (100 MHz, $CDCl_3$) δ 28.3 $((CH_3)_3)$, 42.9 ($NCH_2$), 55.0 ($OCH_2CH$), 62.8 ($OCH_2CH$), 69.4 ($CH_2O$), 80.6 ($C(CH_3)_3$), 115.0 ($C_3$), 115.5 (d, J=21.2 Hz, $C_{3'}$), 128.9 (ArC), 129.2 (d, J=7.7 Hz, $C_{2'}$), 130.3 (ArC), 132.7 (d, J=3.2 Hz, $C_{1'}$), 156.3 (NC(O)O), 158.0 ($C_4$), 162.5 (d, J=245.0 Hz, $C_{4'}$), 171.3 (C(O)); HRMS $(M+H^+)$ $(ESI^+)$ 419.1982 $[M+H^+]$ (calcd for $C_{22}H_{27}FN_2O_5H^+$ 419.1982); Anal. Calcd. for $C_{22}H_{27}FN_2O_5$: C, 63.14; H, 6.50; F, 4.54; N, 6.69. Found: C, 62.84; H, 6.49; F, 4.29; N, 6.67.

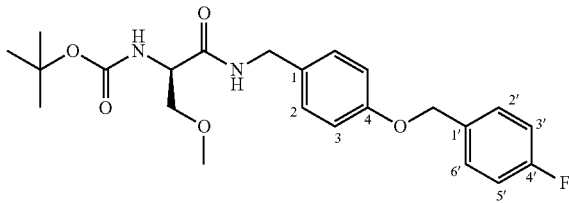 [SMILES: COC[C@@H](NC(=O)OC(C)(C)C)C(=O)NCc1ccc(OCc2ccc(F)cc2)cc1]

Preparation of (R)—N-4-(4-Fluorobenzyloxy)benzyl 2-N-(tert.-Butoxycarbonyl)amino-3-methoxypropionamide $Ag_2O$ (18.80 g, 81.2 mmol) was added to a $CH_3CN$ solution (400 mL) of (R)—N-4-(4-fluorobenzyloxy)benzyl 2-N-(tert.-butoxycarbonyl)amino-3-hydroxypropionamide (6.80 g, 16.3 mmol) and $CH_3I$ (10.12 mL, 162.5 mmol) at room temperature under Ar. The reaction mixture was stirred at room temperature (3 d), filtered, and the filtrate concentrated in vacuo. The residue was purified by flash column chromatography on silica gel with EtOAc/hexanes (3/7) as the eluant to obtain (R)—N-4-(4-fluorobenzyloxy)benzyl 2-N-(tert.-butoxycarbonyl)amino-3-methoxypropionamide as a white solid (6.00 g, 85%): $R_f$=0.59 (317 EtOAc/hexanes); mp 84-87° C.; $[\alpha]^{25.3}_D$ −18.3° (c 1, $CHCl_3$); IR (nujol) 3305, 2880, 1649, 1527, 1458, 1375, 1319, 1241, 1166, 1094, 1050, 913, 864, 920, 677, 506 $cm^{-1}$; $^1H$ NMR (400 MHz, $CDCl_3$) δ 1.42 (s, $(CH_3)_3$), 3.36 (s, $OCH_3$), 3.48 (dd, J=5.6, 9.0 Hz, CHH'), 3.83 (dd, J=4.0, 9.0 Hz, CHH'), 4.20-4.28 (br m, CH), 4.38-4.46 (br m, $CH_2N$), 5.01 (s, $OCH_2$), 5.33-5.42 (br m, OC(O)NH), 6.62-6.69 (br t, $CH_2NH$), 6.90 (d, J=8.4 Hz, 2 ArH), 7.06 (t, J=8.8 Hz, 2 ArH), 7.19 (d, J=8.4 Hz, 2 ArH), 7.37-7.41 (m, 2 ArH); $^{13}C$ NMR (100 MHz, $CDCl_3$) δ 28.3 $((CH_3)_3)$, 42.9 ($NCH_2$), 54.0 ($OCH_2CH$), 59.1 ($OCH_3$), 69.4 ($CH_2O$), 72.1 ($OCH_2CH$), 80.3 ($C(CH_3)_3$), 115.0 (ArC), 115.5 (d, J=21.8 Hz, $C_{3'}$), 128.9 (ArC), 129.3 (d, J=8.3 Hz, $C_{2'}$), 130.6 (ArC), 132.7 (d, J=3.2 Hz, $C_{1'}$), 155.5 (NC(O)O), 158.0 ($C_4$), 162.5 (d, J=245.0 Hz, $C_{4'}$), 170.2 (C(O)); HRMS $(M+H^+)$ $(ESI^+)$ 433.2139 $[M+H^+]$ (calcd for $C_{23}H_{29}FN_2O_5H^+$ 433.2139); Anal. Calcd. for $C_{23}H_{29}FN_2O_5$: C, 63.87; H, 6.76; F, 4.39; N, 6.48. Found: C, 63.92; H, 6.86; F, 4.40; N, 6.53.

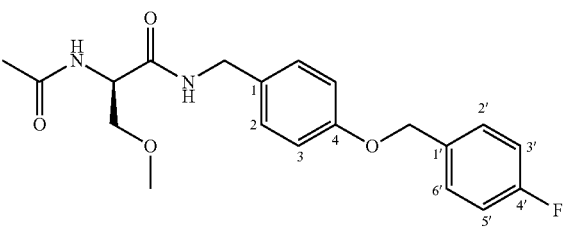 [SMILES: COC[C@@H](NC(C)=O)C(=O)NCc1ccc(OCc2ccc(F)cc2)cc1]

Preparation of (R)—N-4-(4-Fluorobenzyloxy)benzyl 2-Acetamido-3-methoxypropionamide A saturated HCl solution in dioxane (1 mmol/2 mL, 11.57 mL) was added to (R)—N-4-(4-fluorobenzyloxy)benzyl 2-N-(tert.-butoxycarbonyl)amino-3-methoxypropionamide (2.50 g, 5.8 mmol) at 0° C. and the solution was stirred at room temperature (16 h). The reaction solution was concentrated in vacuo and dried (30 min): HRMS $(M+H^+)$ $(ESI^+)$ 333.1624 $[M+H^4]$ (calcd for $C_{18}H_{21}FN_2O_3H^+$ 333.1614); Anal. Calcd. for $C_{18}H_{21}ClFN_2O_3.0.25H_2O$: C, 57.91; H, 6.07; Cl, 9.50; F, 5.09; N, 7.50. Found: C, 57.59; H, 5.86; Cl, 9.47; F, 4.85; N, 7.50.

The residue (1.85 g, 5.6 mmol) was dissolved in $CH_2Cl_2$ (30 mL) and $Et_3N$ (2.36 mL, 16.8 mmol) and AcCl (608 μL, 8.4 mmol) were successively added at 0° C. The mixture was stirred at room temperature (2 h), aqueous 10% citric acid (60 mL) was added, and then the organic layer was separated. The aqueous layer was extracted with $CH_2Cl_2$ (2×30 mL). All of the organic layers were combined, washed with aqueous saturated $NaHCO_3$ (30 mL) and $H_2O$ (30 mL), dried ($MgSO_4$), and concentrated in vacuo. The solid was recrystallized with EtOAc to obtain (R)—N-4-(4-fluorobenzyloxy)benzyl 2-acetamido-3-methoxypropionamide (1.28 g, 61%) as a white solid: $R_f$=0.22 (EtOAc); mp 166-167° C.; $[\alpha]^{25.2}_D$ −19.4° (c 1, $CHCl_3$); IR (nujol) 3287, 3205, 3103, 2924, 2858, 1763, 1636, 1555, 1515, 1457, 1376, 1304, 1238, 1136, 1048, 827, 728, 608, 515 $cm^{-1}$; $^1H$ NMR (400 MHz, $CDCl_3$) δ 2.03 (s, $CH_3CO$), 3.37 (s, $OCH_3$), 3.42 (dd, J=7.6, 9.4 Hz, CHH'), 3.79 (dd, J=4.0, 9.4 Hz, CHH'), 4.40 (d, J=5.2 Hz, $CH_2N$), 4.49-4.54 (m, NC(H)CO), 5.01 (s, $CH_2O$), 6.40 (br d, J=5.6 Hz, $NHC(O)CH_3$), 6.62-6.69 (br t, $CH_2NH$), 6.92 (d, J=8.8 Hz, 2 ArH), 7.07 (t, J=8.8 Hz, 2 ArH), 7.18 (d, J=8.0 Hz, 2 ArH), 7.37-7.41 (m, 2 ArH), addition of excess (R)-(-)-mandelic acid to a $CDCl_3$ solution of (R)—N-4-(4-fluorobenzyloxy)benzyl 2-acetamido-3-methoxypropionamide gave only one signal for the acetyl methyl and one signal for the ether methyl protons; $^{13}C$ NMR (100 MHz, $CDCl_3$) δ 23.1 ($CH_3C(O)$), 43.0 ($NCH_2$), 52.4 ($OCH_2CH$), 59.1 ($OCH_3$), 69.4 ($CH_2O$), 71.7 ($OCH_2CH$), 115.0 ($C_3$), 115.4 (d, J=21.3 Hz, $C_{3'}$), 128.8 (ArC), 129.3 (d, J=7.7 Hz, $C_{2'}$), 130.4 (ArC), 132.6 (d, J=3.3 Hz, $C_{1'}$), 158.0 ($C_4$), 162.5 (d, J=245.1 Hz, $C_{4'}$), 169.8, 170.3 (2C(O)); HRMS $(M+H^+)(ESI^+)$ 375.1720 $[M+H^4]$ (calcd for $C_{20}H_{23}FN_2O_4H^+$ 375.1720); Anal. Calcd. for $C_{20}H_{23}FN_2O_4$: C, 64.16; H, 6.19; F, 5.07; N, 7.48. Found: C, 64.02; H, 6.16; F, 4.99; N, 7.45.

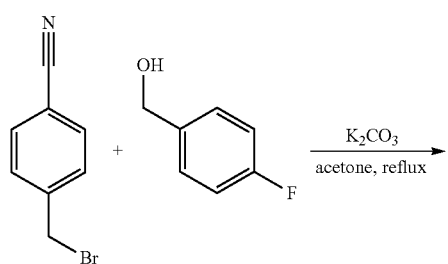

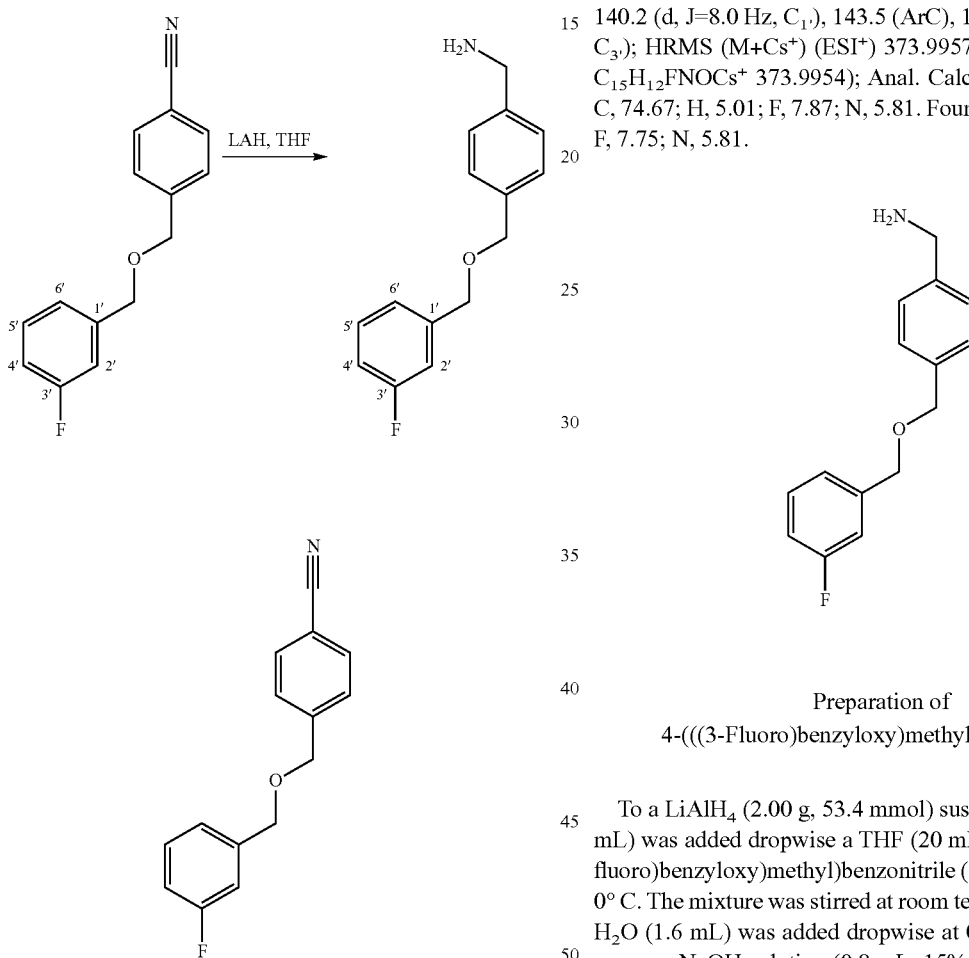

Preparation of
4-(((3-Fluoro)benzyloxy)methyl)benzonitrile 3-(Fluoro)benzylalcohol (5.00 g, 39.6 mmol) in THF (50 mL) was added dropwise at 0° C. to a THF (100 mL) suspension of NaH (60%, 6.3 g, 158.4 mmol). The mixture was stirred at 0° C. (30 min). Then, a THF solution of 4-cyanobenzylbromide (9.30 g, 47.6 mmol) was added dropwise at 0° C. and the mixture was stirred at room temperature (16 h). A saturated aqueous solution of NH$_4$Cl (40 mL) was added dropwise at 0° C. and the layers were separated. The aqueous layer was washed with CH$_2$Cl$_2$ (60 mL). The organics layers were combined, dried (Na$_2$SO$_4$) and concentrated under vacuum. The residue was purified by flash column chromatography on silica gel with EtOAc/hexanes (0/10 to 1/9) as the eluant to obtain 4-((3-fluorobenzyloxy)methyl)benzonitrile as a colorless oil (7.80 g, 81%): R$_f$ 0.65 (hexanes/EtOAc 8/2); IR (nujol) 2863, 2229, 1719, 1595, 1451, 1450, 1360, 1258, 1100, 1018, 945, 862, 790, 687, 554 cm$^{-1}$; $^1$H NMR (CDCl$_3$) δ 4.59 (s, CH$_2$O), 4.61 (s, CH$_2$O), 6.97-7.14 (m, 3 ArH), 7.26-7.37 (m, 1 ArH), 7.47 (d, J=7.5 Hz, 2 ArH), 7.65 (d, J=7.5 Hz, 2 ArH); $^{13}$C NMR (CDCl$_3$) δ 71.2 (CH$_2$O), 71.9 (CH$_2$O), 113.4 (CCN), 114.4 (d, J=21.6 Hz, C$_{2'}$ or C$_{4'}$), 114.7 (d, J=21.6 Hz, C$_{4'}$ or C$_{2'}$), 118.8 (CN), 122.9 (d, J=2.3 Hz, C$_{6'}$), 127.7 (ArC), 130.0 (d, J=9.2 Hz, C$_{6'}$), 132.2 (ArC), 140.2 (d, J=8.0 Hz, C$_{1'}$), 143.5 (ArC), 162.9 (d, J=244.8 Hz, C$_{3'}$); HRMS (M+Cs$^+$) (ESI$^+$) 373.9957 [M+Cs$^+$] (calcd for C$_{15}$H$_{12}$FNOCs$^+$ 373.9954); Anal. Calcd. for C$_{15}$H$_{12}$FNO$_2$: C, 74.67; H, 5.01; F, 7.87; N, 5.81. Found: C, 74.53; H, 4.93; F, 7.75; N, 5.81.

Preparation of
4-(((3-Fluoro)benzyloxy)methyl)benzylamine

To a LiAlH$_4$ (2.00 g, 53.4 mmol) suspension in THF (300 mL) was added dropwise a THF (20 mL) solution of 4-(((3-fluoro)benzyloxy)methyl)benzonitrile (4.30 g, 17.8 mmol) at 0° C. The mixture was stirred at room temperature (16 h) and H$_2$O (1.6 mL) was added dropwise at 0° C. followed by an aqueous NaOH solution (0.8 mL, 15% w/w), and then H$_2$O (1.6 mL). The mixture was stirred at room temperature (2 h), and the precipitate filtered and washed with CH$_2$Cl$_2$. The filtrate was concentrated in vacuo and the solid triturated with Et$_2$O to obtain a white solid (1.60 g, 37%). The solid was used in the next step with no other purification: R$_f$=0.00 (hexanes/EtOAc 8/2); mp >138° C. (decomp.); IR (nujol) 3224, 3100, 3039, 2970, 2843, 1593, 1520, 1456, 1375, 1257, 1143, 1073, 940, 866, 733, 686, 549 cm$^{-1}$; $^1$H NMR (CDCl$_3$) δ 3.87 (s, CH$_2$NH$_2$), 4.47-4.54 (m, 2 CH$_2$O), 7.08-7.45 (m, 8 ArH); $^{13}$C NMR (CDCl$_3$) δ 43.1 (CH$_2$N), 70.4, 71.2 (2 CH$_2$O), 113.8 (d, J=21.7 Hz, C$_{2'}$ or C$_{4'}$), 114.1 (d, J=20.5 Hz, C$_{4'}$ or C$_{2'}$), 123.1 (d, J=2.3 Hz, C$_{6'}$), 127.5 (ArC), 128.1 (ArC), 130.2 (d, J=8.0 Hz, C$_{5'}$), 137.2, 137.3 (2 ArC), 141.4 (d, J=6.8 Hz, C$_{1'}$), 162.1 (d, J=242.5 Hz, C$_{3'}$); HRMS (M+H$^+$) (ESI$^+$) 246.1294 [M+H$^+$] (calcd for C$_{15}$H$_{16}$FNOH$^+$ 246.1294).

Reaction overview

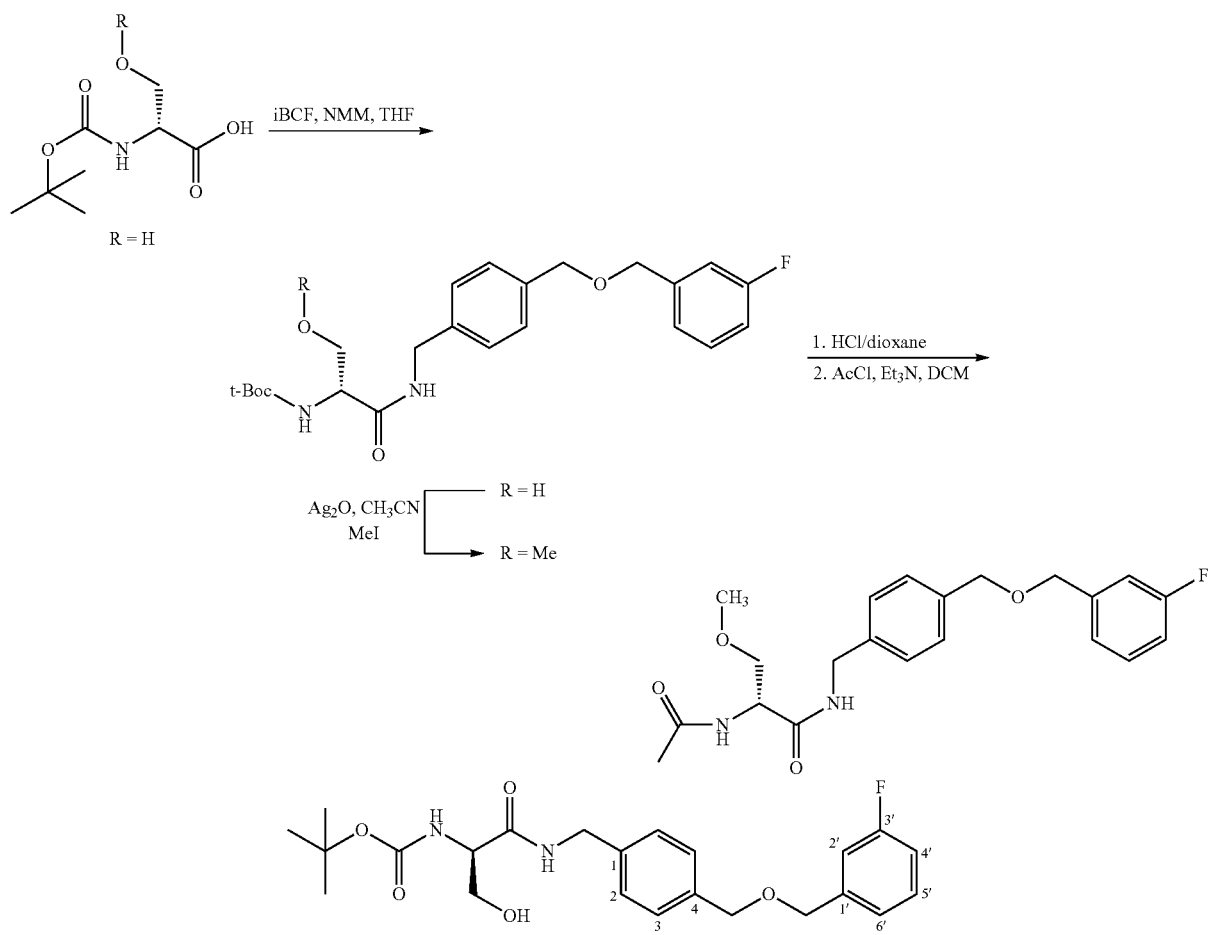

Preparation of (R)—N-4-((3-Fluorobenzyloxy)methyl)benzyl 2-N-(tert.-Butoxycarbonyl)amino-3-hydroxypropionamide A THF solution (100 mL) of (R)-t-Boc-serine (2.35 g, 11.4 mmol) was stirred and cooled at −78° C. under Ar and then 4-methylmorpholine (NMM) (1.5 mL, 13.7 mmol) was added dropwise. After 2 min of stirring at this temperature, isobutylchloroformate (IBCF) (1.8 mL, 13.7 mmol) was added dropwise leading to the precipitation of a white solid, and the reaction was allowed to proceed for additional 2 min, and then 4-(((3-fluoro)benzyloxy)methyl)benzylamine (3.37 g, 13.7 mmol) was added portionwise at −78° C. The mixture was allowed to stir at room temperature (2 h), and the white solid filtered and the organic layer concentrated in vacuo. The residue was purified by flash column chromatography on silica gel with EtOAc/hexanes (30/70 to 100/0) as the eluant to obtain (R)—N-4-((3-fluorobenzyloxy)methyl)benzyl 2-N-(tert.-butoxycarbonyl)amino-3-hydroxypropionamide as a white solid (3.30 g, 66%); $R_f$=0.34 (hexanes/EtOAc 4/6); mp 79-81° C.; $[\alpha]^{25.2}_D$ +23.1° (c 1, CHCl$_3$); IR (nujol) 2954, 2856, 1651, 1527, 1457, 1374, 1307, 1256, 1166, 1075, 1010, 868, 726 cm$^{-1}$; NMR (DMSO-d$_6$) δ 1.39 (s, (CH$_3$)$_3$), 3.54-3.60 (br m, CH$_2$), 3.96-4.02 (m, CH), 4.25-4.36 (br m, CH$_2$N), 4.51 (s, CH$_2$O), 4.53 (s, CH$_2$O), 4.85 (t, J=5.9 Hz, OH), 6.68 (br d, J=8.1 Hz, NH), 7.08-7.30 (m, 7 ArH), 7.36-7.44 (m, 1 ArH), 8.33 (br t, J=5.9 Hz, NH); $^{13}$C NMR (CDCl$_3$) δ 28.2 ((CH$_3$)$_3$), 42.1 (NCH$_2$), 55.0 (OCH$_2$CH), 62.8 (OCH$_2$CH), 71.2 (d, J=2.0 Hz, CH$_2$O), 71.9 (CH$_2$O), 80.6 (C(CH$_3$)$_3$), 114.3 (d, J=21.3 Hz, C$_{2'}$ or C$_{4'}$), 114.4 (d, J=21.1 Hz, C$_{4'}$ or C$_{2'}$), 123.0 (d, J=2.9 Hz, C$_{6'}$), 127.6, 128.0 (2 ArC), 129.9 (d, J=8.0 Hz, C$_{5'}$), 137.2, 137.3 (2 ArC), 140.8 (d, J=7.1 Hz, C$_{1'}$), 156.3 (N(H)C(O)O), 161.4 (d, J=244.2 Hz, C$_{3'}$), 171.3 (C(O)); Anal. Calcd. for C$_{23}$H$_{29}$FN$_2$O$_5$: C, 63.87; H, 6.76; F, 4.39; N, 6.48. Found: C, 63.48; H, 6.79; F, 4.25; N, 6.48.

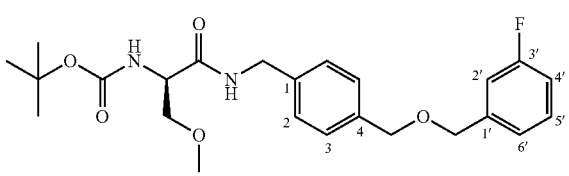 [SMILES: COC[C@@H](NC(=O)OC(C)(C)C)C(=O)NCc1ccc(COCc2cccc(F)c2)cc1]

Preparation of (R)—N-4-((3-Fluorobenzyloxy)methyl)benzyl 2-N-(tert.-Butoxycarbonyl)amino-3-methoxypropionamide Ag$_2$O (8.00 g, 34.7 mmol) was added to a CH$_3$CN solution (200 mL) of (R)—N-4-((3-fluorobenzyloxy)methyl)benzyl 2-N-(tert.-butoxycarbonyl)amino-3-hydroxypropionamide (3.00 g, 6.9 mmol) and CH₃I (4.30 mL, 69.4 mmol) at room temperature under Ar. The reaction mixture was stirred at room temperature (3 d), filtered, and the filtrate concentrated in vacuo. The residue was purified by flash column chromatography on silica gel with EtOAc/hexanes (6/4 to 10/0) as the eluant to obtain (R)—N-4-(((3-fluorobenzyloxy)methyl)benzyl 2-N-(tert.-butoxycarbonyl)amino-3-methoxypropionamide as a colorless oil (1.30 g, 42%): $R_f$=0.35 (5/5 EtOAc/hexanes); $[\alpha]^{25.3}_D$ −17.7° (c 1, CHCl₃); IR (nujol) 2954, 2856, 1651, 1527, 1457, 1374, 1307, 1256, 1166, 1075, 1010, 868, 726 cm⁻¹; ¹H NMR (CDCl₃) δ 1.43 (s, (CH₃)₃), 3.37 (s, OCH₃), 3.50 (dd, J=6.0, 9.3 Hz, CHH'), 3.84 (dd, J=3.8, 9.3 Hz, CHH'), 4.23-4.31 (br m, CH), 4.48 (br d, J=4.5 Hz, CH₂N), 4.53 (s, OCH₂), 4.54 (s, OCH₂), 5.37-5.45 (br m, OC(O)NH), 6.73-6.81 (br 1, CH₂NH), 6.98 (td, J=6.3, 8.4 Hz, 1 ArH), 7.06-7.14 (m, 2 ArH), 7.24-7.34 (m, 5 ArH); ¹³C NMR (CDCl₃) δ 28.2 ((CH₃)₃), 43.2 (NCH₂), 54.0 (OCH₂CH), 59.0 (OCH₃), 71.2 (d, J=1.7 Hz, CH₂O), 71.9, 72.0 (2 CH₂O), 80.3 (C(CH₃)₃), 114.3 (d, J=21.6 Hz, $C_{2'}$ or $C_{4'}$), 114.4 (d, J=21.1 Hz, $C_{4'}$ or $C_{2'}$), 123.0 (d, J=2.9 Hz, $C_{6'}$), 127.5, 128.1 (2 ArC), 129.8 (d, J=8.3 Hz, $C_{5'}$), 137.2, 137.5 (2 ArC), 140.8 (d, J=7.1 Hz, $C_{1'}$), 155.5 (N(H)C(O)O), 162.9 (d, J=244.4 Hz, $C_{3'}$), 170.3 (C(O)).

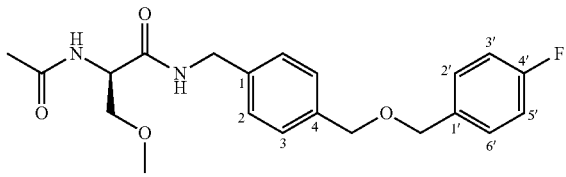 [SMILES: COC[C@@H](NC(C)=O)C(=O)NCc1ccc(COCc2ccc(F)cc2)cc1]

Preparation of (R)—N-4-(((3-Fluoro)benzyloxy)methyl)benzyl 2-Acetamido-3-methoxypropionamide A saturated HCl solution in dioxane (1 mmol/2 mL, 1.2 mL) was added to (R)—N-4-((3-fluorobenzyloxy)methyl)benzyl 2-N-(tert.-butoxycarbonyl)amino-3-methoxypropionamide (1.10 g, 5.8 mmol) at 0° C. and the solution was stirred at room temperature (16 h). The reaction solution was concentrated in vacuo and dried (30 min). The residue was dissolved in CH₂Cl₂ (20 mL) and Et₃N (1.40 mL, 9.8 mmol) and AcCl (356 μL, 4.9 mmol) were successively added at 0° C. The mixture was stirred at room temperature (2 h), aqueous 10% citric acid (60 mL) was added, and then the organic layer was separated. The aqueous layer was extracted with CH₂Cl₂ (2×30 mL). All of the organic layers were combined, washed with aqueous saturated NaHCO₃ (30 mL) and H₂O (30 mL), dried (MgSO₄), and concentrated in vacuo. The solid was recrystallized with EtOAc to obtain (R)—N-4-(((3-fluoro)benzyloxy)methyl)benzyl 2-acetamido-3-methoxypropionamide (450 mg, 47%) as a white solid: $R_f$=0.26 (EtOAc); mp 140-142° C.; $[\alpha]^{25.2}_D$ −21.0° (c 0.5, CHCl₃); IR (nujol) 3275, 3140, 2954, 2915, 2856, 1631, 1550, 1457, 1374, 1248, 1102, 1009, 917, 832, 779, 729, 612, 522 cm⁻¹; ¹H NMR (CDCl₃) δ 2.04 (s, CH₃CO), 3.39 (s, OCH₃), 3.43 (dd, J=7.8, 9.0 Hz, CHH'), 3.82 (dd, J=3.9, 9.0 Hz, CHH'), 4.48 (d, J=6.0 Hz, CH₂N), 4.48-4.56 (m, NC(H)CO), 4.54 (s, CH₂O), 4.55 (s, CH₂O), 6.42 (br d, J=6.6 Hz, NHC(O)CH₃), 6.71-6.79 (br t, CH₂NH), 6.96-7.15 (m, 3 ArH), 7.24-7.35 (m, 5 ArH), addition of excess (R)-(−)-mandelic acid to a CDCl₃ solution of (R)—N-4-(((3-fluoro)benzyloxy)methyl)benzyl 2-acetamido-3-methoxypropionamide gave only one signal for the acetyl methyl and one signal for the ether methyl protons; ¹³C NMR (CDCl₃) δ 23.2 (CH₃), 43.3 (NCH₂), 53.4 (OCH₂CH), 59.1 (OCH₃), 71.3, 71.6, 72.0 (3 CH₂O), 114.4 (d, J=21.4 Hz, $C_{2'}$ or $C_{4'}$), 114.5 (d, J=21.1 Hz, $C_{4'}$ or $C_{2'}$), 123.0 (d, J=2.9 Hz, $C_{3'}$), 127.6, 128.1 (2 ArC), 129.9 (d, J=8.2 Hz, $C_{5'}$), 137.3, 137.4 (2 ArC), 140.9 (d, J=7.1 Hz, $C_{1'}$), 163.0 (d, J=244.4 Hz, $C_{3'}$), 169.9, 170.3 (2C(O)); Anal. Calcd. for $C_{21}H_{25}FN_2O_4$: C, 64.93; H, 6.47; F, 4.89; N, 7.21. Found: C, 64.53; H, 6.47; F, 4.68; N, 7.37.

Preparation of N-(4-(3-Fluorobenzyloxy)benzyl)2-Acetamido-2-(pyridin-2-yl)acetamide

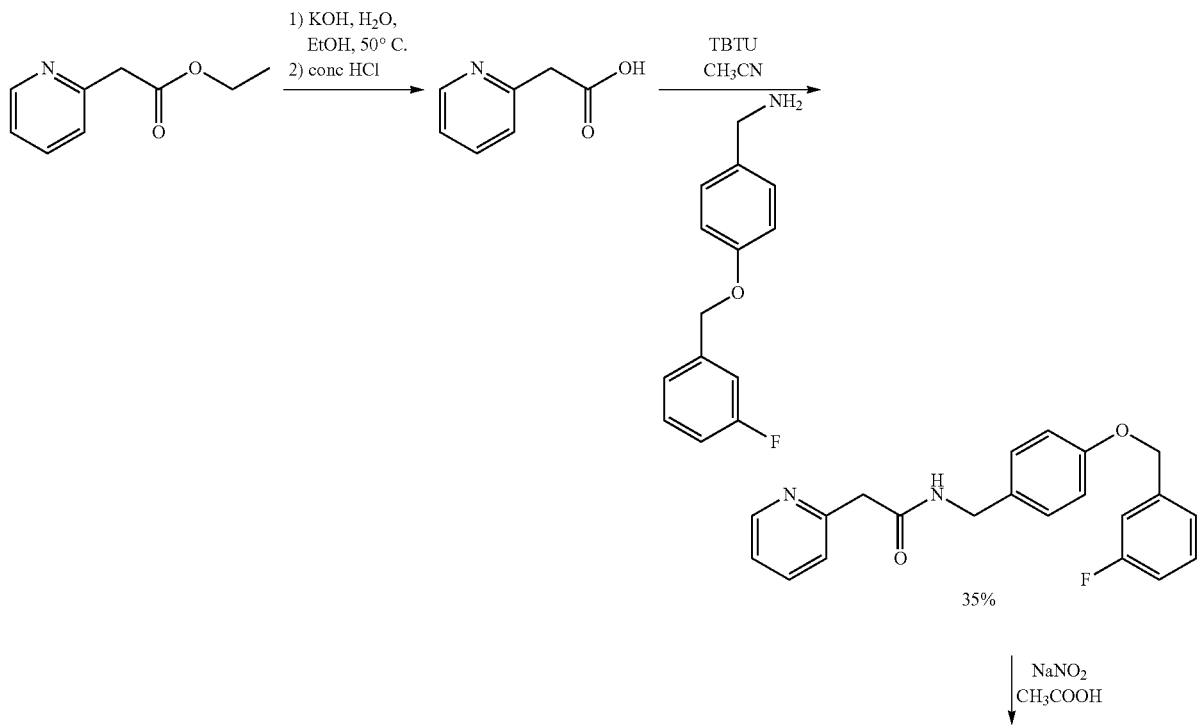

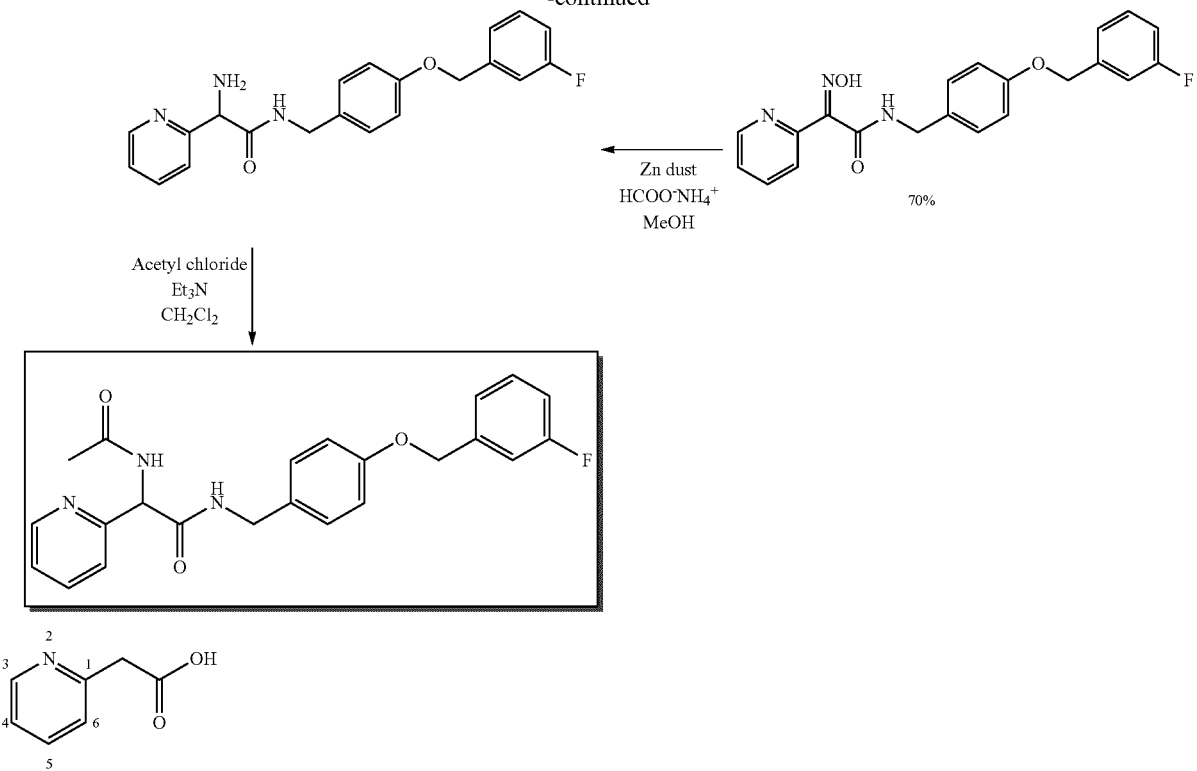

Preparation of 2-(Pyridin-2-yl)acetic Acid (Pranjal Baruah)

To an EtOH solution (40 mL) of ethyl 2-pyridylacetate (5.00 g, 30.27 mmol, 1 equiv) was added an aqueous solution (13 mL) of KOH (2.04 g, 36.32 mmol, 1.2 equiv). The resulting solution was stirred at 50° C. (2 h). The solution was concentrated to one third of the original volume and then washed with Et$_2$O (3×20 mL). The aqueous layer was neutralized with aqueous concentrated HCl (3.0 mL), and then concentrated in vacuo. The crude 2-(pyridin-2-yl)acetic acid (4.15 g) was used without further purification for the next step: $R_f$=0.06 (EtOAc); $^1$H NMR (DMSO-d$_6$) δ 3.93 (s, CH$_2$), 7.54 (dd, J=1.8, 5.4 Hz, H$_4$), 7.60 (d, J=7.9 Hz, H$_6$), 8.06 (dt, J=1.8, 7.9 Hz, H$_5$), 8.64 (d, J=5.4 Hz, H$_3$).

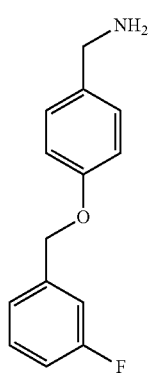 [SMILES: NCc1ccc(OCc2cccc(F)c2)cc1]

Preparation of (4-(3-Fluorobenzyloxy)phenyl)methanamine (Nakamoto, Kazutaka; Tsukada, Itaru; Tanaka, Keigo; Matsukura, Masayuki; Haneda, Toru; Inoue, Satoshi; Ueda, Norihiro; Abe, Shinya; Hata, Katsura; Watanabe, Naoaki, WO 2005033079 (2005).)

A mixture of 4-cyanophenol (11.91 g, 100.0 mmol), K$_2$CO$_3$ (55.20 g, 400.0 mmol), and 3-(fluoro)benzylbromide (22.68 g, 120.0 mmol) were heated in acetone (400 mL) at reflux (5 h). The volatiles were evaporated and the residue was diluted in CH$_2$Cl$_2$ (300 mL), and then washed with H$_2$O (500 mL), dried (MgSO$_4$), and concentrated in vacuo to give white needles (19.81 g, 87%): $R_f$=0.45 (hexanes/EtOAc 9\1); mp 104-105° C.; $^1$H NMR (CDCl$_3$) δ 5.11 (s, CH$_2$O), 6.98-7.20 (m, 5 ArH), 7.33-7.41 (m, 1 ArH), 7.59 (d, J=8.7 Hz, 2 ArH); HRMS (M+Na$^+$) (ESI$^+$) 250.0641 [M+Na$^+$] (calcd for C$_{14}$H$_{10}$NONa$^+$ 250.0641).

To a LiAlH$_4$ (5.02 g, 132.0 mmol) suspension in THF (400 mL) was added dropwise a THF (30 mL) solution of 4-(3-fluorobenzyloxy)benzonitrile (10.00 g, 44.0 mmol) at 0° C. The mixture was stirred at room temperature (16 h) and H$_2$O (4 mL) was added dropwise at 0° C. followed by an aqueous NaOH solution (2 mL, 15% w/w), and then H$_2$O (4 mL). The mixture was stirred at room temperature (2 h), and the precipitate filtered and washed with CH$_2$Cl$_2$. The filtrate was concentrated in vacuo to obtain a white solid (8.82 g, 86%): $R_f$=0.00 (hexanes/EtOAc 9/1); mp 44-45° C.; $^1$H NMR (CDCl$_3$) δ 1.61 (br s, NH$_2$), 3.79 (s, CH$_2$NH$_2$), 5.04 (s, CH$_2$O), 6.90-7.04 (m, 3 ArH) 7.13-7.37 (m, 5 ArH); HRMS (M-NH$_2^+$) (ESI$^+$) 215.088 [M-NH$_2^+$] (calcd for C$_{14}$H$_{12}$O$^+$ 215.087).

119

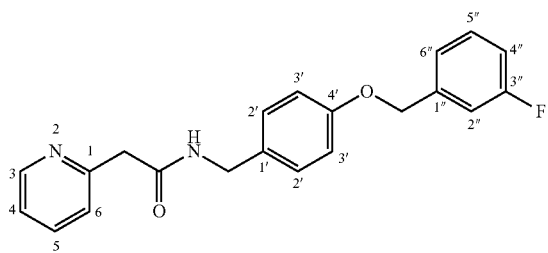 [SMILES: O=C(Cc1ccccn1)NCc1ccc(OCc2cccc(F)c2)cc1]

Preparation of N-4-(3-Fluorobenzyloxy)benzyl 2-(Pyridin-2-yl)acetamide

To a CH$_3$CN solution (20 mL) of 2-(pyridin-2-yl)acetic acid (1.48 g, 10.81 mmol, 1 equiv) at 0° C. was added (4-(3-fluorobenzyloxy)phenyl)methanamine (2.50 g, 10.81 mmol, 1 equiv). Upon addition of DMF (5 mL) the contents of the reaction went into solution, and then TBTU (4.16 g, 12.97 mmol, 1.2 equiv) was added at 0° C. The reaction mixture was stirred at room temperature under Ar (16 h). The reaction mixture was concentrated in vacuo. EtOAc (50 mL) was added, and the organic layer was successively washed with H$_2$O (5×50 mL), brine (2×50 mL), dried (Na$_2$SO$_4$), and concentrated in vacuo. The residue was purified by flash liquid chromatography on silica gel with EtOAc/hexanes (5/5 to 10/0) as the eluent. The white solid was recrystallized with EtOH to obtain N-4-(3-fluorobenzyloxy)benzyl 2-(pyridin-2-yl)acetamide as a white solid (1.48 g, 39%): $R_f$=0.43 (EtOAc); mp 127-129° C.; IR (nujol mull) 3464, 3404, 3338, 3157, 3125, 2850, 1636, 1555, 1456, 1375, 1255, 1146, 1109, 1027, 933, 882, 775, 687, 635, 574, 498, 406 cm$^{-1}$; $^1$H NMR (CDCl$_3$) δ 3.79 (s, CH$_2$C(O)), 4.40 (d, J=5.7 Hz, CH$_2$N), 5.04 (s, CH$_2$O), 6.89 (d, J=8.7 Hz, 2 ArH), 7.01 (dt, J=2.3, 8.7 Hz, 1 ArH), 7.13-7.38 (m, 7 ArH), 7.58-7.68 (br s, NH), 7.69 (dt, J=1.6, 7.7 Hz, H$_5$), 8.51 (d, J=4.2 Hz, H$_3$); $^{13}$C NMR (CDCl$_3$) δ 42.9 (CH$_2$), 45.2 (CH$_2$), 69.2 (d, J=1.7 Hz, CH$_2$O), 114.1 (d, J=21.6 Hz, C$_{2''}$ or C$_{4''}$), 114.8 (d, J=20.5 Hz, C$_{4''}$ or C$_{2''}$), 114.9 (C$_{3'}$), 122.0 (C$_4$ or C$_6$), 122.6 (d, J=2.9 Hz, C$_{6''}$), 124.1 (C$_6$ or C$_4$), 128.9 (C$_{2'}$), 130.1 (d, J=8.6 Hz, C$_{5''}$), 131.0 (C$_{1'}$), 137.1 (C$_5$), 139.6 (d, J=7.4 Hz, C$_{1''}$), 149.1 (C$_3$), 155.6 (C$_{4'}$ or C$_1$), 157.7 (C$_1$ or C$_{4'}$), 163.0 (d, J=224.7 Hz, C$_{3''}$), 169.1 (C(O)); M$_r$ (+ESI) 373.13 [M+Na]$^+$ (calcd for C$_{21}$H$_{19}$FN$_2$O$_2$Na$^+$ 373.13 [M+Na]$^+$); Anal. Calcd for C$_{21}$H$_{19}$FN$_2$O$_2$: C, 71.98; H, 5.47; F, 5.42; N, 8.00. Found: C, 72.12; H, 5.36; F, 5.29; N, 7.98.

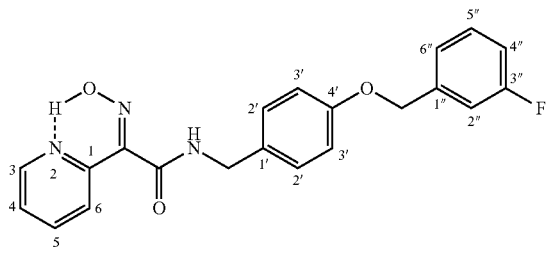

Preparation of N-4-(3-Fluorobenzyloxy)benzyl 2-(Hydroxyimino)-2-(pyridin-2-yl)acetamide To a stirred glacial acetic acid solution (16 mL) of N-4-(3-fluorobenzyloxy)benzyl 2-(pyridin-2-yl)acetamide (2.40 g, 6.85 mmol, 1 equiv) maintained at 0° C. was added portionwise an aqueous solution (5 mL) of NaNO$_2$ (490 mg, 7.05 mmol, 1.03 equiv). The reaction mixture was stirred at room temperature under Ar (16 h) and then H$_2$O was added and the reaction stirred at room temperature (1 h). The reaction mixture was extracted with CH$_2$Cl$_2$ (2×100 mL). The organic layers were combined and washed sequentially with an aqueous saturated NaHCO$_3$ solution (2×100 mL) and brine (2×100 mL), dried (Na$_2$SO$_4$), and concentrated in vacuo. The residue was purified by flash liquid chromatography on silica gel with EtOAc/hexanes (2/8 to 5/5) as the eluent to obtain two different isomers of N-(4-(3-fluorobenzyloxy)benzyl)-2-(hydroxyimino) 2-(pyridin-2-yl)acetamide as a white solid (1.81 g, 70%, approximative ratio 1/1).

Data for the mixture (A and B): $R_f$=0.60, 0.82 (EtOAc); mp 146-148° C.; IR (nujol mull) 3417, 3323, 3275, 3179, 3137, 3091, 2958, 2896, 1622, 1577, 1457, 1374, 1233, 1178, 1088, 1026, 959, 876, 828, 777, 731, 622, 440, 401 cm$^{-1}$; $^1$H NMR (CDCl$_3$) δ 4.52 (d, J=6.0 Hz, CH$_2$N, A or B), 4.58 (d, J=6.0 Hz, CH$_2$N, B or A), 5.06 (s, CH$_2$O, A and B), 6.91-7.05 (m, 3 ArH, A and B), 7.14-7.20 (m, 2 ArH, A and B), 7.27-7.38 (m, 3.5 ArH, A and B), 7.38-7.47 (br s, NH, A or B), 7.48-7.53 (m, ArH, A or B), 7.78 (dt, J=1.7, 7.9 Hz, ArH, A or B), 7.97 (dt, J=1.9, 8.0 Hz, ArH, B or A), 8.09-8.12 (m, ArH, A or B), 8.42-8.44 (m, ArH, A or B), 8.51-8.53 (m, ArH, B or A), 8.60-8.63 (m, ArH, B or A), 11.45-11.53 (br s, NH); $^{13}$C NMR (CDCl$_3$) δ 42.2 (CH$_2$, A or B), 42.9 (CH$_2$, B or A), 69.2 (d, J=0.9 Hz, CH$_2$O, A and B), 114.2 (d, J=16.3 Hz, C$_{2''}$ or C$_{4''}$, A and B), 114.8 (d, J=15.9 Hz, C$_{4''}$ or C$_{2''}$, A or B), 114.8 (d, J=15.9 Hz, C$_{4''}$ or C$_{2''}$, B or A), 122.7 (d, J=2.4 Hz, C$_{6''}$, A and B), 130.1 (d, J=6.2 Hz, C$_{5''}$, A or B), 130.2 (d, J=5.8 Hz, C$_{5''}$, B or A), 139.5 (d, J=5.8 Hz, C$_{1''}$, A or B), 139.6 (d, J=5.3 Hz, C$_{1''}$, B or A), 115.1, 115.1, 122.1, 123.7, 125.2, 125.5, 129.0, 129.2, 129.7, 130.5, 137.6, 138.5, 142.4, 143.0, 144.8, 146.6 (ArC, A and B), 149.9, 152.9 (C(NOH), A and B), 157.9, 158.0, 161.8, 163.2 (ArC, A and B), 164.2, 164.6 (C(O), A and B); M$_r$ (+ESI) 380.19 [M+H]$^+$ (calcd for C$_{21}$H$_{18}$FN$_3$O$_3$H$^+$ 380.14 [M+H]$^+$); Anal. Calcd for C$_{21}$H$_{18}$FN$_3$O$_3$: C, 66.48; H, 4.78; F, 5.01; N, 11.08. Found: C, 66.21; H, 4.81; F, 4.89; N, 10.95.

Data for top spot: $R_f$=0.82 (EtOAc); $^1$H NMR (CDCl$_3$) δ 4.51 (d, J=6.3 Hz, CH$_2$N), 5.06 (s, CH$_2$O), 6.93 (d, J=8.4 Hz, 2 ArH), 7.01 (dt, J=2.1, 8.4 Hz, 1 ArH), 7.12-7.39 (m, 5 ArH), 7.39-7.46 (br s, NH), 7.50 (ddd, J=1.2, 5.1, 7.7 Hz, 1 ArH), 7.97 (dt, J=1.8, 8.1 Hz, 1 ArH), 8.51-8.54 (m, 1 ArH), 8.59-8.63 (m, 1 ArH).

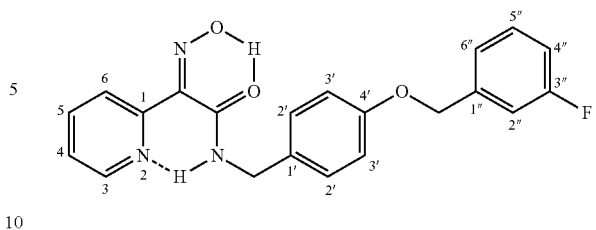

Data for bottom spot: $R_f$=0.60 (EtOAc); mp 167-138° C.; IR (nujol mull) 2919, 2858, 2728, 1622, 1575, 1458, 1375, 1235, 1152, 1041, 960, 828, 726 cm$^{-1}$; $^1$H NMR (CDCl$_3$) δ 4.58 (d, J=5.7 Hz, CH$_2$N), 5.06 (s, CH$_2$O), 6.94-7.39 (m, 9 ArH), 7.78 (dt, J=1.8, 7.9 Hz, 1 ArH), 8.09-8.12 (m, 1 ArH), 8.42-8.44 (m, 1 ArH), 11.40-11.52 (br s, NH); Anal. Calcd for C$_{21}$H$_{18}$FN$_3$O$_3$: C, 66.48; H, 4.78; F, 5.01; N, 11.08. Found: C, 66.26; H, 4.70; F, 4.97; N, 11.06.

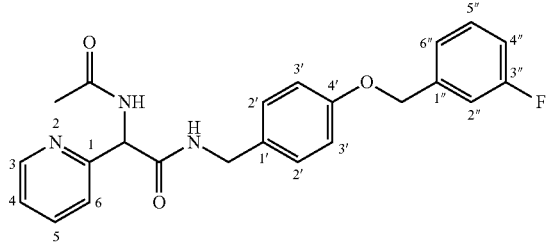

Preparation of N-4-(3-Fluorobenzyloxy)benzyl 2-Acetamido-2-(pyridin-2-yl)acetamide To a solution of N-4-(3-fluorobenzyloxy)benzyl 2-(hydroxyimino) 2-(pyridin-2-yl)acetamide (1.81 g, 4.77 mmol, 1 equiv) in MeOH (95 mL) was added ammonium formate (1.21 g, 19.08 mmol, 4 equiv) as a solid and then the reaction mixture was stirred at room temperature (5 min). Zn dust (Sigma-Aldrich <10 micron, 1.20 g, 19.08 mmol, 4 equiv) was added and the reaction heated at reflux (6 h), and then maintained at room temperature (16 h). The reaction mixture was filtered through Celite®. The filtrate was concentrated and the residue was dissolved in CH$_2$Cl$_2$ (100 mL). The CH$_2$Cl$_2$ layer was washed with a brine (2×100 mL), dried (Na$_2$SO$_4$), and concentrated in vacuo. The crude N-4-(3-fluorobenzyloxy)benzyl 2-amino-2-(pyridin-2-yl)acetamide crude material was used without further purification for the next step: $R_f$=0.00 (EtOAc).

N-4-(3-Fluorobenzyloxy)benzyl 2-amino-2-(pyridin-2-yl)acetamide (4.77 mmol, 1 equiv) was dissolved in CH$_2$Cl$_2$ (100 mL) and then triethylamine (0.8 mL, 5.72 mmol, 1.2 equiv) and acetyl chloride (0.4 mL, 5.72 mmol, 1.2 equiv) were carefully added at 0° C. and the resulting solution was stirred at room temperature (2 h). An aqueous saturated NaHCO$_3$ solution (100 mL) was added and the organic layer was extracted with CH$_2$Cl$_2$ (3×100 mL). The organic layers were combined, dried (Na$_2$SO$_4$), and concentrated in vacuo. The residue was purified by chromatography on silica gel with EtOAc/hexanes (7/3 to 10/0) as the eluent. The residue was recrystallized with EtOAc to obtain N-4-(3-fluorobenzyloxy)benzyl 2-acetamido-2-(pyridin-2-yl)acetamide as a white solid (935 mg, 48%): $R_f$=0.47 (EtOAc); mp 154-155° C.; IR (nujol mull) 3150, 2977, 2888, 1874, 1635, 1542, 1456, 1373, 1249, 1139, 1056, 992, 926, 824, 749, 690, 622, 548, 507, 443 cm$^{-1}$; $^1$H NMR (CDCl$_3$) δ 2.14 (s, C(O)CH$_3$), 4.29-4.41 (m, CH$_2$N), 5.03 (s, CH$_2$O), 5.56 (d, J=6.0 Hz, CH), 6.87 (d, J=9.0 Hz, 2 ArH), 6.98-7.43 (m, 8 ArH, 2 NH), 7.70 (dt, J=1.6, 7.8 Hz, 1 ArH), 8.50-8.52 (m, 1 ArH); $^{13}$C NMR (CDCl$_3$) δ 23.2 (C(O)CH$_3$), 43.2 (CH$_2$N), 58.0 (CH), 69.2 (d, J=2.3 Hz, CH$_2$O), 114.2 (d, J=22.5 Hz, C$_{2''}$ or C$_{4''}$), 114.8 (d, J=21.0 Hz, C$_{4''}$ or C$_{2''}$), 115.0 (C$_{3'}$), 121.0 (C$_4$ or C$_6$), 122.7 (d, J=3.1 Hz, C$_{6''}$), 123.0 (C$_6$ or C$_4$), 128.8 (C$_{2'}$), 130.1 (d, J=7.7 Hz, C$_{5''}$), 130.4 (C$_{1'}$), 137.2 (C$_5$), 139.6 (d, J=6.9 Hz, C$_{1''}$), 148.9 (C$_3$), 155.9 (C$_{4'}$ or C$_1$), 157.9 (C$_1$ or C$_{4'}$), 163.0 (d, J=244.7 Hz, C$_{3''}$), 168.5, 170.3 (2C(O)); Anal. Calcd for C$_{23}$H$_{22}$FN$_3$O$_3$: C, 67.80; H, 5.44; F, 4.66; N, 10.31. Found: C, 67.56; H, 5.38; F, 4.58; N, 10.24.

Preparation of N-4-(3-Fluorobenzyloxy)benzyl 2-Acetamido-2-(thiazol-2-yl)acetamide

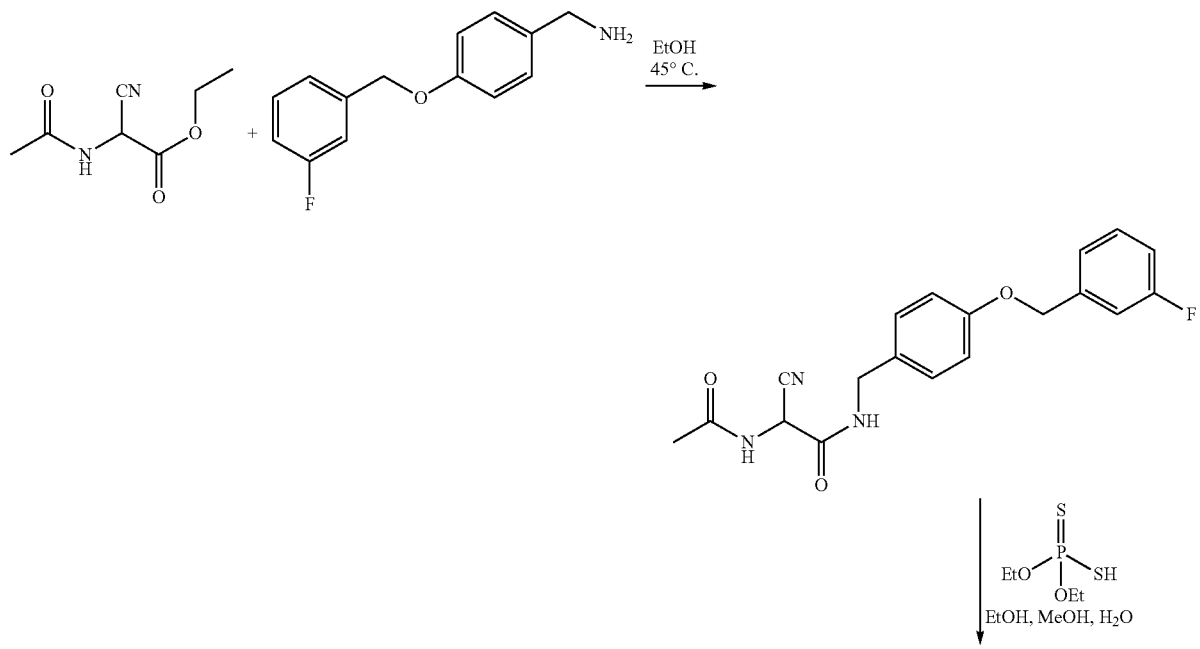

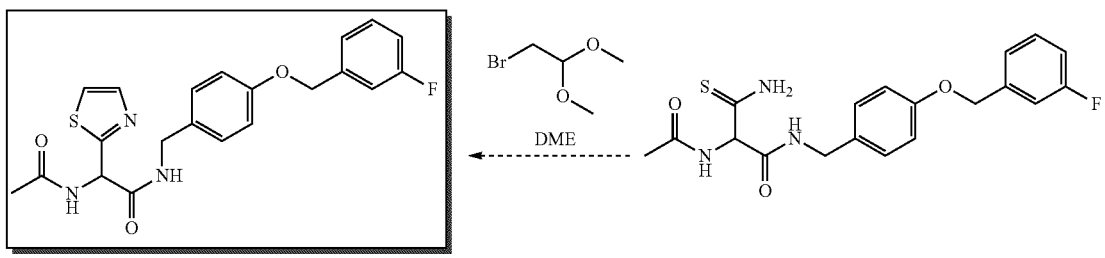

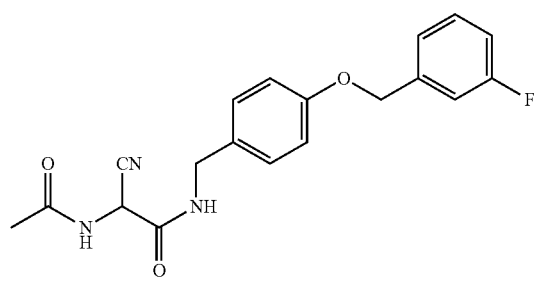

Preparation of N-4-(3-Fluorobenzyloxy)benzyl 2-Acetamido-2-cyano-acetamide

An EtOH solution (9 mL) of ethylacetamidocyanoacetate (809 mg, 4.76 mmol) and (4-(3-fluorobenzyloxy)phenyl)methanamine (2.20 g, 9.51 mmol) was stirred at 45° C. (5 d). The residue was concentrated in vacuo, and then dissolved in $CH_2Cl_2$ (20 mL), and washed with an aqueous 0.1 M HCl solution (10 mL). The $CH_2Cl_2$ layer was concentrated in vacuo. EtOH was added to the residue, and the insoluble white solid was filtered. The filtrate was concentrated in vacuo to obtain an 1:1 mixture of (4-(3-fluorobenzyloxy)phenyl)methanamine and N-4-(3-fluorobenzyloxy)benzyl 2-acetamido-2-cyanoacetamide. Crude N-4-(3-fluorobenzyloxy)benzyl 2-acetamido-2-cyanoacetamide was used without further purification for the next step: $R_f$=0.84 (EtOAc); $^1$H NMR (DMSO-$d_6$) δ 1.93 (s, C(O)CH$_3$), 4.25 (d, J=5.7 Hz, CH$_2$NH), 5.13 (s, CH$_2$O), 5.57 (d, J=8.1 Hz, CHNH), 6.90-7.08 (m, 2 ArH), 7.10-7.36 (m, 4 ArH), 7.38-7.49 (m, 2 ArH), 8.82 (t, J=5.7 Hz, CH$_2$NH), 9.10 (d, J=8.1 Hz, CHNH).

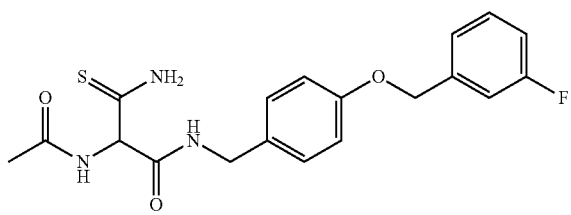 [SMILES: CC(=O)NC(C(=O)NCc1ccc(OCc2cccc(F)c2)cc1)C(N)=S]

Preparation of N-4-(3-Fluorobenzyloxy)benzyl 2-Acetamido-3-amino-2-thiocarbamoylacetamide N-4-(3-Fluorobenzyloxy)benzyl 2-acetamido-2-cyanoacetamide (500 mg, 1.41 mmol, 1 equiv) and O,O'-diethyl dithiophosphate (0.22 mL, 1.41 mmol, 1 equiv) were dissolved in a binary MeOH (3 mL)-EtOH (3 mL) solution containing H$_2$O (13 μL), and the mixture was stirred at room temperature (24 h). The reaction was concentrated in vacuo, and the residue was triturated with EtOAc/hexanes to obtain N-4-(3-fluorobenzyloxy)benzyl 2-acetamido-3-amino-2-thiocarbamoylacetamide as a white solid (180 mg, 33%): $R_f$=0.45 (EtOAc); mp 168-170° C.; IR (nujol mull) 3270, 3194, 3147, 3073, 2934, 2850, 2726, 2681, 2405, 1619, 1514, 1457, 1374, 1303, 1251, 1171, 1048, 961, 928, 860, 823, 776, 727, 677, 562 cm$^{-1}$; $^1$H NMR (acetone-$d_6$) δ 2.02 (s, C(O)CH$_3$), 2.75-2.90 (br s, C(S)NH$_2$), 4.35 (d, J=6.0 Hz, CH$_2$NH), 5.14 (s, CH$_2$O), 5.25 (d, J=6.9 Hz, CHNH), 6.90-6.99 (m, 2 ArH), 7.03-7.12 (m, 1 ArH), 7.18-7.33 (m, 4 ArH), 7.35-7.47 (m, 1 ArH), 7.50-7.58 (br d, CHNH), 7.90-8.10 (br s, CH$_2$NH); $M_r$ (+ESI) 522.04 [M+Cs]$^+$ (100%), 524.03 [M+2+Cs]$^+$ (7%) (calcd for $C_{19}H_{20}FN_3O_3SCs^+$ 522.03 [M+Cs]$^+$).

Preparation of (R)—N-4'-((3"-Fluoro)benzyloxy) benzyl 2-Acetamido-3-methylbutanamide
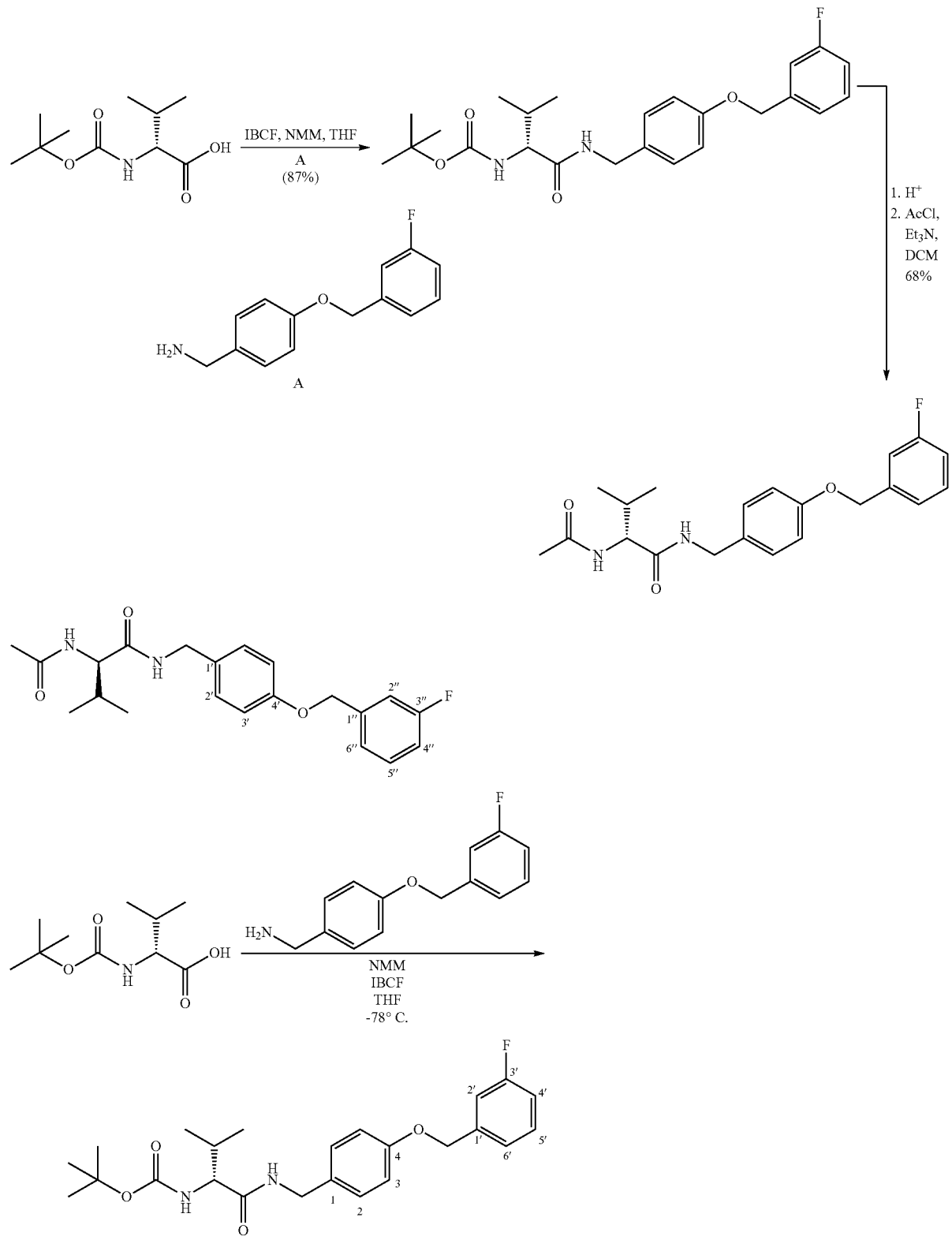

(R)—N-4'-((3"-Fluoro)benzyloxy)benzyl 2-N'-(t-Butoxycarbonyl)amino-3-methylbutanamide Using (R)-2-N-(t-butoxycarbonyl)amino-3-methylbutanoic acid (3.07 g, 14.14 mmol), 4-methylmorpholine (2.02 mL, 18.38 mmol), isobutyl chloroformate (1.84 mL, 15.55 mmol), and (4-(3'-fluoro)benzyloxy)benzylamine (3.43 g, 14.85 mmol) in anhydrous THF (15 mL) gave the crude product that was purified by flash column chromatography ($SiO_2$; 1-10% $MeOH/CH_2Cl_2$) to give the desired product (5.29 g, 87%) as a pale yellow solid: $R_f$ 0.21 (10% EtOAc/hexanes); mp 109-110° C.; $[\alpha]^{25}_D$ +4.3° (c 1.1, $CH_2Cl_2$); IR (nujol) 3298, 2947 (br), 1652, 1530, 1458, 1375, 1301, 1245, 1170, 1017, 879, 777 $cm^{-1}$; $^1H$ NMR (400 MHz, $CDCl_3$) δ 0.91 (d, J=6.8 Hz, $CH(CH_3)(CH_3)'$), 0.95 (d, J=6.8 Hz, $CH(CH_3)(CH_3)'$), 1.41 (s, $C(CH_3)_3$), 2.09-2.19 (m, CH $(CH_3)_2$), 3.86-3.92 (m, CH), 4.23-4.42 (m, $NHCH_2Ph$), 5.04 (s, $OCH_2$), 5.08-5.12 (br d, C(O)NH), 6.36 (t, J=5.2 Hz, $NHCH_2Ph$), 6.88-6.93 (m, 2 ArH), 6.98-7.03 (m, 1 ArH), 7.12-7.22 (m, 4 ArH), 7.31-7.36 (1 ArH); $^{13}C$ NMR (300 MHz, $CDCl_3$) δ 18.1 ($CH(CH_3)CH_3$), 19.6 ($CH(CH_3)CH_3$), 28.5 ($C(CH_3)_3$), 30.9 ($CH(CH_3)CH_3$), 43.1 ($NHCH_2Ph$), 60.4 (CH), 69.4 ($OCH_2$), 80.1 ($C(CH_3)_3$), 114.4 (d, J=21.9 Hz, $C_{4'}$ or $C_{2'}$), 115.0 (d, J=21.2 Hz, $C_{2'}$ or $C_{4'}$), 115.2 ($C_1$), 122.9 (d, J=2.6 Hz, $C_{6'}$), 129.3 (ArC), 130.3 (d, J=8.3 Hz, $C_{5'}$), 130.9 (ArC), 139.8 (d, J=7.1 Hz, $C_{1'}$), 156.1 (OC(O)N), 158.1 ($C_4$), 163.2 (d, J=244.4 Hz, $C_{3'}$), 171.7 (C(O)N); HRMS (ESI) 453.2178 $[M+Na^+]$ (calcd for $C_{24}H_{31}FN_2O_4Na$ 453.2166); Anal. Calcd for $C_{24}H_{31}FN_2O_4$: C, 66.96; H, 7.26; F, 4.41; N, 6.51. Found: O, 67.23; H, 7.22; F, 4.47; N, 6.28.

Preparation of (R)—N-4-((3"-Fluoro)benzyloxy)benzyl 2-Acetamido-3-methylbutanamide Trifluoroacetic acid (2 mL) was added to a $CH_2Cl_2$ (10 mL) solution of solution (R)—N-4'-((3"-fluoro)benzyloxy)benzyl 2-N-(tert-butoxycarbonyl)amino-3-methylbutanamide (1.00 g, 2.3 mmol) at 0° C. and the solution was stirred at room temperature (16 h). The reaction solution was concentrated in vacuo, dried (30 min), and $CH_2Cl_2$ (20 mL) and a saturated aqueous $Na_2CO_3$ solution (20 mL) were added. The layers were separated and the aqueous layer was washed with $CH_2Cl_2$ (2×20 mL). The organic layers were combined and concentrated under vacuum.

The residue was dissolved in $CH_2Cl_2$ (20 mL) and $Et_3N$ (0.49 mL, 3.5 mmol) and AcCl (200 μL, 2.8 mmol) were successively added at 0° C. The mixture was stirred at room temperature (3 h), aqueous 10% citric acid (60 mL) was added, and the organic layer was separated. The aqueous layer was washed with $CH_2Cl_2$ (2×30 mL). All the organic layers were combined, washed with aqueous saturated $NaHCO_3$ (30 mL), and $H_2O$ (30 mL), dried ($MgSO_4$), and concentrated in vacuo. The solid was recrystallized with EtOAc to obtain (R)—N-4'-((3"-fluoro)benzyloxy)benzyl 2-acetamido-3-methylbutanamide (585 mg, 68%) as a white solid: $R_f$=0.26 (EtOAc); mp 199-200° C.; $[\alpha]^{25.2}_D$ +25.6° (c 0.5, MeOH); IR (nujol) 3292, 3215, 3136, 3066, 2917, 2862, 1651, 1457, 1376, 1166, 1073, 950, 728 $cm^{-1}$; $^1H$ NMR (400 MHz, DMSO-$d_6$) δ 0.81 (d, J=3.0 Hz, $(CH_3)_2$), 0.83 (d, J=3.0 Hz, $(CH_3)_2$), 1.87 (s, $CH_3C(O)$), 1.90-1.99 (m, $CH(CH_3)_2$), 4.12-4.43 (dd, J=6.4, 8.8 Hz, CH), 4.19 (d, J=5.8 Hz, $CH_2NH$), 5.11 (s, $CH_2O$), 6.95 (d, J=8.4 Hz, $2H_3$), 7.11-7.19 (m, 3 ArH), 7.24-7.28 (m, 2 ArH), 7.39-7.46 (m, 1 ArH), 7.87 (d, J=8.8 Hz, $NHC(O)CH_3$), 8.38 (t, J=5.8 Hz, NH), addition of excess (R)-(−)-mandelic acid to a $CDCl_3$ solution of the desired compound gave only one signal for the acetyl methyl protons; $^{13}C$ NMR (100 MHz, DMSO-$d_5$) δ 18.1, 19.1 (2 $CH_3$), 24.4 ($CH_3C(O)$), 30.2 ($CH(CH_3)_3$), 41.3 ($NCH_2$), 57.8 (CH), 68.2 (d, J=2.0 Hz, $CH_2O$), 114.0 (d, J=21.9 Hz, $C_{2'}$ or $C_{4'}$), 114.4 (d, J=20.6 Hz, $C_{4'}$ or $C_{2'}$), 114.5 ($C_3$), 123.3 (d, J=2.5 Hz, $C_{6'}$), 128.5 ($C_2$), 130.3 (d, =8.3 Hz, $C_{5'}$), 131.8 ($C_1$), 140.1 (d, J=7.8 Hz, $C_{1'}$), 156.9 ($C_4$), 163.0 (d, J=242.5 Hz, $C_{3'}$), 169.1 (NC(O)O), 170.9 (C(O)); HRMS $(M+Na^+)$ ($ESI^+$) 395.1747 $[M+Na^+]$ (calcd for $C_{21}H_{25}FN_2O_3Na^+$ 395.1747); Anal. Calcd. for $C_{21}H_{25}FN_2O_3$: C, 67.72; H, 6.77; F, 5.10; N, 7.52. Found: C, 67.95; H, 6.71; F, 5.18; N, 7.51.

Preparation of (R)—N-4'-((3"-Fluoro)benzyloxy)benzyl 2-Acetamido-3,3-dimethylbutanamide Reaction Overview

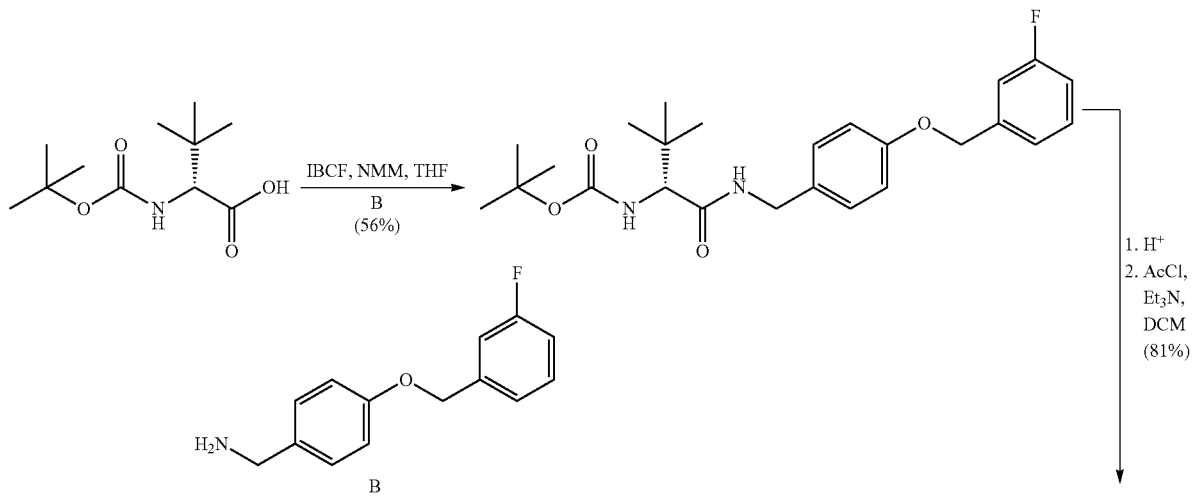

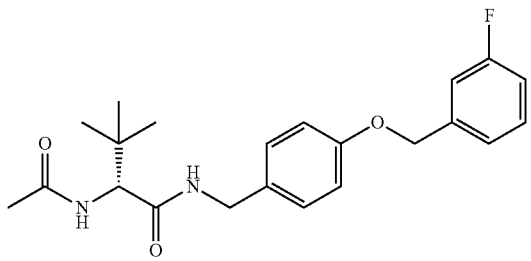

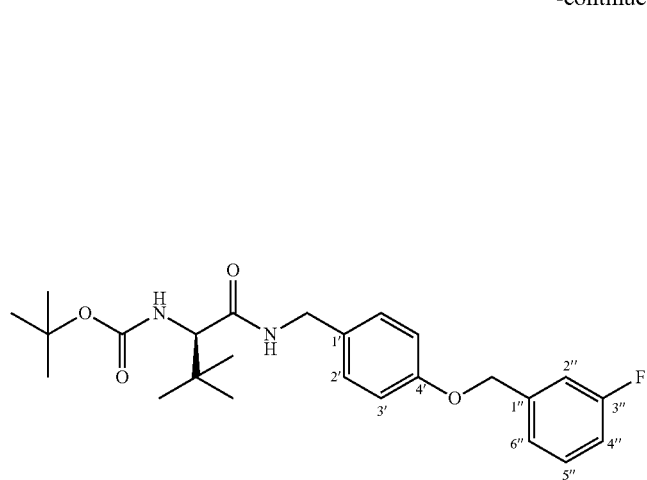

Preparation of (R)—N-4'-((3"-Fluoro)benzyloxy)benzyl 2-N-(tert-Butoxycarbonyl)amino-3,3-dimethylbutanamide A THF solution (120 mL) of (R)-2-tert-butoxycarbonylamino-3,3-dimethylbutyric acid (3.25 g, 14.0 mmol) was stirred and cooled at −78° C. under Ar and then 4-methylmorpholine (NMM) (1.8 mL, 16.8 mmol) was added dropwise. After 2 min of stirring at this temperature, isobutylchloroformate (IBCF) (2.2 mL, 16.8 mmol) was added dropwise leading to the precipitation of a white solid. The reaction was allowed to proceed for additional 2 min and then (4-(3'-fluoro)benzyloxy)benzylamine (3.90 g, 16.8 mmol) was added portionwise at −78° C. The mixture was allowed to stir at room temperature (2 h), and then the white solid filtered and the organic layer concentrated in vacuo. The solid was purified by flash column chromatography on silica gel with EtOAc/hexanes (0/10 to 1/9) as the eluant to obtain (R)—N-4'-((3"-fluoro)benzyloxy)benzyl 2-N-(tert-butoxycarbonyl)amino-3,3-dimethylbutanamide as colorless sticky gum (1.50 g, 56%): $R_f$=0.80 (EtOAc/hexanes 5/5); $[\alpha]^{25.6}_D$ +13.9° (c 1.7, CHCl$_3$); IR (nujol) 3292, 3215, 3136, 3066, 2917, 2862, 1651, 1457, 1376, 1166, 1073, 950, 728 cm$^{-1}$; $^1$H NMR (300 MHz, CDCl$_3$) δ 0.99 (s, (CH$_3$)$_3$), 1.41 (s, (CH$_3$)$_3$C(O)), 3.80 (d, J=9.6 Hz, CH), 4.29 (1/2 ABq, J=5.2, 14.4 Hz, NCHH'), 4.40 (d, J=6.0, 14.4 Hz, NCHH'), 5.04 (s, CH$_2$O), 5.28 (br d, J=9.6 Hz, NH), 6.01-6.10 (br t, NH), 6.90 (d, J=8.7 Hz, 2H$_3$), 6.97-7.04 (m, 1 ArH), 7.11-7.21 (m, 4 ArH), 7.30-7.38 (m, 1 ArH); $^{13}$C NMR (100 MHz, CDCl$_3$) δ 26.6 ((CH$_3$)$_3$), 28.3 ((CH$_3$)$_3$), 34.5 (C(CH$_3$)$_3$), 42.9 (CH$_2$), 62.4 (CH), 69.2 (d, J=1.9 Hz, ArCH$_2$O), 79.7 (OC(CH$_3$)$_3$), 114.1 (d, J=22.5 Hz, C$_{4'}$, or C$_{2'}$), 114.8 (d, J=21.2 Hz, C$_{2'}$ or C$_{4'}$), 115.0 (C$_1$), 122.6 (d, J=3.2 Hz, C$_{6'}$), 129.2 (ArC), 130.1 (d, J=8.4 Hz, C$_{5'}$), 130.6 (ArC), 139.5 (d, J=7.1 Hz, C$_1$), 155.9 (C$_4$), 157.8 (C(O)O), 162.9 (d, J=245.0 Hz, C$_{3'}$), 170.9 (C(O)); MS (M+Na$^+$) (ESI$^+$) 467.2322 [M+Na$^+$] (calcd for C$_{25}$H$_{33}$FN$_2$O$_4$Na$^+$ 467.2322); Anal. Calcd. for C$_{25}$H$_{33}$FN$_2$O$_4$: C, 67.55; H, 7.52; N, 6.30. Found: C, 67.25; H, 7.52; N, 6.09.

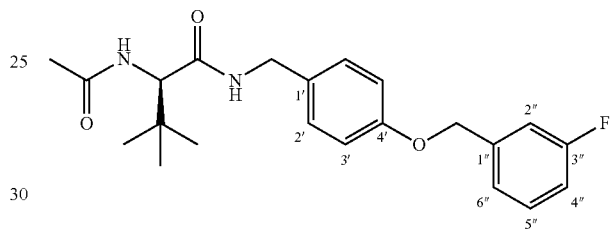

Preparation of (R)—N-4'-((3"-Fluoro)benzyloxy)benzyl 2-Acetamido-3,3-dimethylbutanamide A saturated HCl solution in dioxane (1 mmol/2 mL, 15.8 mL) was added to (R)—N-4'-((3"-fluoro)benzyloxy)benzyl 2-N-(tert-butoxycarbonyl)amino-3,3-dimethylbutanamide (3.50 g, 7.9 mmol) at 0° C. and the solution was stirred at room temperature (16 h). The reaction solution was concentrated in vacuo and dried (30 min). The residue was purified by flash column chromatography on silica gel with EtOAc/MeOH (10/0 to 9/1) as the eluant to obtain (R)—N-4'-((3"-fluoro)benzyloxy)benzyl 2-amino-3,3-dimethylbutanamide as a beige solid (2.40 g, 89%): $R_f$=0.20 (EtOAc); mp 66-67° C.; $[\alpha]^{25.6}_D$ +13.4° (c 1, CHCl$_3$); IR (nujol) 3136, 2950, 1638, 1538, 1457, 1375, 1242, 1177, 1132, 1031, 930, 781, 734, 680, 595 cm$^{-1}$; $^1$H NMR (400 MHz, CDCl$_3$) □ 1.00 (s, (CH$_3$)$_3$), 1.56 (s, NH$_2$), 3.12 (s, CH), 4.38 (d, J=6.4 Hz, NCH$_2$), 5.05 (s, CH$_2$O), 6.90-7.03 (m, 3 ArH, NH), 7.13-7.25 (m, 4 ArH), 7.31-7.37 (m, 1 ArH); $^{13}$C NMR (100 MHz, CDCl$_3$) □ 26.7 ((CH$_3$)$_3$), 34.2 (C(CH$_3$)$_3$), 42.6 (CH$_2$), 64.4 (CH), 69.2 (d, J=1.6 Hz, PhCH$_2$O), 114.1 (d, J=22.5 Hz, C$_{4'}$ or C$_{2'}$), 114.8 (d, J=20.9 Hz, C$_{2'}$ or 115.0 (C$_1$), 122.6 (d, J=3.1 Hz, C$_{6'}$), 129.2 (ArC), 130.1 (d, J=7.7 Hz, C$_{5'}$), 131.2 (ArC), 139.6 (d, J=7.8 Hz, C$_1$), 157.8 (C$_4$), 163.0 (d, J=244.7 Hz, C$_{3'}$), 173.3 (C(O)); MS (M+H$^+$) (ESI$^+$) 345.1978 [M+M$^+$] (calcd for C$_{20}$H$_{25}$FN$_2$O$_2$W 345.1978); Anal. Calcd. for C$_{20}$H$_{25}$FN$_2$O$_2$·H$_2$O: C, 66.28; H, 7.58; F, 5.24; N, 7.73. Found: C, 66.28; H, 7.72; F, 5.40; N, 7.72.

(R)—N-4'-((3"-Fluoro)benzyloxy)benzyl 2-amino-3,3-dimethylbutanamide (1.20 g, 3.3 mmol) was dissolved in CH$_2$Cl$_2$ (40 mL) and Et$_3$N (0.93 mL, 6.6 mmol) and AcCl (0.34 mL, 4.8 mmol) were successively added at 0° C. The mixture was stirred at room temperature (16 h), aqueous 10% citric acid (60 mL) was added, and then the organic layer was separated. The aqueous layer was washed with $CH_2Cl_2$ (2×30 mL). All of the organic layers were combined, washed with aqueous saturated $NaHCO_3$ (30 mL) and $H_2O$ (30 mL), dried ($MgSO_4$), and concentrated in vacuo. The solid was purified by flash column chromatography on silica gel with EtOAc/hexanes (8/2 to 10/0) as the eluant to obtain (R)—N-4'-((3"-fluoro)benzyloxy)benzyl 2-acetamido-3,3-dimethylbutanamide as a white solid (1.03 g, 81%): $R_f$=0.56 (EtOAc); mp 64-66° C.; $[\alpha]^{27.0}_D$ −15.6° (c 1, $CHCl_3$); IR (nujol) 3111, 2938, 2862, 1657, 1557, 1511, 1458, 1373, 1304, 1176, 1044, 930, 826, 768, 723, 680, 569 $cm^{-1}$; $^1H$ NMR (400 MHz, $CDCl_3$) δ 0.99 (s, $(CH_3)_3$), 1.89 (5, $CH_3C(O)$), 4.42 (1/2 ABq, J=5.2, 14.4 Hz, NCHH'), 4.34-4.40 (m, CH, NCHH'), 5.02 (s, $CH_2O$), 6.41 (br d, J=8.8 Hz, $NHC(O)CH_3$), 6.88 (d, J=8.8 Hz, $2H_3$), 6.85-6.96 (br m, NH), 7.00 (t, J=8.4 Hz, 1 ArH), 7.11-7.18 (m, 4 ArH), 7.30-7.36 (m, 1 ArH), addition of excess (R)-(−)-mandelic acid to a $CDCl_3$ solution of the desired compound gave only one signal for the acetyl methyl protons; $^{13}C$ NMR (100 MHz, $CDCl_3$) δ 23.2 ($CH_3C(O)$), 26.6 ($(CH_3)_3$), 34.8 ($C(CH_3)_3$), 43.0 ($NCH_2$), 60.5 (CH), 69.1 (d, J=2.3 Hz, $CH_2O$), 114.1 (d, J=21.7 Hz, $C_{4'}$ or $C_{2'}$), 114.8 (d, J=20.9 Hz, $C_{2'}$ or $C_{4'}$), 115.0 ($C_1$), 122.6 (d, J=3.1 Hz, $C_{6'}$), 129.2 ($C_2$), 130.1 (d, J=8.5 Hz, $C_{5'}$), 130.4 ($C_1$), 139.5 (d, J=7.8 Hz, $C_{1'}$), 157.8 ($C_4$), 162.9 (d, J=244.7 Hz, $C_{3'}$), 170.0, 170.5 (2C(O)); HRMS (M+Na$^+$) (ESI$^+$) 409.1903 [M+Na$^+$] (calcd for $C_{22}H_{27}FN_2O_3Na^+$ 409.1903); Anal. Calcd. for $C_{22}H_{27}FN_2O_3$: C, 68.37; H, 7.04; F, 4.92; N, 7.25. Found: C, 68.31; H, 7.20; F, 5.08; N, 7.25.

Preparation of (R)—N-(3"-Fluorobiphenyl-4-yl)methyl 2-Acetamido-3-methoxypropionamide Reaction Overview

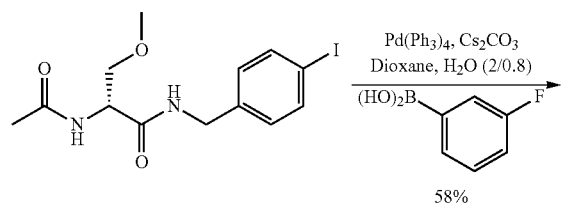

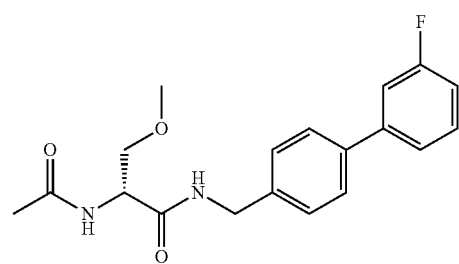

58%

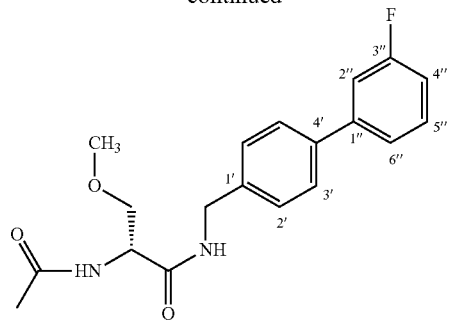

Preparation of (R)—N-(3"-Fluorobiphenyl-4-yl)methyl 2-Acetamido-3-methoxypropionamide To a flame-dried Schlenck tube, under Ar, containing a dioxane (22.5 mL) solution of (R)—N-4'-(iodo)benzyl 2-acetamido-3-methoxypropionamide[1] (1.50 g, 4.0 mmol), palladiumtetrakis(triphenylphosphine) (464 mg, 0.402), and 3-fluorophenylboronic acid (670 mg, 4.80 mmol) was added an aqueous solution (9 mL) of $Cs_2CO_3$ (2.60 g, 8.0 mmol). The mixture was stirred at reflux (16 h). Then MeOH and silica gel were added, and the volatiles were concentrated in vacuo. The residue was purified by flash chromatography on silica gel with EtOAc/MeOH (10/0 to 9/1) as the eluant to obtain (R)—N-(3'-fluorobiphenyl-4-yl)methyl 2-acetamido-3-methoxypropionamide (0.95 g, 60%) as a yellowish solid. To remove traces of palladium impurities, the solid was treated with 6.00 g of resin scavenger (SPM32, PhosPhonics) in $CH_2Cl_2$. The mixture was stirred at room temperature (2 h), filtered, and the filtrate evaporated under vacuum to obtain 800 mg (58%) of (R)—N-(3"-fluorobiphenyl-4-yl)methyl 2-acetamido-3-methoxypropionamide as a white solid: $R_f$=0.22 (EtOAc); mp 170-172° C.; $H^{25.3}_D$=−8.1° (c 0.5, $CHCl_3$); IR (nujol mull) 3288, 2922, 2857, 1642, 1549, 1457, 1376, 1299, 1254, 1190, 1108, 1048, 875, 784, 723, 604 $cm^{-1}$; $^1H$ NMR ($CDCl_3$) δ 2.03 (s, $CH_3C(O)$), 3.39 (s, $OCH_3$), 3.47 (d, J=7.5, 9.3 Hz, CHH'O), 3.81 (d, J=3.9, 9.3 Hz, CHH'O), 4.45-4.55 (m, $CH_2N$), 4.56-4.63 (m, NC(H)CO), 6.53 (br d, J=6.6 Hz, $NHC(O)CH_3$), 6.93-7.07 (m, $CH_2NH$, ArH), 7.23-7.51 (m, 5 ArH), 7.53 (d, J=8.1 Hz, 2 ArH), addition of excess (R)-(−)-mandelic acid to a $CDCl_3$ solution of (R)—N-(3"-fluorobiphenyl-4-yl)methyl 2-acetamido-3-methoxypropionamide gave only one signal for the acetyl methyl and one signal for the ether methyl protons; $^{13}C$ NMR (DMSO-$d_6$) δ 23.2 ($CH_3C(O)$), 43.2 ($CH_2N$), 52.4 ($CHCH_2$), 59.1 ($OCH_3$), 71.7 ($CH_2OCH_3$), 113.8 (d, J=18.8 Hz, $C_{2'}$ or $C_{4'}$), 114.1 (d, J=17.7 Hz, $C_{4'}$ or $C_{2'}$), 122.6 (d, J=2.8 Hz, $C_{6'}$), 127.3, 127.9 ($C_2$, $C_3$), 130.2 (d, J=8.5 Hz, $C_{1'}$ or $C_{5'}$), 137.6 ($C_1$), 139.1 (d, J=2.3 Hz, $C_4$), 142.9 (d, J=8.0 Hz, $C_{5'}$ or $C_{1'}$), 163.2 (d, J=244.2 Hz, $C_{3'}$), 170.1, 170.3 (2C(O)); HRMS (M+Cs$^+$) (ESI$^+$) 477.0591 [M+Cs$^+$] (calcd for $C_{19}H_{21}FN_2O_3Cs^+$ 477.0587); Anal. Calcd. for $C_{19}H_{21}FN_2O_3$: C, 66.26; H, 6.15; F, 5.52; N, 8.13. Found: C, 66.05; H, 6.13; F, 5.32; N, 8.04.

[1] Salome, C.; Salome-Grosjean, E.; Park, K. D.; Morieux, P.; Swendiman, R.; DeMarco, E.; Stables, J. P.; Kohn, H. *J. Med. Chem.* 2010, 53, 1288-1305.

133

Preparation of (R)—N-4'-((3"-Fluoro)phenoxy)benzyl 2-N-Acetamido-3-methoxypropionamide Reaction Overview

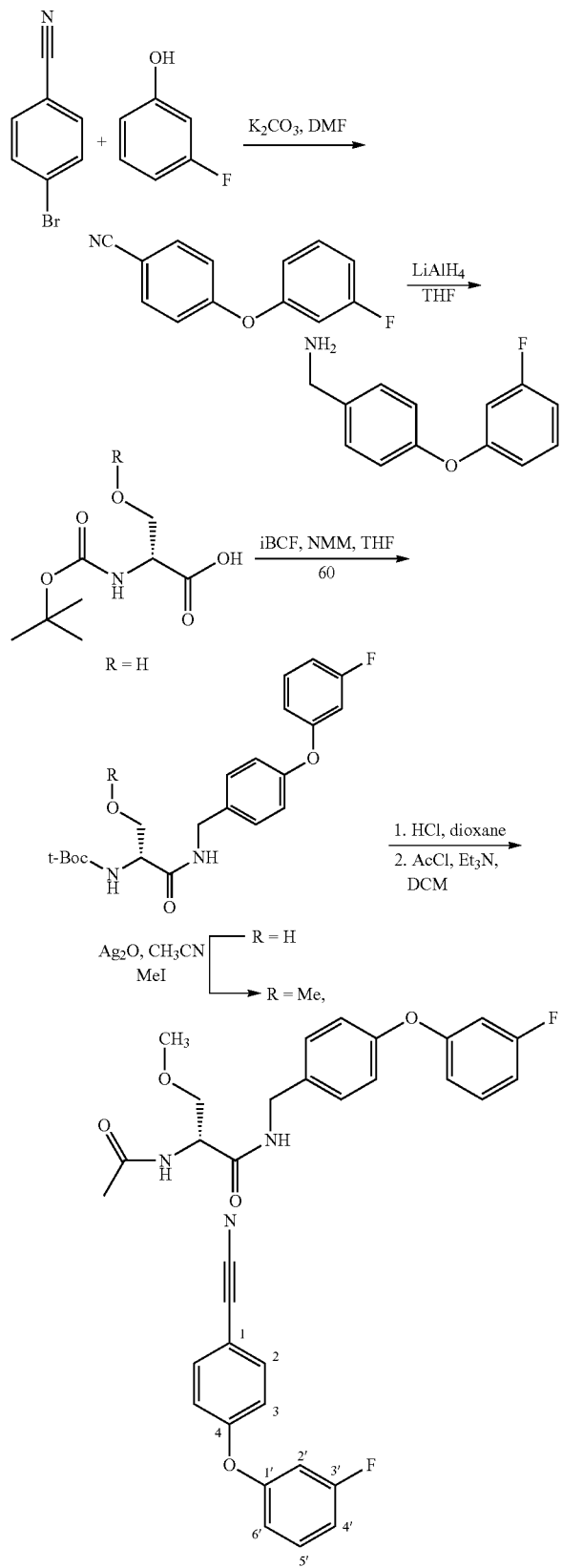

134

Preparation of 4-((3'-Fluoro)phenoxy)benzonitrile

A DMF (83 mL) solution of $K_2CO_3$ (12.60 g, 91.3 mmol), 4-bromobenzonitrile (15.00 g, 83.0 mmol) and 3-fluorophenol (8.2 mL, 91.3 mmol) was stirred at reflux (24 h). DMF was removed by distillation and the residue was purified by flash column chromatography on silica gel with EtOAc/hexanes (0/10 to 5195) as the eluent to obtain 4-((3'-fluoro)phenoxy)benzonitrile as a white solid (9.81 g, 56%): $R_f$=0.54 (EtOAc/hexanes 5/95); mp 67-69° C.; IR (nujol) 3073, 2961, 2912, 2862, 2219, 1593, 1461, 1376, 1265, 1225, 1163, 1119, 954, 869, 830, 788, 677, 543 cm$^{-1}$; $^1$H NMR (300 MHz, CDCl$_3$) δ 6.79 (dt, J=2.1, 9.9 Hz, 1 ArH), 6.84-6.98 (m, 2 ArH), 7.05 (d, J=9.0 Hz, 2H$_3$), 7.32-7.41 (m, 1 ArH), 7.64 (d, J=9.0 Hz, 2H$_2$); $^{13}$C NMR (75 MHz, CDCl$_3$) δ 106.7 (C$_1$), 107.9 (d, J=23.9 Hz, C$_2'$ or C$_{4'}$), 111.9 (d, J=21.1 Hz, C$_{4'}$ or C$_{2'}$), 115.6 (d, J=3.4 Hz, C$_{6'}$), 118.5, 118.6 (CN, C$_3$), 131.0 (d, J=9.7 Hz, C$_{5'}$), 134.2 (C$_2$), 156.2 (d, J=10.3 Hz, C$_{1'}$), 160.7 (C$_4$), 163.6 (d, J=247.1 Hz, C$_{3'}$); HRMS (M+H$^+$) (ESI$^+$) not observed [M+H$^+$] (calcd for C$_{13}$H$_8$FNOH$^+$ 214.0668); Anal. Calcd. for C$_{13}$H$_8$FNO: C, 73.23; H, 3.78; F, 8.91; N, 6.57. Found: C, 73.18; H, 3.69; F, 8.68; N, 6.53.

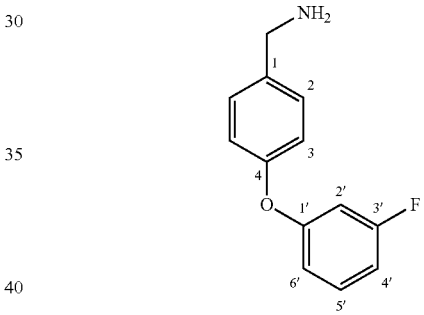

Preparation of 4'-((3"-Fluoro)phenoxy)benzylamine

To a LiAlH$_4$ (3.21 g, 84.5 mmol) suspension in THF (300 mL) was added dropwise a THF (50 mL) solution of 4'-((3% fluoro)phenoxy)benzonitrile (6.00 g, 28.2 mmol) at 0° C. The mixture was stirred at room temperature (16 h) and then H$_2$O (2.5 mL) was added dropwise at 0° C. followed by an aqueous NaOH solution (1.25 mL, 15% w/w) and then H$_2$O (2.5 mL). The mixture was stirred at room temperature (2 h) and the precipitate was filtered, and the pad was washed with CH$_2$Cl$_2$. The filtrate was concentrated in vacuo to give 4.00 g of a colorless oil (65%): $R_f$=0.00 (hexanes/EtOAc 911); $^1$H NMR (300 MHz, CDCl$_3$) δ 1.55 (br s, NH$_2$), 3.87 (s, CH$_2$NH$_2$), 6.66-6.80 (br m, 3 ArH), 7.01 (d, J=7.5 Hz, 2 ArH), 7.24-7.32 (m, 3 ArH); $^{13}$C NMR (100 MHz, CDCl$_3$) δ5.8 (CH$_2$NH$_2$), 105.8 (d, J=24.8 Hz, C$_{2'}$ or C$_{4'}$), 109.7 (d, J=20.9 Hz, C$_{4'}$ or C$_{2'}$), 113.7 (d, J=3.1 Hz, C$_{6'}$), 119.7, 128.7 (2 ArC), 130.4 (d, J=10.0 Hz, C$_{5'}$), 138.8 (C$_2$), 155.0 (C$_4$), 159.1 (d, J=10.9 Hz, C$_{1'}$), 163.5 (d, J=244.2 Hz, C$_{3'}$); HRMS (M-NH$_2$)$^+$ (ESI$^+$) 201.0698 [M-NH$_2$]$^+$ (calcd for C$_{13}$H$_{10}$FO$^+$ 201.0715).

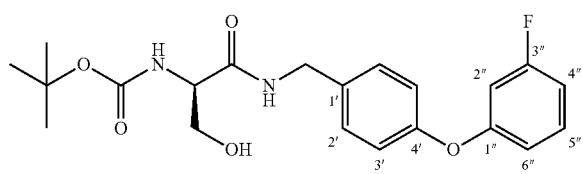 [SMILES: CC(C)(C)OC(=O)N[C@H](CO)C(=O)NCc1ccc(Oc2cccc(F)c2)cc1]

Preparation of (R)—N-4'-((3"-Fluoro)phenoxy)benzyl 2-N-(tert-Butoxycarbonyl)amino-3-hydroxypropionamide A THF solution (150 mL) of (R)-t-Boc-serine (3.00 g, 14.6 mmol) was stirred and cooled at −78° C. under Ar and then 4-methylmorpholine (NMM) (1.9 mL, 17.6 mmol) was added dropwise. After 2 min of stirring at this temperature, isobutylchloroformate (IBCF) (2.3 mL, 17.6 mmol) was added dropwise leading to the precipitation of a white solid, and the reaction was allowed to proceed for additional 2 min, and then 4-((3'-fluoro)phenoxy)benzylamine (3.50 g, 16.1 mmol) was added portionwise at −78° C. The mixture was allowed to stir at room temperature (2 h), and the white solid filtered and the organic layer concentrated in vacuo. The residue was purified by flash column chromatography on silica gel with EtOAc/hexanes (0/10 to 713) as the eluant to obtain (R)—N-4'-((3"-fluoro)phenoxy)benzyl 2-N-(tert-butoxycarbonyl)amino-3-hydroxypropionamide as a sticky white gum (3.55 g, 60%): $R_f$=0.34 (hexanes/EtOAc 5/5); $[\alpha]^{25.9}_D$ +16.3° (c 1, CHCl$_3$); IR (nujol) 3322, 3265, 2917, 2858, 1659, 1600, 1525, 1458, 1375, 1270, 1119, 1011, 961, 849, 766, 670, 579, 510 cm$^{-1}$; $^1$H NMR (400 MHz, CDCl$_3$) δ 1.42 (s, (CH$_3$)$_3$), 3.33-3.44 (br m, OH), 3.64-3.73 (br m, CHH'), 4.06-4.22 (br m, CHH', CH), 4.34-4.52 (br m, CH$_2$NH), 5.67 (d, J=7.2 Hz, NH), 6.64-6.81 (m, 3 ArH), 6.97 (d, J=8.8 Hz, 2 ArH), 7.11-7.19 (br m, NH), 7.21-7.29 (m, 3 ArH); $^{13}$C NMR (100 MHz, CDCl$_3$) δ 28.2 ((CH$_3$)$_3$), 42.7 (NCH$_2$), 54.9 (OCH$_2$CH), 62.7 (OCH$_2$CH), 80.6 (C(CH$_3$)$_3$), 106.0 (d, J=24.0 Hz, C$_{2'}$ or C$_{4'}$), 109.9 (d, J=20.9 Hz, C$_{4'}$ or C$_{2'}$), 113.9 (d, J=3.1 Hz, C$_{6'}$), 119.7, 129.1 (2 ArC), 130.5 (d, J=9.3 Hz, C$_{5'}$), 133.5 (ArC), 155.6 (C$_4$), 156.3 (NHC(O)O), 158.7 (d, J=10.1 Hz, C$_{1'}$), 163.5 (d, J=245.4 Hz, C$_{3'}$), 171.4 (C(O)); HRMS (M+H$^+$) (ESI$^+$) 405.1826 [M+H$^+$] (calcd for C$_{21}$H$_{25}$FN$_2$O$_5$H$^+$ 405.1826); Anal. Calcd. for C$_{21}$H$_{25}$FN$_2$O$_5$.0.05H$_2$O: C, 62.22; H, 6.24; F, 4.69; N, 6.91. Found: C, 61.86; H, 6.53; F, 4.37; N, 6.88.

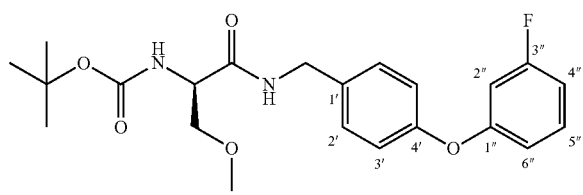 [SMILES: COC[C@@H](NC(=O)OC(C)(C)C)C(=O)NCc1ccc(Oc2cccc(F)c2)cc1]

Preparation of (R)—N-4'-((3"-Fluoro)phenoxy)benzyl 2-N-(tert-Butoxycarbonyl)amino-3-methoxypropionamide Ag$_2$O (8.86 g, 38.4 mmol) was added to a CH$_3$CN solution (150 mL) of (R)—N-4'-((3"-fluoro)phenoxy)benzyl 2-N-(tert-butoxycarbonyl)amino-3-hydroxypropionamide (3.10 g, 7.7 mmol) and CH$_3$I (4.8 mL, 77.0 mmol) at room temperature under Ar. The reaction mixture was stirred at room temperature in the dark (3 d), filtered through Celite®, and the filtrate concentrated in vacuo to obtain a white solid. The solid was purified by flash column chromatography on silica gel with EtOAc/hexanes (5/95 to 50/50) as the eluant to obtain (R)—N-4'-((3"-fluoro)phenoxy)benzyl 2-N-(tert-butoxycarbonyl)amino-3-methoxypropionamide as a colorless oil (3.20 g, quant.): $R_f$=0.42 (1/1 EtOAc/hexanes); IR (nujol) 3156, 2935, 1711, 1672, 1601, 1457, 1372, 1264, 1168, 1118, 960, 855, 774, 680, 507 cm$^{-1}$; $^1$H NMR (400 MHz, CDCl$_3$) δ 1.44 (s, (CH$_3$)$_3$), 3.37 (s, OCH$_3$), 3.50 (dd, J=6.4, 9.2 Hz, CHH'), 3.85 (dd, J=4.0, 9.2 Hz, CHH'), 4.23-4.32 (br m, CH), 4.47 (br t, J=4.4 Hz, CH$_2$NH), 5.36-5.44 (br m, NH), 6.67 (dt, J=2.4, 10.4 Hz, 1 ArH), 6.74-6.71 (m, 2 ArH, NH), 6.99 (d, J=8.4 Hz, 2H$_{3'}$), 7.22-7.29 (m, 3 ArH); $^{13}$C NMR (100 MHz, CDCl$_3$) δ 28.2 ((CH$_3$)$_3$), 42.8 (NCH$_2$), 54.0 (OCH$_2$CH), 59.1 (OCH$_3$), 71.9 (CH$_2$O), 80.3 (C(CH$_3$)$_3$), 105.9 (d, J=24.5 Hz, C$_{2'}$ or C$_{4'}$), 109.9 (d, J=21.2 Hz, C$_{4'}$ or C$_{2'}$), 113.8 (d, J=3.2 Hz, C$_{6'}$), 119.7, 129.0 (2 ArC), 130.5 (d, J=9.7 Hz, C$_{5'}$), 133.7 (ArC), 155.6 (NHC(O)O), 158.8 (d, J=10.9 Hz, C$_{1'}$), 163.5 (d, J=245.0 Hz, C$_{3'}$), 170.3 (C(O)), the remaining aromatic peak was not detected and is believed to overlap with the observed signals; Anal. Calcd. for C$_{22}$H$_{27}$FN$_2$O$_5$: C, 63.14; H, 6.50; F, 4.54; N, 6.69. Found: C, 63.19; H, 6.63; F, 4.37; N, 6.63.

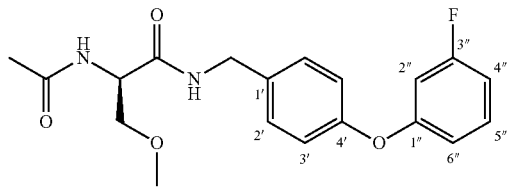 [SMILES: COC[C@@H](NC(C)=O)C(=O)NCc1ccc(Oc2cccc(F)c2)cc1]

Preparation of (R)—N-4'-((3"-Fluoro)phenoxy)benzyl 2-N-Acetamido-3-methoxypropionamide A saturated HCl solution in dioxane (1 mmol/2 mL, 16.7 mL) was added to an Et$_2$O (8 mL) solution of (R)—N-4'-((3"-fluoro)phenoxy)benzyl 2-N-(tert-butoxycarbonyl)amino-3-methoxypropionamide (3.50 g, 8.4 mmol) at 0° C. and the solution was stirred at room temperature (16 h). The reaction solution was concentrated in vacuo and dried (30 min).

The residue was dissolved in CH$_2$Cl$_2$ (40 mL) and Et$_3$N (3.52 mL, 25.1 mmol) and AcCl (0.91 mL, 12.5 mmol) were successively added at 0° C. The mixture was stirred at room temperature (16 h), aqueous 10% citric acid (60 mL) was added, and then the organic layer was separated. The aqueous layer was washed with CH$_2$Cl$_2$ (2×30 mL). All of the organic layers were combined, washed with aqueous saturated NaHCO$_3$ (30 mL) and H$_2$O (30 mL), dried (MgSO$_4$), and concentrated in vacuo. The solid was purified by flash column chromatography on silica gel with EtOAc as the eluant to obtain (R)—N-4'-((3"-fluoro)phenoxy)benzyl 2-N-acetamido-3-methoxypropionamide as a white solid (1.30 g, 43%): $R_f$=0.45 (EtOAc); mp 125-126° C.; $[\alpha]^{25.3}_D$ −14.8° (c 1, CHCl$_3$); IR (nujol) 3148, 2974, 2918, 1637, 1552, 1457, 1377, 1274, 1223, 1126, 963, 846, 764, 725, 606 cm$^{-1}$; NMR (300 MHz, CDCl$_3$) δ 2.04 (s, CH$_3$C(O)), 3.39 (s, OCH$_3$), 3.45 (dd, J=7.5, 9.3 Hz, CHH'), 3.81 (dd, J=4.2, 9.3 Hz, CHH'), 4.45 (d, J=6.0 Hz, CH$_2$NH), 4.53-4.59 (m, CH), 6.48 (br d, J=6.0 Hz, NHC(O)CH$_3$), 6.68 (dt, J=2.4, 10.2 Hz, 1 ArH), 6.74-6.89 (m, 2 ArH, NH), 6.99 (d, J=9.0 Hz, 2H$_3$), 7.21-7.34 (m, 3 ArH), addition of excess (R)-(−)-mandelic acid to a CDCl$_3$ solution of the compound gave only one signal for the acetyl methyl protons; $^{13}$C NMR (100 MHz, CDCl$_3$) δ 23.2 (CH$_3$C(O)), 42.9 (NCH$_2$), 52.4 (OCH$_2$CH), 59.1 (OCH$_3$), 71.6 (CH$_2$O), 106.0 (d, J=24.4 Hz, C$_{2'}$ or C$_{4'}$), 109.9 (d, J=21.3 Hz, C$_{4'}$ or C$_{2'}$), 113.9 (d, J=2.5 Hz, C$_{6'}$), 119.6, 129.0 (2 ArC), 130.5 (d, J=9.6 Hz, C$_{5'}$), 133.6, 155.6 (2 ArC), 158.7 (d, J=10.9 Hz, C$_{1'}$), 163.5 (d, J=245.7 Hz, C$_{3'}$), 170.0, 170.3 (2C(O)); HRMS (M+H$^+$) (ESI$^+$) 361.1564 [M+H$^+$] (calcd for C$_{19}$H$_{21}$FN$_2$O$_4$H$^+$ 361.1563); Anal. Calcd. for C$_{19}$H$_{21}$FN$_2$O$_4$: C, 63.32; H, 5.87; F, 5.27; N, 7.77. Found: C, 63.35; H, 5.84; F, 5.06; N, 7.78.

Preparation of (R)—N-4'-((3"-Fluoro)phenethoxy)benzyl 2-N-Acetamido-3-methoxypropionamide

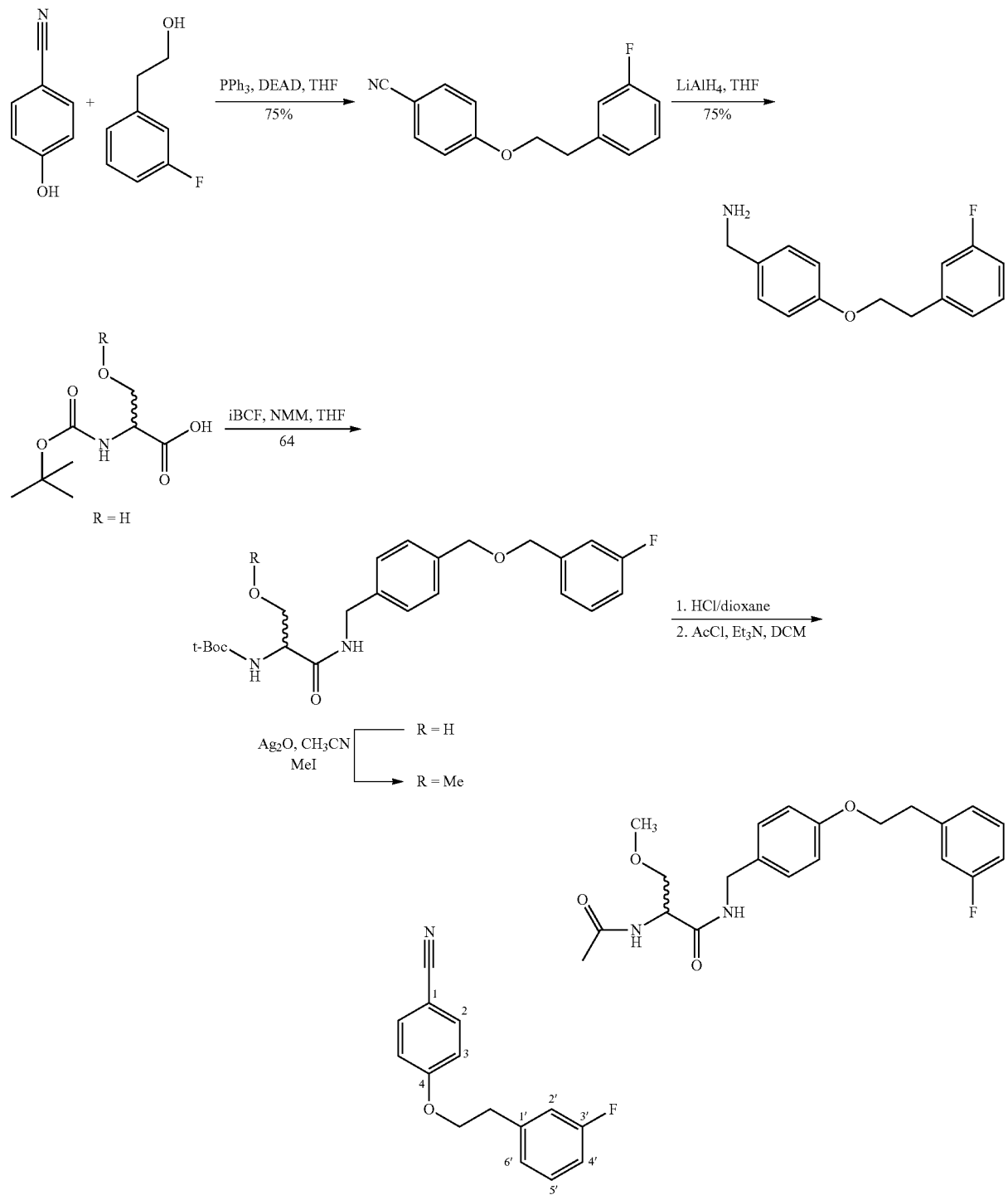

Preparation of 4-((3'-Fluoro)phenethoxy)benzonitrile

A THF (2 mL) solution of 3-(fluoro)phenethyl alcohol (168 mg, 1.2 mmol) and DEAD (205 µL, 1.3 mmol) was very slowly added dropwise at 0° C. to a THF (4 mL) solution of triphenylphosphine (341 mg, 1.3 mmol) and 4-cyanophenol (119 mg, 1.0 mmol). The mixture was stirred at 0° C. (30 min), and then at room temperature (16 h). A saturated aqueous solution of NH$_4$Cl (200 mL) was added dropwise at 0° C. The volatiles were evaporated under vacuum and the residue was purified by flash column chromatography on silica gel with EtOAc/hexanes (0/10 to 2/8) as the eluant to obtain 4-((3'-fluoro)phenethoxy)benzonitrile as a white solid (180 mg, 75%): R$_f$=0.33 (EtOAc/hexanes 1/9); mp 79-81° C.; IR (crystal) 3281, 2909, 2222, 1711, 1643, 1603, 1589, 1506, 1489, 1450, 1418, 1300, 1250, 1171, 1140, 1115, 1057, 1024, 941 cm$^{-1}$; $^1$H NMR (400 MHz, CDCl$_3$) δ 3.11 (t, J=7.0 Hz, CH$_2$), 4.22 (t, J=7.0 Hz, OCH$_2$), 6.92-7.06 (m, 5 ArH), 7.20-7.31 (m, 1 ArH), 7.57 (d, J=8.0 Hz, 2H$_3$); $^{13}$C NMR (100 MHz, CDCl$_3$) δ 35.2 (d, J=1.6 Hz, CH$_2$), 68.5 (CH$_2$O), 104.1 (C$_1$), 113.6 (d, J=21.0 Hz, C$_{2'}$ or C$_{4'}$), 115.2 (C$_3$), 115.9 (d, J=20.9 Hz, C$_{4'}$ or C$_{2'}$), 119.1 (CN), 124.6 (d, J=3.1 Hz, C$_{6'}$), 130.0 (d, J=8.6 Hz, C$_{5'}$), 134.0 (C$_2$), 140.2 (d, J=7.0 Hz, C$_{1'}$), 161.9 (C$_4$), 162.9 (d, J=247.7 Hz, C$_{3'}$); HRMS (M+H$^+$) (ESI$^+$) not observed [M+H$^+$] (calcd for C$_{13}$H$_8$FNOH$^+$ 214.0668); Anal. Calcd. for C$_{15}$H$_{12}$FNO: C, 74.67; H, 5.01; F, 7.87; N, 5.81. Found: C, 74.46; H, 5.11; F, 7.89; N, 5.83.

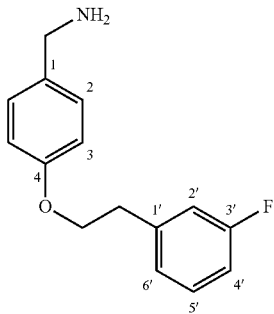 [SMILES: NCc1ccc(OCCc2cccc(F)c2)cc1]

Preparation of 4-(((3'-Fluoro)phenethoxy)benzylamine

To a LiAlH$_4$ (3.80 g, 99.6 mmol) suspension in THF (350 mL) was added dropwise a THF (750 mL) solution of 4-((3'-fluoro)phenethoxy)benzonitrile (8.00 g, 33.2 mmol) at 0° C. The mixture was stirred at room temperature (16 h) and then H$_2$O (3.0 mL) was added dropwise at 0° C. followed by an aqueous NaOH solution (1.5 mL, 15% w/w) and then H$_2$O (3.0 mL). The mixture was stirred at room temperature (2 h) and the precipitate was filtered and washed with CH$_2$Cl$_2$. The filtrate was concentrated in vacuo to give 5.50 g of a colorless oil (68%): R$_f$=0.00 (hexanes/EtOAc 9/1); $^1$H NMR (400 MHz, CDCl$_3$) δ 1.75 (br s, NH$_2$), 3.07 (t, J=6.7 Hz, CH$_2$), 3.79 (s, CH$_2$NH$_2$), 4.16 (t, J=6.7 Hz, OCH$_2$), 6.84-7.06 (m, 5 ArH), 7.20-7.29 (m, 3 ArH); $^{13}$C NMR (100 MHz, CDCl$_3$) δ 35.5 (d, J=1.6 Hz, CH$_2$), 45.8 (CH$_2$NH$_2$), 68.2 (CH$_2$O), 113.3 (d, J=20.9 Hz, C$_{2'}$ or C$_{4'}$), 114.6 (C$_3$), 115.9 (d, J=20.9 Hz, C$_{4'}$ or C$_{2'}$), 124.6 (d, J=3.1 Hz, C$_{6'}$), 128.3 (C$_2$), 129.8 (d, J=8.5 Hz, C$_{5'}$), 135.5 (C$_1$), 140.9 (d, J=7.8 Hz, C$_{1'}$), 157.6 (C$_4$), 162.8 (d, J=243.9 Hz, C$_{3'}$); HRMS (M+H$^+$) (ESI$^+$) 246.1294 [M+H$^+$] (calcd for C$_{16}$H$_{16}$FNOH$^+$ 246.1294); Anal. Calcd. for C$_{16}$H$_{16}$FNO.0.15H$_2$O: C, 72.65; H, 6.62; F, 7.66; N, 5.65. Found: C, 72.61; H, 6.58; F, 7.28; N, 5.46.

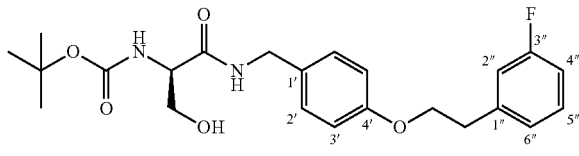 [SMILES: CC(C)(C)OC(=O)N[C@H](CO)C(=O)NCc1ccc(OCCc2cccc(F)c2)cc1]

Preparation of (R)—N-4% ((3"-Fluoro)phenethoxy)benzyl 2-N-(tert-Butoxycarbonyl)amino-3-hydroxypropionamide A THF solution (250 mL) of (R)-t-Boc-serine (5.00 g, 21.6 mmol) was stirred and cooled at −78° C. under Ar and then 4-methylmorpholine (NMM) (2.9 mL, 26.0 mmol) was added dropwise. After 2 min of stirring at this temperature, isobutylchloroformate (IBCF) (3.4 mL, 26.0 mmol) was added dropwise leading to the precipitation of a white solid, and the reaction was allowed to proceed for additional 2 min, and then 4-((3'-fluoro)phenethoxy)benzylamine (6.30 g, 26.0 mmol) was added portionwise at −78° C. The mixture was allowed to stir at room temperature (2 h), and the white solid filtered and the organic layer concentrated in vacuo. The residue was purified by flash column chromatography on silica gel with EtOAc/hexanes (5/5 to 10/0) as the eluant to obtain (R)—N-4'-((3"-fluoro)phenethoxy)benzyl 2-N-(tert-butoxycarbonyl)amino-3-hydroxypropionamide as colorless oil (3.00 g, 32%): R$_f$=0.32 (hexanes/EtOAc 5/5); [α]$^{26.3}_D$ +14.8° (c 1, CHCl$_3$); IR (nujol) 3329, 3281, 3252, 1691, 1657, 1643, 1549, 1524, 1388, 1366, 1300, 1277, 1238, 1171, 1140, 1113, 1034, 957, 781 cm$^{-1}$; $^1$H NMR (400 MHz, CDCl$_3$) δ 1.41 (s, (CH$_3$)$_3$), 3.07 (t, J=6.6 Hz, CH$_2$), 3.34-3.49 (br m, OH), 3.61-3.72 (m, CHH'), 4.05-4.15 (m, OCH$_2$, CH, CHH'), 4.28-4.43 (m, NHCH$_2$), 5.65 (br d, J=7.2 Hz, NH), 6.82 (d, J=7.4 Hz, 2 ArH), 6.89-7.06 (m, NH, 3 ArH), 7.15 (d, J=7.4 Hz, 2 ArH), 7.21-7.29 (m, 1 ArH); $^{13}$C NMR (100 MHz, CDCl$_3$) δ 28.2 ((CH$_3$)$_3$), 35.4 (d, J=1.6 Hz, CH$_2$), 42.9 (NCH$_2$), 54.9 (OCH$_2$CH), 62.8, 68.2 (2 CH$_2$O), 80.5 (C(CH$_3$)$_3$), 113.4 (d, J=20.9 Hz, C$_{2'}$ or C$_{4'}$), 114.7 (C$_3$), 115.8 (d, J=20.9 Hz, C$_{4'}$ or C$_{2'}$), 124.6 (d, J=3.1 Hz, C$_{6'}$), 128.8 (C$_2$), 129.8 (d, J=8.5 Hz, C$_{5'}$), 130.0 (C$_1$), 140.8 (d, J=7.0 Hz, C$_{1'}$), 156.2 (OC(O)NH), 158.1 (C$_4$), 162.8 (d, J=243.9 Hz, C$_{3'}$), 171.2 (C(O)); HRMS (M+Na$^+$) (ESI$^+$) 455.1958 [M+Na$^+$] (calcd for C$_{23}$H$_{29}$FN$_2$O$_5$Na$^+$ 455.1958).

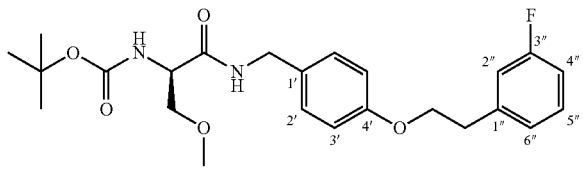 [SMILES: COC[C@@H](NC(=O)OC(C)(C)C)C(=O)NCc1ccc(OCCc2cccc(F)c2)cc1]

Preparation of (R)—N-4'-((3"-Fluoro)phenethoxy)benzyl 2-N-(tert-Butoxycarbonyl)amino-3-methoxypropionamide Ag$_2$O (7.70 g, 33.5 mmol) was added to a CH$_3$CN solution (200 mL) of (R)—N-4'-((3"-fluoro)phenethoxy)benzyl 2-N-(tert-butoxycarbonyl)amino-3-hydroxypropionamide (2.90 g, 6.7 mmol) and CH$_3$I (4.2 mL, 67.0 mmol) at room temperature under Ar. The reaction mixture was stirred at room temperature in the dark (3 d), filtered through Celite®, and the filtrate concentrated in vacuo to obtain a white solid. The solid was purified by flash column chromatography on silica gel with EtOAc/hexanes (3/7 to 6/4) as the eluant to obtain (R)—N-4'-((3''-fluoro)phenethoxy)benzyl 2-N-(tert-butoxycarbonyl)amino-3-methoxypropionamide as a white solid (2.40 g, 80%): $R_f$=0.63 (1/1 EtOAc/hexanes); mp 64-67° C.; $[\alpha]^{25.7}_D$ −16.2° (c 0.5, $CHCl_3$); IR (crystal) 3314, 2928, 1686, 1647, 1414, 1452, 1391, 1317, 1240, 1167, 1138, 1084, 1038, 1020, 912 $cm^{-1}$; $^1H$ NMR (400 MHz, $CDCl_3$) δ 1.42 (s, $(CH_3)_3$), 3.07 (t, J=6.9 Hz, $CH_2$), 3.35 (s, $OCH_3$), 3.46-3.51 (m, CHH'), 3.81 (dd, J=3.8, 9.0 Hz, CHH'), 4.15 (t, J=6.9 Hz, $OCH_2$), 4.19-4.28 (br m, CH), 4.32-4.44 (br m, $CH_2NH$), 5.37-5.45 (br m, NH), 6.65-6.73 (br t, NH), 6.83 (d, J=7.6 Hz, 2 ArH), 6.87-7.05 (m, 3 ArH), 7.17 (d, J=7.6 Hz, 2 ArH), 7.23-7.29 (m, 1 ArH); $^{13}C$ NMR (100 MHz, $CDCl_3$) δ 28.2 (($CH_3)_3$), 35.4 (d, J=1.5 Hz, $CH_2$), 42.9 ($NCH_2$), 54.0 ($OCH_2CH$), 59.0 ($OCH_3$), 68.2 ($OCH_2$), 72.1 ($CH_2OCH_3$), 80.3 ($C(CH_3)_3$), 113.3 (d, J=20.9 Hz, $C_{2'}$ or $C_{4'}$), 114.7 ($C_3$), 115.8 (d, J=20.9 Hz, $C_{4'}$ or $C_{2'}$), 124.6 (d, J=3.1 Hz, $C_{6'}$), 128.8 ($C_2$), 129.8 (d, J=8.5 Hz, $C_{5'}$), 130.3 ($C_1$), 140.8 (d, J=6.9 Hz, $C_{1'}$), 155.5 (OC(O)NH), 158.0 ($C_4$), 162.8 (d, J=244.7 Hz, $C_{3'}$), 170.2 (C(O)); HRMS (M+$Na^+$) ($ESI^+$) 469.2115 [M+$Na^+$] (calcd for $C_{24}H_{31}FN_2O_5Na^+$ 469.2114).

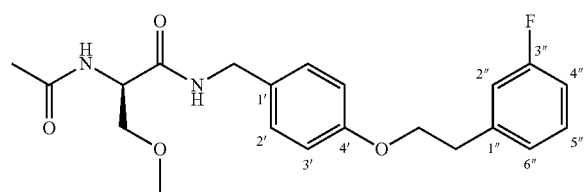 [SMILES: COC[C@@H](NC(C)=O)C(=O)NCc1ccc(OCCc2cccc(F)c2)cc1]

Preparation of (R)—N-4'-((3''-Fluoro)phenethoxy) benzyl 2-N-Acetamido-3-methoxypropionamide A saturated HCl solution in dioxane (1 mmol/2 mL, 10.0 mL) was added to an $Et_2O$ (5 mL) solution of (R)—N-4'-((3''-fluoro)phenethoxy)benzyl 2-N-(tert-butoxycarbonyl)amino-3-methoxypropionamide (2.20 g, 5.0 mmol) at 0° C. and the solution was stirred at room temperature (16 h). The reaction solution was concentrated in vacuo and dried (30 min).

The residue was dissolved in $CH_2Cl_2$ (30 mL) and $Et_3N$ (2.1 mL, 15.0 mmol) and AcCl (0.54 mL, 7.5 mmol) were successively added at 0° C. The mixture was stirred at room temperature (16 h), aqueous 10% citric acid (60 mL) was added, and then the organic layer was separated. The aqueous layer was washed with $CH_2Cl_2$ (2×30 mL). All of the organic layers were combined, washed with aqueous saturated $NaHCO_3$ (30 mL) and $H_2O$ (30 mL), dried ($MgSO_4$), and concentrated in vacuo. The solid was recrystallized with EtOAc to obtain (R)—N-4'-((3''-fluoro)phenethoxy)benzyl 2-N-acetamido-3-methoxypropionamide as a white solid (1.30 g, 66%): $R_f$=0.28 (EtOAc); mp 147-148° C.; $[\alpha]^{25.2}_D$ −16.6° (c 0.5, $CHCl_3$); IR (crystal) 3323, 3240, 3001, 2938, 1738, 1634, 1553, 1541, 1514, 1456, 1368, 1304, 1231, 1217, 1207, 1175, 1134, 1109, 1097, 1034, 1007, 980, 864, 822 $cm^{-1}$; $^1H$ NMR (400 MHz, $CDCl_3$) δ 2.02 (s, $CH_3C(O)$), 3.08 (t, J=7.1 Hz, $CH_2$), 3.36 (s, $OCH_3$), 3.39-3.44 (m, CHH'), 3.79 (dd, J=4.8, 9.6 Hz, CHH'), 4.15 (t, J=7.1 Hz, $OCH_2$), 4.33-4.44 (m, $CH_2NH$), 4.49-4.54 (m, CH), 6.44 (br d, J=6.4 Hz, $NHC(O)CH_3$), 6.65-6.73 (br t, NH), 6.84 (d, J=8.0 Hz, 2 ArH), 6.90-7.06 (m, 3 ArH), 7.16 (d, J=8.0 Hz, 2 ArH), 7.23-7.29 (m, 1 ArH), addition of excess (R)-(−)-mandelic acid to a $CDCl_3$ solution of (R)—N-4'-((3''-fluoro)phenethoxy)benzyl 2-N-acetamido-3-methoxypropionamide gave only one signal for the acetyl methyl and one signal for the ether methyl protons; $^{13}C$ NMR (100 MHz, $CDCl_3$) δ 23.2 ($CH_3C(O)$), 35.4 (d, J=1.6 Hz, $CH_2$), 43.0 ($NCH_2$), 52.4 ($OCH_2CH$), 59.0 ($OCH_3$), 68.2 ($OCH_2$), 71.6 ($CH_2O$), 113.4 (d, J=21.0 Hz, $C_{2'}$ or $C_{4'}$), 114.7 ($C_3$), 115.8 (d, J=20.9 Hz, $C_{4'}$ or $C_{2'}$), 124.6 (d, J=2.3 Hz, $C_{6'}$), 128.8 ($C_2$), 129.8 (d, J=7.7 Hz, $C_{5'}$), 130.1 ($C_1$), 140.8 (d, J=7.8 Hz, $C_{1'}$), 158.1 ($C_4$), 162.8 (d, J=243.9 Hz, $C_{3'}$), 169.8, 170.2 (2C(O)); HRMS (M+$Na^+$) ($ESI^+$) 411.1696 [M+$Na^+$] (calcd for $C_{21}H_{25}FN_2O_4Na^+$ 411.1691); Anal. Calcd. for $C_{21}H_{25}FN_2O_4$: C, 64.93; H, 6.49; F, 4.89; N, 7.21. Found: C, 64.98; H, 6.57; F, 4.84; N, 7.10.

Preparation of (R)—N-4'-(Benzyloxy)benzyl 2-N-Acetamido-3-methoxypropionamide Reaction Overview

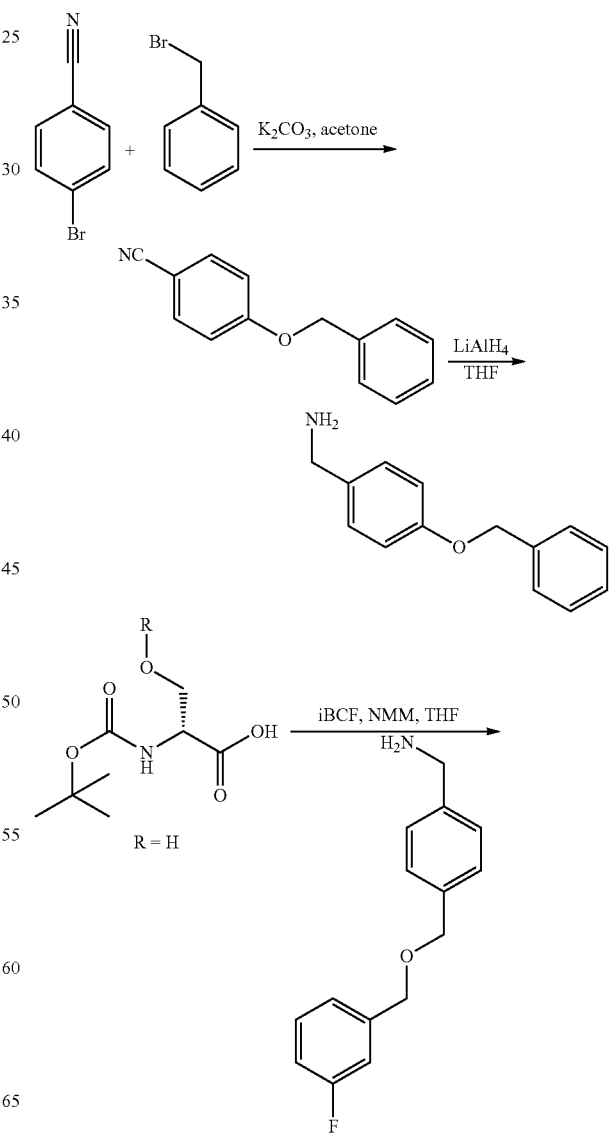

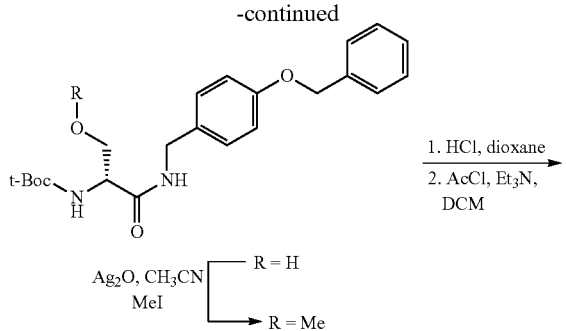
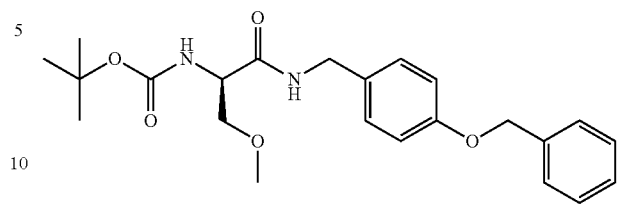

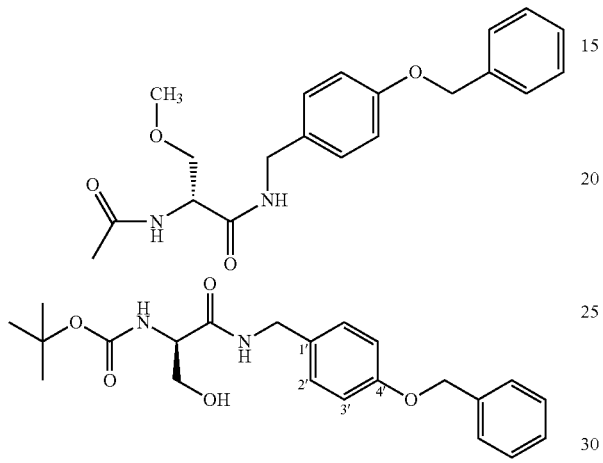

Preparation of (R)—N-4'-(Benzyloxy)benzyl 2-N-(tert-Butoxycarbonyl)amino-3-hydroxypropionamide A THF solution (250 mL) of (R)-t-Boc-serine (5.00 g, 21.6 mmol) was stirred and cooled at −78° C. under Ar and then 4-methylmorpholine (NMM) (2.9 mL, 26.0 mmol) was added dropwise. After 2 min of stirring at this temperature, isobutylchloroformate (IBCF) (3.4 mL, 26.0 mmol) was added dropwise leading to the precipitation of a white solid, and the reaction was allowed to proceed for additional 2 min, and then 4-(benzyloxy)benzylamine[2] (5.20 g, 26.0 mmol) was added portionwise at −78° C. The mixture was allowed to stir at room temperature (2 h), and the white solid filtered and the organic layer concentrated in vacuo. The residue was purified by flash column chromatography on silica gel with EtOAc/hexanes (5/5 to 10/0) as the eluant to obtain (R)—N-4'-(benzyloxy)benzyl 2-N-(tert-butoxycarbonyl)amino-3-hydroxypropionamide as a white solid (6.30 g, 73%): $R_f$=0:31 (hexanes/EtOAc 5/5); mp 64-67° C.; $[\alpha]^{25.3}_D$ +18.0° (c 1, CHCl$_3$); IR (crystal) 3327, 2982, 2936, 2876, 1713, 1684, 1657, 1549, 1514, 1456, 1389, 1368, 1302, 1277, 1236, 1167, 1107, 1034, 1007 cm$^{-1}$; $^1$H NMR (400 MHz, CDCl$_3$) δ 1.41 (s, (CH$_3$)$_3$), 3.20-3.51 (br m, OH), 3.61-3.70 (br m, CHH'), 4.02-4.19 (br m, CHH', CH), 4.26-4.46 (br m, CH$_2$NH), 5.04 (s, OCH$_2$), 5.59-5.68 (br m, NH), 6.91 (d, J=8.4 Hz, 2 ArH), 6.95-7.08 (br m, NH), 7.16 (d, J=8.4 Hz, 2 ArH), 6.30-7.43 (m, 5 ArH); $^{13}$C NMR (100 MHz, CDCl$_3$) δ 28.2 ((CH$_3$)$_3$), 42.9 (NCH$_2$), 54.9 (OCH$_2$CH), 62.8 (OCH$_2$CH), 70.0 (OCH$_2$), 80.6 (C(CH$_3$)$_3$), 115.0, 127.4, 128.0, 128.6, 128.8, 130.1, 136.9 (7 ArH), 156.2 (NHC(O)O), 158.2 (C$_4$), 171.2 (C(O)); HRMS (M+Na$^+$) (ESI$^+$) 423.1896 [M+Na$^+$] (calcd for C$_{22}$H$_{28}$N$_2$O$_5$Na$^+$ 423.1896); Anal. Calcd. for C$_{22}$H$_{28}$N$_2$O$_5$: C, 65.98; H, 7.05; N, 7.00. Found: C, 66.05; H, 7.15; N, 7.04.

[2] Coburger, C.; Wollmann, J.; Baumert, C.; Krug, M.; Molnar, J.; Lage, H.; Hilgeroth, A. *J. Med. Chem.* 2008, 51, 5871-5874

Preparation of (R)—N-4'-(Benzyloxy)benzyl 2-N-(tert-Butoxycarbonyl)amino-3-methoxypropionamide Ag$_2$O (14.40 g, 62.5 mmol) was added to a CH$_3$CN solution (350 mL) of (R)—N-4'-(benzyloxy)benzyl 2-N-(tert-butoxycarbonyl)amino-3-hydroxypropionamide (5.00 g, 12.5 mmol) and CH$_3$I (7.8 mL, 125.0 mmol) at room temperature under Ar. The reaction mixture was stirred at room temperature in the dark (3 d), filtered through Celite®, and the filtrate concentrated in vacuo to obtain a white solid. The solid was purified by flash column chromatography on silica gel with EtOAc/hexanes (515) as the eluant to obtain (R)—N-4'-(benzyloxy)benzyl 2-N-(tert-butoxycarbonyl)amino-3-methoxypropionamide as a white solid (5.10 g, quant.): $R_f$=0.57 (1/1 EtOAc/hexanes); mp 103-104° C.; $[\alpha]^{25.7}_D$ −38.0° (c 0.5, CHCl$_3$); IR (crystal) 3312, 2930, 1684, 1647, 1551, 1514, 1450, 1389, 1364, 1315, 1285, 1240, 1167, 1109, 1086, 1045, 1024 cm$^{-1}$; $^1$H NMR (400 MHz, CDCl$_3$) δ 1.43 (s, (CH$_3$)$_3$), 3.36 (s, OCH$_3$), 3.46-3.51 (br m, CHH'), 3.83 (dd, J=3.2, 9.6 Hz, CHH'), 4.21-4.30 (br m, CH), 4.36-4.45 (br m, CH$_2$NH), 5.06 (s, OCH$_2$), 5.33-5.44 (br m, NH), 6.61-6.66 (br t, NH), 6.93 (d, J=7.0 Hz, 2 ArH), 7.18 (d, J=7.0 Hz, 2 ArH), 7.29-7.44 (m, 5 ArH); $^{13}$C NMR (100 MHz, CDCl$_3$) δ 28.2 ((CH$_3$)$_3$), 43.0 (NCH$_2$), 54.0 (OCH$_2$CH), 59.0 (OCH$_3$), 70.0, 72.0 (2 OCH$_2$), 80.3 (C(CH$_3$)$_3$), 115.0, 127.4, 127.9, 128.6, 128.8, 130.3, 136.9 (7 ArH), 155.5 (NHC(O)O), 158.2 (C$_4$), 170.1 (C(O)); HRMS (M+Na$^+$) (ESI$^+$) 437.2052 [M+Na$^+$] (calcd for C$_{23}$H$_{30}$N$_2$O$_5$Na$^+$ 437.2052); Anal. Calcd. for C$_{23}$H$_{30}$N$_2$O$_5$: C, 66.65; H, 7.30; N, 6.76. Found: C, 66.90; H, 7.25; N, 6.84.

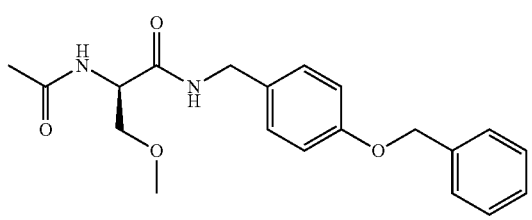 [SMILES: COC[C@@H](NC(C)=O)C(=O)NCc1ccc(OCc2ccccc2)cc1]

Preparation of (R)—N-4'-(Benzyloxy)benzyl 2-N-Acetamido-3-methoxypropionamide A saturated HCl solution in dioxane (1 mmol/2 mL, 24.1 mL) was added to an Et$_2$O (10 mL) solution of (R)—N-4'-(benzyloxy)benzyl 2-N-(tert-butoxycarbonyl)amino-3-methoxypropionamide (5.00 g, 12.1 mmol) at 0° C. and the solution was stirred at room temperature (16 h). The reaction solution was concentrated in vacuo and dried (30 min).

The residue was dissolved in $CH_2Cl_2$ (60 mL) and $Et_3N$ (5.1 mL, 36.3 mmol) and AcCl (1.4 mL, 18.8 mmol) were successively added at 0° C. The mixture was stirred at room temperature (16 h), aqueous 10% citric acid (60 mL) was added, and then the organic layer was separated. The aqueous layer was washed with $CH_2Cl_2$ (2×30 mL). All of the organic layers were combined, washed with aqueous saturated $NaHCO_3$ (30 mL) and $H_2O$ (30 mL), dried ($MgSO_4$), and concentrated in vacuo. The solid was recrystallized with EtOAc to obtain (R)—N-4'-(benzyloxy)benzyl 2-N-acetamido-3-methoxypropionamide as a white solid (2.60 g, 60%): $R_f$=0.28 (EtOAc); mp 149° C.; $[\alpha]^{25.1}_D$ –26.8° (c 0.5, $CHCl_3$); IR (crystal) 3283, 3028, 2940, 1738, 1719, 1636, 1551, 1514, 1454, 1433, 1368, 1304, 1229, 1217, 1177, 1140, 1099, 1036, 1026, 910, 810 cm$^{-1}$; $^1$H NMR (400 MHz, $CDCl_3$) δ 2.02 (s, $CH_3C(O)$), 3.36 (s, $CH_3$), 3.39-3.44 (br m, CHH'), 4.02-3.79 (dd, J=4.2, 9.4 Hz, CHH'), 4.36-4.44 (m, $CH_2NH$), 4.48-4.55 (m, CH), 5.05 (s, $OCH_2$), 6.42 (br d, J=6.0 Hz, NH), 6.64-6.71 (br m, NH), 6.93 (d, J=7.8 Hz, 2 ArH), 7.18 (d, J=7.8 Hz, 2 ArH), 7.29-7.44 (m, 5 ArH), addition of excess (R)-(–)-mandelic acid to a $CDCl_3$ solution of (R)—N-4'-(benzyloxy)benzyl 2-N-acetamido-3-methoxypropionamide gave only one signal for the acetyl methyl and one signal for the ether methyl protons; $^{13}$C NMR (100 MHz, $CDCl_3$) δ 23.2 ($CH_3C(O)$), 43.0 ($NCH_2$), 52.4 ($OCH_2CH$), 59.0 ($OCH_3$), 70.0, 71.6 (2 $OCH_2$), 115.0, 127.4, 128.0, 128.6, 128.8, 130.2, 136.8 (7 ArH), 158.2 ($C_4$), 169.8, 170.2 (C(O)); HRMS (M+Na$^+$) (ESI$^+$) 379.1634 [M+Na$^+$] (calcd for $C_{20}H_{24}N_2O_4Na^+$ 379.1634); Anal. Calcd. for $C_{20}H_{24}N_2O_4$: C, 67.40; H, 6.79; N, 7.86. Found: C, 67.12; H, 6.68; N, 7.80.

Example 4

Assay Procedures

1. Whole Animal Pharmacology Studies: Anti-Nociceptive/Anti-Neuropathic Pain Properties In Vivo
   A. Writhing Test, Mouse.

Dose-dependent efficacy of test compounds will be determined in the acetic acid (writhing) test in which intraperitoneal injection of a chemical irritant induces specific (writhing) movements that are counted over a defined time period. This unspecific test with some tonic chemically induced nociceptive aspects usually gives positive results for all psychoactive drugs and muscle relaxants. Therefore, this result is taken as a first indication that the test compound may have anti-nociceptive properties, and further studies will be performed to support this hypothesis and to investigate the in vivo profile of the compound.

B. Formalin Test, Mouse and Rat

The formalin test is a chemically induced tonic pain model in which biphasic changes of nociceptive behavior (Dubuisson & Dennis, 1977; Wheeler-Aceto & Cowan, 1991; Abbott et al., 1995) are assessed. Spinal/supraspinal plasticity of nociception is considered as a molecular basis for neuropathic pain particularly during the second (late) phase of the test (Dubuisson & Dennis, 1977; Coderre et al., 1990; Coderre & Melzack, 1992), during which most clinically used drugs against neuropathic pain are active. These features have resulted in the formalin test's being accepted as a valid model of persistent clinical pain (Tjolsen et al., 1992).

For active compounds in the mouse formalin test, the compound is then tested in the rat formalin test by use of a more sophisticated assessment, the weighted behavioral scoring method described by Dubuisson and Dennis (1977). Freely moving animals undergo observational assessment of the position of the left hind paw according to a rating score scaled 0-3 before and 10, 20, 30 and 40 min after injection of 0.05 ml of sterile 2.5% formalin under the skin on the dorsal surface of the paw. The test compound is administered i.p. just prior to formalin injection.

C. Chronic Constriction Injury (Bennett Model) Rat.

The effectiveness of the test compound in reducing spontaneous chronic pain, mechanical allodynia, and thermal hyperalgesia is tested using the chronic constriction injury (CCI) model of peripheral neuropathy, one of the best characterized in vivo animal models used to study chronic pain due to peripheral nerve injury (Bennett & Xie, 1988). In this model, loose ligatures are placed around the sciatic nerve, which produces axonal swelling and a partial deafferentation manifested as a significant but incomplete loss of axons in the distal portion of the peripheral nerve (Basbaum et al., 1991). One of the prominent behaviors seen following sciatic nerve ligation is the appearance of hind paw guarding, thought to be an indication of an ongoing spontaneous chronic pain. Support for this idea is derived from reports of increased spinal cord neural activity (Price et al., 1991; Mao et al., 1992) and increased spontaneous neuronal discharge in spinothalamic tract neurons (Palecek et al., 1992) and in the ventrobasal thalamus (Guilbaud et al., 1990) in the absence of overt peripheral stimulation. In addition to the appearance of spontaneous pain behaviors, several abnormalities in stimulus-evoked pain occur as a result of CCI, including thermal hyperalgesia and mechanical allodynia (Bennett & Xie, 1988; Bennett, 1993; Kingery et al., 1993). The development of these abnormal stimulus-evoked pain symptoms has also been reported as occurring in areas outside the territory of the damaged nerve, i.e., areas innervated by uninjured nerves (Kingery et al., 1993; Tal & Bennett, 1994).

Behavioral tests for spontaneous pain, thermal hyperalgesia, and mechanical allodynia are conducted to evaluate different components of neuropathic pain. Baseline data for each test is collected prior to any experimental procedure. In addition, 13-25 days after CCI surgery all animals are tested for the development of chronic pain behavior 1 day prior to the day of vehicle (0.04 ml sterile water/10 g body weight) or drug administration and after vehicle/drug administration. The sequence of the tests will be (1) spontaneous pain-related behavior, (2) mechanical allodynia, (3) thermal hyperalgesia, so as to minimize the influence of one test on the result of the next. The testing procedures and results are presented separately for each aspect of chronic pain. Either 0 (vehicle, 0.04 ml/10 g body weight), 5, 10, 20, or 40 m/kg of test compound is administered i.p. 15 min before the first behavior test.

Spontaneous pain (ongoing pain without an apparent external stimulus) of the ligated paw is assessed for 5 min following a 10 min acclimation period by use of a rating score (weighted behavior score scaled 0-5) according to the method of Attal et al. (1990).

Thermal hyperalgesia is assessed by means of withdrawal latency in response to radiant heat applied to the subplantar surface of the ligated rat hind paw, according to Hargreaves and coworkers (1988). As compared with the baseline latency, a significant decrease in the (post-operative) latency of foot withdrawal in response to the thermal stimulus is interpreted as presence of thermal hyperalgesia following chronic constriction injury.

Mechanical sensitivity and allodynia of the ligated rat hind paw is quantified by brisk foot withdrawal in response to normally innocuous mechanical stimuli as described previously (Möller et al., 1998). Responsiveness to mechanical stimuli is tested with a calibrated electronic Von Frey pressure algometer connected to a computerized data collection system. A significant decrease in the postoperative versus the baseline pressure (g/mm$^2$) necessary to elicit a brisk foot withdrawal in response to this mechanical stimulus is interpreted as mechanical allodynia.

D. Randall-Selitto Paw Pressure Test, Rat.

Potential anti-nociceptive efficacy of the test compounds is also assessed in a rat experimental model of acute inflammation using a modified Randall and Selitto procedure (Randall & Selitto, 1957). Acute inflammation is induced by injection of s.c. carrageenan (1.0 mg in 0.1 ml saline/paw), an unspecific inflammatory agent, into the plantar surface of one hind paw. Mechanical sensitivity and nociceptive thresholds are measured using an algesimeter device that exerts a constantly increasing mechanical force (10 mmHg/sec) at which the rat vocalizes or struggles or withdraws it paw. The Randall and Selitto mechanical paw pressure test is a standard method for testing the efficacy of new compounds for alleviating acute inflammatory pain.

The test compound or vehicle (sterile water, 0.04 ml/10 g body weight) is administered i.p. after carrageenan but before the start of behavioral testing. As compared with the response threshold of vehicle-treated controls, an increase in the pressure required to produce a behavior response is interpreted as anti-nociception.

E. Tail Flick Test, Mouse and Rat.

Test compounds are additionally tested for potential activity in acute spinal thermal nociception using the tail flick test. In this model of acute thermal spinal/reflex hyperalgesia, radiant heat is applied to the animal's tail approximately 1 cm (mouse) to 2 cm (rat) from the tip and the time latency for withdrawal reaction is automatically assessed by an algometer. A defined maximal stimulus time prevents tissue damage. This test, described by D'Amour and Smith (1941) is widely used as an assay for the anti-nociceptive efficacy of pharmacological agents and is highly predictive of acute analgesic efficacy in humans (Ness & Gebhart, 1986; Kiritsy-Roy et al., 1994). Usually pure analgesics of the opioid type are most active; neither adjuvants like amitriptyline nor NSAIDs (non-steroidal anti-inflammatory drugs) are active.

F. Chronic Inflammatory Pain Model (Freund's Complete Adjuvant (FCA) Model), Rat.

For similar methods, see procedure described by Stoehr et al. (2006). FCA (100 uL) is administered subcutaneously to the dorsal aspect of the left hind paw of the rat leading to the formation of a localized edema, a model of chronic inflammatory pain. The edema is observed within 2 h, and typically peaks by 6 h, and lasts for ~7 d. To measure the effect of the test compound on mechanical allodynia in the FCA model, a modified Randall-Selitto method (Analgesy-Meter, Ugo Basile, Italy) can be utilized. Here, the animal's paw is placed on a small plinth under a cone-shaped pusher. Then, increasing force is applied until either vocalization or withdrawal of the paw occurs. The minimum force required to elicit this response is termed the paw pressure threshold. Accordingly, initial basal (control) readings are measured in absence of the test compound, and then the test compound is administered orally. The paw pressure thresholds are determined 30, 60, and 180 min post administration. The FCA method provides the paw edema/volume using a plethysmometer (Ugo Basile, Italy). Here, the paw of the rat is immersed in a reservoir of water and the volume of water displaced indicated the paw volume. Using this method, the initial basal (control) readings are measured, and then the test compound is administered orally and the paw volume measured 30 and 60 min post administration.

G. Tumor Necrosis Factor-Alpha (TNF) Model of Muscle Pain, Rat.

Chronic muscle pain occurs with high frequency. Using the method described by Beyreuther et al. (2007) recombinant rat TNF (diluted) is injected (im) during short isofluorane narcosis bilaterally either into the gastrocnemius or into the biceps brachii muscle of rats. Typically, pressure hyperalgesia is maximal after 18 h. Mechanical withdrawal thresholds to muscle pressure are measured with an algesimeter (UgoBasile, Comerio, Italy). Here, the rat crawls into the sock, the hind limbs positioned so that increasing pressure can be applied onto the gastrocnemius muscle (maximum typically 250 g), and the pressure needed to elicit withdrawal is recorded. The test compounds are typically administered ip and then the paw pressure was tested 30-60 min post administration. Similarly, the grip strength of the fore limbs can be determined using a digital grip force meter (DFIS series, Chatillon, Greensboro, N.C.). Here, the rat is positioned to grab the grid with the fore limbs and then gently pulled so that the grip strength can be determined. Again, the test compound is administered ip prior to measurement.

H. Diabetic Neuropathy-Streptozotocin Model of Diabetic Neuropathic Pain, rat. For a representative protocol, see Beyreuther et al. (2006). Diabetes is induced by intravenous injections of streptozocin in the left magna. Blood glucose levels are determined before each phase of behavioral testing. Tests for allodynia (cold bath (4° C.); warm plate (38° C.) are run 10 days after induction of diabetes with streptozotocin and tests for hyperalgesia (paw pressure and hot plate at 52° C.) and dynamic mechanical allodynia (brushing tests) are typically run on day 21.

2. Whole Animal Pharmacology Studies: In Vivo Anticonvulsant and Antiepileptic Properties A. Maximal Electroconvulsive Shock, Mice and Rat.

The maximal electroconvulsive shock (MES) test is regarded as a standard screen for anticonvulsant activity in terms of inhibition of seizure spread in generalized tonic-clonic seizures.

Groups of at least 8 male albino CF No. 1 mice or male albino Sprague-Dawley rats are treated with 10 mL/kg i.p. or 4 mL/kg p.o. of the test compound solution, respectively. The electrical stimulus in the MES test is 50 mA at 60 Hz for mice and 150 mA at 60 Hz for rats, both delivered for 0.2 sec. Abolition of the hind leg tonic extensor component of the seizure is used as the endpoint.

B. Hippocampal Kindling, Rat.

The kindling model provides a tool to predict a test compound's activity in complex partial seizures.

Male albino Sprague-Dawley rats (n=8) are kindled to a Stage 5 behavioral seizure. They are treated with an appropriate i.p. dose of the test compound after a 1-week, stimulus-free period. The test compound is evaluated for its effect on kindled motor seizures (seizures scores of 4 and 5), limbic behavior seizures (seizure scores between 1 and 3) and after-discharge duration. After 15 min, each rat is stimulated every 30 min for 3-4 h. Following each stimulation, individual seizure scores and after-discharge duration are recorded. The group mean and standard error of the mean (SEM) are calculated for each parameter.

C. Chemoconvulsant-Induced Seizures, Mice.

The pentylenetetrazole (Metrazol, Met) model is considered to be a model of myoclonic seizures. Other chemoconvulsants like the GABA$_A$ antagonist bicuculline (Bic), and the chloride-channel blocker picrotoxin (Pic) induce generalized tonic-clonic convulsions. By use of these models, the test compound's anticonvulsant effects on these mechanisms can be studied.

In male albino CF No. 1 mice, the test compound is dosed i.p. at 25 mg/kg (concomitantly with 85 mg Met/kg s.c.), 50 mg/kg (Bic: 2.7 mg/kg s.c.), and 30 mg/kg (Pic: 2.5 mg/kg s.c.) (Wolf et al., 1996). In rats, effects of the test compound dosed at 250 mg/kg p.o. on clonic seizures induced by a does of 70 mg Met/kg s.c. is examined. Absence of a 3-sec clonic episode is used as the endpoint for protection in these tests. Animals that received either Met or Bic are observed for at least 30 min for the presence or absence of a seizure. Those that received Pic are observed for 45-60 min because the onset of action for this convulsant is slightly longer. The timed i.v. infusion (0.34 mL/min) of 0.5% Met in heparinized saline to mice is used to determine if the test compound possesses the potential to elevate the seizure threshold for the chemoconvulsant. The endpoints measured in this test are the time to "first twitch" of whole body and time to "sustained clonus" of forelimbs. Results obtained with groups of 10 mice are then converted to mg/kg of Met required to induce each endpoint.

D. Frings Audiogenic Seizures, Mice.

The Frings audiogenic seizure (AGS)-susceptible mouse model is useful for gross screening of anticonvulsant activity although it cannot predict a test compound's activity against a specific type of epilepsy. Male and female Frings AGS-susceptible mice are treated with the test compound. Groups of at least 8 mice are employed for $ED_{50}$ calculation. At the time of peak effect (TPE), as determined in the MES test, individual mice are exposed to a sound stimulus of 110 decibels (11 KHz), delivered for 20 sec in a plexiglass cylinder. Sound-induced seizures are characterized by wild running followed by loss of righting reflex with forelimb and hindlimb tonic extension. Mice not displaying hindlimb tonic extension are considered protected.

E. Self-Sustaining Status Epilepticus (SSSE), Rat.

Groups of 5 male Wistar rats are treated with either 50 mg/kg i.v. of test compound dissolved in 10% DMSO or fosphenyloin (equivalent to 50 mg/kg phenyloin) 10 min after the end of perforant path stimulation. Control animals (n=6) are injected i.v. with vehicle (10% DMSO). In the control animals, symptoms of SSSE are limbic seizures, which recurred with different frequency for up to 24 h after the end of electrical stimulation. Continuous spikes between seizures are recorded.

Histological examination of brain sections are collected 72 h after status epilepticus to reveal the extent of the effects of the compound tested and control rates to see if it may be neuroprotective. The sections selected for quantitation contained dorsal hippocampus and posterior to the bregma. Damage to the pyramidal cell layer is assessed by counting damaged neurons in the subiculum, CA1, CA3, CA3c, and the hilus in the dorsal hippocampus. Neurons are counted only if the majority of the nucleus are present in the section. Damaged neurons are counted if they were distinctly eosinophilic or distinctly pyknotic or both.

F. Chemically Induced, Self-Sustaining Status Epilepticus, Rat (Cobalt/Homocysteine Model of SSSE).

The test compound at i.p. doses of 10, 20, 40, 80, or 100 mg/kg is tested in male Sprague-Dawley rats with cobalt/homocysteine-induced status epilepticus (8/group). Rats are treated with the test compound immediately following the second generalized tonic-clonic seizures (GTCS) after homocysteine injection.

3. Whole Animal Pharmacology Studies: Essential Tremors

Rat Harmaline Model of Essential Tremors, Rats.

Employing the method described by Stoehr et al. (2008) rats are given the test compound Ip typically 30 min before harmaline administration or saline as a control. The rats are placed in individual plexiglass cages for behavioral assessment. Two individuals independently record their observations and these individuals are blind to the treatment protocol. Defined are the latency of tremor onset (the time between harmaline administration and the appearance of tremors); and the intensity of tremors as defined by Arsaduddin (2004) which are first recorded at tremor onset. These observations are recorded every 30 min post harmaline administration over a 2 h period.

4. Whole Animal Pharmacology Studies: Neuroprotective/Anti-Ischemic Properties

A. Focal Ischemia, Rats.

Permanent MCAO in male Wistar rats (n=5/group) is accomplished by ligating the MCA while the animals are under anesthesia. An initial dose of the test compound or the respective volume of the vehicle (PBS) is administered 15 min before occlusion, followed by a 5 mg/kg/h i.v. infusion for 4 h; control rats received saline. On the fourth day after MCAO, the animals are sacrificed by decapitation, the brains immediately removed and frozen (−70° C.). Coronal sections (20 μm) are made, stained with 2% crystal violet and the ischemic infarct volume (total ischemic area in $mm^2$) quantitatively assessed by an Image Analyzer.

B. Focal Ischemia, Rats.

Groups of 10 Sprague-Dawley rats are treated with either the test compound or the vehicle starting at 30 min after initiation of the temporal occlusion of the MCA (90 min). Measurements include arterial blood pressure and blood gasses, neurological scoring, infarct volume (uncorrected and corrected), percent hemispheric infarct volume, and edema volume.

5. Whole Animal Pharmacology Studies: Bi-Polar Disorders

Unfortunately, there are no standard animal models of bipolar disorder. A number of competing models with varying degrees of documentation have been proposed. They mimic some aspects of bipolar disorder and include: (a) chlordiazepoxide-amphetamine model (to study antimanic properties of compounds); (b) forced swim test that is sometimes used to study the effect of a drug on bipolar depression, however, this model seems to be better for the identification of treatments for unipolar depression; (c) cocaine and intracranial self stimulation (ICSS) test that appears to have some utility but it is not a validated model of bipolar disorder (when the rat is in a cocaine withdrawal state, the assay can be used to study the effect of a test compound on bipolar depression) (Tomasiewicz et al., 2008, Tomasiewicz et al., 2006, Carlezon and Chartoff, 2007); and (d) clock mutant mice assay (Roybal et al., 2007).

6, Pharmacodynamic Tolerance

Induction of tolerance is assessed by testing the decrease in protection against MES and decrease in hexobarbital sleep time. Four groups of 8 male Sprague-Dawley rats each are treated p.o. daily for 4 days with vehicle (groups 1 and 2), an MED $ED_{50}$ dose of the test compound (group 3) or a large dose of the test compound (group 4). On day 5, animals in groups 2, 3 and 4 received an MES $ED_{50}$ dose of the test compound and those in group 1 received another dose of the vehicle. All groups are test at the time of peak effect for drug efficacy against MES-induced tonic extension described under anticonvulsant and antiepileptic properties in vivo. Following the MES test, animals in group 4 receive the test compound in a dose equal to the difference between the $ED_{50}$ and 100 mg/kg.

On day 6, all groups are tested for sleep time response (time from loss to regaining of righting reflex) to a standard dose (100 mg/kg i.p.) of hexobarbital. The hexobarbital sleep time test provides an assessment of hepatic drug metabolism and is employed to provide an early indication of whether altered drug efficacy could result from pharmacokinetic tolerance rather than, or in addition to, pharmacodynamic tolerance. Following the performance of this test, all animal groups receive the same treatment that they received on day 1. Day 7 has a similar dosing allocation except that group 2 receives 10 mg/kg of the test compound. On days 8 and 9, 4 rats from each of the 4 groups are euthanized. Blood is collected for sALT activity, which is an indicator of possible liver damage.

7. Therapeutic Index

Tests are conducted in groups of at least 8 mice or rats to determine the intrinsic neurotoxicity (neuromuscular impairment) after administration of the test compound by the route of administration to be used in the pharmacology studies. Neurotoxicity is determined in male CF No 1 mice by the rotarod procedure. Inability of the mouse to maintain its equilibrium in 3 trials during 1 min on this rotating rod (6 rpm) is used as an indication of such impairment. In Sprague-Dawley rats, minimal motor impairment (MMI) is determined by overt evidence of ataxia, abnormal gait, and stance.

8. Mechanistic Studies

A. Receptor Binding (Displacement) Assays.

Test compounds will be tested for in vitro receptor binding activity in a number of test systems at 10 μm that include different receptors, ion channels, growth factor receptors, and secondary messengers. The compounds will be tested to see if they displace binding of radiolabeled ligands to the following receptors: adenosine, $α_1$, $α_2$, $β$, dopamine-1, dopamine-2, $GABA_A$, $GABA_B$, serotonin-1, serotonin-2, NMDA, kainate, quisqualate, glycine (strychnine-sensitive), benzodiazepine, phencyclidine, MK-801, angiotensin II type 2, vasopressin, CCK (central and peripheral), substance P, substance K, NPY, neurotensin, somatostatin, VIP, ANF1, and EFG. In addition, the compounds will be tested if they inhibit carbonic anhydrase activity in vitro. Compounds will also be tested to see if they are active against calcium (type N, T and L), chloride and potassium (low conductance) channels and if they influence secondary messenger systems tested (e.g., forskolin, phorbol ester, $IP_3$). Further, compound testing (10 μm) will be conducted against glutamate receptor subtypes and other glycine binding sites (e.g., AMPA, kainate, NMDA agonist).

B. Gated Ion-Channel Interaction.

To gain insight into the underlying molecular mode of action of the compounds, they are tested for GABA or glutamate receptor-gated ion channel interaction by means of whole cell, patch-clamp electrophysiological recordings in primary cultures (14-21 days in vitro) of cortical neurons from 15-gestational day-old Swiss Webster mouse fetuses. Two distinct protocols can be used to investigate the effects of the test compounds on agonist-evoked, whole cell currents: an acute protocol for detection of direct drug-ion channel interaction and a pre-treatment protocol to assess possible slow binding kinetics or indirect mechanisms of drug-ion channel interaction. In addition agonist-independent currents mediated by the compound itself can be detected by the pretreatment protocol.

The effect of the test compounds on voltage-gated $Na^+$ channels are investigated in the NIE-115 neuroblastoma cell line (n=6 cells) under $Ca^{2+}$ and $K^+$ channel blockage condition (presence of $CdCl_2$ and tetraethylammonium chloride). $Na^+$ channels are activated by hyperpolarizing the cells from −80 to +60 mV in 10-mV increments in control and at 1 and 2 min following incubation of the test compound. As some antiepileptic compounds have voltage-dependent mechanisms of action, effects of the test compounds are also tested on cells held at a more depolarized holding potential (−60 mV).

For details on proposed mechanistic sodium channel investigations with Professors Lees (Errington et al., 2008) and Cummins (Sheets et al., 2008) see comparable studies conducted on lacosamide. Key studies include (1) examination of steady-state fast and slow inactivation of voltage-gated sodium channels in N1E-115 cells; (2) examination of the activity of selected compounds on recombinant $Na_v1.3$, and 1.7 sodium currents expressed in peripheral sensory HEK293 neurons and $Na_v1.8$-type TTX-R currents from DRG neurons using whole-cell patch clamp electrophysiology where both steady-state fast inactivation and slow inactivation is monitored, and the determination of IC50 values for inhibition of these channels. The results of these studies will be compared with lacosamide and safinamide (where appropriate).

C. Monoamine Oxidase Inhibition Assay.

Monoamine oxidase (MAO) A and B enzymatic activities are assessed with a radioenzymatic assay using $^{14}C$-serotonin (5-HT) and $^{14}C$-phenylethylamine (PEA) as selective substrates for MAO-A and MAO-B, respectively, according to a well-consolidated procedure (Drukarch & van Muiswinkel, 2000; Robinson et al., 1968).

The mitochrondrial pellet (500 μg protein) is resuspended in 200 μL of 0.1 M phosphate buffer, pH 7.40, and is added to 50 μL of the solution of the inhibitor or of buffer and incubated for 30 min at 37° C. (preincubation). Then, the substrate in 50 μL of buffer (5 μM $^{14}C$-5-HT or 0.5 μM $^{14}C$-PEA) is added, and the assay mixture is incubated at 37° C. for 30 min (5-HT) or for 10 min (PEA). The reaction is stopped by adding 0.2 mL of HCl or perchloric acid for 5-HT or PEA, respectively. After centrifugation, the acidic radioactive metabolites are extracted with 3 mL of diethyl ether (for 5-HT) or toluene (for PEA), and the radioactivity of the organic phase was measured by liquid scintillation spectrometry at 90% efficiency. The enzymatic activity is expressed as nanomoles of substrate transformed per milligram of protein per minute (nmol $mg^{-1}$ $min^{-1}$). Drug inhibition curves are obtained from five to eight different concentrations ($10^{-10}$-$10^{-5}$ M), each in duplicate, and the IC50 is determined using nonlinear regression analysis (GraphPad best-fitting computer program).

REFERENCES

Abbott F V, Franklin K B J, Westbrook, R F (1995). The formalin test: Scoring properties of the first and second phases of the pain response in rats. Pain 60:91-102.

Altal N, Jazat F, Kayser V, Guilbaud G (1990). Further evidence for "pain-related" behaviors in a model of unilateral peripheral mononeuropathy. Pain 41:235-251.

Basbaum A I, Gautron M, Jazat F, Mayes M, Guilbaud G (1991). The spectrum of fiber loss in a model of neuropathic pain in the rat: An electron microscopic study. Pain 47:359-367.

Bennett G J, Zie Y K (1988). A peripheral mononeuropathy in rat that produces disorders of pain sensation like those seen in man [see comments]. Pain 33:87-107.

Beyreuther B, Callizot N, Stoehr T (2006). Antinociceptive efficacy of lacosamide in a rat model for painful diabetic neuropathy. Eur J. Pharmacol, 538, 64-70

Beyreuther B K, Geis C, Stoehr T, Sommer C (2007). Antihyperalgesic efficacy of lacosamide in a rat model for muscle pain induced by TNF. Neuropharmacology 52, 1312-1317.

Carlezon W A Jr, Chartoff E H. (2007) Intracranial self-stimulation (ICSS) in rodents to study the neurobiology of motivation. Nat. Protoc. 2, 2987-95.

Coderre T J, Melzack R (1992). The contribution of excitatory amino acids to central sensitization and persistent nociception after formalin-induced tissue injury. J Neurosci 12:3665-3670.

Coderre T J, Vaccarino A L, Melzack R (1990). Central nervous system plasticity in the tonic pain response to subcutaneous formalin injection. Brain Res 535:155-158.

D'Amour F E, Smith D L (1941). A method of determining loss of pain sensation. J Pharmacol Exp Ther 72:74-79.

Drukarch B, van Muiswinkel F L (2000). Drug treatment of Parkinson's disease. Time for phase II. Biochem. Pharmacol 59:1023-1031.

Dubuisson D, Dennis S G (1977). The formalin test: A quantitative study of the analgesic effects of morphine and brain stem stimulation in rats and cats. Pain 4:161-174.

Errington A C, Stoehr T, Heers C, Lees G (2008). The investigational anticonvulsant lacosamide selectively enhances slow inactivation of voltage-gated sodium channels. Mol Pharm 73, 157-169.

Goussakov I, Chartoff E H, Tsvetkov E, Gerety L P, Meloni E G, Carlezon W A Jr, Bolshakov V Y. (2006) LTP in the lateral amygdala during cocaine withdrawal. Eur J. Neurosci. 23, 239-50.

Guilbaud G, Benoist J M, Jazat F, Gautron M (1990). Neuronal responsiveness in the ventrovasal thalamic complex of rats with an experimental peripheral mononeuropathy. J neurophysiol 64:1637-1554.

Kingery W S, Castellote J M, Wang E E (1993). A loose ligature-induced mononeuropathy produces hyperalgesia and mechano-allodynia in the territory of an uninjured nerve. Pain 55:297-304.

Kiritsy-Roy J A, Shyu B C, Danneman P J, Morrow T J, Belczynski C, Casey K L (1944). Spinal antinociception mediated by a cocaine-sensitive dopaminergic supraspinal mechanism. Brain Res 644:109-116.

Mao J, Price D D, Coghill R C, Mayer D J, Hayes R L (1992). Spatial patterns of spinal core [14C]-2-deoxyglucose metabolic activity in a rat model of painful peripheral mononeuropathy [published erratum appears in Pain 51(3):389]. Pain 50:89-100.

Möller K A, Johansson B, Berge O G (1998). Assessing mechanical allodynia in the rat paw with a new electronic algometer. J Neurosci Methods 84:41-47.

Ness T J, Gebhart G F (1986). Centrifugal modulation of the rat tail flick reflex evoked by graded noxious heating of the tail. 386:41-52.

Palecek J, Paleckova V, Dougherty P M, Carlton S M, Willis W D (1992). Responses of spinothalamic tract cells to mechanical and thermal stimulation of skin in rats with experimental peripheral neuropathy. J Neurophysiol 67:1562-1573

Price D D, Mao J, Coghill R C, D'Avella D, Cicciarello R, Fiori M G, Mayer D J, Hayes R L (1991). Regional changes in spinal cord glucose metabolism in a rat model of painful neuropathy. Brain Res 564:314-318.

Randall L O, Selitto J J (1957). A method for measurement of analgesic activity on inflamed tissue. Arch Int Pharmacodyn Ther 111:409-419.

Robinson D S, Lovenberg W, Keiser H (1968). Sjoerdsma effects of drugs on human blood platelet and plasma amine oxidase activity in vitro and in vivo. Biochem Pharmacol 17:109-119.

Roybal K, Theobold D, Graham A, DiNieri J A, Russo S J, Krishnan V, Chakravarty S, Peevey J, Oehrlein N, Birnbaum S, Vitaterna M H, Orsulak P, Takahashi J S, Nestler E J, Carlezon W A Jr, McClung C A. (2007) Mania-like behavior induced by disruption of CLOCK. Proc Natl Acad Sci 104, 6406-11.

Sheets, P L, Heers, C, Stoehr T, Cummins, T R (2008) Differential block of sensory neuronal voltage-gated sodium channels by lacosamide [(2R)-2-(acetylamino)-N-benzyl-3-methoxypropanamide], lidocaine, and carbamazepine. J. Pharmacol. Exp. Ther 326, 88-89.

Stoehr T, Krause E, Selve N (2006) Lacosamide displays potent antinociceptive effects in animal models for inflammatory pain. Europ. J. Pain 10, 241-249

Stoehr T, Lekieffre, D, Freitag J (2008) Lacosamide, the new anticonvulsant, effectively reduces harmaline-induced tremors in rats. Eur. J. Pharmacol 589, 114-116.

Tal M, Bennett G J (1994). Extra-territorial pain in rats with a peripheral mononeuropathy: Mechano-hyperalgesia and mechano-allodynia in the territory of an uninjured nerve. Pain 57:375-382.

Tomasiewicz H C, Mague S D, Cohen B M, Carlezon W A Jr. (2006) Behavioral effects of short-term administration of lithium and valproic acid in rats. Brain Res. 1093, 83-94.

Tomasiewicz H C, Todtenkopf M S, Chartoff E H, Cohen B M, Carlezon W A Jr. (2008) The kappa-opioid agonist U69,593 blocks cocaine-induced enhancement of brain stimulation reward. Biol Psychiatry 64, 982-8.

Tjolsen A, Berg O-G, Hunskaar S, Rosland J H, Hole K (1992). The formalin test: An evaluation of the method. Pain 51:5-17.

Wheeler-Aceto H, Cowan A (1991). Standardization of the rat paw formalin test for the evaluation of analgesics. Psychopharmacology Berl, 104:33-44.

TABLE 3

Novel Neurological Agents: Structure-Activity Relationship of R Group[a]

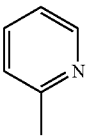

| Cpd No | R | Stereo | Mice (ip)[b] | | | | Rat (po)[f] | | |
| --- | --- | --- | --- | --- | --- | --- | --- | --- | --- |
| | | | Mes,[c] $ED_{50}$ | 6 Hz, $ED_{50}$ | Tox,[d] $TD_{50}$ | PI[e] | MES,[c] $ED_{50}$ | Tox,[g] $TD_{50}$ | PI[e] |
| 5 | H | — | >100, <300 [4.0] >30, >100 [2] | | >300 [0.5 and 4.0] | | 31 [1.0] (18-53) | >500 [1.0] | >16 |
| (R)-6 | (R)-Me | R | >30, <100 [0.5 and 4] | | >300 [0.5] | | 31 [4.0] (21-44) | >500 [4.0] | >16 |
| (S)-6 | (S)-Me | S | >100, <300 [0.5] >300 [4.0] | | >300 [0.5] | | >30 [0.25 to 4.0] | >30 [0.25 to 4.0] | |
| (R)-7 | (R)-i-Pr | R | >300 [0.5 and 4] | | >300 [0.5 and 4] | | >30 | >30 | |
| (R)-8 | (R)-t-Bu | R | >300 [0.5 and 4] | | >300 [0.5 and 4] | | | | |
| (R, S)-9 | (2-pyridylmethyl) | R, S | 28 [0.5] (20-36) | | 210 [2.0] (160-190) | 7.6 | >30 [4] | >30 [4] | |
| (R)-10 | (R)-CH$_2$OMe | R | 13 [0.25] (11-16) | ~10 [0.25] | 26 [0.5] (21-34) | 2 | 14 [0.5] (6.1-27) | >500 [0.5] | >36 |
| (S)-10 | (S)-CH$_2$OMe | S | >300 | | >300 | | | | |
| | (S)-4[h] | | 8.0 (7.0-9.1) | | 630 (560-700) | | | | |
| | (R)-4[h] | | 7.2 (5.9-8.9) | | 580 (410-830) | | | | |
| | (R)-3[i] | | 4.5 [0.5] (3.7-5.5) | | 27 [0.25] (26-28) | | 3.9 [2.0] (2.9-6.2) | >500 | |
| | phenytoin[j] | | 9.5 [2.0] (8.1-10) | | 66 [2.0] (53-72) | 6.9 | 30 [4.0] (22-39) | | >100 |
| | phenobarbital[j] | | 22 [1.0] (15-23) | | 69 [0.5] (63-73) | 3.2 | 9.1 [5.0] (7.6-12) | 61 [0.5] (44-96) | 6.7 |
| | valproate[j] | | 270 [0.25] (250-340) | | 430 [0.25] (370-450) | 1.6 | 490 [0.5] (350-730) | 280 [0.5] (190-350) | 0.6 |

[a]The compounds were tested through the auspices of the NINDS ASP.
[b]The compounds were administered intraperitoneally. $ED_{50}$ and $TD_{50}$ values are in milligrams per kilogram.
[c]MES = maximal electroshock seizure test.
[d]$TD_{50}$ value determined from the rotorod test.
[e]PI = protective index ($TD_{50}/ED_{50}$).
[f]The compounds were acministered orally. $ED_{50}$ and $TD_{50}$ values are in milligrams per kilogram.
[g]Tox = behavioral toxicity.
[h]Ref 30.
[i]Ref 16.
[j]Ref 32.

TABLE 2

Novel Neurological Agents: Structure-Activity Relationship of X'-Y'-Z' Group[a]

| Cpd No | -X'-Y'-Z'- | Mice (ip)[b] | | | | Rat (po)[f] | | |
|---|---|---|---|---|---|---|---|---|
| | | MES, [c]ED$_{50}$ | 6 Hz, ED$_{50}$ | Tox, [d]Td$_{50}$ | PI[e] | MES, [c]ED$_{50}$ | Tox, [g]TD$_{50}$ | PI[e] |
| (R)-11 | — | >10, <30 [0.5] | <30 [0.5] | >100, <300 [0.5] | | 2.4 [1.0] (1-3.9) | >500 | >250 |
| (R)-12 | —O— | 5.5 [0.25] (3.2-6.3) | ~10 [0.5] | 23 [0.25] (18-28) | 4.2 | <10 [0.25-2.0] | >10 [0.25-4.0] | |
| (R)-13 | —(CH$_2$)$_2$— | >10, <30 [0.5] | | >30, <100 [0.5] | | <30 [1] | >30 [1] | |
| (R)-14 | —CH=CH— | >30, <100 [0.5] | <30 [0.25] | >100, <300 [0.5] | | ~30 [1.0, 4.0] | >30 [0.25, 4.0] | |
| (R)-15 | —≡— | >30, <100 [1.0, 4.0] | | >100, <300 [4.0] | | 1.4 [4.0] (0.7-2.2) | >63, >125 [4] | |
| (R)-16 | —CH$_2$O— | 5.9 [0.25] (4.3-7.3) | | 10 [0.25] (9.1-13) | 1.8 | 19 [2] (13-25) | >400 [0.5] | >21 |
| (R)-17 | —N(H)CH$_2$— | >10, <30 [0.5] | | >30, <100 [0.5] | | | | |
| (R)-10 | —OCH$_2$— | 13 [0.25] (11-16) | ~10 [0.25] | 26 [0.5] (21-34) | 2 | 1.4 [0.5] (6.1-27) | >500 [0.5] | >36 |
| (R)-18 | —CH$_2$OCH$_2$— | >30, <100 [0.5] | | >30, <100 [0.5] | | | | |
| (R)-19 | —OCH$_2$CH$_2$— | >30, <100 [0.5, 4.0] | | >30, <100 [0.5] | | | | |

[a]The compounds were tested through the auspices of NINDS ASP.
[b]The compounds were administered intraperitoneally. ED$_{50}$ and TD$_{50}$ values are in milligrams per kilogram.
[c]MES = maximal electroshock seizure test.
[d]TD$_{50}$ value determined from the rotorod test.
[e]PI = protective index (TD$_{50}$/ED$_{50}$).
[f]The compounds were administered orally. ED$_{50}$ and TD$_{50}$ values are in milligrams per kilogram.
[g]TOX = behavioral toxicity.
[h]Ref 30.
[i]Ref 16.
[j]Ref 32.

TABLE 3

Novel Neurological Agents: Structure-Activity Relationship of Terminal Ring Group[a]

| Cpd No | R' | Mice (ip)[b] | | | | Rat (po)[f] | | |
|---|---|---|---|---|---|---|---|---|
| | | MES, [c]ED$_{50}$ | 6 Hz, ED$_{50}$ | Tox, [d]TD$_{50}$ | PI[e] | MES, [c]ED$_{50}$ | Tox, [g]TD$_{50}$ | PI[e] |
| (R)-20 | — | 5.8 [0.25] (4.4-7.2) | | 22 [0.25] (19-25) | 3.8 | 5.6 [0.25] (4.2-6.4) | >250 [1.0] | >45 |
| (R)-21 | 2-F | 6.7 [0.25] (4.8-9.1) | | 37 [0.5] (29-48) | 5.5 | 11 [0.5] (7.9-13) | >500 | >45 |
| (R)-10 | 3-F | 13 [0.25] (11-16) | ~10 [0.25] | 26 [0.5] (21-34) | 2 | 14 [0.5] (6.1-27) | >500 [0.5] | >36 |
| (R)-22 | 4-F | >10, <30 [0.5] | | >30, <100 [0.5] | | 5.8 [0.5] (4.3-7.3) | >500 | >86 |

[a]The compounds were tested through the auspices of the NINDS ASP.
[b]The compounds were administered intraperitoneally. ED$_{50}$ and TD$_{50}$ values are in milligrams per kilogram.
[c]MES = maximal electroshock seizure test.
[d]TD$_{50}$ value determined from the rotorod test.
[e]PI = protective index (TD$_{50}$/ED$_{50}$).
[f]The compounds were administered orally. ED$_{50}$ and TD$_{50}$ values are in milligrams per kilogram.
[g]Tox = behavioral toxicity.
[h]Ref 30.
[i]Ref 16.
[j]Ref 32.

TABLE 5

Novels Neurological agents: Advanced Neurological Test Data

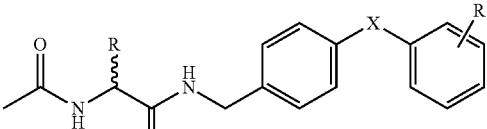

| | | | Formalin Test (mice, ip)[a] | | | Preliminary Hippocampal Kindling Test | | | Hippocampal |
|---|---|---|---|---|---|---|---|---|---|
| | | | Acute | | | (Rats) | | | |
| | | | Dose (mg/ | (%) (SEM) | Inflammatory (%) | Seizure Score | | After discharge duration (sec) | Kindled Rats (ip) $ED_{50}$ (interval) |
| R | X | $R_1$ | kg) | [p Value] | [p Value] | Pre-drug | Drug | Pre-drug Drug | (mg/kg) |
| (R)-$CH_2OMe$ | $OCH_2$ | -mF- | 15 | 35 (4.7) [<0.01] | 44 (10) [<0.01] | 4-5 | 0 | 21-47 0 | 12 (7.6-18) |
| lacosamide | | | 5 | 86 [>0.05] | 31 [<0.01] | | | | 14 |
| phenytoin | | | 6 | 66 (21) [>0.05] | 21 (5) [<0.01] | 4-5 | 3 | 42-72 51 | 34 (21-45) |
| pheno-barbital | | | | | | | | | 20 (14-28) |
| valproate | | | 300 | 66 (5) [<0.05] | 67 (20) [>0.05] | | | | 214 (150-280) |

[a]Results are presented as mean ± SEM. Mean value for duration of licking expressed as a percent of control. Data were considered in the early phase (Acute) and the late phase

TABLE 4

Activities in the Formalin Pain Assay (mice, ip) and Partial Sciatic Nerve Ligation Model (rats, ip)

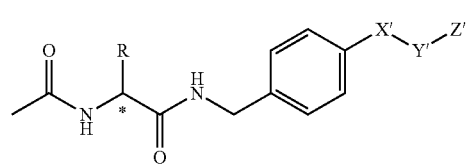

| R | Dose (mg) | Acute (%) | Inflam. (%) |
|---|---|---|---|
| | Formalin Assay | | |
| H | 16 | 100 | 44 |
| $OCF_3$ | 4.0 | 52 | 50 |
| $N_3$ | 8.0 | 59 | 106 |
| $CF_3$ | 25 | 80 | 70 |
| $OCH_2Ph(mF)$ | 15 | 35 | 44 |
| | Partial Sciatic Nerve Ligation Assay | | |
| $OCH_2Ph(mF)$ | 12 | 11.2 fold attenuation of mechanical allodynia at 1 h (p < 0.05) | |

The foregoing is illustrative of the present invention, and is not to be construed as limiting thereof. The invention is defined by the following claims, with equivalents of the claims to be included therein.

We claim:
1. A compound of Formula Ib:

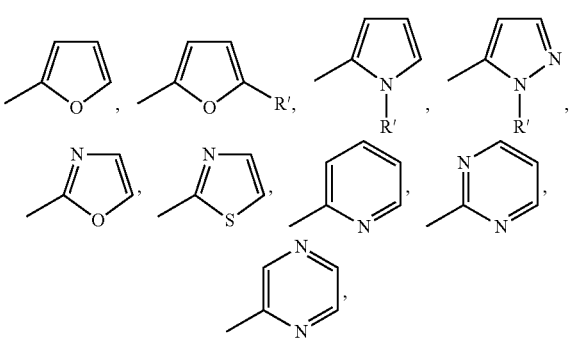

(Ib)

wherein:
R is:

$N(R')OR'$, $CH_2OCH_3$, $CH_2OCH_2CH_3$, $CH_2OCH(CH_3)_2$, $CH_2OCD_3$, $CH_2OCD_2CD_3$, $CH_2OCD_2CH_3$, $CH_2OCD(CH_3)_2$, $CH_2OCD(CD_3)_2$, $CH_2OCF_2H$, $CH_3$, $CD_3$, $CF_3$, $CH_2F$, $CH_2CH_3$, $(CH_2)_2CH_3$, $CH(CH_3)_2$, $(CH_2)_3CH_3$, $C(CH_3)_3$;

each R' is independently selected H or lower alkyl, unsubstituted or substituted with 1-3 electron-withdrawing or electron-donating groups;

X' is a covalent bond or a linker that consist of one, two, or three connected atoms and which atoms may or may not be substituted;

Y' is an aromatic or heteroaromatic moiety, unsubstituted or substituted with 1-3 electron-withdrawing or electron-donating groups; and Z' is H, F, Cl, Br, I, $CF_3$, CN, $OCF_3$, or $N_3$;

or a pharmaceutically acceptable salt or prodrug thereof.

2. The compound of claim 1, wherein X' is a covalent bond.

3. The compound of claim 1 wherein Z' is F, Cl, or $OCF_3$.

4. The compound of claim 1 wherein R is —$CH_2OCH_3$.

5. The compound of claim 1, wherein said compound is selected from the group consisting of:

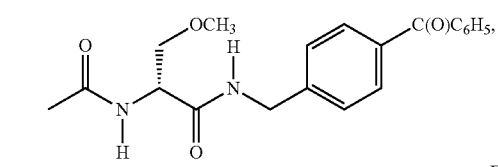

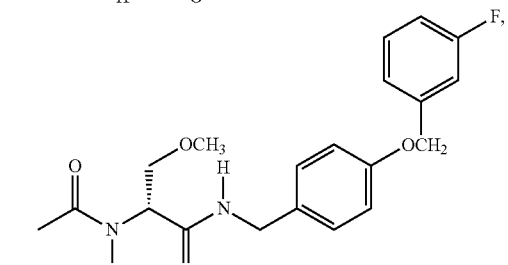

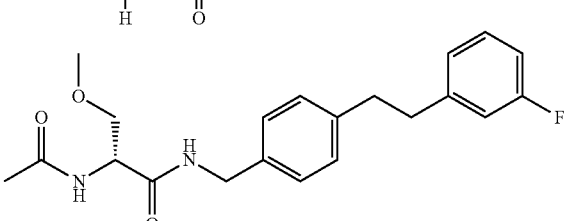

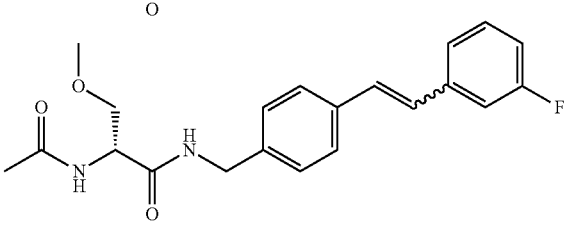

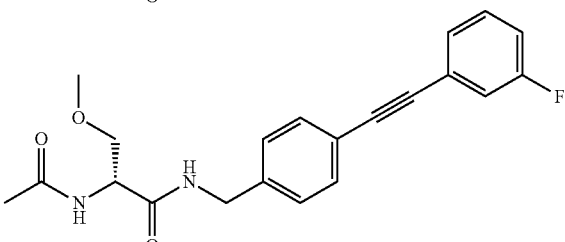

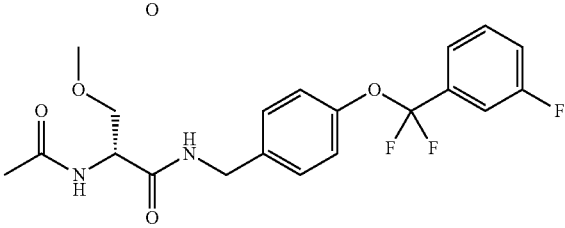

-continued

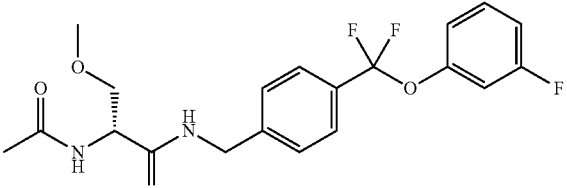

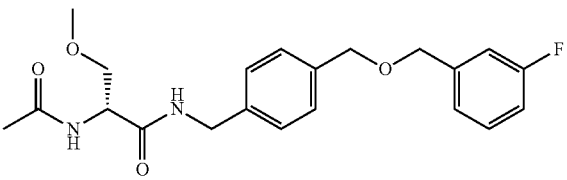

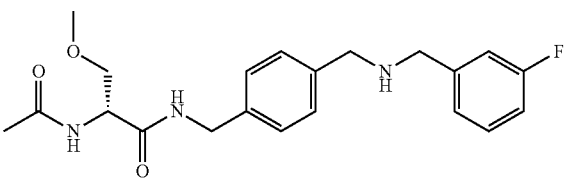

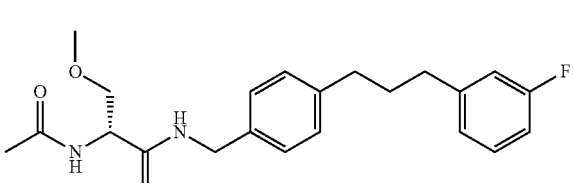

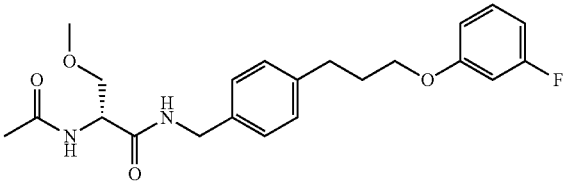

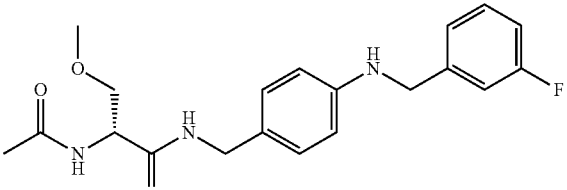

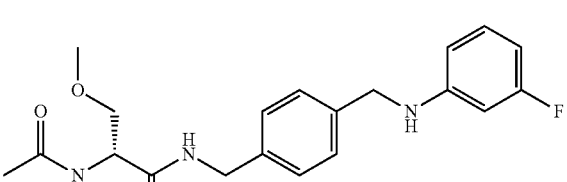

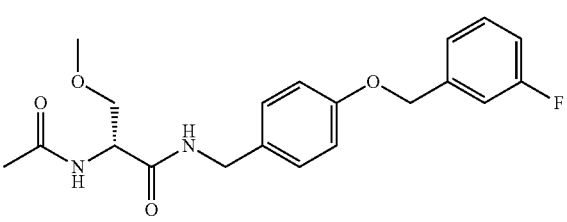

163
-continued
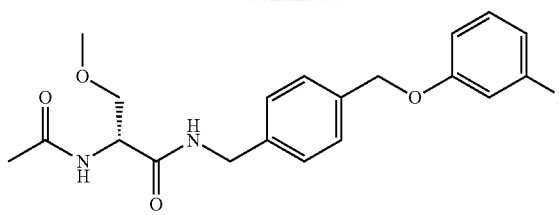
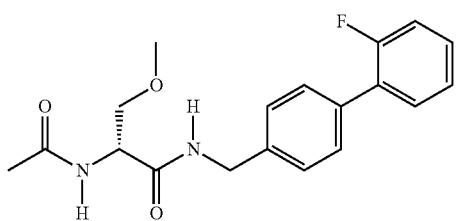
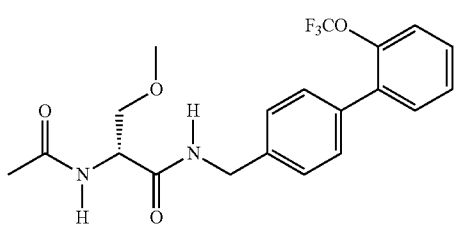
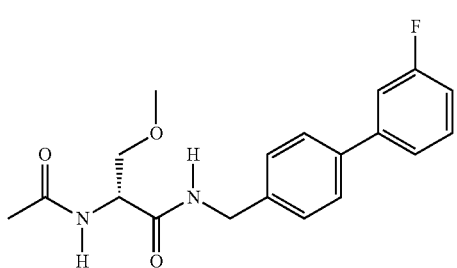
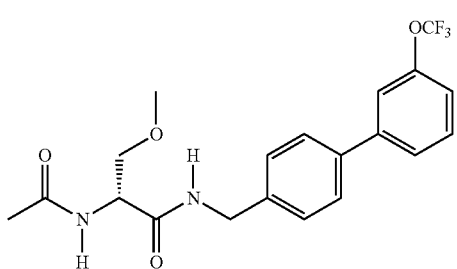
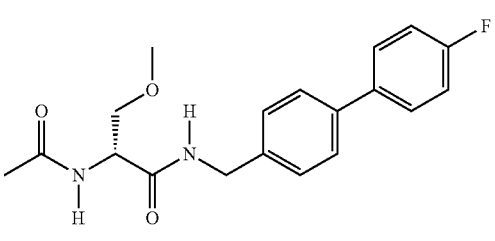
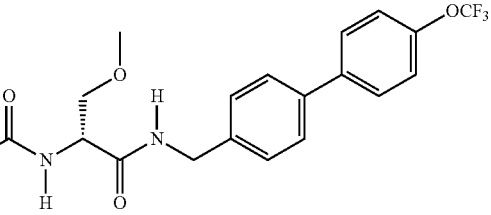
164
-continued
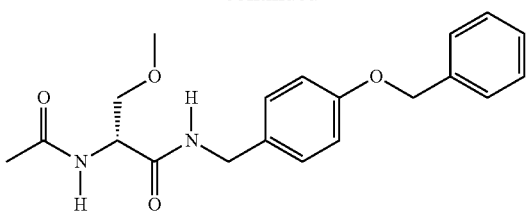
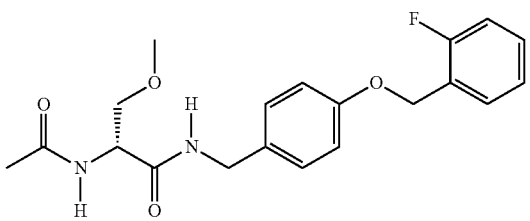
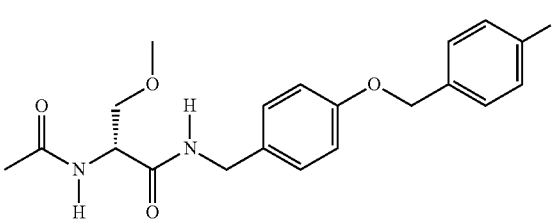
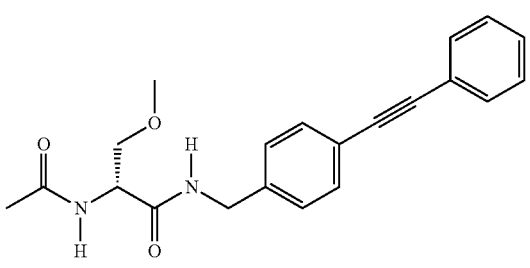
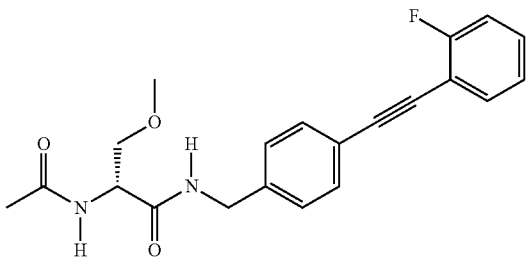
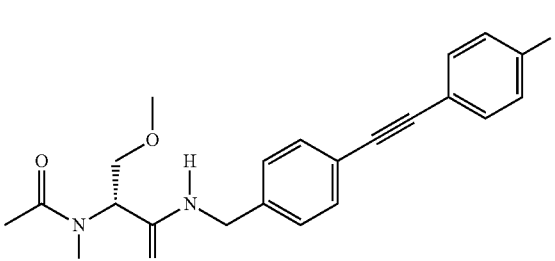
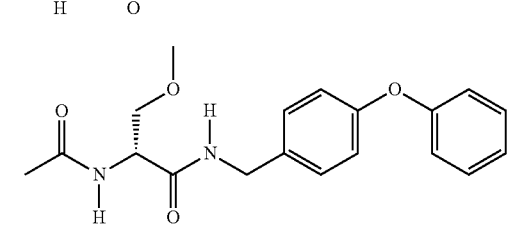

-continued

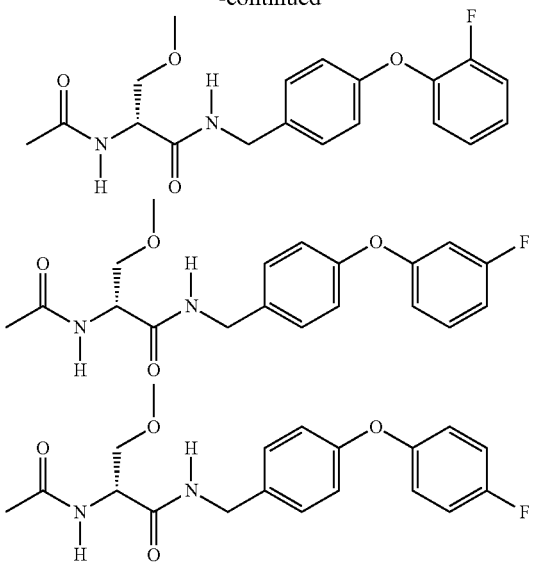

and pharmaceutically acceptable salts thereof.

6. The compound of claim 1 in the D-amino acid configuration, the L-amino acid configuration, or as a racemic mixture thereof.

7. The compound of claim 1 in the D-amino acid configuration.

8. A pharmaceutical composition comprising a compound of claim 1 in a pharmaceutically acceptable carrier.

9. The composition of claim 8 further comprising at least one neurological active agent in addition to said compound of Formula Ib.

10. The composition of claim 8 in oral administration form.

11. A method of treating a neurological disorder in a mammalian subject in need thereof, comprising administering said subject a compound of claim 1 in a treatment effective amount, wherein said neurological disorder is acute or chronic pain, migraine, neuropathic pain, fibromyalgia, bipolar disorders, convulsions, a seizure disorder, mania, epilepsy, epileptogenesis, dyskinesia, tremors, anxiety, depression, or ischemia.

12. The method of claim 11, wherein said neurological disorder is epilepsy.

13. The method of claim 11, wherein said neurological disorder is neuropathic pain.

14. The method of claim 11, wherein said subject is a human subject.

15. The method of claim 11, further comprising concurrently administering said subject at least one neurological active agent in addition to said compound of Formula Ib in a treatment effective amount.

* * * * *

UNITED STATES PATENT AND TRADEMARK OFFICE
CERTIFICATE OF CORRECTION

PATENT NO. : 8,829,033 B2  
APPLICATION NO. : 13/395588  
DATED : September 9, 2014  
INVENTOR(S) : Kohn et al.

Page 1 of 1

It is certified that error appears in the above-identified patent and that said Letters Patent is hereby corrected as shown below:

In the Specification

Column 1, GOVERNMENT FUNDING, Lines 16-24, Please replace the paragraph to read as follows:

"This invention was made with government support under Grant Nos. NS054112 & RR025747 awarded by the National Institutes of Health. The government has certain rights in the invention."

Signed and Sealed this  
Eighteenth Day of November, 2014

Michelle K. Lee  
*Deputy Director of the United States Patent and Trademark Office*